US011918592B2

(12) United States Patent
Marineau et al.

(10) Patent No.: US 11,918,592 B2
(45) Date of Patent: Mar. 5, 2024

(54) INHIBITORS OF CYCLIN DEPENDENT KINASE 7 (CDK7)

(71) Applicant: Syros Pharmaceuticals, Inc., Cambridge, MA (US)

(72) Inventors: Jason J. Marineau, Franklin, MA (US); Claudio Edmundo Chuaqui, Arlington, MA (US); Stephane Ciblat, Montreal (CA); Anzhelika Kabro, Montreal (CA); Henri Piras, Montreal (CA); Kenneth Matthew Whitmore, Montreal (CA); Kate-Lyn Lund, Lachine (CA); Michael Bradley, Houston, TX (US)

(73) Assignee: Syros Pharmaceuticals, Inc., Cambridge, MA (US)

( * ) Notice: Subject to any disclaimer, the term of this patent is extended or adjusted under 35 U.S.C. 154(b) by 520 days.

(21) Appl. No.: 16/962,809

(22) PCT Filed: Jan. 16, 2019

(86) PCT No.: PCT/US2019/013860
§ 371 (c)(1),
(2) Date: Jul. 16, 2020

(87) PCT Pub. No.: WO2019/143730
PCT Pub. Date: Jul. 25, 2019

(65) Prior Publication Data
US 2022/0000890 A1 Jan. 6, 2022

Related U.S. Application Data

(60) Provisional application No. 62/617,888, filed on Jan. 16, 2018.

(51) Int. Cl.
| | |
|---|---|
| C07D 403/04 | (2006.01) |
| C07D 403/14 | (2006.01) |
| C07D 413/14 | (2006.01) |
| A61P 35/00 | (2006.01) |
| A61K 31/675 | (2006.01) |
| A61K 31/506 | (2006.01) |
| A61K 31/5377 | (2006.01) |
| A61K 45/06 | (2006.01) |
| C07D 471/04 | (2006.01) |
| C07D 487/08 | (2006.01) |
| C07F 9/6558 | (2006.01) |

(52) U.S. Cl.
CPC .......... *A61K 31/675* (2013.01); *A61K 31/506* (2013.01); *A61K 31/5377* (2013.01); *A61K 45/06* (2013.01); *A61P 35/00* (2018.01); *C07D 403/04* (2013.01); *C07D 403/14* (2013.01); *C07D 413/14* (2013.01); *C07D 471/04* (2013.01); *C07D 487/08* (2013.01); *C07F 9/65583* (2013.01)

(58) Field of Classification Search
CPC .. C07D 403/04; C07D 403/14; C07D 413/14; A61P 35/00
See application file for complete search history.

(56) References Cited

U.S. PATENT DOCUMENTS

| | | |
|---|---|---|
| 7,615,562 B2 | 11/2009 | Bollbuck et al. |
| 9,012,462 B2 | 4/2015 | Wang et al. |
| 9,561,228 B2 | 2/2017 | Haq et al. |
| 2011/0160237 A1 | 6/2011 | Ali et al. |
| 2014/0031360 A1 | 1/2014 | Wang et al. |
| 2019/0276440 A1 | 9/2019 | Zhao et al. |
| 2020/0190126 A1 | 6/2020 | Marineau et al. |

FOREIGN PATENT DOCUMENTS

| | | |
|---|---|---|
| WO | 2006038001 A1 | 4/2006 |
| WO | 2006096564 A1 | 9/2006 |
| WO | 2008137105 A1 | 11/2008 |
| WO | 2012078777 A1 | 6/2012 |
| WO | 2015058126 A1 | 4/2015 |

(Continued)

OTHER PUBLICATIONS

Browne et al. "A Chemoproteomic Strategy for Direct and Proteome-Wide Covalent Inhibitor Target-Site dentification," Journal of the American Chemical Society, 2019, 141:191-203.

Gao et al. "Overcoming Resistance to the THZ Series of Covalent Transcriptional CDK Inhibitors," Cell Chemical Biology, 2018, 25:135-142.

Geng et al. "Targeting CDK12-mediated transcription regulation in anaplastic thyroid carcinoma," Biochemical and Biophysical Research Communications, 2019, 520:544-550.

(Continued)

*Primary Examiner* — Samira J Jean-Louis
(74) *Attorney, Agent, or Firm* — Goodwin Procter LLP

(57) ABSTRACT

The present invention provides, inter alia, compounds having the structures of formulas described herein; pharmaceutically acceptable salts, solvates, hydrates, tautomers, and isotopic forms thereof; and compositions (e.g., pharmaceutical compositions and kits) containing one or more of the foregoing. Also provided are methods of administering and uses involving the compounds and/or pharmaceutical compositions for treating or preventing disease. The disease can be a proliferative disease, such as a cancer (e.g., a blood cancer (e.g., a leukemia or lymphoma), a brain cancer, a breast cancer, melanoma, multiple myeloma, or an ovarian cancer) a benign neoplasm, pathologic angiogenesis, or a fibrotic disease. While no aspect of the invention is limited by the biological events that may transpire, administering a compound or other composition described herein may selectively inhibit the aberrant expression or activity of cyclin-dependent kinase 7 (CDK7) and, thereby, induce cellular apoptosis and/or inhibit the transcription of disease-related genes in the patient (or in a biological sample).

26 Claims, 16 Drawing Sheets

(56) References Cited

FOREIGN PATENT DOCUMENTS

| | | |
|---|---|---|
| WO | 2015058163 A2 | 4/2015 |
| WO | 2015154039 A2 | 10/2015 |
| WO | 2015188777 A1 | 12/2015 |
| WO | 2015195228 A1 | 12/2015 |
| WO | 2018013867 A1 | 1/2018 |
| WO | 2018098473 A1 | 5/2018 |
| WO | 2019143719 A1 | 7/2019 |
| WO | 2019143730 A1 | 7/2019 |
| WO | 2019204781 A1 | 10/2019 |
| WO | 2019217757 A1 | 11/2019 |

OTHER PUBLICATIONS

Hu et al., "An Oral and Selective CDK7 Inhibitor Demonstrates Substantial Anti-tumor Effect in Breast and Ovarian Cancer Models," 30th EORTC-NCI-AACR Molecular Targets and Cancer Symposium, Abstract No. 96, 2018.

Hu et al., "SY-5609, an Orally Available Selective CDK7 Inhibitor, Demonstrates Broad Anti-tumor Activity In Vivo," American Association for Cancer Research (AACH) Annual Meeting, Abstract No. 4421, 2019.

Iniguez et al. "EWS/FLI Confers Tumor Cell Synthetic Lethality to CDK12 Inhibition in Ewing Sarcoma, " Cancer Cell, 2018, 33:202-216.

International Search Report for PCT/US2017/042017 dated Oct. 13, 2017.

International Search Report for PCT/US2019/013845 dated Mar. 14, 2019.

International Search Report for PCT/US2019/013860 dated Mar. 22, 2019.

International Search Report for PCT/US2019/59542 dated Feb. 11, 2020.

Ito et al. "Discovery of 3-Benzyl-1-(trans-4-((5-cyanopyridin-2-yl)amino)cyclohexyl)-1-arylurea Derivatives as Novel and Selective Cyclin-Dependent Kinase 12 (CDK12) Inhibitors," Journal of Medicinal Chemistry, 2018, 61:7710-7728.

Johannes et al. "Structure-Based Design of Selective Noncovalent CDK12 Inhibitors," ChemMedChem, 2018, 13:231-235.

Johannessen et al., "Preclinical Evaluation of PK, PD, and Anti-tumor Activity of the Oral, Non-covalent, Potent and Highly Selective CDK7 Inhibitor, SY-5609, Provides Rationale for Clinical Development in Multiple Solid Tumor Indications," 31st EORTC-NCI-AACR Molecular Targets and Cancer Symposium, Abstract No. C091, 2019.

Krajewska et al. "CDK12 loss in cancer cells affects DNA damage response genes through premature cleavage and polyadenylation," Nature Communications, 2019, 10(1):1-16.

Olson et al. "Development of a Selective CDK7 Covalent Inhibitor Reveals Predominant Cell-Cycle Phenotype," Cell Chemical Biology, 2019, 26:792-803.

Zhang et al. "Covalent targeting of remote cysteine residues to develop CDK12 and CDK13 inhibitors," Nature Chemical Biology, 2016, 12:876-884.

| Compound | Done as | ¹H NMR | Calcd. Mass | Found Mass (MH⁺) |
|---|---|---|---|---|
| 100 | Following steps 6-7 of Example 1 substituting tert-butyl N-[(1S,2S)-2-aminocyclohexyl]carbamate for tert-butyl N-[(1S,2S)-2-aminoindan-1-yl]carbamate | ¹H NMR (400MHz, DMSO) δ 12.43 (br, 1 H), 8.65-8.36 (m, 2 H), 8.19-7.87 (m, 5H), 7.53-7.48 (m, 1 H), 4.04-4.01 (m, 1H), 3.29-2.99 (m, 1 H), 2.12-1.88 (m, 2H), 1.80-1.64 (m, 2 H), 1.57-1.18 (m, 4 H) | 400.4 | 401.2 |
| 101 | Following steps 6-7 of Example 1 substituting tert-butyl N-[(1S,2S)-2-aminocyclopentyl]carbamate for tert-butyl N-[(1S,2S)-2-aminoindan-1-yl]carbamate | ¹H NMR (400MHz, DMSO) δ 12.36 (br, 1 H), 8.66-8.53 (m, 1 H), 8.32-7.94 (m, 5 H), 7.51-7.49 (m, 1 H), 4.32 (br, 1H), 3.60-3.46 (m, 1 H), 2.22-2.03 (m, 2 H), 1.81-1.50 (m, 4 H) | 386.37 | 387.2 |
| 102 | Following steps 6-7 of Example 1 substituting tert-butyl-(R)-(morpholin-3-ylmethyl)carbamate for tert-butyl N-[(1S,2S)-2-aminocyclohexyl]carbamate | ¹H NMR (400MHz, DMSO) δ 12.41 (br, 1 H), 9.50-9.37 (m, 2H), 8.66 (s, 1 H), 8.58 (d, J = 8 Hz, 1 H), 8.31-8.03 (m, 3 H), 7.54-7.48 (m, 1 H), 4.00-3.97 (m, 1H), 3.78-3.47 (m, 6 H), 3.31-3.18 (m, 1 H), 3.13-2.94 (m, 1 H) | 402.37 | 403.2 |
| 103 | Following steps 6-7 of Example 1 substituting tert-butyl N-[(1S,2S)-2-aminocyclobutyl]carbamate for tert-butyl N-[(1S,2S)-2-aminoindan-1-yl]carbamate | ¹H NMR (400MHz, D₂O) δ 8.52 (1H), 8.00 (d, J = 8 Hz, 1 H), 7.81 (br, 1 H), 7.33 (br, 1 H), 4.45-4.39 (br, 1H), 3.80-3.70 (br, 1H), 2.40 (d, J=8.4 Hz, 1H), 2.24 (br, 1 H), 1.97-1.92 (br, 1H) | 372.35 | 373.2 |
| 104 | Following steps 6-7 of Example 1 substituting tert-butyl (2S,4S)-4-amino-2-methylpyrrolidine-1-carboxylate for tert-butyl N-[(1S,2S)-2-aminoindan-1-yl]carbamate | 1H NMR (400MHz, METHANOL-d4) δ = 8.65 - 8.52 (m, 2H), 8.16 (br s, 1H), 7.93 (br s, 1H), 7.51 (br s, 1H), 4.02 (br s, 1H), 3.77 (dd, J=6.4, 12.5 Hz, 1H), 3.50 - 3.41 (m, 1H), 3.38 - 3.32 (m, 1H), 2.48 - 2.39 (m, 1H), 2.16 (br s, 1H), 1.48 (d, J=6.6 Hz, 3H) | 386.15 | 387.2 |
| 105 | Following steps 6-7 of Example 1 substituting (S)-1-isopropylpyrrolidin-3-amine for tert-butyl N-[(1S,2S)-2-aminoindan-1-yl]carbamate | 1H NMR (400MHz, METHANOL-d4) δ = 8.65 - 8.52 (m, 2H), 8.04 (s, 1H), 7.89 (s, 1H), 7.44 (br d, J=8.3 Hz, 1H), 4.72 (br s, 1H), 3.61 - 3.35 (m, 2H), 3.28 - 2.99 (m, 3H), 2.56 - 2.43 (m, 1H), 2.13 (br dd, J=6.1, 13.0 Hz, 1H), 1.29 (br s, 6H) | 414.18 | 415.3 |

FIG. 2 (Cont.)

| Compound | Done as | $^1$H NMR | Calcd. Mass | Found Mass (MH$^+$) |
|---|---|---|---|---|
| 106 | Example 14 | $^1$H NMR (400 MHz, MeOD-d4) δ 8.65 (br, 1 H), 8.41 (br, 1H), 8.17 (br, 1H), 7.93 (br, 1H), 7.59-7.47 (br, 1H), 4.76-4.64 (br, 1H), 4.54-4.82 (br, 1H), 4.28-4.26 (t, J=5.2, 1H), 2.56 (br, 1H), 2.25-2.20 (br, 1H), 1.96-1.71 (m, 3 H), 1.81-1.76 (dd, J=13.6 Hz, 4.8 Hz, 1 H) | 398.38 | 399.1 |
| 107 | Following steps 6-7 of Example 1 substituting tert-butyl cis-3-amino-4-hydroxypyrrolidine-1-carboxylate for tert-butyl N-[(1S,2S)-2-aminoindan-1-yl]carbamate | 1H NMR (400MHz, METHANOL-d4) δ = 8.70 (br s, 1H), 8.60 - 8.36 (m, 1H), 8.24 (br s, 1H), 7.94 (br s, 1H), 7.58 (br s, 1H), 4.60 (br s, 1H), 3.80 - 3.63 (m, 2H), 3.56 - 3.47 (m, 1H), 3.44 - 3.36 (m, 2H) | 388.13 | 389.1 |
| 108 | Following steps 6-7 of Example 1 substituting tert-butyl (2R,4S)-4-amino-2-methylpyrrolidine-1-carboxylate for tert-butyl N-[(1S,2S)-2-aminoindan-1-yl]carbamate | 1H NMR (400MHz, METHANOL-d4) δ = 8.65 (s, 1H), 8.54 (br s, 1H), 8.11 (s, 1H), 7.91 (s, 1H), 7.49 (br s, 1H), 4.85 - 4.54 (m, 1H), 3.82 - 3.65 (m, 2H), 3.38 (br dd, J=5.9, 12.1 Hz, 1H), 2.78 - 2.66 (m, 1H), 1.95 - 1.80 (m, 1H), 1.52 (br d, J=6.6 Hz, 3H) | 386.15 | 387.1 |
| 109 | Following steps 6-7 of Example 1 substituting (S)-1-methylpyrrolidin-3-amine for tert-butyl N-[(1S,2S)-2-aminoindan-1-yl]carbamate | 1H NMR (400MHz, METHANOL-d4) δ = 8.67 - 8.46 (m, 2H), 8.46 (br s, 1H), 8.06 (s, 1H), 7.90 (s, 1H), 7.51 - 7.36 (m, 1H), 4.75 (br s, 1H), 3.69 - 3.34 (m, 4H), 2.99 - 2.77 (m, 3H), 2.64 - 2.50 (m, 1H), 2.23 (br d, J=6.8 Hz, 1H) | 386.15 | 387.2 |
| 110 | Following steps 6-7 of Example 1 substituting tert-butyl trans-3-amino-4-fluoropyrrolidine-1-carboxylate for tert-butyl N-[(1S,2S)-2-aminoindan-1-yl]carbamate | 1H NMR (400MHz, METHANOL-d4) δ = 8.64 (br s, 1H), 8.51 (br s, 1H), 8.45 (s, 1H), 8.08 (s, 1H), 7.92 - 7.86 (m, 1H), 7.46 - 7.38 (m, 1H), 5.51 - 5.22 (m, 1H), 4.81 - 4.62 (m, 1H), 3.79 - 3.60 (m, 1H), 3.48 (br s, 2H), 3.38 - 3.34 (m, 1H) | 390.12 | 391.0 |
| 111 | Following steps 6-7 of Example 1 substituting tert-butyl trans-3-amino-4-ethoxypyrrolidine-1-carboxylate for tert-butyl N-[(1S,2S)-2-aminoindan-1-yl]carbamate | 1H NMR (400MHz, METHANOL-d4) δ = 8.64 (br s, 1H), 8.52 (br s, 1H), 8.05 (br s, 1H), 7.89 (s, 1H), 7.43 (d, J=8.4 Hz, 1H), 4.79 - 4.52 (m, 1H), 4.33 - 4.12 (m, 1H), 3.70 (br dd, J=6.5, 12.7 Hz, 1H), 3.49 - 3.36 (m, 5H) | 416.16 | 417.1 |

FIG. 2 (Cont.)

| Compound | Done as | ¹H NMR | Calcd. Mass | Found Mass (MH⁺) |
|---|---|---|---|---|
| 112 | Following steps 6-7 of Example 1 substituting tert-butyl (2S,4R)-4-amino-2-(hydroxymethyl)pyrrolidine-1-carboxylate for tert-butyl N-[(1S,2S)-2-aminoindan-1-yl]carbamate | 1H NMR (400MHz, METHANOL-d4) δ = 8.60 (br s, 1H), 8.55 (s, 1H), 8.51 - 8.32 (m, 1H), 8.06 (s, 1H), 7.89 (s, 1H), 7.45 (br d, J=8.4 Hz, 1H), 4.72 (br s, 1H), 3.91 - 3.73 (m, 2H), 3.65 (dd, J=6.2, 11.5 Hz, 1H), 3.59 - 3.46 (m, 1H), 3.28 - 3.17 (m, 1H), 2.22 - 2.14 (m, 2H) | 402.14 | 403.0 |
| 113 | Following steps 6-7 of Example 1 substituting tert-butyl trans-3-amino-4-(4-chlorophenyl)pyrrolidine-1-carboxylate for tert-butyl N-[(1S,2S)-2-aminoindan-1-yl]carbamate | 1H NMR (400MHz, METHANOL-d4) δ = 8.56 - 8.49 (m, 3H), 8.00 (br s, 1H), 7.91 (br s, 1H), 7.47 - 7.28 (m, 5H), 3.99 - 3.76 (m, 3H), 3.43 (br t, J=11.1 Hz, 3H) | 482.12 | 483.0 |
| 114 | Example 14 | ¹H NMR (400 MHz, MeOD-d4) δ 8.66-8.23 (m, 2H), 8.11-7.99 (m, 1H), 7.90 (br s, 1H), 7.51-7.40 (m, 1H), 4.66-4.59 (m, 1H), 4.56-4.42 (m, 1H), 4.28 -4.20 (m, 1H), 2.56-2.45 (m, 1H), 2.28 -2.17 (m, 1H), 2.08 -1.68 (m, 4H) | 398.15 | 399.2 |
| 115 | Example 14 | ¹H NMR (400 MHz, MeOD-d4) δ 8.66-8.24 (m, 2H), 8.05 (s, 1H), 7.90 (s, 1H), 7.49 - 7.40 (m, 1H), 4.66-4.36 (m, 2H), 4.24-4.13 (m, 1H), 2.54-2.39 (m, 1H), 2.28 -2.12 (m, 1H), 2.06-1.64 (m, 4H) | 398.15 | 399.2 |
| 116 | Example 2 | ¹H NMR (400 MHz, MeOD-d4) δ 8.63 (brs, 1H), 8.53 (brs, 1H), 8.49 (brs, 0.5H), 7.91 (brs, 1H), 7.40 (brs, 1H), 7.12 (brs, 1H), 4.33-4.70 (m, 1H), 3.63 (brs, 1H), 2.34-2.49 (m, 4H), 2.28 (s, 4H), 1.71-2.12 (m, 2H) | 442.17 | 443.1 |
| 117 | Example 3 | ¹H NMR (400 MHz, MeOD-d4) δ 8.69 (s, 2H), 8.52-8.15 (m, 3H), 8.06-7.76 (m, 2H), 4.79-4.28 (m, 1H), 3.82-3.50 (m, 1H), 2.48-2.24 (m, 2H), 2.00-1.74 (m, 4H) | 444.13 | 445 |
| 118 | Starting with Example 4 product and following step 3 of Example 3 | ¹H NMR (400 MHz, MeOD-d4) δ8.49-8.74 (m, 2H), 7.95 (br s, 1H), 7.43 (br s, 1H), 7.16 (br s, 1H), 4.25 (br s, 1H), 3.42-3.56 (m, 1H), 2.46 (s, 3H), 2.31 (s, 5H), 1.61-1.99 (m, 4H) | 456.19 | 457.2 |

FIG. 2 (Cont.)

| Compound | Done as | $^1$H NMR | Calcd. Mass | Found Mass (MH$^+$) |
|---|---|---|---|---|
| 119 | Example 1 | $^1$H NMR (400 MHz, MeOD-d4) δ 8.77 - 8.56 (m, 2H), 8.51 (s, 1H), 8.27 - 7.99 (m, 1H), 7.89 (s, 1H), 7.54-7.30 (m, 5H), 4.77 (br. s, 2H), 3.63-3.50 (m, 1H), 3.29 -3.07 (m, 1H) | 434.15 | 435.1 |
| 120 | Example 10 | $^1$H NMR (400 MHz, MeOD-d4) δ 8.89 (br. d, J = 7.5 Hz, 1H), 8.78 (br. s, 1H), 8.46 (s, 1H), 7.97 (s, 1H), 7.58 (br. d, J = 8.1 Hz, 1H), 4.14 (br. s, 2H), 2.35-2.24 (m, 1H), 2.22-2.14 (m, 1H), 2.11 (br. s, 3H), 2.07-1.96 (m, 2H), 1.88 (br. s, 2H) | 428.16 | 429.1 |
| 121 | Starting with the product from Step 3 of Example 5 and substituting morpholine instead of pyrrolidine, then following steps 3 and 4 of Example 6 | $^1$H NMR (400 MHz, MeOD-d4) δ 8.55 (br. s, 1H), 8.34 (br. s, 1H), 8.04 (br. s, 1H), 7.90 (br. s, 1H), 7.45 (br. d, J = 6.6 Hz, 1H), 4.68-4.53 (m, 1H), 3.91-3.42 (m, 4H), 3.23-2.65 (m, 5H), 2.32-2.00 (m, 2H), 1.88-1.61 (m, 4H) | 456.19 | 457.2 |
| 122 | Starting with the product from Step 3 of Example 5 and following steps 4 and 5 of Example 6 | $^1$H NMR (400 MHz, MeOD-d4) δ 8.66 (br. s, 1H), 8.53 (br. s, 1H), 8.29-7.85 (m, 2H), 7.45 (br. s, 1H), 4.67 (br. d, J = 6.4 Hz, 1H), 3.69-3.34 (m, 3H), 3.28-2.90 (m, 2H), 2.40-1.48 (m, 10H) | 440.19 | 441.2 |
| 123 | Example 5 | $^1$H NMR (400 MHz, MeOD-d4) δ 8.67 - 8.59 (m, 2H), 8.58 - 8.52 (m, 0.51H), 8.13 (br.s., 1H), 7.91 (br.s., 1H), 7.46 (br.d., J = 8.2 Hz, 1H), 4.73-4.35 (m, 1H), 4.32-4.16 (m, 1H), 3.70 (br.s., 1H), 3.47 (br.s., 3H), 3.11 (br.s., 2H), 3.01-2.84 (m, 1H), 2.40 -2.14 (m, 2H), 1.93 (br.s., 4H) | 444.19 | 445.1 |
| 124 | Example 10, steps 1-2, followed by Example 7, steps 3 and 4 | $^1$H NMR (400 MHz, MeOD-d4) δ 8.73 (br s, 1H), 8.68-8.41 (m, 1H), 8.37-8.09 (m, 1H), 8.06-7.83 (m, 1H), 7.75-7.36 (m, 1H), 4.64 (br s, 1H), 3.83 (br d, J = 17.2 Hz, 1H), 3.00 (br s, 3H), 2.84 (br d, J = 15.3 Hz, 3H), 2.52-2.17 (m, 2H), 1.95 (br s, 4H) | 414.18 | 415.1 |
| 125 | Example 8 | $^1$H NMR (400 MHz, MeOD-d4) δ 8.51-8.88 (m, 2H), 8.40 (s, 1H), 7.97 (brs, 1H), 7.48 - 7.70 (m, 1H),, 4.16-4.70 (m, 2H), 2.17 -2.53 (m, 2H), 1.82-2.06 (m, 3H), 1.47 -1.65 (m, 2H) | 414.14 | 415.1 |

FIG. 2 (Cont.)

| Compound | Done as | $^1$H NMR | Calcd. Mass | Found Mass (MH$^+$) |
|---|---|---|---|---|
| 126 | Example 7 | $^1$H NMR (400 MHz, MeOD-d4) δ 8.44-8.74 (m, 2H), 8.12-8.34 (m, 1H), 7.93 (brd, J = 11.5 Hz, 1H), 7.39 - 7.76 (m, 1H), 5.10 (brs, 1H), 3.74-4.12 (m, 1H), 2.71-3.06 (m, 6H), 2.23-2.62 (m, 2H), 1.83-2.20 (m, 2H) | 400.16 | 401.2 |
| 127 | Steps 1-6 of Example 12 substituting tert-butyl N-[(1S,2S)-2-aminocyclopentyl]carbamate for tert-butyl N-[(1S,2S)-2-aminocyclobutyl]carbamate in step 4. | $^1$H NMR (400 MHz, MeOD-d4) δ 9.39 (br. d, J = 7.7 Hz, 1H), 9.49-8.86 (m, 1H), 8.72 (s, 1H), 8.38-8.20 (m, 1H), 7.61 (br. d, J = 7.3 Hz, 1H), 4.86-4.29 (m, 1H), 3.85-3.55 (m, 1H), 2.68-2.25 (m, 8H), 2.03-1.77 (m, 4H) | 457.18 | 458.1 |
| 128 | Example 11 | $^1$H NMR (400 MHz, MeOD-d4) δ 8.58 (s, 1H), 8.55-8.13 (m, 1H), 8.04 (br.s., 1H), 7.92-7.76 (m, 1H), 7.52-7.29 (m, 1H), 4.59-4.20 (m, 1H), 3.48 (br.s., 1H), 3.16-2.74 (m, 2H), 2.20 (br.s., 2H), 1.90-1.59 (m, 4H), 1.34-0.57 (m, 3H) | 414.18 | 415.2 |
| 129 | Example 12 | $^1$H NMR (400 MHz, MeOD-d4) δ 9.11 (br d, J = 7.9 Hz, 1H), 8.69 (s, 1H), 8.12 (s, 1H), 7.46 (br d, J = 7.9 Hz, 1H), 4.43 (br d, J = 7.9 Hz, 1H), 3.66 (br d, J = 7.0 Hz, 1H), 2.60 (s, 3H), 2.44 (s, 3H), 2.43-2.24 (m, 2H), 2.12-1.88 (m, 2H) | 443.17 | 444.2 |
| 130 | Following Example 6, steps 1-3, substituting morpholine for pyrrolidine at step 3, and then step 5 of Example 6 | $^1$H NMR (400 MHz, MeOD-d4) δ 8.72-8.38 (m, 2H), 8.25-8.09 (m, 1H), 7.99 - 7.86 (m, 1H), 7.72-7.42 (m, 1H), 5.19 -4.93 (m, 2H), 4.17 -3.74 (m, 3H), 3.70 -3.40 (m, 3H), 3.12 (br d, J = 13.4 Hz, 2H), 2.63-1.90 (m, 4H) | 442.17 | 443.2 |
| 131 | Example 9 | $^1$H NMR (400 MHz, MeOD-d4) δ 8.58 (s, 1H), 8.52-8.17 (m, 1H), 8.03 (br.s., 1H), 7.93-7.74 (m, 1H), 7.57-7.26 (m, 1H), 3.89-3.56 (m, 1H), 3.38 (br.s., 1H), 3.13-2.70 (m, 2H), 2.54-2.10 (m, 2H), 2.02-1.75 (m, 2H), 1.30-0.80 (m, 3H) | 400.16 | 401.1 |
| 132 | Following Example 6, steps 1-4, substituting morpholine for pyrrolidine at step 4 and then step 6 of Example 6 | $^1$H NMR (400 MHz, MeOD-d4) δ 8.76-8.41 (m, 2H), 8.29 - 8.09 (m, 1H), 8.01-7.87 (m, 1H), 7.77 - 7.41 (m, 1H), 5.13 (br s, 2H), 4.17 -3.75 (m, 3H), 3.70 -3.39 (m, 3H), 3.12 (br d, J = 7.2 Hz, 2H), 2.59 -1.93 (m, 4H). | 442.17 | 443.2 |
| 133 | Following Example 6, steps 1-4, substituting 2-methoxyethan-1-amine for pyrrolidine at step 4, and then step 5 of Example 6 | $^1$H NMR (400 MHz, MeOD-d4) δ 8.72 (br s, 1H), 8.68 - 8.32 (m, 1H), 8.20 (br s, 1H), 8.06-7.94 (m, 1H), 7.70 - 7.48 (m, 1H), 4.03-3.66 (m, 3H), 3.61-3.46 (m, 2H), 3.35-3.10 (m, 4H), 2.64-2.27 (m, 2H), 2.20 -1.98 (m, 2H) | 430.17 | 431.1 |

FIG. 2 (Cont.)

| Compound | Done as | ¹H NMR | Calcd. Mass | Found Mass (MH⁺) |
|---|---|---|---|---|
| 134 | Following Example 6, steps 1-4, substituting 2-methoxyethan-1-amine for pyrrolidine at step 4, and ten step 6 of Example 6 | ¹H NMR (400 MHz, MeOD-d4) δ 8.72 (brs, 1H), 8.68 - 8.32 (m, 1H), 8.20 (brs, 1H), 8.06-7.94 (m, 1H), 7.70 - 7.48 (m, 1H), 4.03-3.66 (m, 3H), 3.61-3.46 (m, 2H), 3.35-3.10 (m, 4H), 2.64-2.27 (m, 2H), 2.20 -1.98 (m, 2H) | 430.17 | 431.2 |
| 135 | Example 6 | ¹H NMR (400 MHz, MeOD-d4) δ 8.66 (s, 1H), 8.60 - 8.26 (m, 1H), 8.10 (s, 1H), 7.90 (br s, 1H), 7.61-7.38 (m, 1H), 3.91-3.38 (m, 3H), 3.21-2.97 (m, 2H), 2.50 -1.72 (m, 9H) | 426.18 | 427.1 |
| 136 | Example 6 | ¹H NMR (400 MHz, MeOD-d4) δ 8.67 (s, 1H), 8.62-8.31 (m, 1H), 8.12 (br s, 1H), 7.98 - 7.83 (m, 1H), 7.66-7.39 (m, 1H), 3.98 -3.76 (m, 1H), 3.71-3.40 (m, 2H), 3.17 -2.94 (m, 2H), 2.55-1.60 (m, 9H) | 426.18 | 427.1 |
| 137 | Example 13 | ¹H NMR (400 MHz, MeOD-d4) δ 8.73-8.47 (m, 2H), 8.30 (br s, 1H), 7.61-7.11 (m, 2H), 5.05-4.92 (m, 1H), 4.61 (t, J = 4.3 Hz, 1H), 4.33 (br s, 1H), 2.82-2.54 (m, 1H), 2.48 (s, 3H), 2.32 (s, 3H), 2.30-2.22 (m, 1H), 2.18-1.92 (m, 3H), 1.88 (br dd, J = 4.4, 13.9 Hz, 1H) | 468.19 | 469.2 |
| 138 | Example 13 | ¹H NMR (400 MHz, MeOD-d4) δ 8.55-8.30 (m, 2H), 8.20-7.84 (m, 1H), 7.44-6.94 (m, 2H), 4.85-4.75 (m, 1H), 4.72 (s, 1H), 4.44 (t, J = 4.3 Hz, 1H), 4.16 (br s, 1H), 2.60-2.37 (m, 1H), 2.31 (s, 3H), 2.15 (s, 3H), 2.14-2.08 (m, 1H), 1.99-1.74 (m, 3H), 1.71 (br dd, J = 4.3, 14.0 Hz, 1H) | 468.19 | 469.1 |
| 139 | Steps 1-4 of Example 12, followed by steps 3-5 of Example 13 | ¹H NMR (400 MHz, MeOH-d4) δ 9.32-8.83 (m, 1H), 8.68 (s, 1H), 8.19 (br d, J = 12.8 Hz, 1H), 7.70 - 7.47 (m, 1H), 4.71-4.43 (m, 1H), 4.28 (br s, 1H), 3.38 -3.32 (m, 1H), 2.62 (br s, 4H), 2.45 (br s, 3H), 2.25 (ddd, J = 4.6, 9.1, 13.4 Hz, 1H), 2.12-1.73 (m, 4H) | 469.18 | 470.2 |
| 140 | Steps 1-4 of Example 12, followed by steps 3-4 and 6 of Example 13 | ¹H NMR (400 MHz, MeOH-d4) δ 9.34-8.82 (m, 1H), 8.67 (s, 1H), 8.19 (br d, J = 13.7 Hz, 1H), 7.74-7.45 (m, 1H), 4.75-4.43 (m, 1H), 4.28 (br s, 1H), 3.35 (br s, 1H), 2.62 (br s, 4H), 2.45 (br s, 3H), 2.34-2.18 (m, 1H), 2.10 -1.71 (m, 4H) | 469.18 | 470.1 |

FIG. 2 (Cont.)

| Compound | Done as | ¹H NMR | Calcd. Mass | Found Mass (MH⁺) |
|---|---|---|---|---|
| 141 | Example 15 | ¹H NMR (400 MHz, MeOD-d4) δ 8.95 - 8.77 (m, 1H), 8.65 - 8.43 (m, 1H), 8.01 (s, 1H), 7.34 (br. d, $J$ = 8.4 Hz, 1H), 4.83 - 4.53 (m, 1H), 3.50 (br. d, $J$ = 15.9 Hz, 1H), 3.19 - 3.01 (m, 3H), 2.93 (br. s, 1H), 2.73 (t, $J$ = 12.8 Hz, 1H), 2.45 (s, 4H), 2.18 (br. s, 1H), 1.95 (br. s, 1H), 1.88 - 1.81 (m, 1H), 1.80 - 1.65 (m, 2H). | 497.22 | 498.2 |
| 142 | Example 16 | ¹H NMR (400 MHz, MeOD-d4) δ 8.94 - 8.77 (m, 1H), 8.63 - 8.46 (m, 1H), 8.01 (s, 1H), 7.34 (br. d, $J$ = 7.9 Hz, 1H), 4.83 - 4.53 (m, 1H), 3.50 (br. d, $J$ = 15.0 Hz, 1H), 3.17 - 2.98 (m, 3H), 2.92 (br. s, 1H), 2.73 (t, $J$ = 12.6 Hz, 1H), 2.60 (s, 3H), 2.45 (s, 3H), 2.43 - 2.32 (m, 1H), 2.17 (br. s, 1H), 1.95 (br. s, 1H), 1.84 (br.s, 2H), 1.79 - 1.68 (m, 2H) | 497.22 | 498.2 |
| 143 | Example 17 | ¹H NMR (400 MHz, MeOD-d4) δ 8.64 - 8.33 (m, 2H), 7.89 (s, 1H), 7.40 (s, 1H), 7.12 (dd, $J$ = 1.2, 8.3 Hz, 1H), 4.74 - 4.49 (m, 1H), 2.80 - 2.73 (m, 1H), 2.66 (br. s, 4H), 2.44 (s, 3H), 2.29 (s, 3H), 2.26 - 2.13 (m, 1H), 2.13 - 1.99 (m, 1H), 1.84 - 1.57 (m, 8H) | 510.24 | 511.1 |
| 144 | Example 18 | ¹H NMR (400 MHz, MeOD-d4) δ 8.99 - 8.58 (m, 2H), 8.54 (br.s., 1H), 8.10 - 7.93 (m, 1H), 7.35 (br.s., 1H), 4.69 (br.s., 1H), 3.63 - 3.33 (m, 4H), 3.11 (br.d., $J$ = 17.2 Hz, 1H), 2.61 (s, 3H), 2.46 (s, 3H), 2.27 (br.s., 2H), 2.03 (br.s., 3H), 1.95 - 1.72 (m, 5H) | 511.23 | 512.2 |
| 145 | Example 19 | ¹H NMR (400 MHz, MeOD-d4) δ 9.03 - 8.58 (m, 2H), 8.55 (br.s., 1H), 8.06 (br.s., 1H), 7.44 - 7.29 (m, 1H), 4.42 - 4.28 (m, 1H), 3.47 - 3.34 (m, 1H), 3.12 - 2.97 (m, 1H), 2.78 - 2.65 (m, 1H), 2.61 (s, 3H), 2.46 (s, 3H), 2.26 (br.s., 2H), 1.88 (br.s., 4H), 1.31 (br.s., 2H), 0.76 - 0.60 (m, 1H) | 485.22 | 486.2 |
| 146 | Example 20 | ¹H NMR (400 MHz, MeOD-d4) δ 8.99 - 8.64 (m, 2H), 8.60 (br.s., 0.635H), 8.08 - 7.93 (m, 1H), 7.34 (br.d., $J$ = 7.7 Hz, 1H), 4.43 (br.s., 1H), 4.27 - 4.02 (m, 3H), 3.96 - 3.74 (m, 1H), 3.71 - 3.47 (m, 1H), 2.61 (s, 3H), 2.46 (s, 4H), 2.33 - 2.06 (m, 3H), 1.98 - 1.57 (m, 4H) | 497.22 | 498.2 |

FIG. 2 (Cont.)

| Compound | Done as | $^1$H NMR | Calcd. Mass | Found Mass (MH$^+$) |
|---|---|---|---|---|
| 147 | Example 21 | $^1$H NMR (400 MHz, DMSO-d6) δ 12.32 - 12.00 (m, 1H), 8.74 (br.s., 1H), 8.57 (s, 1H), 7.91 (s, 1H), 7.71 (br.d., J = 7.8 Hz, 1H), 7.34 (d, J = 8.3 Hz, 1H), 6.08 - 5.67 (m, 1H), 4.13 (quin, J = 7.0 Hz, 1H), 3.15 - 3.10 (m, 2H), 2.94 (br.s., 1H), 2.60 (s, 3H), 2.43 (s, 3H), 2.16 - 2.05 (m, 1H), 2.01 - 1.91 (m, 1H), 1.75 - 1.66 (m, 2H), 1.65 - 1.55 (m, 1H), 1.41 (dd, J = 7.1, 13.0 Hz, 1H) | 521.20 | 522.2 |
| 148 | Example 22 | $^1$H NMR (400 MHz, MeOD-d4) δ 9.45 - 8.91 (m, 1H), 8.73 (br. s, 1H), 8.41 - 8.19 (m, 1H), 7.84 - 7.54 (m, 1H), 5.64 - 5.21 (m, 1H), 5.08 (br. s, 1H), 4.23 - 3.78 (m, 3H), 3.77 - 3.41 (m, 2H), 2.72 - 2.58 (m, 3H), 2.56 - 2.17 (m, 7H), 2.17 - 1.84 (m, 4H) | 529.22 | 530.2 |
| 149 | Example 23 | $^1$H NMR (400 MHz, MeOD-d4) δ 8.97 - 8.66 (m, 1H), 8.62 (br.s., 0.564H), 8.55 (br.s., 1H), 8.07 - 7.94 (m, 1H), 7.45 - 7.30 (m, 1H), 4.83 - 4.74 (m, 1H), 3.51 - 3.33 (m, 1H), 3.12 - 2.73 (m, 4H), 2.61 (s, 3H), 2.46 (s, 3H), 2.36 (br.s., 1H), 2.12 (br.s., 1H), 2.02 - 1.66 (m, 6H) | 497.22 | 498.2 |
| 150 | Example 24 | $^1$H NMR (400 MHz, MeOD-d4) δ 9.27 - 8.75 (m, 1H), 8.69 (br. s, 1H), 8.29 - 8.05 (m, 1H), 7.75 - 7.39 (m, 1H), 5.59 - 5.19 (m, 1H), 5.01 (br. s, 1H), 3.90 (br. s, 3H), 3.49 (br. s, 2H), 2.61 (br. s, 3H), 2.51 - 2.26 (m, 6H), 1.97 (br. s, 4H), 2.09 - 1.70 (m, 1H) | 529.22 | 530.2 |
| 151 | Example 25 | $^1$H NMR (400MHz, MeOD-d4) δ = 9.04 - 8.53 (m, 2H), 8.48 (br s, 1H), 8.07 (br s, 1H), 7.35 (br d, J = 7.9 Hz, 1H), 4.65 - 3.97 (m, 2H), 3.61 - 3.33 (m, 4H), 2.60 (s, 3H), 2.45 (s, 3H), 2.37 - 2.16 (m, 2H), 1.93 (br s, 4H) | 503.21 | 504.2 |
| 152 | Example 26 | $^1$H NMR (400MHz, MeOD-d4) δ 9.02 - 8.57 (m, 2H), 8.55 (s, 0.751H), 8.12 - 7.92 (m, 1H), 7.35 (br. d., J = 7.8 Hz, 1H), 4.50 - 4.14 (m, 1H), 3.76 - 3.36 (m, 5H), 3.28 - 2.81 (m, 3H), 2.61 (s, 3H), 2.46 (s, 3H), 2.39 - 1.55 (m, 6H) | 515.23 | 516.2 |

FIG. 2 (Cont.)

| Compound | Done as | $^1$H NMR | Calcd. Mass | Found Mass (MH$^+$) |
|---|---|---|---|---|
| 153 | Example 27 | $^1$H NMR: (400MHz, MeOD-d4) δ 10.24 - 9.38 (m, 1H), 8.86 - 8.35 (m, 2H), 7.96 (br. s, 1H), 7.21 - 7.04 (m, 1H), 5.55 (br. s, 1H), 4.51 (br. s, 1H), 3.90 (br. s, 1H), 3.26 (br. s, 3H), 2.93 - 2.77 (m, 2H), 2.74 (br. s, 1H), 2.61 (br. s, 3H), 2.48 (br. d, J = 3.1 Hz, 3H), 2.27 (br. s, 1H), 2.04 (br. d, J = 5.9 Hz, 2H), 1.89 - 1.67 (m, 5H) | 541.24 | 542.2 |
| 154 | Example 28 | $^1$H NMR (400MHz, DMSO-d6) δ 8.86 - 8.69 (m, 1H), 8.57 (s, 1H), 8.20 (br. s, 1H), 7.92 (s, 1H), 7.81 - 7.70 (m, 1H), 7.35 (d, J = 8.4 Hz, 1H), 4.23 - 4.11 (m, 1H), 3.44 (br. s, 2H), 3.19 - 3.09 (m, 1H), 2.69 (br. s, 2H), 2.60 (s, 3H), 2.43 (s, 3H), 2.17 - 1.92 (m, 2H), 1.70 (quin, J = 6.8 Hz, 2H), 1.66 - 1.55 (m, 1H), 1.50 - 1.39 (m, 1H) | 501.21 | 502.1 |
| 155 | Example 29 | $^1$H NMR (400 MHz, MeOD-d4) δ ppm 9.18 - 8.60 (m, 2H), 8.10 (br. s, 1H), 7.43 (br. d, J=7.6 Hz, 1H), 5.57 - 5.10 (m, 1H), 4.45 (br. s, 4H), 4.06 - 3.40 (m, 2H), 2.61 (s, 3H), 2.45 (s, 3H), 2.27 (br. s, 2H), 2.03 - 1.73 (m, 4H) | 515.21 | 516.2 |
| 156 | Example 30 | $^1$H NMR (400 MHz, MeOD-d4) δ 8.99 - 8.67 (m, 1H), 8.64 - 8.46 (m, 1H), 7.99 (s, 1H), 7.36 (br. s, 1H), 5.21 - 4.93 (m, 1H), 4.43 - 4.21 (m, 1H), 3.82 - 3.39 (m, 2H), 3.30 (br. s, 2H), 2.90 (br. s, 1H), 2.60 (s, 3H), 2.45 (s, 3H), 2.27 - 2.12 (m, 1H), 2.00 - 1.89 (m, 1H), 1.86 - 1.74 (m, 2H), 1.69 - 1.58 (m, 1H), 1.46 (br. d, J = 6.2 Hz, 1H) | 515.21 | 516.2 |
| 157 | Example 31 | $^1$H NMR (400 MHz, MeOD-d4) δ 8.96-8.69 (m, 2H), 8.54 (s, 0.78H), 7.45 (br d, J = 8.6 Hz, 1H), 4.30 (br d, J = 6.2 Hz, 1H), 3.50 (br d, J = 7.3 Hz, 1H), 2.66 (s, 3H), 2.50 (s, 3H), 2.38-2.20 (m, 2H), 1.92 (br s, 3H), 1.84-1.64 (m, 1H) | 458.18 | 459.2 |
| 158 | Example 32 | $^1$H NMR (400 MHz, MeOD-d4) δ 9.09-8.47 (m, 2H), 8.09 (br. d, J = 7.6 Hz, 2H), 4.13 (br. s, 1H), 3.28-3.20 (m, 1H), 2.70 (s, 3H), 2.38-2.01 (m, 2H), 1.90-1.41 (m, 4H) | 460.14 | 461.1 |
| 159 | Example 33 | $^1$H NMR (400MHz, MeOD-d4) δ 9.00 - 8.54 (m, 2H), 8.52 (br.s., 0.512H), 8.03 (br.s., 1H), 7.35 (br.s., 1H), 4.59 - 4.35 (m, 1H), 4.33 - 4.10 (m, 2H), 3.99 - 3.34 (m, 3H), 3.28 - 3.16 (m, 1H), 2.61 (s, 3H), 2.46 (s, 3H), 2.33 - 1.99 (m, 2H), 1.98 - 1.49 (m, 4H) | 513.21 | 514.3 |

FIG. 2 (Cont.)

| Compound | Done as | ¹H NMR | Calcd. Mass | Found Mass (MH⁺) |
|---|---|---|---|---|
| 160 | Example 34 | ¹H NMR (400 MHz, MeOD-d4) δ 9.01 - 8.61 (m, 2H), 8.59 - 8.53 (m, 1H), 8.12 - 7.91 (m, 1H), 7.38 (br. s, 1H), 4.61 (br. s, 1H), 3.69 (q, J = 8.2 Hz, 1H), 3.06 (br. s, 2H), 2.63 (s, 3H), 2.48 (s, 4H), 2.28 (br. s, 1H), 2.11 - 1.81 (m, 2H), 1.32 (br. s, 2H), 1.04 - 0.86 (m, 1H) | 471.20 | 472.2 |
| 161 | Example 35 | ¹H NMR (400 MHz, MeOD-d4) δ 8.85-8.47 (m, 2H), 8.16 (br s, 1H), 7.64 (br s, 1H), 4.05 (q, J = 7.50 Hz, 1H), 3.19 (q, J = 7.13 Hz, 1H), 2.30-2.18 (m, 1H), 2.13 (s, 3H), 2.10 (s, 3H), 2.08-1.98 (m, 1H), 1.79 (br s, 2H), 1.63 (br s, 1H), 1.48 (br s, 1H) | 462.15 | 463.1 |
| 162 | Example 36 | ¹H NMR (400 MHz, MeOD-d4) δ 8.82 (br. s, 1H), 8.68 (s, 1H), 8.38-8.16 (m, 1H), 7.83-7.59 (m, 1H), 4.73-4.27 (m, 1H), 3.91-3.53 (m, 1H), 2.49-2.24 (m, 2H), 2.12 (br. d, J = 14.03 Hz, 6H), 2.01-1.74 (m, 4H) | 480.17 | 481.1 |
| 163 | Example 37 | ¹H NMR (400MHz, MeOD-d4) δ 8.99 - 8.53 (m, 2H), 8.49 (br. s, 0.4H), 8.02 (br s, 1H), 7.36 (br. s, 1H), 4.59 - 4.33 (m, 2H), 4.23 (br. s, 1H), 3.99 - 3.43 (m, 4H), 2.61 (s, 3H), 2.46 (s, 3H), 2.31 - 1.98 (m, 2H), 1.83 (br. s, 4H) | 513.21 | 514.2 |
| 164 | Example 38 | ¹H NMR (400 MHz, DMSO-d6) δ 12.54 (br. s, 1H), 11.85 - 11.12 (m, 1H), 8.92 (br d, J = 7.9 Hz, 1H), 8.73 - 8.54 (m, 1H), 8.42 - 8.21 (m, 1H), 8.03 - 7.88 (m, 1H), 7.61 - 7.28 (m, 3H), 4.55 - 4.30 (m, 2H), 4.22 (br. s, 2H), 3.98 - 3.69 (m, 3H), 3.32 - 2.89 (m, 3H), 2.60 (s, 3H), 2.43 (s, 3H), 2.29 - 1.99 (m, 2H), 1.88 - 1.53 (m, 4H) | 527.23 | 528.2 |
| 165 | Example 39 | ¹H NMR (400 MHz, DMSO-d6) δ 12.54 (br. s, 1H), 11.80 - 11.06 (m, 1H), 8.91 (br d, J = 8.1 Hz, 0.5H), 8.75 - 8.56 (m, 1H), 8.39 - 8.21 (m, 1H), 8.04 - 7.89 (m, 1H), 7.63 - 7.32 (m, 1H), 4.55 - 4.13 (m, 3H), 4.04 (br. s, 2H), 3.80 (br. s, 2H), 3.34 - 2.87 (m, 3H), 2.60 (s, 3H), 2.43 (s, 3H), 2.28 - 1.97 (m, 2H), 1.89 - 1.53 (m, 4H) | 527.23 | 528.2 |

FIG. 2 (Cont.)

| Compound | Done as | $^1$H NMR | Calcd. Mass | Found Mass (MH$^+$) |
|---|---|---|---|---|
| 166 | Example 40 | $^1$H NMR (400MHz, DMSO-d6) δ 12.42 (br s, 1H), 8.90 (br d, $J$ = 8.2 Hz, 0.5 H), 8.67 - 8.56 (m, 1H), 8.08 - 7.87 (m, 2H), 7.45 - 7.29 (m, 1H), 4.12 (br s, 1H), 3.74 - 3.41 (m, 7H), 2.86 (br d, $J$ = 15.0 Hz, 1H), 2.59 (br d, $J$ = 5.7 Hz, 3H), 2.42 (br d, $J$ = 4.9 Hz, 3H), 2.07 (br s, 1H), 1.87 - 1.54 (m, 4H), 1.40 (br s, 1H) | 533.20 | 534.2 |
| 167 | Example 41 | $^1$H NMR (400MHz, MeOD-d4) δ 8.96 - 8.64 (m, 1H), 8.56 (br d, $J$ = 18.8 Hz, 1H), 7.98 (br s, 1H), 7.35 (br d, $J$ = 6.1 Hz, 1H), 4.58 (br s, 1H), 4.31 (br d, $J$ = 17.2 Hz, 1H), 3.88 - 3.42 (m, 4H), 2.93 (br s, 1H), 2.60 (s, 3H), 2.45 (s, 3H), 2.29 - 2.14 (m, 1H), 2.00 - 1.87 (m, 1H), 1.87 - 1.74 (m, 2H), 1.74 - 1.62 (m, 1H), 1.56 - 1.41 (m, 1H) | 533.20 | 534.2 |
| 168 | Example 42 | $^1$H NMR (400 MHz, MeOD-d4) δ 8.72 - 8.45 (m, 2H), 8.18 (br. s, 1H), 7.97 - 7.57 (m, 1H), 6.86 (br. s, 1H), 4.23 (br. s, 1H), 3.55 - 3.39 (m, 1H), 2.26 (br. s, 2H), 2.00 - 1.53 (m, 4H). | 411.11 | 412.1 |

INHIBITORS OF CYCLIN DEPENDENT KINASE 7 (CDK7)

CROSS-REFERENCE TO RELATED APPLICATIONS

This application is a national stage application under 35 U.S.C. 371 of International Application No. PCT/US2019/013860 filed on Jan. 16, 2019, which claims the benefit of the priority of U.S. Provisional Application 62/617,888 filed on Jan. 16, 2018, the disclosure of each of which is incorporated herein by reference in its entirety.

BACKGROUND OF THE INVENTION

Kinases that are members of the cyclin-dependent kinase (CDK) family play critical roles in cellular proliferation. Among the mammalian CDKs, CDK7 has uniquely consolidated kinase activities that help regulate both the cell cycle and gene transcription. In the cytosol, CDK7 exists within a heterotrimeric complex and is thought to function as a CDK1/2-activating kinase (CAK); phosphorylation of conserved residues in CDK1/2 by CDK7 is required for full catalytic activity and cell cycle progression. In the nucleus, CDK7 forms the kinase core of the RNA polymerase (RNAP) II general transcription factor complex and phosphorylates its C-terminal domain (CTD), a requisite step in initiating gene transcription. By both activating CDK1/2 and phosphorylating the CTD of RNAP II, CDK7 supports critical facets of cellular proliferation, cell cycling, and gene transcription.

Although some progress has been made, it is difficult to develop selective inhibitors of CDK7 because its sequence and structure are similar to the sequences and structures of other CDKs. Thus, there is still an unmet need for selective CDK7 inhibitors.

SUMMARY OF THE INVENTION

Described herein are selective CDK7 inhibitors (compounds) having structures as illustrated by the present formulas (e.g., Formula (I), (II), and (III)) and pharmaceutically acceptable salts, solvates (e.g., hydrates), tautomers, and isotopic forms thereof. These compounds preferably demonstrate greater specificity for CDK7 than for one or more of CDK2, CDK9, and CDK12 (e.g., at least 10-, 100-, or 1,000-fold greater specificity) when assessed in an enzymatic assay that measures the $IC_{50}$ of the compound. Also described are compositions containing a compound described herein (e.g., a pharmaceutical composition or kit) and methods of using the compounds (or salts, solvates (e.g., hydrates), tautomers, and isotopic forms thereof), pharmaceutical compositions, or kits to treat or prevent a disease associated with aberrant CDK7 expression (e.g., overexpression or misexpression) or activity (e.g., overactivity). The disease can be a proliferative disease (e.g., a cancer such as a blood cancer (e.g., leukemia) breast cancer, melanoma, multiple myeloma, ovarian cancer (or any other cancer described further below), a benign neoplasm, or a condition characterized by pathologic angiogenesis, or a fibrotic disease). The fibrotic disease can be NASH (non-alcoholic steatohepatitis) or NAFLD (non-alcoholic fatty liver disease), which can progress to cirrhosis of the liver and eventual liver failure; any other disease or chronic damage to the liver that results in fibrosis (e.g., alcoholism or hepatitis); scleroderma, which can progress to systemic scleroderma (also known as systemic sclerosis (SSc)); any other disease characterized by cutaneous fibrosis or resulting in pulmonary fibrosis (e.g., cystic fibrosis, multiple sclerosis, rheumatoid arthritis, systemic lupus erythematosus (SLE), or idiopathic pulmonary fibrosis); kidney fibrosis (e.g., as occurs in connection with chronic kidney disease such as Alport Syndrome, glomerulonephritis, polycystic kidney disease, and reflux nephropathy); and cardiac (e.g., endomyocardial) fibrosis, which is a common phenomenon in heart or cardiovascular diseases such as ischemic heart disease, atherosclerosis, arteriosclerosis, and inherited cardiomyopathies, as well as in Behcet's disease, diabetes, and ageing. The disease can also be an infectious disease (e.g., a viral infection caused by an influenza virus, human immunodeficiency virus (HIV), herpes virus, or human papilloma vims (HPV)) or a disease caused by or associated with expanded repeats of simple nucleotide tracts including, but not limited to, Huntington's Disease (HD), myotonic dystrophy (e.g., DM1 and DM2), and some forms of amyotrophic lateral sclerosis (ALS). Diseases caused by or associated with an expanded repeat are also known in the art as trinucleotide repeat disorders, trinucleotide repeat expansion disorders, triplet repeat expansion disorders, and codon reiteration disorders. In these genetic diseases, trinucleotide repeats in certain genes or introns exceed the stable threshold observed in healthy patients.

More specifically, described herein are compounds of Formula (I):

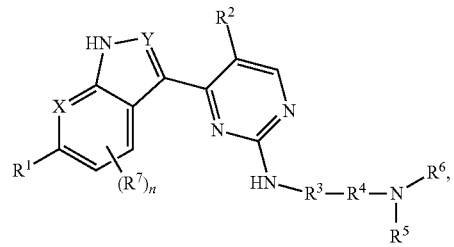

and pharmaceutically acceptable salts, solvates (e.g., hydrates), tautomers, and isotopic forms thereof, wherein X, Y, each of $R^1$-$R^7$, n and subvariables thereof are as defined herein. For ease of reading, we may not refer to both a compound of the invention and a pharmaceutically acceptable salt thereof when describing each and every composition, method, and use within the scope of the invention. It is to be understood that where a compound of the invention can be used, a pharmaceutically acceptable salt thereof may also be useful, and making that determination is well within the ability of one of ordinary skill in the art.

While pharmaceutical compositions within the scope of the invention are described further below, we note here that they can contain a compound described herein (e.g., a compound of Formula (I), (II), or (III) or a pharmaceutically acceptable salt, solvate (e.g., hydrate), tautomer, or isotopic form thereof) and a pharmaceutically acceptable excipient. The active ingredient (e.g., the compound), regardless of its precise chemical form (e.g., isomeric or isotopic forms), can be present in a therapeutically or prophylactic ally effective amount, and the pharmaceutical compositions described herein can be packaged in unit dosages, fractions thereof or multiples thereof.

In addition to administering a composition described herein to a patient who has been diagnosed as having a disease described herein, the compositions of the invention can be used ex vivo to alter CDK7 expression or activity in a biological sample (e.g., a cultured cell line or a blood or tissue sample obtained from a patient). In any circumstance in which a compound or composition described herein is administered to a patient, the patient may have been diagnosed with a disease that is associated with aberrant expression or activity of CDK7, and any of the methods of treatment or uses described herein can include a step of determining whether CDK7 expression or activity is aberrant in a biological sample obtained from the patient. This information may also be obtained indirectly. Thus, the methods of treatment and uses described herein can include a step of administering/using a compound or composition described herein, where, prior to the administration/use, a biological sample obtained from the patient has been determined to exhibit aberrant (e.g., elevated) CDK7 expression or activity.

The kits can include a container with a compound of Formula (I) or a pharmaceutically acceptable salt, solvate (e.g., hydrate), tautomer, or isotopic form thereof, or a pharmaceutical composition thereof. In certain embodiments, the kits described herein further include instructions (in written or other form) for administering a compound described herein (e.g., a compound of Formula (I) or a pharmaceutically acceptable salt, solvate (e.g., hydrate), tautomer, or isotopic form thereof, or the pharmaceutical composition thereof. Paraphernalia (e.g., a syringe, needles, tubing, gloves, bandages, tape, local anesthetics, etc. . . . ) may also be included.

The following definitions apply to the compositions and methods described herein unless the context clearly indicates otherwise. It will be evident to one of ordinary skill in the art that the definitions apply to grammatical variants of these terms, some of which are particularly mentioned below (e.g., "administration" and "administering"). The chemical elements are identified in accordance with the Periodic Table of the Elements, CAS version, Handbook of Chemistry and Physics, 75$^{th}$ Ed. Additionally, general principles of organic chemistry that may facilitate the production of the compounds described herein can be found in "Organic Chemistry," Thomas Sorrell, University Science Books, Sausalito, 1999; "March's Advanced Organic Chemistry," 5$^{th}$ Ed., Ed. Smith and March, John Wiley & Sons, New York, 2001; Larock, "Comprehensive Organic Transformations," VCH Publishers, Inc., New York, 1989; and Carruthers, "Some Modern Methods of Organic Synthesis," 3$^{rd}$ Edition, Cambridge University Press, Cambridge, 1987.

The term "about," when used in reference to a value, signifies any value or range of values that is plus-or-minus 10% of the stated value (e.g., within plus-or-minus 1%, 2%, 3%, 4%, 5%, 6%, 7%, 8%, 9% or 10% of the stated value). For example, a dose of about 10 mg means any dose as low as 10% less than 10 mg (9 mg), any dose as high as 10% more than 10 mg (11 mg), and any dose or dosage range therebetween (e.g., 9-11 mg; 9.1-10.9 mg; 9.2-10.8 mg; and so on). In case of any doubt, the stated value is included; about 10 mg includes 10 mg. Where a stated value cannot be exceeded (e.g., 100%), "about" means a value or range of values that is up to and including 10% less than the stated value (e.g., a purity of about 100% means 90%-100% pure (e.g., 95%-100% pure, 96%-100% pure, 97%-100% pure etc. . . . )).

The term "administration" and variants thereof, such as "administering," refer to the application of a compound described herein, a form thereof (e.g., a pharmaceutically acceptable salt or solvate) or a composition containing any such compounds or forms (e.g., a pharmaceutical composition) to a patient (e.g., a human patient) or system (e.g., a cell- or tissue-containing system maintained ex vivo (e.g., any cell, tissue, or organ culture, which may be maintained by conventional or new techniques). One of ordinary skill in the art will know a variety of routes that may, in appropriate circumstances, be utilized for administration to a patient or system. For example, the route of administration to a patient may be oral (i.e., by swallowing a pharmaceutical composition) or parenteral (a term encompassing any route of administration that is not oral; e.g., intra-arterial or intravenous, intra-articular, intracranial, intralesional, intramuscular, intraperitoneal, or intrathecal). Preferably, the compositions are administered orally, subcutaneously, intralesionally, intraperitoneally or intravenously. Any pharmaceutical composition described herein can be sterile and/or in an orally available or injectable form made using techniques and excipients known in the art (including those described further herein).

Further, the route of administration to a patient can be bronchial (e.g., by bronchial instillation), by mouth (i.e., oral), dermal (which may be or comprise topical application to the dermis or intradermal, interdermal, or transdermal administration), intragastric or enteral (i.e., directly to the stomach or intestine, respectively), intramedullary, intramuscular, intranasal, intraperitoneal, intrathecal, intravenous (or intra-arterial), intraventricular, by application to or injection into a specific organ (e.g., intrahepatic), mucosal (e.g., buccal, rectal, sublingual, or vaginal), subcutaneous, tracheal (e.g., by intratracheal instillation), or ocular (e.g., topical, subconjunctival, or intravitreal). Administration can involve continuous dosing (e.g., by oral administration or perfusion) for a selected time (e.g., over or every 1-3 hours; 3-6 hours; over a period of 12 hours; over a period of 24 hours; etc. . . . ), intermittent dosing (e.g., a plurality of doses separated in time), and/or periodic dosing (e.g., doses separated by a common period of time (e.g., every so many hours, daily, weekly, twice per week, etc.)).

The terms "aliphatic" and "aliphatic group" mean a branched, unbranched (i.e., straight-chain) or cyclic hydrocarbon group that is substituted or unsubstituted and either completely saturated or having one or more units of unsaturation. The cyclic aliphatic group is a monocyclic hydrocarbon group that is not aromatic and that has a single point of attachment to the molecule (i.e., compound) of which it is a part. We may refer to such cyclic groups as "cycloaliphatic," "carbocycle," "carbocyclyl," or "cycloalkyl." Unless otherwise specified, aliphatic groups contain 1-6 aliphatic carbon atoms ("$C_1$-$C_6$"; e.g., $C_1$-$C_2$, $C_1$-$C_3$, $C_1$-$C_4$, $C_1$-$C_5$, or $C_1$-$C_6$). Thus, suitable aliphatic groups include, but are not limited to, substituted or unsubstituted alkyl, alkenyl, and alkynyl groups and hybrids thereof such as (cycloalkyl)alkyl, (cycloalkenyl)alkyl and (cycloalkyl)alkenyl.

An "alkyl" is a hydrocarbon group containing 1 to 12 carbon atoms (e.g., 1, 2, 3, 4, 5, 6, 7, 8, 9, 10, 11, or 12 carbon atoms) that form a branched or unbranched (i.e., straight) chain that is saturated and monovalent. Suitable alkyl groups include methyl, ethyl, n- and iso-propyl, n-, sec-, iso- and tert-butyl, n-, sec-, and iso-pentyl, neopentyl, n- and sec-hexyl, etc. The term "alkylene" means a branched or unbranched (i.e., straight chain) bivalent alkyl group. Exemplary alkylenes include —$CH_2$—, —$CH_2CH_2$—, —$CH(CH_3)$—, —$CH_2CH(CH_3)$—, —$CH(CH_3)CH_2$—, etc. An "alkylene chain" can be a polymethylene group (i.e., —$(CH_2)_n$—), where "n" is a positive integer from 1 to 6 (e.g., 1, 2, 3, 4, 5, or 6, or ranges therebetween, such as 1-2, 1-3, 1-4, etc.). A substituted alkylene chain is a bivalent alkyl group in which at least one hydrogen atom is replaced with a substituent.

The term "angiogenesis" refers to the formation and growth of new blood vessels. Normal angiogenesis occurs in healthy patients during development and in the context of wound healing. However, patients suffering from many different diseases, including cancer, diabetes (particularly the progression to blindness associated therewith), age-related macular degeneration, rheumatoid arthritis, and psoriasis, experience excessive and detrimental angiogenesis. Angiogenesis is detrimental when it produces blood vessels that support diseased cells (e.g., tumor cells), destroy normal tissues (e.g., tissue within the eye), or facilitates tumor metastases. We may refer to such unwanted angiogenesis as "pathologic angiogenesis."

The terms "aryl" and "aryl ring" describe monocyclic, bicyclic and tricyclic ring systems having a total of six to 14 ring atoms, each of which is carbon. Further, at least one ring in the system is aromatic, and each ring in the system contains three to seven ring members. The aryl ring can include, but is not limited to, phenyl (Ph), biphenyl, naphthyl, and anthracyl, which may bear one or more substituents. In some embodiments, an aromatic ring is fused to one or more non-aromatic rings (e.g., indanyl, naphthimidyl, phthalimidyl, tetrahydronaphthyl, or tetrahydronaphthyl, and the like).

Two events or entities are "associated" with one another if one or more features of the first (e.g., its presence, level, activity, and/or form) are correlated with a feature of the second. For example, a first entity (e.g., a CDK7), gene expression profile, genetic signature (i.e., a single or combined group of genes in a cell with a uniquely characteristic pattern of gene expression), metabolite, or event (e.g., loss of cell cycle control in CDK7-positive cells)) is associated with a particular disease, if its presence, level, activity, and/or form correlates with the incidence of, severity of, and/or susceptibility to the disease (e.g., a cancer disclosed herein). Associations are typically assessed across a relevant population. Two or more entities are physically "associated" with one another if they interact, directly or indirectly, so that they are and/or remain in physical proximity with one another in a given circumstance (e.g., within a cell maintained under physiological conditions (e.g., within cell culture) or within a pharmaceutical composition). Entities that are physically associated with one another can be covalently linked to one another or non-covalently associated by, for example, hydrogen bonds, van der Waals forces, hydrophobic interactions, magnetism, or combinations thereof.

The terms "binding" and variants thereof (such as "bound" and "bind(s)") refer to a covalent or non-covalent association of two or more entities (e.g., a compound and an agent within a pharmaceutical composition or a compound and its target within a cell). "Direct" binding or direct association occurs when the two entities physically contact one another (e.g., through a chemical bond) whereas indirect binding or indirect association occurs when one of the entities physically contacts one or more intermediate entities that bring the entities into physical proximity with one another (e.g., within a complex). Binding can be assessed in a variety of contexts (e.g., in full or partial isolation or in more complex, naturally occurring or model systems (e.g., in a tissue, organ, or cell in vivo or maintained in a tissue culture environment)).

The term "biologically active" describes an agent (e.g., a compound described herein) that produces an observable biological effect or result in a biological system or model thereof (e.g., in a human, other animal, or a system maintained in vitro). The "biological activity" can result from binding between the agent and a target (e.g., a CDK7), and it may result in modulation (e.g., induction, enhancement, or inhibition) of a biological pathway or event (e.g., a cellular activity (e.g., immunostimulation) or proliferation). The presence of biological activity and, optionally, its extent, can be assessed using known and/or standard methods to detect an immediate or downstream product or event associated with the biological activity, and any of the methods described herein can include a step of assessing such activity.

The term "biological sample" refers to a sample obtained or derived from a biological source of interest (e.g., a tissue or organism (e.g., an animal or human patient) or cell culture). The biological sample can contain a biological cell, tissue or fluid or any combination thereof. For example, a biological sample can be or can include ascites; blood; blood cells; bodily fluid(s), any of which may include or exclude cells; bone marrow; cerebrospinal fluid (CSF); feces; flexural fluid; free floating nucleic acids; gynecological fluids; immune infiltrates; lymph; peritoneal fluid; plasma; saliva; sputum; surgically-obtained specimens; tissue scraped or swabbed from the skin or a mucus membrane (e.g., in the nose, mouth, or vagina); tissue or fine needle biopsy samples; urine; washings or lavages such as a ductal lavage or broncheoalveolar lavage; or other body fluids, tissues, secretions, and/or excretions. A biological sample may include cancer cells or immune cells, such as NK cells and/or macrophages, which are found in many tissues and organs, including the spleen and lymph nodes. Cells (e.g., NK cells, macrophages, and cancer cells) within the sample may have been obtained from an individual for whom a treatment is intended. Samples used in the form in which they were obtained may be referred to as "primary" samples, and samples that have been further manipulated (e.g., by adding or removing one or more components to/from the sample) may be referred to as "secondary" or "processed" samples. Such processed samples can contain or be enriched for a particular cell type (e.g., a CDK7-expressing cell such as a macrophage or tumor cell), cellular component (e.g., a membrane fraction), or cellular material (e.g., one or more cellular proteins, including one or more of a CDK7, DNA, or RNA (e.g., mRNA), which may have been subjected to amplification).

The term "cancer" refers to a disease in which cells exhibit an aberrant growth phenotype characterized by loss of control of cell proliferation to an extent that will be detrimental to a patient having the disease; such cells can be referred to as a "cancer cell," a "tumor cell," or a "malignant cell." A cancer can be classified by the type of tissue in which it originated (histological type) and/or by the primary site in the body in which the cancer first developed. Based on histological type, cancers are generally grouped into six major categories: carcinomas; sarcomas; myelomas; leukemias; lymphomas; and mixed types. A cancer treated as described herein can be of any one of these types and may comprise cells that are precancerous (e.g., benign), malignant, pre-metastatic, metastatic, and/or non-metastatic. A patient who has a malignancy or malignant lesion has a cancer. The present disclosure specifically identifies certain cancers to which its teachings may be particularly relevant, and one or more of these cancers may be characterized by a solid tumor or by a hematologic tumor, which may also be known as a blood cancer (e.g., of a type described herein).

The term "comparable" refers to two or more items (e.g., agents, entities, situations, sets of conditions, etc.) that are not identical to one another but are sufficiently similar to permit comparison therebetween so that one of ordinary skill in the art will appreciate that conclusions may reasonably be drawn based on differences or similarities observed. Comparable sets of conditions, circumstances, individuals, or populations are characterized by a plurality of substantially identical features and one or a small number of varied features. One of ordinary skill in the art will understand, in context, what degree of identity is required in any given circumstance for two or more items to be considered comparable. For example, two items are comparable to one another when they have in common a sufficient number and type of substantially identical features to warrant a reasonable conclusion that any differences in results obtained or phenomena observed with the items are caused by or are indicative of the variation in those features that are varied. A comparable item can serve as a "control." For example, a "control patient/population" can be an untreated patient/population who is afflicted with the same disease as a patient/population being treated.

The term "combination therapy" refers to those situations in which a patient is exposed to two or more therapeutic regimens (e.g., two or more therapeutic agents) to treat a single disease (e.g., a cancer). The two or more regimens may be administered simultaneously or sequentially (e.g., all "doses" of a first regimen are administered prior to administration of any dose(s) of a second regimen by the same or a different route of administration). For clarity, combination therapy does not require that individual agents be administered together in a single composition (or even necessarily at the same time), although in some embodiments, two or more agents (e.g., compounds described herein) may be administered together in a single composition or even as a combination compound (e.g., associated in a single chemical complex or covalent entity). In any of the compositions or methods described herein, a compound of Formula I can be a "first" agent.

The term "compound" means a chemical compound (e.g., a compound represented by a structural Formula depicted herein, a sub-genus thereof, or a species thereof). Any given compound can be biologically, therapeutically, or prophylactically active (e.g., when contained in a pharmaceutical composition in an effective amount) and can be provided and/or utilized (e.g., used in a biological assay, administered to a patient, incorporated into a medicament, or otherwise used as described herein) in any of a variety of forms.

A "disease" is a pathologic state regardless of whether the disease is commonly referred to as a condition, disorder, syndrome, or the like (e.g., a myeloproliferative disorder is a disease).

The terms "dosage form," "formulation," and "preparation" are used to refer to compositions containing a compound or other biologically and/or therapeutically active agent that is suitable for administration to a patient. The term "unit dosage form" refers to a physically discrete unit of a compound or other biologically and/or therapeutically active agent (e.g., a therapeutic or diagnostic agent) formulated for administration to a patient. Typically, each such unit contains a predetermined quantity of the active agent, which may be the amount prescribed for a single dose (i.e., an amount expected to correlate with a desired outcome when administered as part of a therapeutic regimen) or a fraction thereof. One of ordinary skill in the art will appreciate that the total amount of a therapeutic composition or agent administered to a particular patient is determined by one or more attending physicians and may involve administration of multiple unit dosage forms.

The term "dosing regimen" refers to the unit dosage form(s) administered to, or prescribed for, a patient, and typically includes more than one dose separated by periods of time (e.g., as described elsewhere herein). The dosage form(s) administered within a dosing regimen can be of the same unit dose amount or of different amounts. For example, a dosing regimen can comprises a first dose in a first dose amount, followed by one or more additional doses in a second dose amount that is the same as or different from the first dose amount.

An "effective amount" of a compound of Formula (I) refers to an amount sufficient to elicit the desired biological response (e.g., treating or preventing the disease). As will be appreciated by one of ordinary skill in the art, the effective amount of a compound described herein may vary depending on such factors as the desired biological endpoint, the pharmacokinetics of the compound, the disease being treated, the mode of administration, and the age and health of the patient. An effective amount encompasses therapeutic and prophylactic treatment. For example, in treating cancer, an effective amount of an inventive compound may reduce the tumor burden or stop the growth or spread of a tumor.

The term "excipient" refers to an adjuvant, carrier, diluent, or other vehicle with which a compound or composition described herein is administered or otherwise used. The excipient can be a sterile or sterilizable liquid, such as a water (e.g., water for injection), an aqueous solution (e.g., an isotonic salt solution (e.g., 0.9% NaCl), Ringer's solution, or a solution comprising 1,3-BO butanediol), or a natural or synthetic oil (e.g., a petroleum-based or mineral oil, an animal oil, or a vegetable oil (e.g., a peanut, soybean, sesame, or canola oil)). The oil may also be a nonvolatile oil of any animal or plant origin (i.e., a "fixed" oil). Sterile, fixed oils are conventionally employed as solvents and suspending media.

The excipient can be a solid; a liquid that includes one or more solid components (e.g., a salt, for example, a "normal saline"); a mixture of solids; or a mixture of liquids. The excipient may have characteristics that make it useful as a binding agent, buffering agent, diluent, disintegrating agent, dispersing agent, emulsifier, granulating agent, lubricating agent, preservative, or surface-active agent. Excipients include, but are not limited to, alumina, aluminum stearate, a buffer (e.g., a phosphate salt (e.g., disodium hydrogen phosphate or potassium hydrogen phosphate) a sodium salt (e.g., sodium chloride), a zinc salt, or other salts or electrolytes), a cellulose-based substance (e.g., sodium carboxymethylcellulose), colloidal silica, glycine, an ion exchanger, lecithin, polyethylene glycol, potassium sorbate, protamine sulfate, a serum protein (e.g., human serum albumin), sorbic acid, a partial glyceride mixture of saturated vegetable fatty acids, magnesium trisilicate, polyvinyl pyrrolidone, a polyethylene-polyoxypropylene-block polymer, a polyacrylate, water, wax, and wool fat.

The term "fused" refers to two rings within a compound that are joined and share at least one atom. An atom where two fused rings join is called a "bridgehead" atom. "Spirofused" systems are bicyclic systems in which the two rings share only one atom. For fused systems sharing at least two atoms, bridgehead atoms may be adjacent and connected by a bond, or they may be non-adjacent and have additional atoms connecting them to each other. A fused ring system in which the bridgehead atoms are non-adjacent is called a "bridged" system, and systems with bridgehead atoms connected by a bond are "non-bridged." Rings that may be fused together include cycloalkyls, heterocycloalkyls, aryls, heteroaryls, and combinations thereof. A "benzofused" ring is a ring which is fused to two adjacent carbons of a benzene ring. Examples of bridged fused ring systems include norbornane, bicyclo[2.2.2]octane, and quinuclidine. Examples of non-bridged fused systems include naphthalene, quinoline, indole, decalin, and tetrahydroisoquinoline. Examples of benzofused rings include pyrrole benzofused to give indole, and cyclopentane benzofused to give indane.

"Halo" or "halogen" refers to fluorine (fluoro, —F), chlorine (chloro, —Cl), bromine (bromo, —Br), or iodine (iodo, —I).

As used herein, a "heteroatom" is nitrogen, oxygen, sulfur or phosphorous.

The term "heteroaromatic ring" refers to a monocyclic, bicyclic or polycyclic ring or ring system in which at least one ring is both aromatic and comprises a heteroatom; and wherein no other rings are heterocyclyl (as defined below). A ring that is aromatic and includes a heteroatom can contain 1, 2, 3, or 4 independently selected ring heteroatoms.

The term "heteroaryl" refers to a radical of a heteroaromatic ring or ring system. Representative heteroaryl groups include ring systems where (i) each ring comprises a heteroatom and is aromatic (e.g., imidazolyl, oxazolyl, thiazolyl, triazolyl, pyrrolyl, furanyl, thiophenyl, pyrazolyl, pyridinyl, pyrazinyl, pyridazinyl, pyrimidinyl, indolizinyl, purinyl, naphthyridinyl, and pteridinyl); (ii) one ring is aromatic and comprises a heteroatom, and each additional ring is either aromatic or carbocyclyl (e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, 5,6,7,8-tetrahydroquinolinyl and 5,6,7,8-tetrahydroisoquinolinyl); and (iii) one ring is aromatic and comprises a heteroatom, and is fused to a carbocyclyl, and the aromatic ring shares a bridgehead heteroatom with the carbocyclic ring (e.g., 5,6,7,8-tetrahydroindolizinyl). The heteroaryl can be a monocyclic or bicyclic ring, in which case each of the rings contains 5 or 6 ring atoms and 1, 2, 3, or 4 of the ring atoms are heteroatoms (i.e., independently, N, O, S, or P).

The terms "heterocycle," "heterocyclyl," and "heterocyclic radical/ring," are used interchangeably and refer to a stable 4- to 7-membered monocyclic, 7-11-membered bicyclic, or 10-16-membered tricyclic heterocyclic chemical structure that is either saturated or partially unsaturated, and that has, in addition to carbon atoms, one or more (e.g., 1-4) heteroatoms, as defined herein. A heterocyclic ring can be attached to its pendant group at any heteroatom or carbon atom that results in a stable structure, and any of the ring atoms can be optionally substituted (i.e., substituted or unsubstituted). For example, in a saturated or partially unsaturated ring having 1-3 heteroatoms selected from oxygen, sulfur or nitrogen, the nitrogen moiety may be N (as in 3,4-dihydro-2H-pyrrolyl-), NH (as in pyrrolidinyl-), NR^ (as in N-substituted 2-pyrrolidinyl) or +NR^ (as in N-substituted 1-pyrrolidinyl). Examples of a saturated or partially unsaturated heterocycle include, without limitation, tetrahydrofuranyl, tetrahydrothiophenyl, pyrrolidinyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl, as well as chemical structures in which a heterocyclyl ring is fused to one or more aryl, heterocyclyl, or cycloaliphatic rings (e.g., indolinyl, 3H-indolyl, chromanyl, 1,2,3,4-tetrahydroisoquinolinyl and 1,2,3,4-tetrahydroquinolinyl). When a heterocyclic ring is fused to an aryl ring, we refer to that heterocyclic ring using the term "heterocyclo." A "saturated heterocyclic ring" refers to a saturated ring having one or more heteroatoms, wherein the ring is monocyclic or fused to one or more saturated cycloaliphatic rings.

The term "hydrate" refers to a compound that is bound to water. The amount of water contained in the hydrate can be expressed as a ratio of the number of water molecules to the number of compound molecules. Thus, a hydrate of a compound may be represented by a general formula such as R·x $H_2O$, where R is the compound and x is a number greater than 0. For example, where x is 1, the hydrate is a monohydrate; where x is 0.5, the hydrate is a hemihydrate; where x is 2, the hydrate is a dihydrate; and where x is 6, the hydrate is a hexahydrate. A hydrate is a type of solvate.

"Improve(s)," "increase(s)" or "reduce(s)/decrease(s)" are terms used to characterize the manner in which a value has changed relative to a reference value. For example, a measurement obtained from a patient (or a biological sample obtained therefrom) prior to treatment can be increased or reduced/decreased relative to that measurement obtained during or after treatment in the same patient, a control patient, on average in a patient population, or biological sample(s) obtained therefrom. The value may be improved in either event, depending on whether an increase or decrease is associated with a positive therapeutic outcome.

The term "inhibitor" refers to an agent, including a compound described herein or a variant form thereof (e.g., a pharmaceutically acceptable salt or solvate), whose presence (e.g., at a certain level or in a certain form) correlates with a decrease in the expression or activity of another agent (i.e., the inhibited agent or target) or a decrease in the occurrence of an event (e.g., tumor progression or metastasis). In some embodiments, an inhibitor exerts its influence on a target by binding to the target, directly or indirectly. In other embodiments, an inhibitor exerts its influence by binding and/or otherwise altering a regulator of the target, so that the expression and/or activity of the target is reduced. Inhibition can be assessed in silico, in vitro (e.g., in a cell, tissue, or organ culture or system), or in vivo (e.g., in a patient or animal model).

An "isotopic form" of a compound described herein (e.g., a compound of Formula (I)) is a form in which one or more elements of the compound have been replaced with an isotopic variant of that element. Where a compound contains an isotopic substitution, it can be, e.g., $^2H$ or $^3H$ for H; $^nC$, $^{13}C$ or $^{14}C$ for $^{12}C$; $^{13}N$ or $^{15}N$ for $^{14}N$; $^{17}O$ or $^{18}O$ for $^{16}O$; $^{36}Cl$ for $^{35}Cl$; $^{18}F$ for $^{19}F$; $^{131}I$ for $^{127}I$; etc. Such compounds have use, for example, as analytical tools, as probes in biological assays, and/or as therapeutic or prophylactic agents for use in accordance with the present invention. In particular, an isotopic substitution of deuterium ($^2H$) for hydrogen is known to potentially slow down metabolism, shift metabolism to other sites on the compound, slow down racemization and/or have other effects on the pharmacokinetics of the compound that may be therapeutically beneficial. In particular, deuterated forms of a compound described herein (or other forms thereof, such as salts or solvates) are embodiments of the present invention; such forms include deuterium in place of one or more of the hydrogen atoms in the compound but no other isotopic variants (e.g., no isotopes of $^{12}C$, $^{14}N$, or $^{18}O$).

The terms "neoplasm" and "tumor" are used herein interchangeably and refer to an abnormal mass of tissue in which the growth of the mass surpasses and is not coordinated with the growth of a normal tissue. A neoplasm or tumor may be "benign" or "malignant" depending on the following characteristics: the degree of cellular differentiation (including morphology and functionality), rate of growth, local invasion, and metastasis. A "benign neoplasm" is generally well differentiated, has a slower growth rate than a malignant neoplasm, and remains localized to the site of origin (i.e., does not have the capacity to infiltrate, invade, or metastasize to distant sites). Benign neoplasms include, but are not limited to, acrochordons, adenomas, chondromas, intraepithelial neoplasias, lentigos, lipoma, sebaceous hyperplasias, seborrheic keratoses, and senile angiomas. The benign neoplasm can also be tuberous sclerosis, or tuberous sclerosis complex (TSC) or epiloia (derived from "epilepsy, low intelligence, adenoma sebaceum"). Benign neoplasms can later give rise to malignant neoplasms (believed to occur as a result of genetic changes in a subpopulation of the tumor's neoplastic cells), and such neoplasms are referred to as "pre-malignant neoplasms." An exemplary pre-malignant neoplasm is a teratoma. In contrast, a "malignant neoplasm" is generally poorly differentiated (anaplasia) and grows rapidly with progressive infiltration, invasion, and destruction of surrounding tissue. Malignant neoplasms also generally have the capacity to metastasize to distant sites.

A compound described herein can contain one or more "optionally substituted" moieties. By "substituted," we mean that one or more hydrogens of the designated moiety are replaced with a suitable substituent. Unless otherwise indicated, an "optionally substituted" moiety can have any one or more hydrogen atoms replaced with a suitable substituent. When more than one hydrogen in any given moiety is replaced with a suitable substituent, each substituent is independently selected. Therefore, each substituent on a multiply substituted moiety may be either the same or different from any other substituent on that moiety. It should be understood that an "optionally substituted" moiety may be, but is not necessarily, substituted. Thus, an "optionally substituted moiety may also be unsubstituted. For example, "optionally substituted phenyl" encompasses "substituted phenyl" and "unsubstituted phenyl;" an "optionally substituted alkyl" encompasses "substituted alkyl" and "unsubstituted alkyl;" a substitutable carbon atom may be a "substituted carbon atom" or an "unsubstituted carbon atom;" and so forth. Combinations of substituents on a specific moiety or on the compound itself are those that result in the formation of stable or otherwise chemically feasible compounds. The term "substitutable carbon atom" as used herein mean a carbon atom that is structurally depicted as being bound to one or more hydrogen atoms (with the understanding that, as is generally understood in the art, a hydrogen atom bound to a carbon atom may not be shown as "H" in such structures, but rather is implicit).

Suitable monovalent substituents on a substitutable carbon atom of an optionally substituted group (e.g., an alkyl, alkenyl, alkynyl, alkylene, alkenylene, alkynylene or the carbon atom of a carbocyclyl, aryl, heterocyclyl or heteroaryl) can be, independently, deuterium; halo; —$NO_2$; —CN; —$N_3$; —$(CH_2)_{0-4}R^\circ$; —$(CH_2)_{0-4}OR^\circ$; —O—$(CH_2)_{0-4}C(O)OR^\circ$; —$(CH_2)_{0-4}SR^\circ$; —$(CH_2)_{0-4}N(R^\circ)_2$; —$(CH_2)_{0-4}C(O)N(R^\circ)_2$; —$(CH_2)_{0-4}N(R^\circ)C(O)R^\circ$; —$(CH_2)_{0-4}N(R^\circ)C(O)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$(CH_2)_{0-4}C(O)R^\circ$; —$(CH_2)_{0-4}C(O)OR^\circ$; —$(CH_2)_{0-4}—C(O)—N(R^\circ)—S(O)_2—R^\circ$; —$(CH_2)_{0-4}OC(O)R$; —$(CH_2)_{0-4}C(O)NR^\circ_2$; —$(CH_2)_{0-4}OC(O)NR^\circ_2$; —$C(O)N(OR^\circ)R^\circ$; —$C(NOR^\circ)R^\circ$; —$C(NOR^\circ)NR^\circ_2$; —$C(NCN)NR^\circ_2$; —$(CH_2)_{0-4}S(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)R^\circ$; —$C(NR^\circ)NR^\circ_2$; —$P(O)(OR^\circ)_2$; —$P(O)(OR^\circ)R^\circ$; —$P(O)R^\circ_2$; —$OP(O)(OR^\circ)_2$; —$OP(O)(OR^\circ)R^\circ$; —$OP(O)R^\circ_2$; or —$SiR^\circ_3$, where each $R^\circ$ is optionally substituted as defined below and is, independently, hydrogen, deuterium, $C_{1-6}$ aliphatic, or a 5-6-membered saturated, partially unsaturated, or aryl ring having 0-4 heteroatoms independently selected from nitrogen, oxygen, or sulfur; or, notwithstanding the definition above, two independent occurrences of $R^\circ$, taken together with their intervening atom(s), may form a 3-7-membered heterocyclic ring having 1-3 heteroatoms independently selected from nitrogen, oxygen, sulfur or phosphorous.

Suitable monovalent substituents on $R^\circ$ (or the ring formed by taking two independent occurrences of $R^\circ$ together with their intervening atoms), can be, independently, halo, —CN, —$NO_2$, —$N_3$, —$R^\bullet$, —$(CH_2)_{0-2}OH$, —$(CH_2)_{0-2}OR^\bullet$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}NH_2$, —$(CH_2)_{0-2}NHR^\bullet$, or —$(CH_2)_{0-2}NR^\bullet_2$, where each $R^\bullet$ is, independently, $C_{1-4}$ aliphatic or a 5-6-membered saturated, partially unsaturated, or aryl ring having 0-4 heteroatoms independently selected from nitrogen, oxygen, or sulfur, and where each $R^\circ$ is optionally substituted with one or more independently selected halogens.

Suitable divalent substituents on a saturated carbon atom of an optionally substituted group include the following: =O, =NN($R^*$)$_2$, =NNR*S(O)$_2$R*, =NR*, =NOR*, and =NCN; where each R* is, independently, hydrogen, deuterium, $C_{1-6}$ aliphatic or a 5-6-membered saturated, partially unsaturated, or aryl ring having 0-4 heteroatoms independently selected from nitrogen, oxygen or sulfur. Notwithstanding the above, two independent occurrences of R*, taken together with their intervening atom(s), can form a 3-7-membered heterocyclic ring having 1-2 heteroatoms independently selected from nitrogen or sulfur, where each R* is optionally substituted with one or more substituents selected from deuterium, halo, —$R^\bullet$, —OH, —$OR^\bullet$, —CN, —C(O)OH, —$C(O)OR^\bullet$, —$NH_2$, —$NHR^\bullet$, —$NR^\bullet_2$, and $NO_2$.

Suitable substituents on a substitutable nitrogen of an optionally substituted group include —$R^\dagger$, —$N(R^\dagger)_2$; —$C(O)R^\dagger$, —$C(O)OR^\dagger$, —$C(O)N(R^\dagger)_2$, —$S(O)_2R^\dagger$, —$S(O)_2N(R^\dagger)_2$—$N(R^\dagger)S(O)_2R^\dagger$, —$C(NR^\dagger)N(R^\dagger)_2$, —$C(NOR^\dagger)N(R^\dagger)_2$, or —$C(NCN)N)R^\dagger)_2$, with each $R^\dagger$ being, independently, hydrogen, a $C_{1-6}$ aliphatic, or a 5-7-membered saturated, partially unsaturated, or aryl ring having 0-4 heteroatoms independently selected from nitrogen, oxygen, or sulfur; or notwithstanding the definition above, two independent occurrences of $R^\dagger$, taken together with their intervening atom(s), may form a 3-7-membered saturated, partially unsaturated, or aryl heterocyclyl having 1-3 heteroatoms independently selected from nitrogen, oxygen or sulfur, wherein each $R^\dagger$ is optionally and independently substituted with one or more substituents independently selected from deuterium, halo, —$R^\bullet$, —OH, —$OR^\bullet$, —CN, —$NH_2$, —$NHR^\bullet$, —$NR^\bullet_2$, and —$NO_2$.

"Partially unsaturated," when used to refer to a chemical group, means the group includes at least one double or triple bond. A partially unsaturated ring or ring system is a ring or ring moiety other than aryl or heteroaryl that includes at least one double or triple bond and may include multiple sites of unsaturation.

A "patient" is any organism to which a compound described herein (or any variant thereof, as also described herein (e.g., a salt or solvate) is administered in accordance with the present invention e.g., for experimental, diagnostic, prophylactic, and/or therapeutic purposes. Typical patients include animals (e.g., mammals such as mice, rats, rabbits, non-human primates, and humans; birds; insects; worms; etc.). A patient can be suffering from a disease described herein (e.g., a proliferative disease, such as cancer or a benign neoplasm).

A "pharmaceutical composition" is a composition in which an active agent (e.g., an active pharmaceutical ingredient (e.g., a compound described herein)) is formulated together with one or more pharmaceutically acceptable excipients. The active agent can be present in a unit dose amount appropriate for administration in a therapeutic regimen that shows a statistically significant probability of achieving a predetermined therapeutic effect when administered to patients of a relevant population. The pharmaceutical composition may be specially formulated for administration in solid or liquid form, including forms made for oral or parenteral (e.g., intravenous) administration. For parenteral administration, the composition can be formulated, for example, as a sterile solution or suspension for subcutaneous, intramuscular, intravenous, intra-arterial, intraperitoneal, or epidural injection. Pharmaceutical compositions comprising an active agent (e.g., a compound described herein and, optionally, a second agent, as described herein) can also be formulated as sustained-release formulations or as a cream, ointment, controlled-release patch, or spray for topical application. Creams, ointments, foams, gels, and pastes can also be applied to mucus membranes lining the nose, mouth, vagina, and rectum. Any of the compounds described herein and any pharmaceutical composition containing such a compound may also be referred to as a "medicament."

The term "pharmaceutically acceptable," when applied to an excipient used to formulate a composition disclosed herein (e.g., a pharmaceutical composition), means an excipient that is compatible with the other ingredients of the composition and not prohibitively deleterious to a patient (e.g., it is sufficiently non-toxic in the amount required and/or administered (e.g., in a unit dosage form). When applied to a salt (e.g., a salt of a compound described herein), "pharmaceutically acceptable" refers to the salt form of a compound that is, within the scope of sound medical judgment, suitable for use in contact with the tissues of humans and lower animals without prohibitive toxicity, irritation, allergic response and the like, and that is commensurate with a reasonable benefit/risk ratio. Pharmaceutically acceptable salts are well known in the art (see, e.g., Berge et al., *J. Pharmaceutical Sciences*, 66:1-19, 1977). Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as lower alkyl sulfonate, aryl sulfonate, carboxylate, halide, hydroxide, nitrate, phosphate, and sulfate.

When applied to a composition (e.g., a pharmaceutical composition), the term "pharmaceutically acceptable" indicates that the composition is suitable for administration to a patient by virtue of being non-contaminated (e.g., sterile) and non-toxic (i.e., generally safe; not expected to be poisonous).

A "prophylactically effective amount" of a compound described herein is an amount sufficient to delay the onset of a disease for a period of time that is substantially longer than expected (e.g., as evidenced by the absence of the signs and symptoms associated with the disease). A prophylactically effective amount can be an amount that improves overall prophylaxis or enhances the prophylactic efficacy of another prophylactic agent (a "second" prophylactic agent (e.g., a "second" compound)).

A "proliferative disease" is a disease that occurs due to abnormal growth or extension by the multiplication of cells (Walker, *Cambridge Dictionary of Biology*; Cambridge University Press: Cambridge, UK, 1990). A proliferative disease can be associated with the pathological proliferation of normally quiescent or normally dividing cells; the pathological migration of cells from their normal location (e.g., metastasis of neoplastic cells); the pathological expression of proteolytic enzymes such as the matrix metalloproteinases (e.g., collagenases, gelatinases, and elastases); and/or pathologic angiogenesis, as occurs in proliferative retinopathies and tumor metastases. Exemplary proliferative diseases include cancers, which may also be referred to as "malignant neoplasms," benign neoplasms, and pathologic angiogenesis.

A "sign or symptom is reduced" when one or more objective signs or subjective symptoms of a disease are reduced in magnitude (e.g., intensity, severity, etc.) and/or frequency. A delay in the onset of a particular sign or symptom is one form of reducing the frequency of that sign or symptom. Reducing a sign or symptom can be achieved by, e.g., a "therapeutically active" compound optionally administered in an effective amount, as described herein.

The term "solvate" refers to a compound bound to a solvent, usually by a solvolysis reaction. This physical association may include hydrogen bonding. Solvents that can be used in the reaction include water, methanol, ethanol, acetic acid, DMSO (dimethyl sulfoxide), THF (tetrahydrofuran), diethyl ether, and the like. A compound of Formula I or (la) can be prepared, e.g., in crystalline form, and then solvated. The solvate can be pharmaceutically acceptable and can be either a stoichiometric or non-stoichiometric solvate. In certain instances, the solvate will be capable of isolation, for example, when one or more solvent molecules are incorporated in the crystal lattice of a crystalline solid. "Solvate" encompasses both solution-phase and isolable solvates, and representative solvates include hydrates, ethanolates, and methanolates.

The term "specific," as used herein with reference to an agent (e.g., a compound) having an activity (e.g., inhibition of a target), means that the agent discriminates between potential target entities or states. For example, an agent binds "specifically" to its intended target (or otherwise specifically inhibits its target) if it preferentially binds or otherwise inhibits the expression or activity of that target in the presence of one or more alternative targets. Although the invention is not so limited, a specific and direct interaction can depend upon recognition of a particular structural feature of the target (e.g., an epitope, a cleft, or a binding site). Specificity need not be absolute; the degree of specificity need only be enough to result in an effective treatment without unacceptable side effects. The specificity of an agent can be evaluated by comparing the effect of the agent on an intended target or state relative to its effect on a distinct target or state. The effects on the intended and distinct targets can each be determined or the effect on the intended target can be determined and compared to a reference standard developed at an earlier time (e.g., a reference specific binding agent or a reference non-specific binding agent). In some embodiments, the agent does not detectably bind the competing alternative target under conditions in which it detectably (and, preferably, significantly) binds its intended target and/or does not detectably inhibit the expression or activity of the competing target under conditions in which it detectably (and, preferably, significantly) inhibits the expression or activity of its intended target. A compound of the invention may exhibit, with respect to its target(s), a higher on-rate, lower off-rate, increased affinity, decreased dissociation, and/or increased stability compared with the competing alternative target, and any of these parameters can be assessed in methods of the invention.

As used herein with regard to a compound, the term "stable," means the compound is not rendered inactive or substantially inactive when it is subjected to conditions that allow for its production, detection, recovery, purification, or use as described herein.

The invention encompasses "stereoisomeric forms" of a compound described herein (e.g., an optical and/or structural isomer). The stereoisomers of any referenced or depicted structure can be enantiomers and diastereomers (e.g., cis/trans isomers and conformational isomers). These include the R and S configurations for each asymmetric center, Z and E double bond isomers, and Z and E conformational isomers. Compositions containing a single type of stereochemical isomer as well as enantiomeric, diastereomeric, and geometric (or conformational) mixtures of the present compounds are within the scope of the invention. Where a particular enantiomer is preferred, it can be provided substantially free of the corresponding enantiomer, and may also be referred to as "optically enriched," meaning that the compound is made up of a significantly greater proportion of one enantiomer. For example, a plurality of the compound molecules can be made up of at least about 90% by weight of the preferred enantiomer (e.g., at least about 95%, 98%, or 99% by weight). Preferred enantiomers can be isolated from racemic mixtures by methods known in the art, including chiral high pressure liquid chromatography (HPLC) and the formation and crystallization of chiral salts. They can also be prepared by asymmetric syntheses. If needed, one could consult, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972).

The term "substantially" refers to the qualitative condition of exhibiting a characteristic or property of interest to a total or near-total extent or degree. One of ordinary skill in the art will understand that biological and chemical phenomena rarely, if ever, go to completion and/or proceed to completeness or achieve or avoid an absolute result. The term "substantially" may therefore be used to capture the potential lack of completeness inherent in many biological and chemical phenomena. For example, a chemical reaction may be characterized as substantially complete even though the yield is well below 100%. Certain features may also be deemed "substantially identical" when they are about the same and/or exhibit about the same activity. For example, two nearly identical compounds that produce about the same effect on an event (e.g., cellular proliferation) may be described as substantially similar. With regard to the purity of a compound or composition, "substantially pure" is defined below.

The term "substantially pure," when used to refer to a compound described herein, means that a preparation of the compound is more than about 85% (w/w) compound (e.g., more than about 90%, 95%, 97%, 98%, 99%, or 99.9%).

An individual who is "susceptible to" a disease (e.g., a proliferative disease, such as cancer) has a greater than average risk for developing the disease. Such an individual may not yet display any symptoms of the disease and may not have not been diagnosed with the disease. Such an individual may have been exposed to conditions associated with development of the disease (e.g., exposure to a carcinogen). Susceptibility can be assessed by one of ordinary skill in the art and can be determined relative to a population-based risk.

The term "tautomer" refers to a structural or constitutional isomer of a compound; tautomers are compounds having the same molecular formula but different atomic organization and bonding patterns. Tautomeric compounds readily interconvert and vary from one another in the displacement of hydrogen atoms and electrons. Thus, two tautomeric compounds may be in equilibrium through the movement of n electrons and an atom (usually H). For example, enols and ketones are tautomers because they are rapidly interconverted by treatment with either acid or base. Tautomeric compounds may exhibit improved chemical reactivity and biological activity relative to the comparable non-tautomeric compound.

A "therapeutic regimen" refers to a dosing regimen that, when administered across a relevant population, is correlated with a desired therapeutic outcome.

The term "treatment," and linguistic variants thereof, such as "treat(s)" and "treating," refer to any use of a compound or pharmaceutical composition described herein to partially or substantially completely alleviate, ameliorate, relieve, inhibit, reduce the severity of, and/or reduce the incidence of one or more signs or symptoms of a particular disease (e.g., a proliferative disease such as cancer). The patient being treated (or who has been identified as a candidate for treatment) may exhibit only early signs or symptoms of the disease or may exhibit one or more established or advanced signs or symptoms of the disease. "Treatment" is distinguished from "prophylaxis," which relates to delaying the onset of one or more signs or symptoms of a disease. In that case, the patient may not exhibit signs and/or symptoms of the disease and/or may be known to have one or more susceptibility factors that are statistically correlated with increased risk of development of the relevant disease. However, once a patient exhibits signs or symptoms of a disease and has been treated, treatment may be continued to delay or prevent recurrence.

A "therapeutically effective amount" of a compound described herein is an amount sufficient to treat a disease in a population of patients. A therapeutically effective amount is an amount that provides a therapeutic benefit in the treatment of a disease (e.g., by treating one or more signs or symptoms associated with the disease). A therapeutically effective amount of a compound described herein can also be an amount that enhances the therapeutic efficacy of another therapeutic agent (a "second" therapeutic agent (e.g., a "second" compound)).

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "premalignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

Many embodiments of the invention are explicitly set forth herein. Other embodiments will be apparent from the Detailed Description, the Drawings, the Examples, and the claims.

BRIEF DESCRIPTION OF THE DRAWINGS

FIG. 2 is a Table disclosing synthetic details and characteristics of selected compounds, including their NMR (nuclear magnetic resonance) and MS (mass spectroscopy) values.

DETAILED DESCRIPTION

Figure 1:
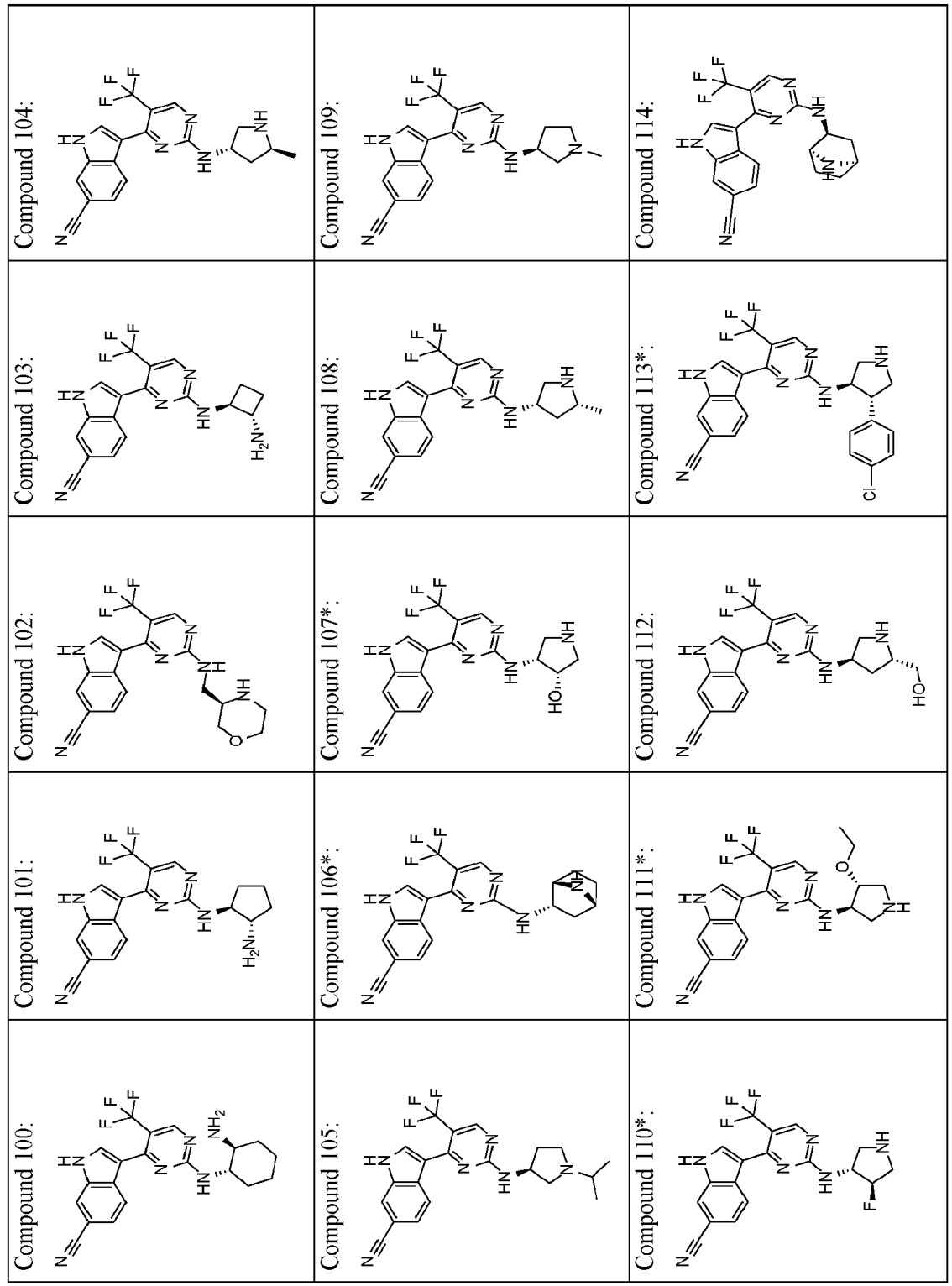
FIG. 1 is a Table disclosing, by compound number and structure, exemplary compounds of the invention. "*" indicates relative stereochemistry (shown for Compounds 106, 107, 110, 111 and 113).
Figure 1:
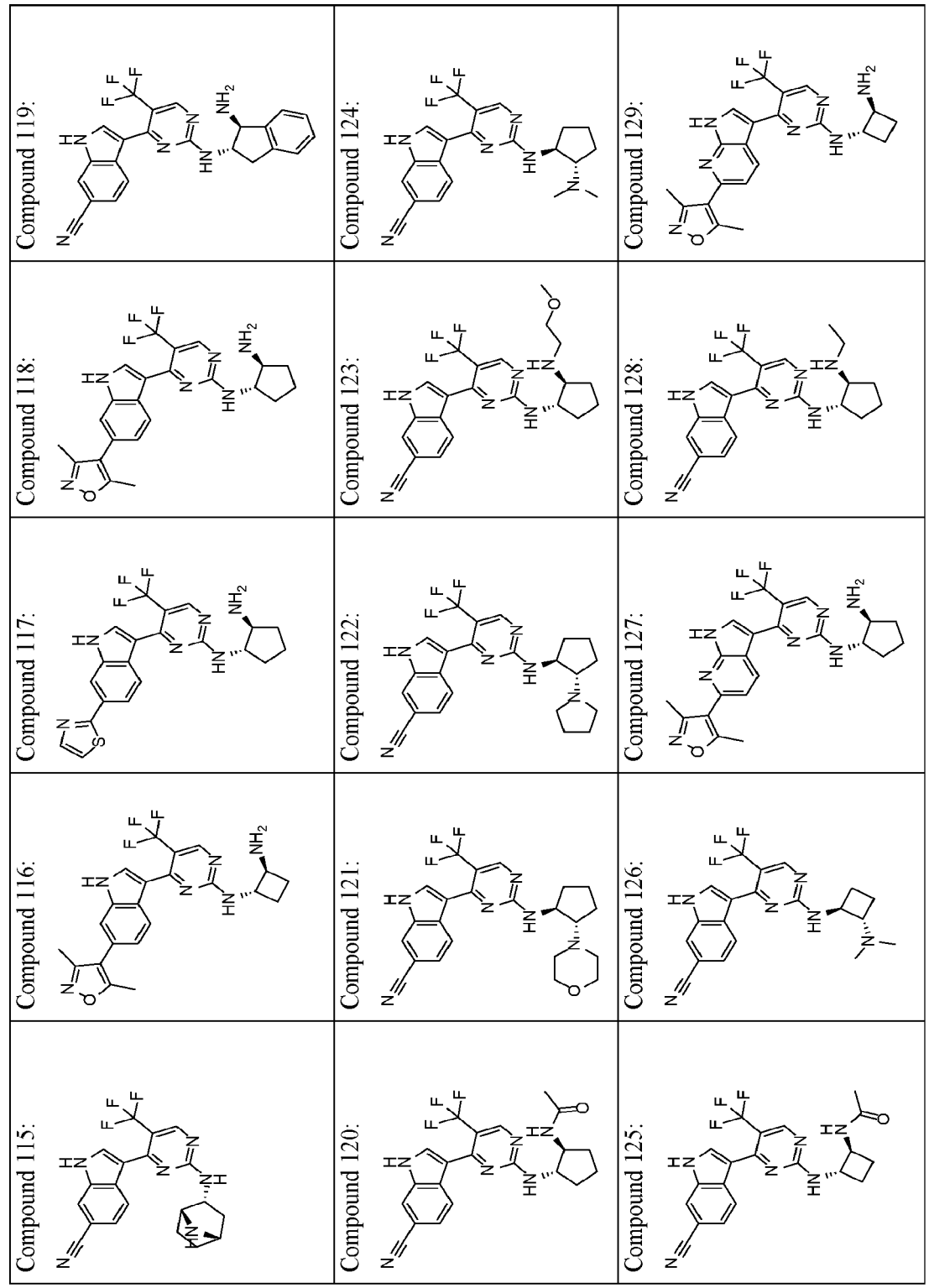
Figure 1:
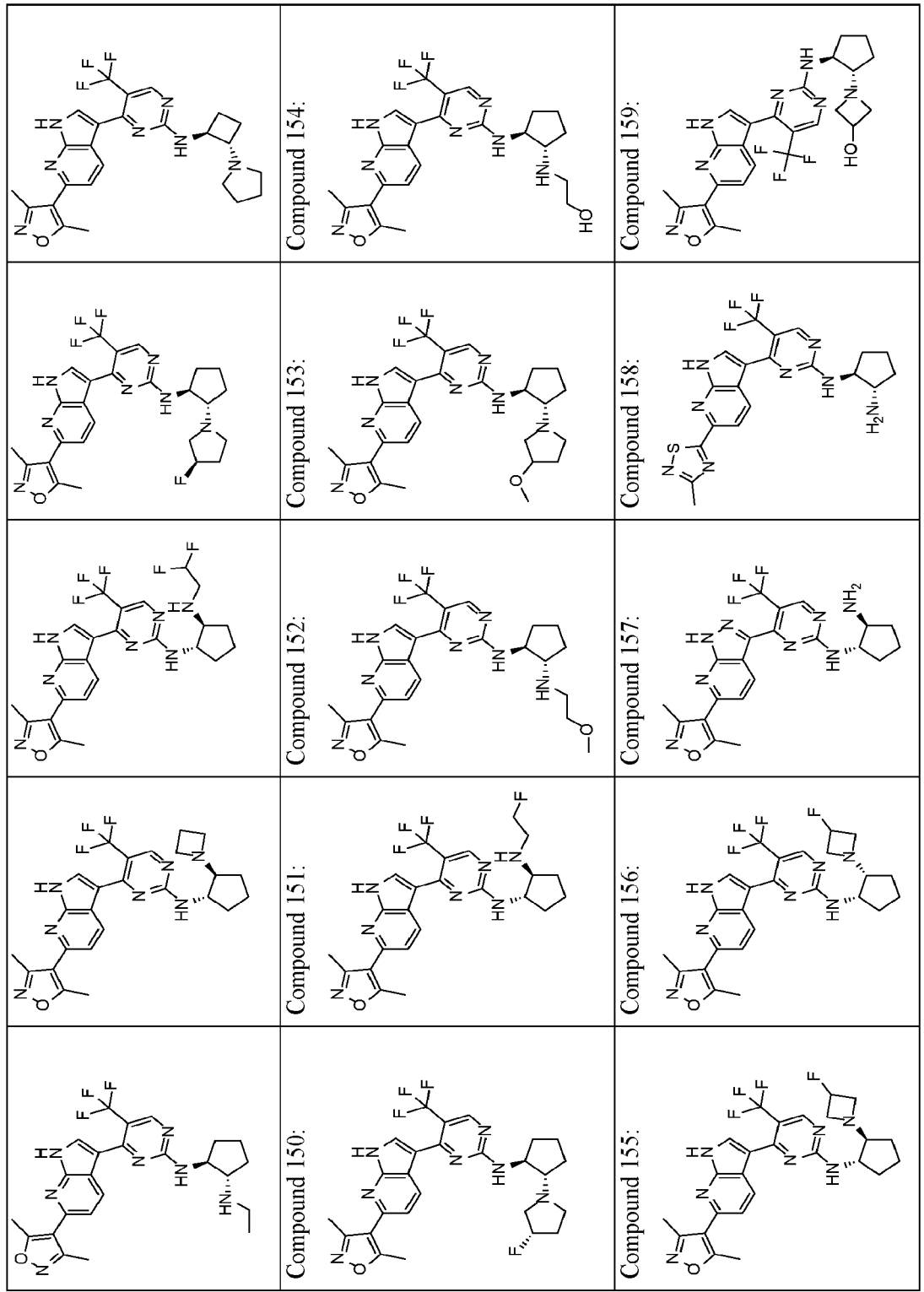
Figure 1:
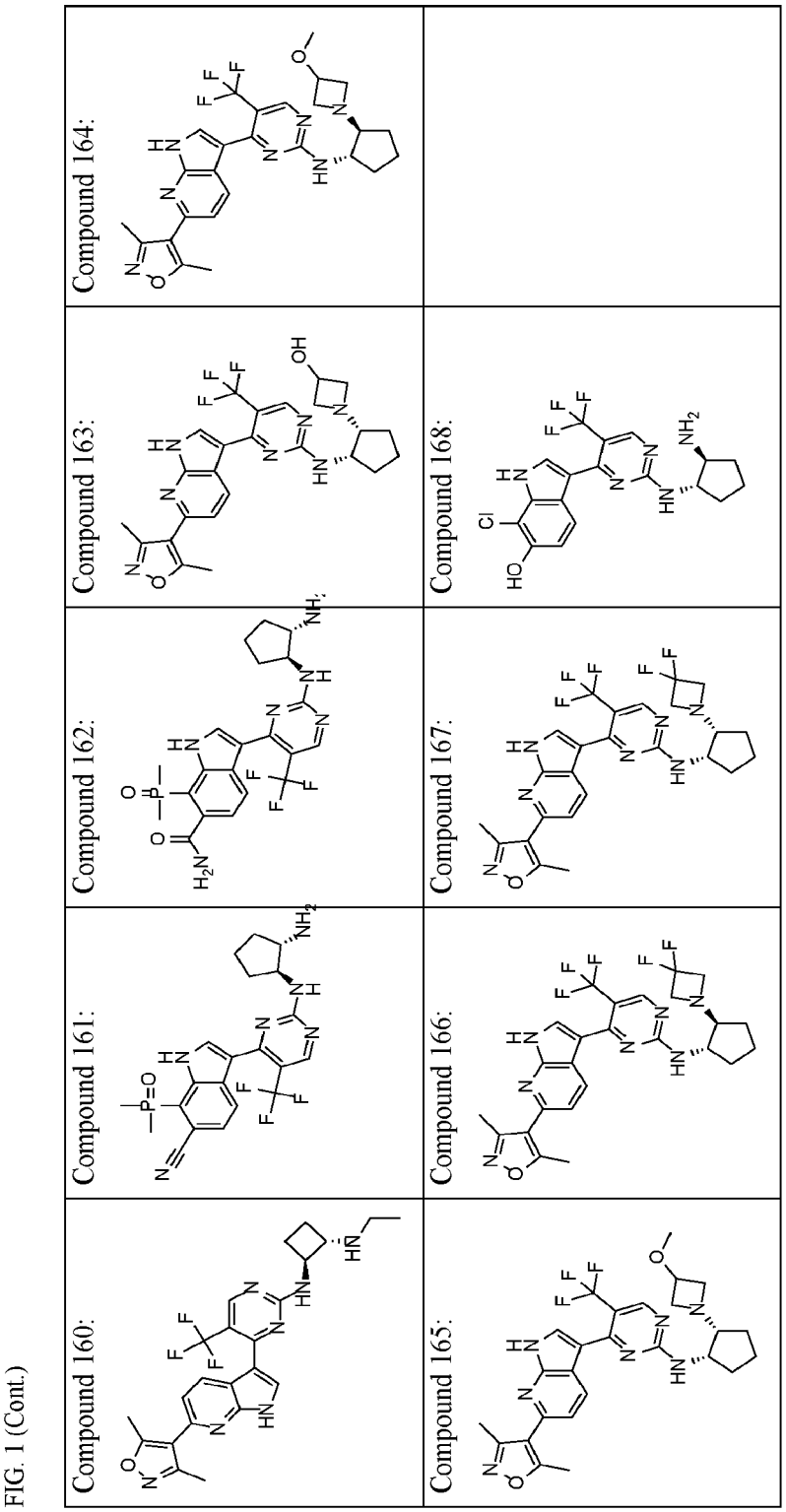

Described herein are compounds of Formula (I):

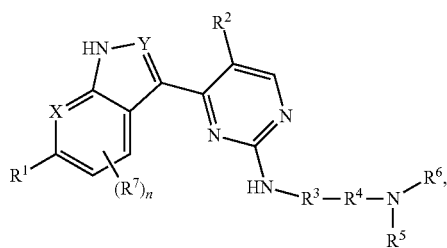

and pharmaceutically acceptable salts, solvates (e.g., hydrates), tautomers, stereoisomers, and isotopic forms thereof, wherein: X is N or CH; Y is N or CH; $R^1$ is: —CN or one of the following heteroaryl groups

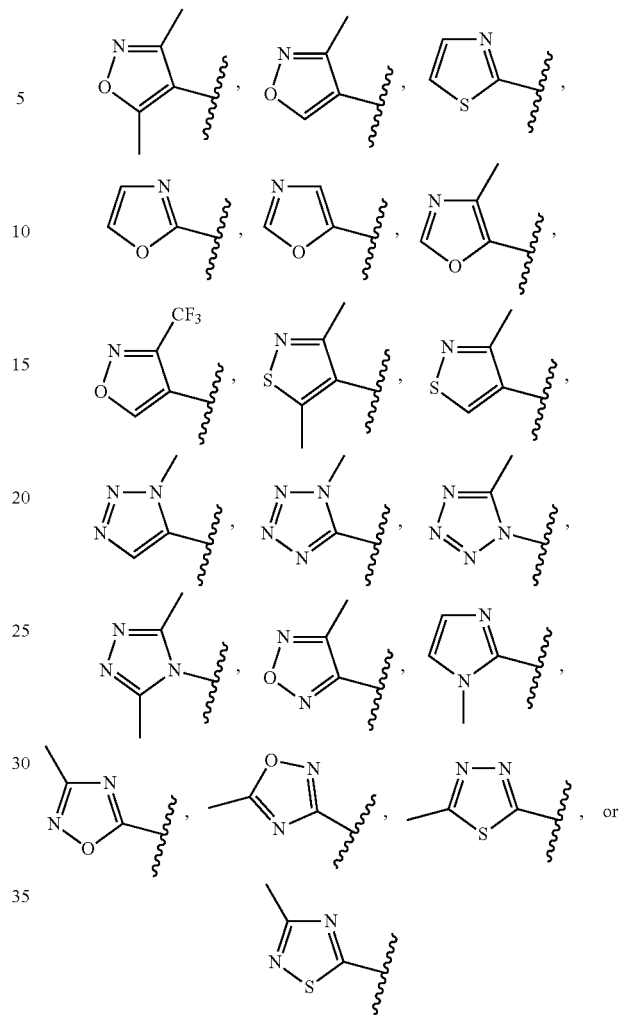

wherein any heteroaryl portion of $R^1$ is optionally substituted at up to two substitutable carbon atoms with, independently, halo, —CN, —OH, —NH$_2$, —NH(C$_1$-C$_4$ alkyl), —N(C$_1$-C$_4$ alkyl)$_2$, C$_1$-C$_4$ alkyl, —O—(C$_1$-C$_4$ alkyl), —(C$_1$-C$_4$ alkylene)-O—(C$_1$-C$_4$ alkyl), or —S(O)$_2$—(C$_1$-C$_4$ alkyl);

$R^2$ is fluoro, chloro, —CN, or C$_1$-C$_4$ alkyl optionally substituted with fluoro;

$R^3$, $R^4$, and $R^5$ are as follows:

(i) $R^3$ is CH, $R^4$ is CH, $R^3$ and $R^4$ are taken together to form an optionally substituted and optionally benzofused cycloalkyl and $R^5$ is hydrogen or C$_1$-C$_4$ alkyl or is taken together with $R^6$ to form an optionally substituted and optionally benzofused saturated monocyclic or bicyclic heterocyclyl; or (ii) $R^3$ is C or CH, $R^5$ is C, CH or CH$_2$, $R^3$ and $R^5$ are taken together with $R^4$ and the intervening nitrogen atom to form a saturated monocyclic heterocyclyl other than piperdine, wherein the saturated monocyclic heterocyclyl is optionally substituted and optionally fused to a cycloalkyl, saturated heterocyclyl, or phenyl ring, and $R^4$ is C, CH, or CH$_2$; or (iii) $R^4$ is C or CH, $R^5$ is C, CH or CH$_2$, $R^4$ and $R^5$ are taken together with the intervening nitrogen atom to form an optionally substituted and optionally benzofused saturated monocyclic or bicyclic heterocyclyl, and $R^3$ is CH$_2$;

$R^6$ is hydrogen, —$C_1$-$C_4$ alkyl, —C(O)—($C_1$-$C_4$ alkyl), —C(O)—($C_1$-$C_4$ alkylene)-N($R^7$)$_2$, —($C_1$-$C_4$ alkylene)-O—($C_1$-$C_4$ alkyl), —C(O)-aryl, or —S(O)$_2$-aryl;

each $R^7$ is, independently, halo, —CN, —OH, —NH$_2$, —NH($C_1$-$C_4$ alkyl), N($C_1$-$C_4$ alkyl)$_2$, —$C_1$-$C_4$ alkyl, —O—($C_1$-$C_4$ alkyl), —($C_1$-$C_4$ alkylene)-O—($C_1$-$C_4$ alkyl) or —S(O)$_2$—($C_1$-$C_4$ alkyl);

n is 0, 1, 2, 3 or 4;

each saturated heterocyclyl, cycloalkyl, or aryl is optionally substituted with up to four substituents independently selected from halo, —CN, —OH, —NH$_2$, —NH($C_1$-$C_4$ alkyl), N($C_1$-$C_4$ alkyl)$_2$, —$C_1$-$C_4$ alkyl, —O—($C_1$-$C_4$ alkyl), —($C_1$-$C_4$ alkylene)-O—($C_1$-$C_4$ alkyl), and optionally substituted phenyl; and each $C_1$-$C_4$ alkyl and $C_1$-$C_4$ alkylene is optionally substituted with up to five substituents, each substituent being, independently, halo, —CN, —OH, —NH$_2$, —NH(unsubstituted $C_1$-$C_4$ alkyl), N(unsubstituted $C_1$-$C_4$ alkyl)$_2$, and —O-(unsubstituted $C_1$-$C_4$ alkyl).

In connection with option (ii) above, when $R^3$ and $R^5$ are taken together with $R^4$ and the intervening nitrogen atom to form a saturated monocyclic heterocyclyl other than piperdine, $R^3$ is C when the saturated monocyclic heterocyclyl is fused to a cycloalkyl or saturated heterocyclyl in which R3 is a bridgehead atom; $R^4$ is CH when the saturated monocyclic heterocyclyl is fused to a cycloalkyl or saturated heterocyclyl in which $R^4$ is a bridgehead atom; $R^4$ is C when the saturated monocyclic heterocyclyl is fused to phenyl in which $R^4$ is a bridgehead atom; $R^5$ is CH when the saturated monocyclic heterocyclyl is fused to a cycloalkyl or saturated heterocyclyl in which $R^5$ is a bridgehead atom; and $R^5$ is C when the saturated monocyclic heterocyclyl is fused to phenyl in which $R^5$ is a bridgehead atom.

In connection with option (iii) above, $R^4$ and $R^5$ are taken together with the intervening nitrogen atom to form a saturated monocyclic or bicyclic heterocyclyl, $R^4$ is C when $R^4$ and $R^5$ are taken together with the intervening nitrogen atom to form a saturated bicyclic heterocyclyl and $R^4$ is a bridgehead atom in that bicyclic heterocyclyl; $R^5$ is CH when $R^4$ and $R^5$ are taken together with the intervening nitrogen atom to form a saturated bicyclic heterocyclyl and $R^5$ is a bridgehead atom in that bicyclic heterocyclyl; and $R^5$ is C when the saturated monocyclic or bicyclic heterocyclyl is benzofused and $R^5$ is a bridgehead atom in that benzfusion. X can additionally be C($R^{10}$), wherein $R^{10}$ is halo (e.g., fluoro) or —P(O)(CH$_3$)$_2$. $R^1$ can additionally be —OH or —C(O)—NH$_2$.

When $R^3$ is C or CH, $R^5$ is C, CH or CH$_2$, $R^3$ and $R^5$ are taken together with $R^4$ and the intervening nitrogen atom to form a saturated monocyclic heterocyclyl other than piperdine, and $R^4$ is C, CH, or CH$_2$; $R^5$ and $R^6$ also are taken together to form a saturated heterocyclyl that is fused to the ring formed by taking $R^3$ and $R^5$ together. For example, $R^3$, $R^4$, $R^5$ and $R^6$ can form a 1-azabicyclo-3-yl moiety, such as 1-azabicyclo[3.2.2]nonan-3-yl:

$R^1$ can be —CN,

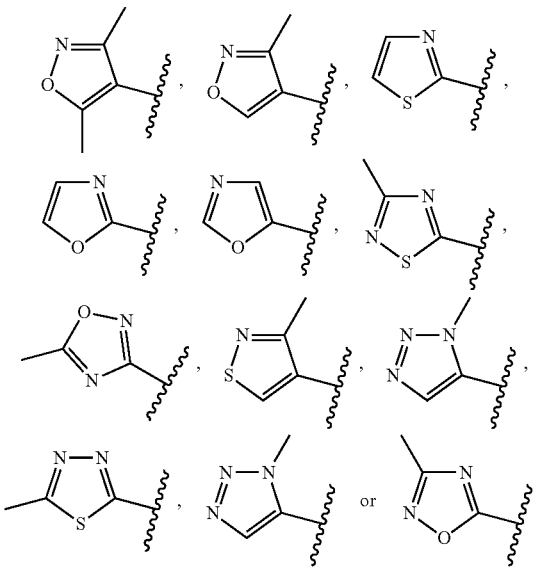

More specifically, $R^1$ can be —CN,

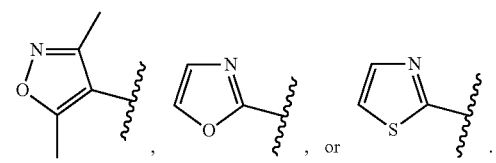

More specifically, $R^1$ can be —CN,

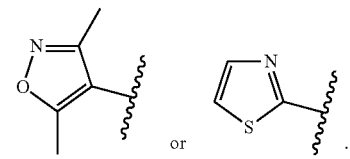

Even more specifically, $R^1$ can be —CN.

In other embodiments, $R^1$ is —C(O)—NH$_2$ or —OH.

$R^2$ can be -chloro or —CF$_3$ (e.g., —CF$_3$).

$R^3$ and $R^4$ can be taken together to form an optionally substituted and optionally benzofused cycloalkyl resulting in a compound of Formula Ia:

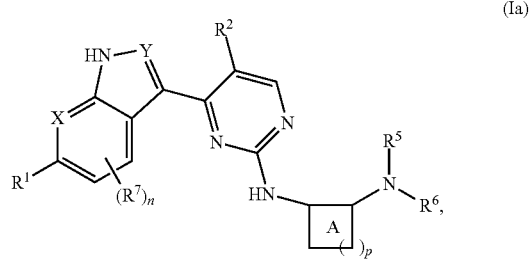

(Ia)

or a pharmaceutically acceptable salt, solvate (e.g., hydrate), tautomer, or isotopic form thereof, wherein p is 0, 1, 2, 3, 4, or 5, resulting in ring A being an optionally substituted and optionally benzofused cycloalkyl. Ring A can be optionally substituted cyclobutyl (optionally benzofused) or cyclopentyl (optionally benzofused). More specifically, ring A can be an unsubstituted cyclobutyl or cyclopentyl (except for the —N(R$^5$)(R$^6$) substituent depicted in Formula Ia), wherein the cyclobutyl or cyclopentyl is optionally benzofused. In some embodiments, Y is CH. In some embodiments, X is N, CH, C(Cl), or C(P(O)(CH$_3$)$_2$). R$^2$ can be —CF$_3$ and R$^1$ can be —OH, —CN, —C(O)NH$_2$,

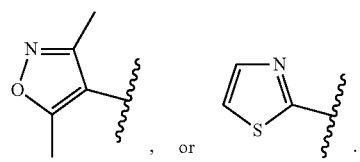

, or .

Where R$^3$ and R$^4$ are taken together to form unsubstituted cyclobutyl or cyclopentyl (each optionally benzofused), R$^5$ is hydrogen or —CH$_3$, R$^6$ is hydrogen, —C$_1$-C$_4$ alkyl, or —(C$_1$-C$_4$ alkylene)-O—(C$_1$-C$_4$ alkyl), or R$^5$ and R$^6$ are taken together with the nitrogen atom to which they are bound to form a saturated heterocyclyl. R$^6$ can be hydrogen, —CH$_2$CH$_2$OCH$_3$, or —CH$_2$CH$_3$, or R$^5$ and R$^6$ can be taken together with the nitrogen atom to which they are bound to form morpholin-4-yl, pyrrolidin-1-yl (e.g., R$^6$ can be hydrogen or —CH$_2$CH$_3$).

Where R$^3$ and R$^4$ are taken together to form unsubstituted cyclobutyl or cyclopentyl, wherein the cyclobutyl or cyclopentyl is optionally benzofused, R$^5$ is hydrogen or —CH$_3$, and R$^6$ is selected from hydrogen, —C$_1$-C$_4$ alkyl, halo-substituted —C$_1$-C$_4$ alkyl, hydroxy-substituted —C$_1$-C$_4$ alkyl, and —(C$_1$-C$_4$ alkylene)-O—(C$_1$-C$_4$ alkyl), or R$^5$ and R$^6$ are taken together with the nitrogen atom to which they are bound to form a saturated heterocyclyl optionally substituted with 1-4 substituents independently selected from halo, —OH, —C$_1$-C$_4$ alkyl, and —O—(C$_1$-C$_4$ alkyl). In specific aspects of these embodiments, R$^6$ is selected from hydrogen, —CH$_2$CH$_3$, —CH$_2$CH$_2$OH, —CH$_2$CH$_2$OCH$_3$, —CH$_2$CH$_2$CH$_2$F, or —CH$_2$CHF$_2$, or R$^5$ and R$^6$ are taken together with the nitrogen atom to which they are bound to form morpholin-4-yl, pyrrolidin-1-yl, azetidine-1-yl, 3,3-difluoroazertidin-1-yl, 3-methoxyazetidin-1-yl, 3-hydroxyazetidin-1-yl, 3-fluoroazetidin-1-yl, 3-methoxypyrrolidin-1-yl, or 3-fluoropyrrolidin-1-yl.

In compounds of Formula Ia, the stereochemistry around ring A can be as depicted in Formula Ia-1:

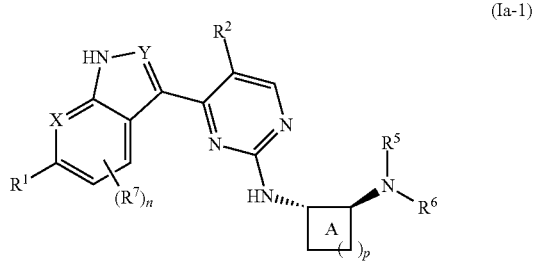

(Ia-1)

or Formula Ia-2:

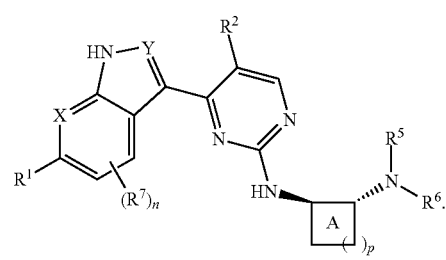

(Ia-2)

In some embodiments of Formula I, R$^3$ and R$^5$ are taken together with R$^4$ and the intervening nitrogen atom to form a saturated monocyclic heterocyclyl other than piperdine, wherein the saturated monocyclic heterocyclyl is optionally substituted and optionally fused to a cycloalkyl, saturated heterocyclyl, or phenyl ring resulting in a compound of Formula Ib:

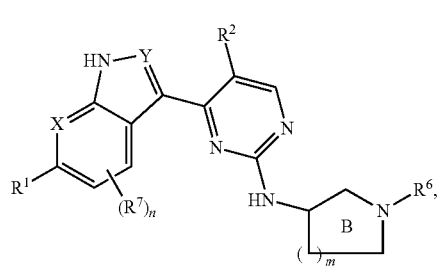

(Ib)

or a pharmaceutically acceptable salt, solvate (e.g., hydrate), tautomer, and isotopic form thereof, wherein m is 0, 1, 3, or 4, resulting in ring B being a saturated monocyclic heterocyclyl other than piperdine, wherein ring B is optionally substituted and optionally fused to a cycloalkyl, saturated heterocyclyl, or phenyl ring. Ring B can be optionally substituted pyrrolidin-3-yl or optionally substituted 7-azabicyclo[2.2.1]heptan-2-yl; and R$^6$ can be hydrogen or —CH$_3$. More specifically, ring B is 7-azabicyclo[2.2.1]heptan-2-yl and R$^6$ is hydrogen. Ring B can also be optionally substituted on a ring carbon atom with one or two substituents independently selected from halo, —OH, C$_1$-C$_4$ alkyl, —O—C$_1$-C$_4$ alkyl, C$_1$-C$_4$ alkylene-OH, or optionally substituted phenyl. More specifically, ring B can be optionally substituted on a ring carbon atom with substituents selected from fluoro, —OH, —CH$_3$, —OCH$_2$CH$_3$, —CH$_2$OH, and fluoro-substituted phenyl. In some embodiments, R$^6$ forms a bridged bicyclic with ring B (i.e., R$^5$ and R$^6$ are taken together to form a ring that is fused to ring B, which is formed by taking R$^3$ and R$^5$ together). In more specific aspects of these embodiments, ring B is taken together with R to form 1-azabicyclo[3.2.2]nonan-3-yl:

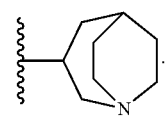 [SMILES: *C1CC2CCN(CC2)C1]

.

In some embodiments of Formula Ib, the stereochemistry around ring B is as depicted in Formula Ib-1

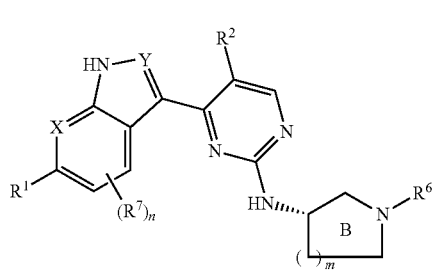

(Ib-1)

or Formula Ib-2

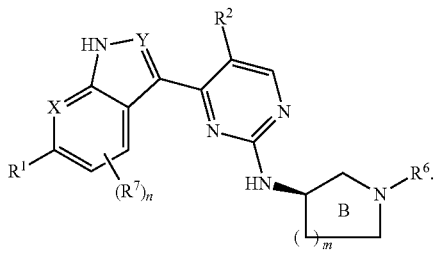

(Ib-2)

In compounds of Formula I, $R^4$ and $R^5$ can be taken together with the intervening nitrogen atom to form an optionally substituted and optionally benzofused saturated monocyclic or bicyclic heterocyclyl resulting in a compound of Formula Ic.

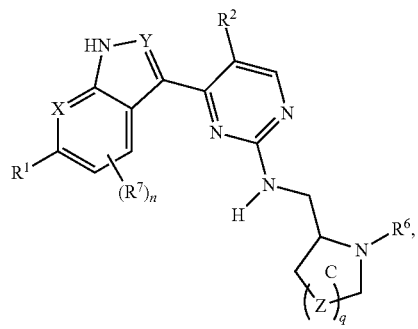

(Ic)

wherein ring C is optionally substituted and optionally benzofused, wherein q is 0, 1, 2, 3, or 4; each Z is independently —C($R^8$)$_2$, N($R^9$), O, or S, each $R^8$ is, independently, hydrogen, halo, —CN, —OH, —NH$_2$, —NH(C$_1$-C$_4$ alkyl), N(C$_1$-C$_4$ alkyl)$_2$, —C$_1$-C$_4$ alkyl, —O—(C$_1$-C$_4$ alkyl), —(C$_1$-C$_4$ alkylene)-O—(C$_1$-C$_4$ alkyl), or optionally substituted phenyl; and each $R^9$ is, independently, hydrogen or —C$_1$-C$_4$ alkyl.

The stereochemistry around ring C can be as depicted in Formula Ic-1:

(Ic-1)

or Formula Ic-2:

(Ic-2)

In some embodiments of Formula I, Ia, Ia-1, Ia-2, Ib, Ib-1, Ib-2, Ic, Ic-1, or Ic-2, at least one of X or Y is CH. In some embodiments, Y is CH and X is N. In other embodiments, X is CH and Y is N. In other embodiments, X is CH and Y is CH.

In some embodiments of Formula I, Ia, Ia-1, Ia-2, Ib, Ib-1, Ib-2, Ic, Ic-1, or Ic-2, n is 0.

In one embodiment, the invention features a compound of Formula II:

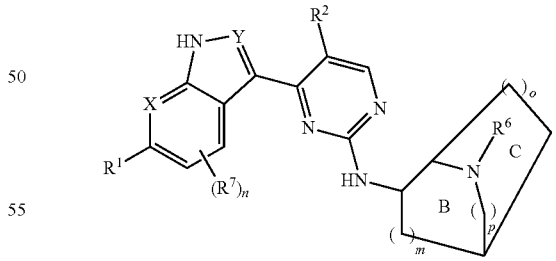

or a pharmaceutically acceptable salt, solvate, tautomer, stereoisomer, or isotopic form thereof, wherein:
 ring B is optionally substituted;
 ring C is optionally substituted;
 X is N, CH, or C($R^{10}$), wherein $R^{10}$ is halo or —P(O)(CH$_3$)$_2$;
 Y is N or CH;
 $R^1$ is —OH, —CN, —C(O)NH$_2$, or one of the following heteroaryl groups

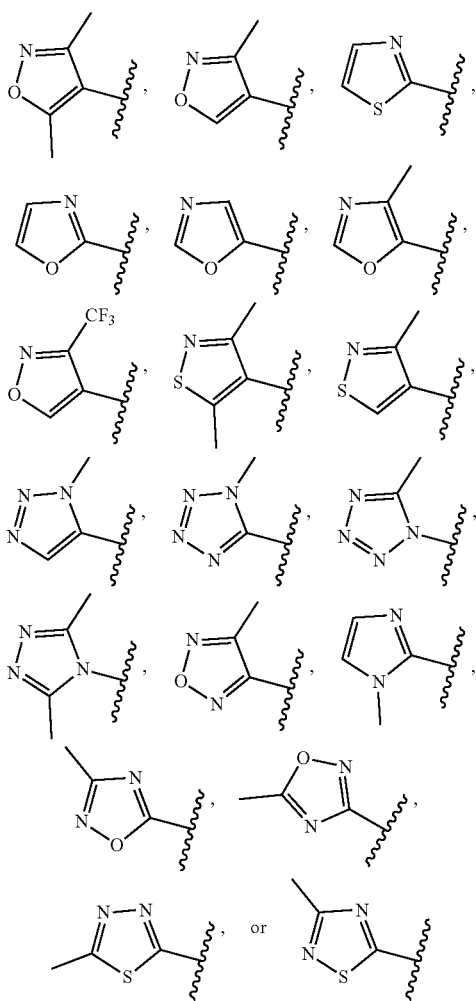

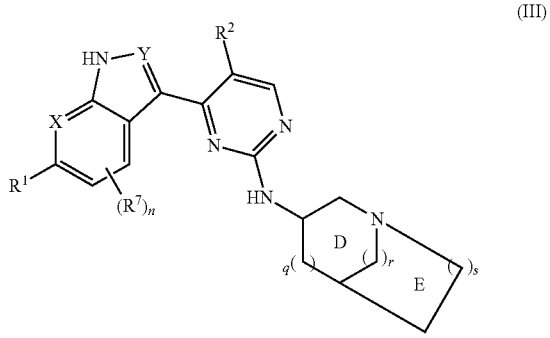

wherein any heteroaryl portion of $R^1$ is optionally substituted at up to two substitutable carbon atoms with a substituent independently selected from halo, —CN, —OH, —NH$_2$, —NH(C$_1$-C$_4$ alkyl), —N(C$_1$-C$_4$ alkyl)$_2$, C$_1$-C$_4$ alkyl, —O—(C$_1$-C$_4$ alkyl), —(C$_1$-C$_4$ alkylene)-O—(C$_1$-C$_4$ alkyl), and —S(O)$_2$—(C$_1$-C$_4$ alkyl);

$R^2$ is fluoro, chloro, —CN, or C$_1$-C$_4$ alkyl optionally substituted with fluoro;

$R^6$ is hydrogen, —C$_1$-C$_4$ alkyl, —C(O)—(C$_1$-C$_4$ alkyl), —C(O)—(C$_1$-C$_4$ alkylene)-N(R$^7$)$_2$, —(C$_1$-C$_4$ alkylene)-O—(C$_1$-C$_4$ alkyl), —C(O)-aryl, or —S(O)$_2$-aryl;

each $R^7$ is, independently, halo, —CN, —OH, —NH$_2$, —NH(C$_1$-C$_4$ alkyl), N(C$_1$-C$_4$ alkyl)$_2$, —C$_1$-C$_4$ alkyl, —O—(C$_1$-C$_4$ alkyl), —(C$_1$-C$_4$ alkylene)-O—(C$_1$-C$_4$ alkyl) or —S(O)$_2$—(C$_1$-C$_4$ alkyl);

m is 0, 1, 2, 3 or 4;

n is 0, 1, 2, 3 or 4;

is 0, 1, 2, 3 or 4;

p is 0, 1, 2, 3 or 4;

wherein m+p does not equal 2;

each saturated heterocyclyl, cycloalkyl, or aryl is optionally substituted with up to four substituents independently selected from halo, —CN, —OH, —NH$_2$, —NH(C$_1$-C$_4$ alkyl), N(C$_1$-C$_4$ alkyl)$_2$, —C$_1$-C$_4$ alkyl, —O—(C$_1$-C$_4$ alkyl), —(C$_1$-C$_4$ alkylene)-O—(C$_1$-C$_4$ alkyl), and an optionally substituted phenyl; and each C$_1$-C$_4$ alkyl and C$_1$-C$_4$ alkylene is optionally substituted with up to five substituents independently selected from halo, —CN, —OH, —NH$_2$, —NH(unsubstituted C$_1$-C$_4$ alkyl), N(unsubstituted C$_1$-C$_4$ alkyl)$_2$, and —O-(unsubstituted C$_1$-C$_4$ alkyl).

In one embodiment, the invention features a compound of Formula III:

(III)

or a pharmaceutically acceptable salt, solvate, tautomer, stereoisomer, or isotopic form thereof, wherein:

ring D is optionally substituted;

ring E is optionally substituted;

X is N, CH, or C(R$^{10}$), wherein R$^{10}$ is halo or —P(O)(CH$_3$)$_2$;

Y is N or CH;

$R^1$ is —OH, —CN, —C(O)NH$_2$, or one of the following heteroaryl groups

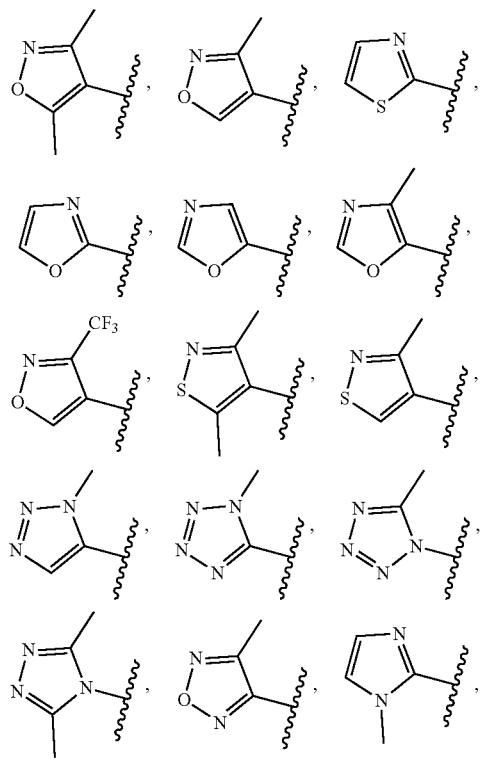

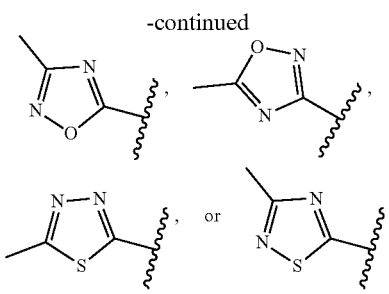

wherein any heteroaryl portion of $R^1$ is optionally substituted at up to two substitutable carbon atoms with a substituent independently selected from halo, —CN, —OH, —NH$_2$, —NH(C$_1$-C$_4$ alkyl), —N(C$_1$-C$_4$ alkyl)$_2$, C$_1$-C$_4$ alkyl, —O—(C$_1$-C$_4$ alkyl), —(C$_1$-C$_4$ alkylene)-O—(C$_1$-C$_4$ alkyl), and —S(O)$_2$—(C$_1$-C$_4$ alkyl);

$R^2$ is fluoro, chloro, —CN, or C$_1$-C$_4$ alkyl optionally substituted with fluoro;

each $R^7$ is, independently, halo, —CN, —OH, —NH$_2$, —NH(C$_1$-C$_4$ alkyl), N(C$_1$-C$_4$ alkyl)$_2$, —C$_1$-C$_4$ alkyl, —O—(C$_1$-C$_4$ alkyl), —(C$_1$-C$_4$ alkyl)-O—(C$_1$-C$_4$ alkyl) or —S(O)$_2$—(C$_1$-C$_4$ alkyl);

n is 0, 1, 2, 3 or 4; q is 0, 1, 2, 3 or 4; r is 0, 1, 2, 3 or 4; s is 0, 1, 2, 3 or 4; wherein q+r does not equal 2;

each saturated heterocyclyl, cycloalkyl, or aryl is optionally substituted with up to four substituents independently selected from halo, —CN, —OH, —NH$_2$, —NH(C$_1$-C$_4$ alkyl), N(C$_1$-C$_4$ alkyl)$_2$, —C$_1$-C$_4$ alkyl, —O—(C$_1$-C$_4$ alkyl), —(C$_1$-C$_4$ alkylene)-O—(C$_1$-C$_4$ alkyl), and an optionally substituted phenyl; and each C$_1$-C$_4$ alkyl and C$_1$-C$_4$ alkylene is optionally substituted with up to five substituents independently selected from halo, —CN, —OH, —NH$_2$, —NH(unsubstituted C$_1$-C$_4$ alkyl), N(unsubstituted C$_1$-C$_4$ alkyl)$_2$, and —O-(unsubstituted C$_1$-C$_4$ alkyl).

Any compound described herein can be prepared using methods described herein and/or known in the art. Techniques useful in synthesizing these compounds are accessible to one of ordinary skill in the art, and the discussion below illustrates certain of the diverse methods available for use in assembling them. The discussion is not intended to limit the scope of useful reactions or reaction sequences. Any pharmaceutical composition described herein can be prepared by methods known in the art of pharmacology. In general, such preparatory methods include the steps of bringing the compound (e.g., a compound of formula (I); the "active ingredient") into association with an excipient and/or one or more other accessory ingredients or "second" agents, and then, if necessary and/or desirable, shaping and/or packaging the product into a desired single- or multi-dose unit and/or packaging the composition within a kit.

Compounds and/or other compositions provided herein (e.g., pharmaceutical compositions) have a variety of uses, including in research and/or clinical settings (e.g., in methods of providing a diagnosis or prognosis and in prophylactic or therapeutic treatment methods).

In some embodiments, a provided compound and/or composition is considered to be specific for a given kinase or set of kinases when it shows at least or about 2-fold, 3-fold, 4-fold, 5-fold, 10-fold, 15-fold, 20-fold, 50-fold, 100-fold or more activity for the specific kinase(s) than for one or more appropriate comparator kinase(s) (e.g., for CDK7 relative to one or more of CDK2, CDK9, and/or CDK12). One of ordinary skill in the art will recognize the evaluating specificity in terms of "fold difference" is only one applicable measure. For example, specificity can be expressed as a "percent difference." For example, a provided compound and/or composition is considered to be specific for CDK7 when it shows at least 101%, 105%, 110%, 120%, 130%, 140%, 150%, 200%, 300%, 400%, 500% or more activity for CDK7 than for one or more of CDK2, CDK9, and/or CDK12.

Compounds of the present disclosure can be prepared and administered in a wide variety of oral and parenteral dosage forms. Thus, the compounds of the present disclosure can be formulated for administration by injection (e.g. intravenously, intramuscularly, intracutaneously, subcutaneously, or intraperitoneally). The compounds can also be formulated for administration by inhalation (e.g., intranasally) or by insufflation. In other embodiments, the compounds described herein can be formulated for topical or transdermal administration (i.e., they can be in a dosage form suitable for administration by the various routes just described).

For preparing pharmaceutical compositions including a compound described herein, pharmaceutically acceptable carriers can be added in either solid or liquid form or a combination thereof. Solid dosage form preparations within the scope of the present invention include powders, tablets, pills, capsules, cachets, suppositories, and dispersible granules. A solid carrier can be a substance that may also act as a diluent, flavoring agent, binder, preservative, tablet disintegrating agent, or an encapsulating material. In powders, the carrier is a finely divided solid in a mixture with the finely divided active component (e.g., a compound described herein, e.g., a compound conforming to the structure of Formula II). In tablets, the active component is mixed with the carrier having the necessary binding properties in suitable proportions and compacted in the shape and size desired. Pharmaceutical compositions, including those formulated as powders and tablets, can contain from about 5% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Tablets, powders, capsules, pills, cachets, and lozenges can be used as solid dosage forms suitable for oral administration. For preparing suppositories, a low melting wax, such as a mixture of fatty acid glycerides or cocoa butter, is melted and the active component is dispersed therein.

Liquid form preparations include solutions, suspensions, and emulsions, for example, water or water/propylene glycol solutions. For parenteral injection, liquid preparations can be formulated in solution in aqueous polyethylene glycol solution. When parenteral application is needed or desired, particularly suitable admixtures for the compounds of the invention are injectable, sterile solutions, preferably oily or aqueous solutions, as well as suspensions, emulsions, or implants, including suppositories. In some embodiments, suitable carriers for parenteral administration will be selected for human administration.

In particular, carriers for parenteral administration include aqueous solutions of dextrose, saline, pure water, ethanol, glycerol, glycerol formal, polyethylene glycol, propylene glycol, peanut oil, sesame oil, polyoxyethylene-block polymers, pyrrolidine, N-methyl pyrrolidione, and the like. Ampoules are convenient unit dosage forms. The compounds of the present disclosure can also be incorporated into liposomes or administered via transdermal pumps or patches. Pharmaceutical admixtures suitable for use in the present disclosure include those described, for example, in Pharmaceutical Sciences (17th Ed., Mack Pub. Co., Easton, PA) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical compositions are preferably in unit dosage form. The unit dosage form can be a packaged preparation, the package containing discrete quantities of preparation, such as packeted tablets, capsules, and powders in vials or ampoules. Unit dosage forms can also be capsules, tablets, cachets, lozenges, or the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition (e.g., polysorbate 20, 60, and 80; Pluronic® F-68, F-84, and P-103; cyclodextrin; and polyoxyl 35 castor oil). Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

Compositions of the present invention may additionally include components to provide sustained release and/or comfort (e.g., high molecular weight, anionic mucomimetic polymers, gelling polysaccharides, and finely-divided drug carrier substrates). These components are discussed in detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present disclosure include compositions wherein the active ingredient is contained in a therapeutically effective amount, i.e., in an amount effective to achieve its intended purpose. The actual amount effective for a particular application will depend, inter alia, on the condition being treated. For example, when administered in methods to a subject with cancer, such compositions will contain an amount of active ingredient effective to achieve the desired result.

The dosage and frequency (single or multiple doses) of compound administered can vary depending on a variety of factors, including route of administration; the size, age, sex, health, body weight, body mass index, and diet of the recipient; nature and extent of symptoms of the disease being treated; any concurrent treatment; and complications from any disease or treatment regimen. Other therapeutic regimens or agents can be used in conjunction with the methods and compounds of the present disclosure.

For any compound, any variant form thereof (e.g., any salt or solvate), or any pharmaceutical composition described herein, the therapeutically effective amount can be initially determined from, or informed by data generated in, cell culture assays and/or animal models of disease. For example, a dose for humans can be formulated to achieve a concentration that has been found to be effective in animals. The dosage in humans can be adjusted by, for example, monitoring kinase inhibition, the signs an symptoms of the disease being treated, and side effects and subsequently adjusting the dosage upwards or downwards.

Dosages may be varied depending upon the requirements of the patient and the compound being employed. The dose administered to a patient should be sufficient to effect a beneficial therapeutic response in the patient over time. The size of the dose also will also be determined by the existence, nature, and extent of any adverse side effects. Generally, treatment is initiated with smaller dosages, which are less than the optimum dose of the compound. Thereafter, the dosage is increased by small increments until the optimum effect under a desired circumstance is reached. In some embodiments, the concentration of compound is about 0.001% to 10% w/v (e.g., about 0.1% to about 5% w/v). In some embodiments, the concentration range is 0.1% to 5% w/v. Concentrations, dosage amounts, and intervals can be adjusted in each individual patient to provide levels of the administered compound effective for the particular disease being treated. This will provide a therapeutic regimen commensurate with the severity of the patient's disease.

The disease to be treated or prevented using a compound described herein (e.g., a compound of Formula (I), or a pharmaceutically acceptable salt, solvate (e.g., hydrate), tautomer, stereoisomer, or an isotopically labeled derivative thereof, or compositions containing any of the foregoing will typically be associated with aberrant expression or activity of CDK7. For example, a gene encoding CDK7 can be overexpressed or misexpressed (i.e., expressed at abnormally high levels in a tissue where it is normally expressed; expressed or overexpressed in a tissue where it is not normally expressed; or expressed at a time during which it is not normally expressed). The activity of the encoded protein can also be increased, and aberrant expression or activity can be relative to the expression or activity in a comparable patient, population of patients, biological sample, or plurality of biological samples that do not manifest signs or symptoms of the disease in question. Both expression and activity may be aberrant, or only activity may be aberrant.

Methods of testing patients and biological samples for levels of CDK7 expression or activity are within the scope of the invention and may be performed prior to, during, or after treatment as described herein. CDK7 levels can be tested and compared between healthy patients and patients having a disease; between treated and untreated patients; between biological samples from healthy tissues and diseased tissues (whether treated or untreated); and between biological samples that represent models of a disease disclosed herein. Although no aspect of the invention is limited by the cellular mechanisms that result from contacting a cell described herein (whether in a patient or a biological sample ex vivo) with a compound or other composition described herein, this contact may cause cytotoxicity via induction of apoptosis, and assessing cytotoxicity can be a part of the methods of testing patients and biological samples prior to, during, or after treatment.

As noted, the proliferative disease to be treated or prevented using the compounds described herein or pharmaceutically acceptable salts, solvates (e.g., hydrates), tautomers, stereoisomers, isotopically labeled derivatives, and compositions thereof include the cancers described herein, particularly when a given cancer is known to be or found to be associated with aberrant CDK7 expression or activity. The proliferative disease can be a cancer associated with dependence on BCL-2 anti-apoptotic proteins (e.g., MCL-1 and/or XIAP); with overexpression of MYC; with overexpression of CDK18; with overexpression of CDK19; with overexpression of FGFR1; with overexpression of CDK6; with overexpression of CCND2; or with overexpression of CDKN2A. In certain embodiments, the proliferative disease is a cancer associated with the absence of, or suppression of, a wild-type RB1 gene.

In certain embodiments, the proliferative disease is a blood cancer, which may also be referred to as a hematopoietic or hematological cancer or malignancy. More specifically and in various embodiments, the blood cancer can be a leukemia such as acute lymphocytic leukemia (ALL; e.g., B cell ALL or T cell ALL), acute myelocytic leukemia (AML; e.g., B cell AML or T cell AML), chronic myelocytic leukemia (CML; e.g., B cell CML or T cell CML), chronic lymphocytic leukemia (CLL; e.g., B cell CLL (e.g., hairy cell leukemia) or T cell CLL), chronic neutrophilic leukemia (CNL), or chronic myelomonocytic leukemia (CMML). The blood cancer can also be a lymphoma such as Hodgkin lymphoma (HL; e.g., B cell HL or T cell HL), non-Hodgkin lymphoma (NHL; e.g., B cell NHL or T cell NHL), follicular lymphoma, chronic lymphocytic leukemia/small lymphocytic lymphoma (CLL/SLL), mantle cell lymphoma (MCL), a marginal zone B cell lymphoma (e.g., splenic marginal zone B cell lymphoma), primary mediastinal B cell lymphoma (e.g., splenic marginal zone B cell lymphoma), primary mediastinal B cell lymphoma, Burkitt lymphoma, lymphoplasmacytic lymphoma (i.e., Waldenstrom's macroglobulinemia), immunoblastic large cell lymphoma, precursor B lymphoblastic lymphoma, or primary central nervous system (CNS) lymphoma. The B cell NHL can be diffuse large cell lymphoma (DLCL; e.g., diffuse large B cell lymphoma), and the T cell NHL can be precursor T lymphoblastic lymphoma or a peripheral T cell lymphoma (PTCL). In turn, the PTCL can be a cutaneous T cell lymphoma (CTCL) such as mycosis fungoides or Sezary syndrome, angioimmunoblastic T cell lymphoma, extranodal natural killer T cell lymphoma, enteropathy type T cell lymphoma, subcutaneous anniculitis-like T cell lymphoma, or anaplastic large cell lymphoma. While the invention is not limited to treating or preventing blood cancers having any particular cause or presentation, stem cells within the bone marrow may proliferate, thereby becoming a dominant cell type within the bone marrow and a target for a compound described herein. Leukemic cells can accumulate in the blood and infiltrate organs such as the lymph nodes, spleen, liver, and kidney. In some embodiments, a compound of the present disclosure is useful in the treatment or prevention of a leukemia or lymphoma.

In other embodiments, the proliferative disease is characterized by a solid tumor considered to be either of its primary location or metastatic. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy (also known as monoclonal gammopathy of unknown significance (MGUS); biliary cancer (e.g., cholangiocarcinoma); bladder cancer; breast cancer (e.g., adenocarcinoma of the breast, papillary carcinoma of the breast, mammary cancer, or medullary carcinoma of the breast, any of which may be present in subjects having a particular profile, such as an HR+(ER+ or PR+), HR− (having neither estrogen nor progesterone receptors), a triple negative breast cancer (TNBC; ER−/PR−/HER2−), or a triple-positive breast cancer); brain cancer (e.g., meningioma, glioblastoma, glioma (e.g., astrocytoma, oligodendroglioma), medulloblastoma, or neuroblastoma); bronchus cancer; carcinoid tumor carcinoid tumor, which may be benign; cervical cancer (e.g., cervical adenocarcinoma); choriocarcinoma; chordoma; craniopharyngioma; colorectal cancer (e.g., colon cancer, rectal cancer, or colorectal adenocarcinoma; connective tissue cancer; epithelial carcinoma; ependymoma; endotheliosarcoma (e.g., Kaposi's sarcoma or multiple idiopathic hemorrhagic sarcoma); endometrial cancer (e.g., uterine cancer or uterine sarcoma); esophageal cancer (e.g., adenocarcinoma of the esophagus or Barrett's adenocarcinoma; Ewing's sarcoma (or other pediatric sarcoma, such as embryonal rhabdomyosarcoma or alveolar rhabdomyosarcoma); eye cancer (e.g., intraocular melanoma or retinoblastoma); familial hypereosinophilia; gallbladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma)), throat cancer (e.g., laryngeal cancer, pharyngeal cancer, nasopharyngeal cancer, oropharyngeal cancer)); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer or small intestine cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The proliferative disease can be associated with pathologic angiogenesis, and the methods of the invention (and uses of the compounds and other compositions described herein) encompass inhibiting pathologic angiogenesis in the context of cancer treatment.

As noted, the patient for which administration is contemplated includes, but is not limited to, a human (i.e., a male, female or transgendered person of any age group, e.g., a pediatric patient (e.g., infant, child, adolescent) or adult patient (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). Thus, the patient may be a domesticated animal. The non-human animal may be a transgenic animal (e.g., an animal valuable in research, such as a transgenic mouse or transgenic pig).

A cell used or treated as described herein may be a healthy cell or an unhealthy or abnormal cell (e.g., a cancer cell, tumor cell, or other cell that is proliferating uncontrollably). A compound of the invention may be administered to any such cell in vitro or in vivo. In various embodiments, the cell is: a cancer cell; a tumor cell; a proliferating cell; a blood cell (e.g., a lymphocyte); an endothelial cell; or an immune cell. In various embodiments, the cancer cell is: a leukemia cell; a CLL cell; a CMML cell; an AML cell; a breast cancer or ovarian cancer cell; a melanoma cell; a multiple myeloma cell; or a cell of any other cancer or disease disclosed herein.

In certain embodiments, the methods described herein comprise the additional step of administering one or more additional pharmaceutical agents in combination with the compound of Formula (I) a pharmaceutically acceptable salt thereof, or compositions comprising such compound or pharmaceutically acceptable salt thereof. Such additional pharmaceutical agents ("second" agents) include, but are not limited to, anti-proliferative agents, anti-cancer agents, antidiabetic agents, anti-inflammatory agents, immunosuppressant agents, and a pain-relieving agent. The additional pharmaceutical agent(s) may synergistically augment inhibition of CDK7 induced by the inventive compounds or compositions of this invention in the biological sample or patient. Thus, the combination of the inventive compounds or compositions and the additional pharmaceutical agent(s) may be useful in treating proliferative diseases resistant to a treatment using the additional pharmaceutical agent(s) without the inventive compounds or compositions.

As indicated, the present invention provides the compounds described herein (e.g., a compound of Formula (I)) and pharmaceutically acceptable salts, solvates (e.g., hydrates), tautomers, isotopic forms, and compositions thereof (e.g., pharmaceutical compositions), for use in the treatment of a proliferative disease or any other disease described herein in a patient. While the compounds, variants thereof, compositions containing them, and methods of use are not limited according to the underlying mechanism of action, we note that use may result in an inhibition of cell growth by, for example, promoting apoptosis or altering the expression or activity of disease-related genes.

EXAMPLES

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., Protecting Groups in Organic Synthesis, Second Edition, Wiley, New York, 1991, and references cited therein.

Example 1. 3-[2-[[(1S,2S)-1-aminoindan-2-yl]-amino]-5-(trifluoromethyl)pyrimidin-4-yl]-1H-indole-6-carbonitrile (Compound 119)

Step 1: (1S,2R)-1-amino-2,3-dihydro-1H-inden-2-ol

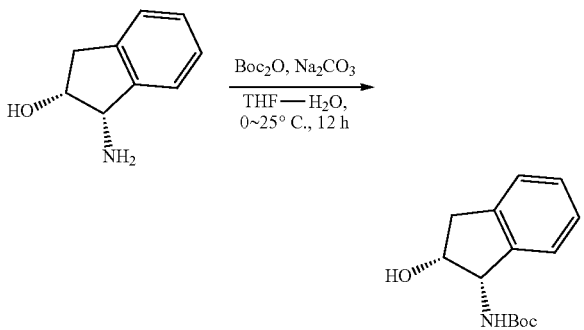

To a solution of (1S,2R)-1-amino-2,3-dihydro-1H-inden-2-ol 1 (1 g, 6.70 mmol, 1 eq) and $Na_2CO_3$ (2.13 g, 20.11 mmol, 3 eq) in THF (tetrahydrofuran; 30 mL) and $H_2O$ (6 mL) was added $BOC_2O$ (di-t-butyl dicarbonate; 1.90 g, 8.71 mmol, 2.00 mL, 1.3 eq) at 0° C. Then the mixture was stirred at 25° C. for 12 h. The reaction mixture was poured into water (100 mL) and extracted with ethyl acetate (30 mL×4). The combined organic phase was washed with brine (30 mL), dried with anhydrous $Na_2SO_4$, filtered and concentrated in vacuum. The residue was purified by silica gel chromatography (PE:EtOAc (ethyl acetate)=99:1-50:50) to afford tert-butyl ((1S,2R)-2-hydroxy-2,3-dihydro-1H-inden-1-yl)carbamate (1.6 g, 5.78 mmol, 86.17% yield, 90% purity) as light yellow solid.

Step 2: (1S,2R)-1-((tert-butoxycarbonyl)amino)-2,3-dihydro-1H-inden-2-yl methanesulfonate

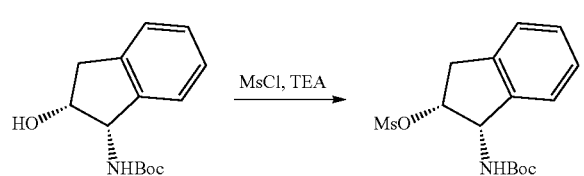 [SMILES: CC(C)(C)OC(=O)N[C@H]1c2ccccc2C[C@H]1O ; CC(C)(C)OC(=O)N[C@H]1c2ccccc2C[C@H]1OS(C)(=O)=O]

To a solution of tert-butyl ((1S,2R)-2-hydroxy-2,3-dihydro-1H-inden-1-yl)carbamate (1.5 g, 6.02 mmol, 1 eq) and TEA (triethylamine; 913.25 mg, 9.03 mmol, 1.26 mL, 1.5 eq) in DCM (dichloromethane; 25 mL) was added MsCl (758.14 mg, 6.62 mmol, 512.26 µL, 1.1 eq) at 0° C. The mixture was stirred at 25° C. for 12 h. The residue was poured into water (20 mL). The aqueous phase was extracted with ethyl acetate (20 mL×3). The combined organic phase was dried over anhydrous $Na_2SO_4$, filtered and concentrated in vacuum to afford the -(1S,2R)-1-((tert-butoxycarbonyl)amino)-2,3-dihydro-1H-inden-2-yl methanesulfonate as white solid.

Step 3: Tert-butyl ((1S,2S)-2-azido-2,3-dihydro-1H-inden-1-yl)carbamate

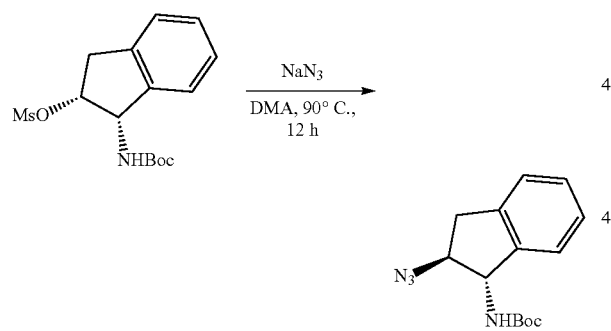

A solution of (1S,2R)-1-((tert-butoxycarbonyl)amino)-2,3-dihydro-1H-inden-2-yl methanesulfonate (1.9 g, 5.80 mmol, 1 eq) and $NaN_3$ (565.92 mg, 8.71 mmol, 1.5 eq) in DMA (dimethyl adipate; 20 mL) was stirred at 90° C. for 12 h. The reaction mixture was poured into sat. (saturated) $NaHCO_3$ (50 mL). The aqueous phase was extracted with ethyl acetate (50 mL×2). The combined organic phase was washed with brine (50 mL×2), dried over anhydrous $Na_2SO_4$, filtered and concentrated in vacuum to remove half of the solvent to afford tert-butyl ((1S,2S)-2-azido-2,3-dihydro-1H-inden-1-yl)carbamate (A solution in EtOAc) as brown oil and used directly.

Step 4: Tert-butyl ((1S,2S)-2-amino-2,3-dihydro-1H-inden-1-yl)carbamate

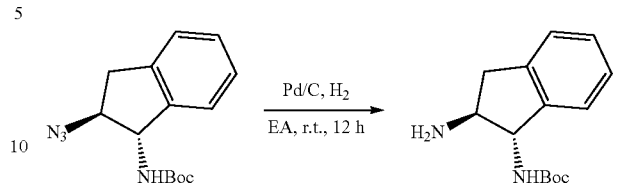

To a solution of tert-butyl ((1S,2S)-2-azido-2,3-dihydro-1H-inden-1-yl)carbamate (A solution in EtOAc) in EtOAc (30 mL) was added Pd/C (0.5 g, 10% purity) under $N_2$. The suspension was degassed under vacuum and purged with $H_2$ several times. The mixture was stirred under $H_2$ (15 psi) at 25° C. for 12 h. The reaction mixture was filtered and the filtrate was concentrated. The crude product was purified by silica gel chromatography eluted with Petroleum ether/Ethyl acetate=2:1/0:1 to afford the title compound as (1.2 g, 4.35 mmol, 90% purity) as yellow solid

Step 5: 3-[2-chloro-5-(trifluoromethyl) pyrimidin-4-yl]-1H-indole-6-carbonitrile

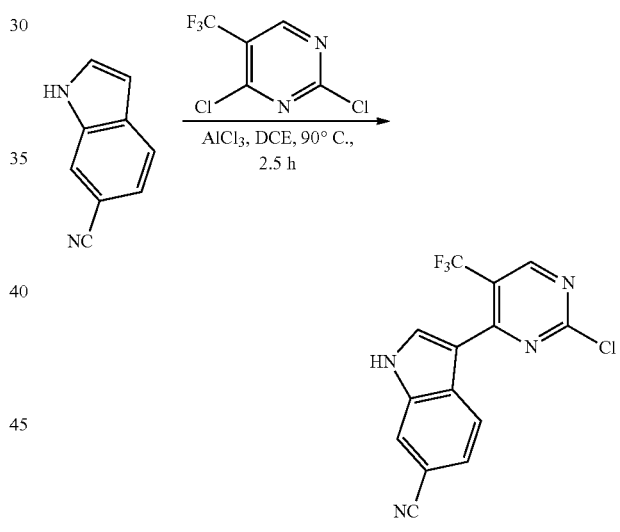

To a solution of 2, 4-dichloro-5-(trifluoromethyl)pyrimidine (30.53 g, 140.69 mmol, 2 eq) in DCE (1,2-dichloroethane; 250 mL) was added $AlCl_3$ (19.70 g, 147.72 mmol, 8.07 mL, 2.1 eq). The mixture was stirred at 90° C. for 0.5 h. Then 1H-indole-6-carbonitrile (10 g, 70.34 mmol, 1 eq) was added and the resulting solution was stirred at 90° C. for 2 h. The residue was dissolved in MeOH (methanol; 100 mL) and poured into ice-water (1000 mL) and stirred for 5 min. The solids were formed and filtered to collect the cake. The cake was washed with MeOH (500 mL), filtered and concentrated in vacuum. The residue was purified by silica gel chromatography (PE:EtOAc=1:1) to afford the title compound (10 g, 26.34 mmol, 37.45% yield, 85% purity) as yellow solid.

Step 6: Tert-butyl N-[(1S,2S)-2-[[4-(6-cyano-1H-indol-3-yl)-5-(trifluoromethyl)pyrimidin-2-yl]-amino]-2,3-dihydro-1H-inden-1-yl)]-carbamate

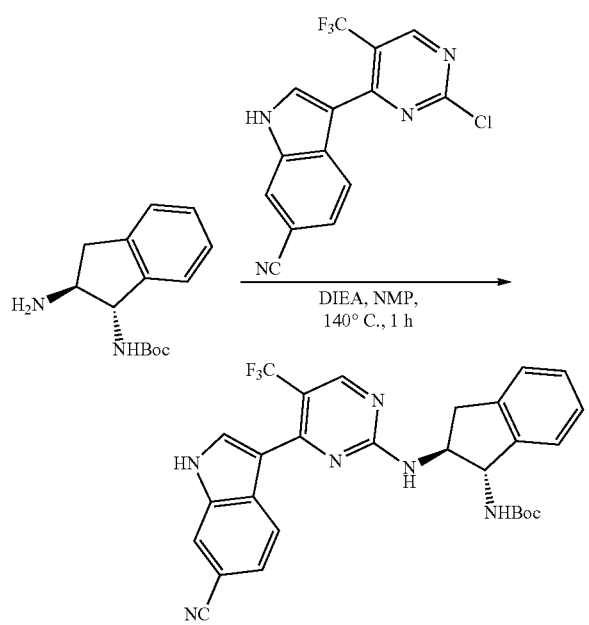

To a solution of tert-butyl ((1S,2S)-2-amino-2,3-dihydro-1H-inden-1-yl)carbamate (0.2 g, 805.41 μmol, 1 eq), 3-[2-chloro-5-(trifluoromethyl)pyrimidin-4-yl]-1H-indole-6-carbonitrile (259.88 mg, 805.41 μmol, 1 eq) in NMP (N-methyl-2-pyrrolidone; 2 mL) was added DIEA (520.47 mg, 4.03 mmol, 701.44 μL, 5 eq). The mixture was stirred at 140° C. for 1 h, and then was poured into water (30 mL). The aqueous phase was extracted with ethyl acetate (20 mL×3). The combined organic phase was washed with brine (30 mL×2), dried over anhydrous Na₂SO₄, filtered and concentrated in vacuum. The residue was purified by silica gel chromatography (100-200 mesh silica gel, Petroleum ether/Ethyl acetate=10/1,3/1) to afford the title compound (0.12 g, 193.07 μmol, 86% purity) as brown solid.

Step 7: 3-[2-[[(1S,2S)-1-amino-2,3-dihydro-1H-inden-2-yl]-amino]-5-(trifluoromethyl)pyrimidin-4-yl]-1H-indole-6-carbonitrile

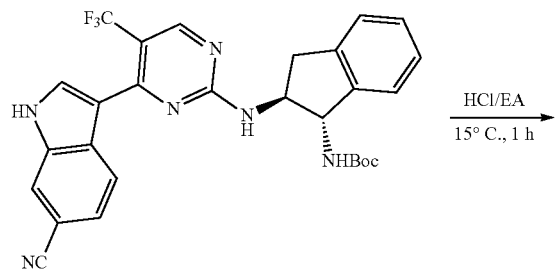

-continued

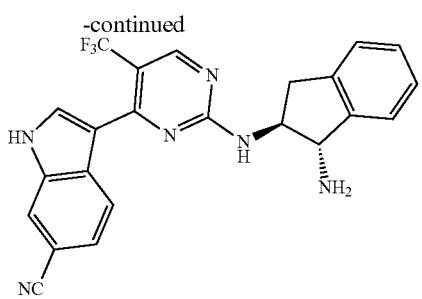

A solution of Tert-butyl N-[(1S,2S)-2-[[4-(6-cyano-1H-indol-3-yl)-5-(trifluoromethyl)pyrimidin-2-yl]-amino]-2,3-dihydro-1H-inden-1-yl) (0.1 g, 187.08 μmol, 1 eq) in HCl/EtOAc (10 mL) was stirred at 15° C. for 1 h. The reaction mixture was filtered and the filter cake was collected. The residue was purified by prep-HPLC (high pressure liquid chromatography; FA) to afford the 3-[2-[[(1S,2S)-1-amino-2,3-dihydro-1H-inden-2-yl]-amino]-5-(trifluoromethyl)pyrimidin-4-yl]-1H-indole-6-carbonitrile (48.9 mg, 100.73 μmol, 53.85% yield, 98.97% purity, FA) as white solid.

Example 2. (1S,2S)—N2-[4-[6-(3,5-dimethylisoxazol-4-yl)-1H-indol-3-yl]-5-(trifluoromethyl)pyrimidin-2-yl]cyclobutane-1,2-diamine (Compound 116)

Step 1: 6-bromo-3-[2-chloro-5-(trifluoromethyl)pyrimidin-4-yl]-1H-indole

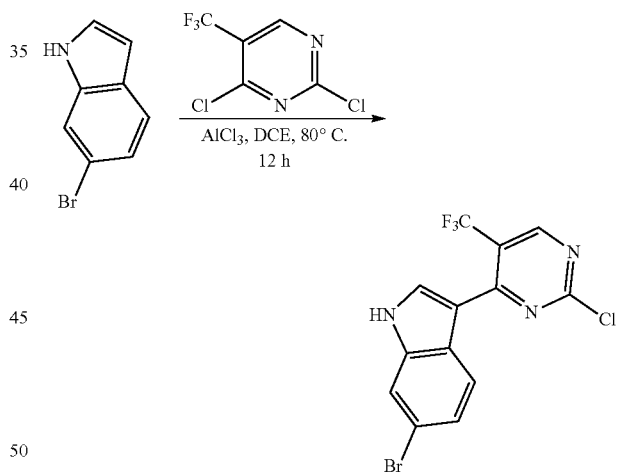

To a solution of 2,4-dichloro-5-(trifluoromethyl)pyrimidine (22.58 g, 104.06 mmol, 1.2 eq) in DCE (200 mL) was added AlCl₃ (15.03 g, 112.73 mmol, 6.16 mL, 1.3 eq). The mixture was stirred at 80° C. for 0.5 h. Then 6-bromo-1H-indole (17 g, 86.72 mmol, 1 eq) was added to the solution at 80° C. The mixture was stirred at 80° C. for 11.5 h. The reaction mixture was diluted with water (1500 mL) and extracted with EtOAc (500 mL×3). The combined organic layers were washed with brine (200 mL×3), dried over Na₂SO₄, filtered and concentrated under reduced pressure to give a residue. The residue was purified by column chromatography (SiO₂, PE/EtOAc=10/1 to 3/1), then the residue was washed with MeOH (200 mL), filtered to afford the title compound (9.9 g, 26.29 mmol, 30.32% yield, 100% purity) as white solid.

Step 2: Tert-butyl N-[(1S,2S)-2-[[4-(6-bromo-1H-indol-3-yl)-5-(trifluoromethyl) pyrimidin-2-yl]-amino]-cyclobutyl]-carbamate

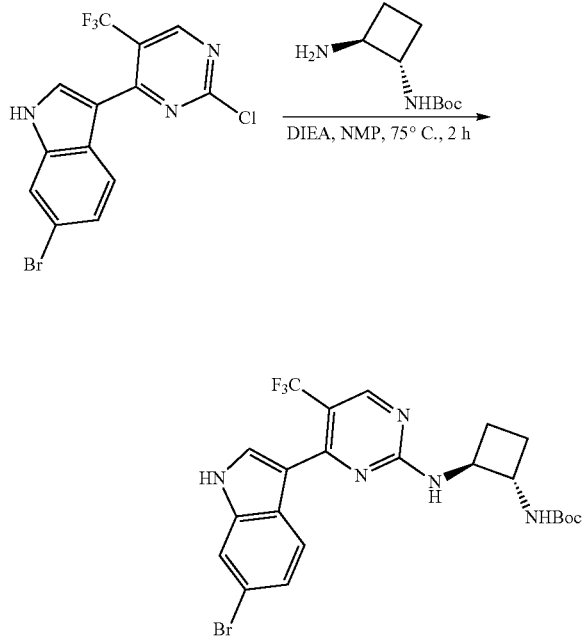

A mixture of 6-bromo-3-[2-chloro-5-(trifluoromethyl)pyrimidin-4-yl]-1H-indole (100 mg, 265.56 µmol, 1 eq), tert-butyl N-[(1S,2S)-2-aminocyclobutyl]carbamate (49.46 mg, 265.56 µmol, 1 eq) and DIEA (171.61 mg, 1.33 mmol, 231.28 µL, 5 eq) in NMP (0.6 mL) was stirred for 2 h at 75° C. under N₂. The reaction mixture was poured into water (10 mL), and then extracted with EtOAc (10 mL×3). The combined organic layer was washed with brine (20 mL), dried over Na₂SO₄, filtered and concentrated under reduced pressure to give a residue. The residue was purified by MPLC (SiO₂, PE/EtOAc=5/1 to 1/1,500 mL) to afford the title compound (150 mg, 87.5% purity) as yellow solid.

Step 3: Tert-butyl N-[(1S,2S)-2-[[4-[6-(3,5-dimethylisoxazol-4-yl)-1H-indol-3-yl]-5-(trifluoromethyl) pyrimidin-2-yl]amino]cyclobutyl]carbamate

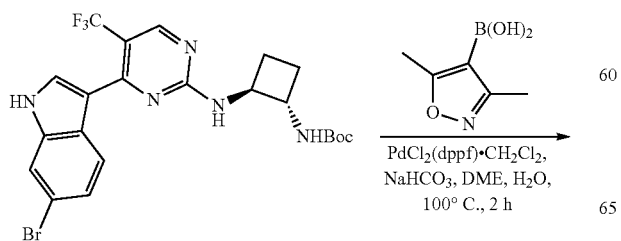

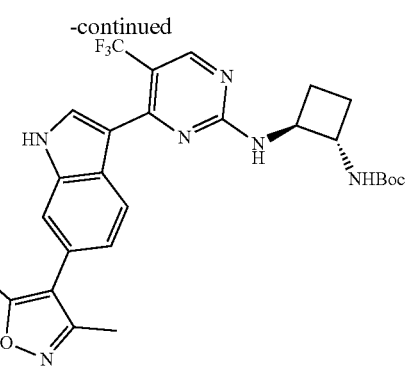

To a solution of tert-butyl N-[(1S,2S)-2-[[4-(6-bromo-1H-indol-3-yl)-5-(trifluoromethyl)-pyrimidin-2-yl]amino]cyclobutyl]carbamate (130 mg, 246.98 µmol, 1 eq) in DME (dimethoxyethane; 1.5 mL) and H₂O (0.5 mL) was added NaHCO₃ (62.25 mg, 740.95 µmol, 28.82 µL, 3 eq), Pd(dppf)Cl₂·CH₂Cl₂ (20.17 mg, 24.70 µmol, 0.1 eq) and (3,5-dimethylisoxazol-4-yl)boronic acid (69.62 mg, 493.97 µmol, 2 eq). The reaction was stirred for 2 hr at 100° C. under N₂. The reaction mixture was poured into water (5 mL) and then extracted with EtOAc (10 mL×3). The combined organic layer was washed with brine (20 mL), dried over Na₂SO₄, filtered and concentrated under reduced pressure to give a residue that was purified by MPLC (SiO₂, PE/EtOAc=10/1 to 1/1,600 mL) to afford the title compound (70 mg, 93.4% purity) as a yellow solid.

Step 4: (1S,2S)—N2-[4-[6-(3,5-dimethylisoxazol-4-yl)-1H-indol-3-yl]-5-(trifluoromethyl)pyrimidin-2-yl]cyclobutane-1,2-diamine

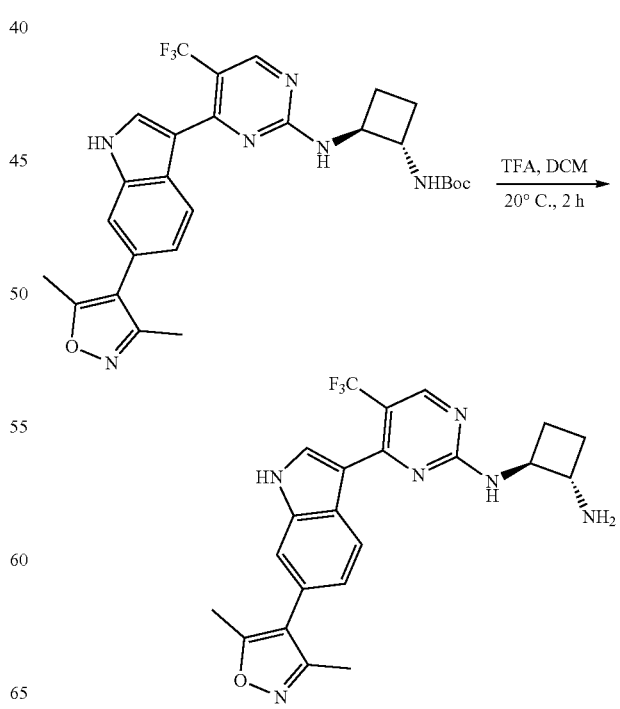

A mixture of tert-butyl N-[(1S,2S)-2-[[4-[6-(3,5-dimethylisoxazol-4-yl)-1H-indol-3-yl]-5-(trifluoromethyl)pyrimidin-2-yl]amino]cyclobutyl]carbamate (50 mg, 92.16 µmol, 1 eq) and TFA (trifluoroacetic acid; 105.08 mg, 921.57 µmol, 68.23 µL, 10 eq) in DCM (5 mL) was stirred at 20° C. for 2 hr. The mixture was poured into water (5 mL), and extracted with EtOAc (20 mL×3). The mixture was concentrated to give the residue. The crude product was purified by prep-HPLC (FA condition) to afford the title compound (42.3 mg, 100% purity, FA) as white solid.

Example 3. (1S,2S)—N1-[4-(6-thiazol-2-yl-1H-indol-3-yl)-5-(trifluoromethyl)pyrimidin-2-yl]-cyclopentane-1,2-diamine (Compound 117)

Step 1: Tert-butyl N-[(2S)-2-[[4-[6-(4,4,5,5-tetramethyl-1,3,2-dioxaborolan-2-yl)-1-(2-trimethylsilylethoxymethyl) indol-3-yl]-5-(trifluoromethyl)pyrimidin-2-yl]-amino]-cyclopentyl]-carbamate

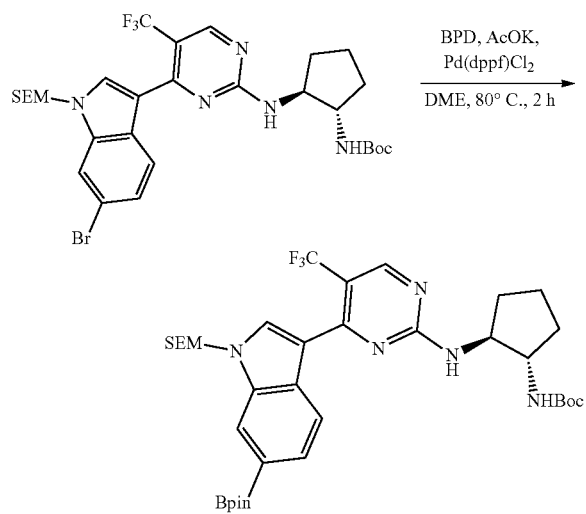

A mixture of tert-butyl N-[(2S)-2-[[4-[6-bromo-1-(2-trimethylsilylethoxymethyl) indol-3-yl]-5-(trifluoromethyl)pyrimidin-2-yl]-amino]-cyclopentyl]-carbamate (see Example 4, steps 1-2; 0.17 g, 253.49 µmol, 1 eq), 4,4,5,5-tetramethyl-2-(4,4,5,5-tetramethyl-1,3,2-dioxaborolan-2-yl)-1,3,2-dioxaborolane (128.74 mg, 506.98 µmol, 2 eq), Pd(dppf)C$_{1-2}$ (18.55 mg, 25.35 µmol, 0.1 eq) and AcOK (74.63 mg, 760.47 µmol, 3 eq) in DME (2 mL) was stirred at 80° C. for 2 h under N$_2$ atmosphere. The reaction mixture was diluted with water (30 mL) and extracted with ethyl acetate (10 mL×2). The combined organic layers were washed with brine (20 mL×2), dried over Na$_2$SO$_4$, filtered and concentrated under reduced pressure to afford the title compound (0.3 g, crude) as a yellow oil. It was used to next step directly.

Step 2: Tert-butyl N-[(2S)-2-[[4-[6-thiazol-2-yl-1-(2-trimethylsilylethoxymethyl) indol-3-yl]-5-(trifluoromethyl)pyrimidin-2-yl]-amino]-cyclopentyl]-carbamate

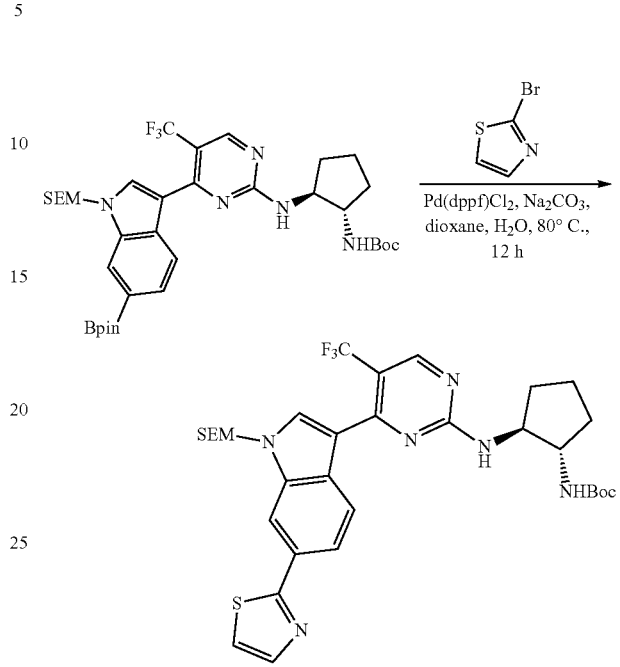

A mixture of tert-butyl N-[(2S)-2-[[4-[6-(4,4,5,5-tetramethyl-1,3,2-dioxaborolan-2-yl)-1-(2-trimethylsilylethoxymethyl) indol-3-yl]-5-(trifluoromethyl)pyrimidin-2-yl]-amino]-cyclopentyl]-carbamate (0.3 g, 418.00 µmol, 1 eq), 2-bromothiazole (89.13 mg, 543.40 µmol, 48.97 µL, 1.3 eq), Pd(dppf)C$_{1-2}$ (30.59 mg, 41.80 µmol, 0.1 eq) and Na$_2$CO$_3$ (88.61 mg, 836.00 µmol, 2 eq) in dioxane (3 mL), H$_2$O (0.6 mL) was degassed and purged with N$_2$ for 3 times, and then the mixture was stirred at 80° C. for 12 h under N$_2$ atmosphere. The reaction mixture was diluted with water (100 mL) and extracted with ethyl acetate (50 mL×2). The combined organic layers were washed with brine (100 mL×2), dried over Na$_2$SO$_4$, filtered and concentrated under reduced pressure to give a residue. The residue was purified by column chromatography (SiO$_2$, Petroleum ether/Ethyl acetate=30:1 to 10:1) to afford the title compound (90 mg) as a yellow solid.
(The reaction was combined with another reaction in 50 mg scale for purification).

Step 3: (1S,2S)—N1-[4-(6-thiazol-2-yl-1H-indol-3-yl)-5-(trifluoromethyl)pyrimidin-2-yl]-cyclopentane-1,2-diamine

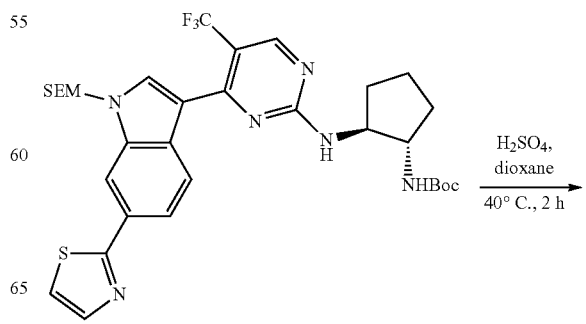

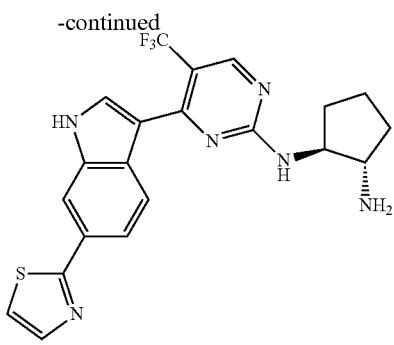

To a solution of tert-butyl N-[(2S)-2-[[4-[6-thiazol-2-yl-1-(2-trimethylsilylethoxy methyl) indol-3-yl]-5-(trifluoromethyl)pyrimidin-2-yl]-amino]-cyclopentyl]-carbamate (80 mg, 118.54 µmol, 1 eq) in dioxane (1 mL) was added H₂SO₄ (1.16 g, 11.85 mmol, 631.90 µL, 100 eq). The mixture was stirred at 40° C. for 2 h. The mixture was adjusted pH to 8 with saturated aqueous Na₂CO₃ and extracted with EtOAc (10 mL×3). The combined organic layers were washed with brine (30 mL×2), dried over Na₂SO₄, filtered and concentrated under reduced pressure to give a residue. The residue was purified by prep-HPLC (HCl condition) to afford the title compound (7 mg, HCl salt) as a yellow solid.

Example 4. Tert-butyl N-[(2S)-2-[[4-[6-(3,5-dimethylisoxazol-4-yl)-1-(2-trimethyl silylethoxymethyl) indol-3-yl]-5-(trifluoromethyl)pyrimidin-2-yl]-amino]-cyclopentyl]-Carbamate Useful in the Synthesis of Compound 118

Step 1: 2-[[6-bromo-3-[2-chloro-5-(trifluoromethyl)pyrimidin-4-yl]-indol-1-yl]-methoxy]-ethyl-trimethyl-silane

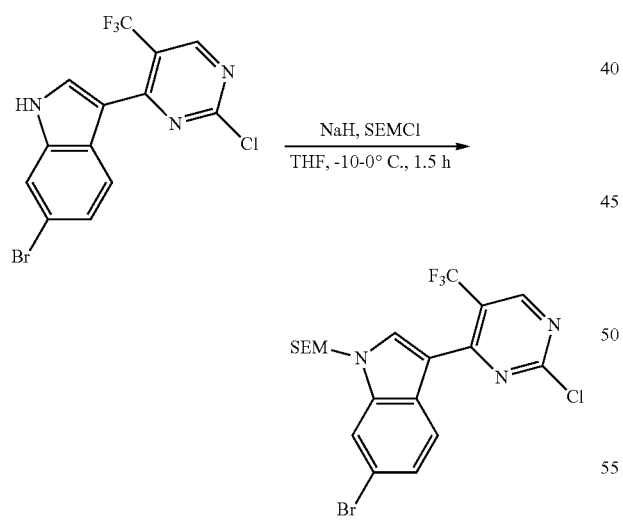

To a solution of 6-bromo-3-[2-chloro-5-(trifluoromethyl) pyrimidin-4-yl]-1H-indole (2 g, 5.31 mmol, 1 eq) in THF (20 mL) was added NaH (254.94 mg, 6.37 mmol, 60% purity, 1.2 eq) at −10° C. After addition, the mixture was stirred at this temperature for 30 min, and then 2-(chloromethoxy) ethyl-trimethyl-silane (1.33 g, 7.97 mmol, 1.41 mL, 1.5 eq) was added dropwise at −10° C. The resulting mixture was stirred at 0° C. for 1 h. The reaction mixture was diluted with water (150 mL) and extracted with ethyl acetate (80 mL×2). The combined organic layers were washed with brine (200 mL×2), dried over Na₂SO₄, filtered and concentrated under reduced pressure to give a residue. The residue was purified by column chromatography (SiO₂, Petroleum ether/Ethyl acetate=50:1 to 20:1) to afford the title compound (2.6 g) as a white solid.

Step 2: Tert-butyl-N-[(2S)-2-[[4-[6-bromo-1-(2-trimethylsilylethoxymethyl) indol-3-yl]-5-(trifluoromethyl)pyrimidin-2-yl]-amino]-cyclopentyl]-carbamate

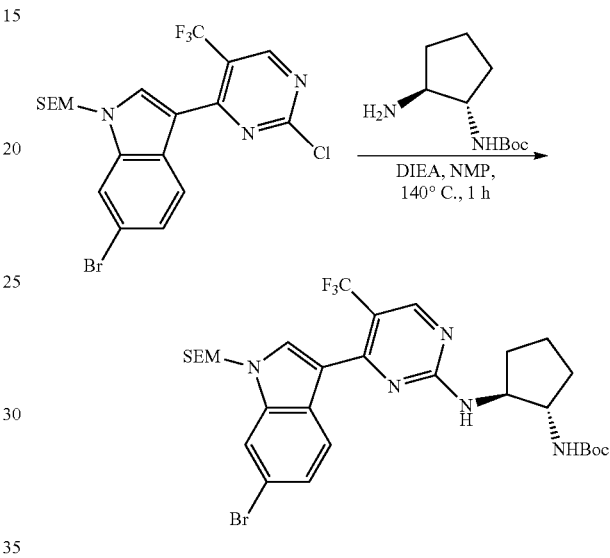

To a solution of 2-[[6-bromo-3-[2-chloro-5-(trifluoromethyl)pyrimidin-4-yl]-indol-1-yl]-methoxy]-ethyl-trimethyl-silane (358.50 mg, 707.35 µmol, 1 eq) and tert-butyl N-[(2S)-2-aminocyclopentyl]-carbamate (170 mg, 848.82 µmol, 1.2 eq) in NMP (4 mL) was added DIEA (274.25 mg, 2.12 mmol, 369.62 µL, 3 eq). The mixture was stirred at 140° C. for 1 h. The reaction mixture was diluted with H₂O 40 mL and extracted with EtOAc (15 mL×3). The combined organic layers were washed with brine (50 mL×2), dried over Na₂SO₄, filtered and concentrated under reduced pressure to give a residue. The residue was purified by column chromatography (SiO₂, Petroleum ether/Ethyl acetate=19:1 to 9:1) to afford the title compound (335 mg).

Step 3: Tert-butyl N-[(2S)-2-[[4-[6-(3,5-dimethyl-isoxazol-4-yl)-1-(2-trimethyl silylethoxymethyl) indol-3-yl]-5-(trifluoromethyl)pyrimidin-2-yl]-amino]-cyclopentyl]-carbamate

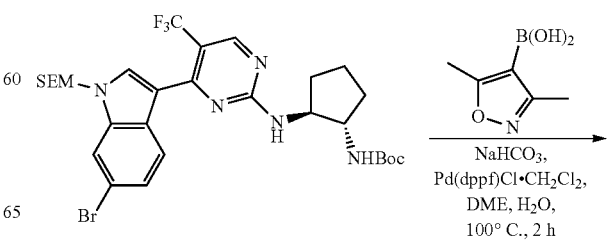

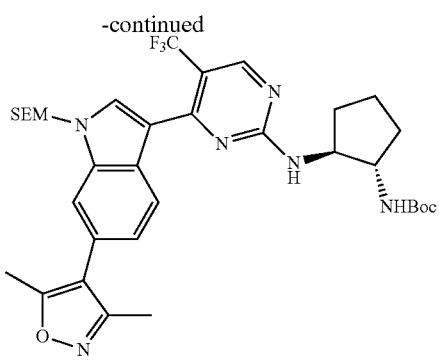

A mixture of tert-butyl N-[(2S)-2-[[4-[6-bromo-1-(2-trimethylsilylethoxymethyl)indol-3-yl]-5-(trifluoromethyl)pyrimidin-2-yl]-amino]-cyclopentyl]-carbamate (210 mg, 313.14 µmol, 1 eq), (3,5-dimethylisoxazol-4-yl) boronic acid (88.26 mg, 626.27 µmol, 2 eq), Pd(dppf)Cl$_2$·CH$_2$Cl$_2$ (25.57 mg, 31.31 µmol, 0.1 eq), NaHCO$_3$ (78.92 mg, 939.41 µmol, 36.54 µL, 3 eq) in DME (3 mL) and H$_2$O (1 mL) was degassed and purged with N$_2$ for 3 times, and then the mixture was stirred at 100° C. for 2 h under N$_2$ atmosphere. The reaction mixture was diluted with H$_2$O 50 mL and extracted with EtOAc (20 mL×3). The combined organic layers were washed with brine (50 mL×2), dried over Na$_2$SO$_4$, filtered and concentrated under reduced pressure to give a residue. The residue was purified by column chromatography (SiO$_2$, PE/EtOAc=19:1 to 15:1) to afford the title compound (100 mg) as a yellow oil.

Example 5. 3-[2-[[(1S,2S)-2-(2-methoxyethylamino) cyclopentyl]-amino]-5-(trifluoromethyl)pyrimidin-4-yl]-1H-indole-6-carbonitrile (Compound 123)

Step 1: 3-[2-chloro-5-(trifluoromethyl)pyrimidin-4-yl]-1-(2-trimethylsilylethoxymethyl) indazole-6-carbonitrile

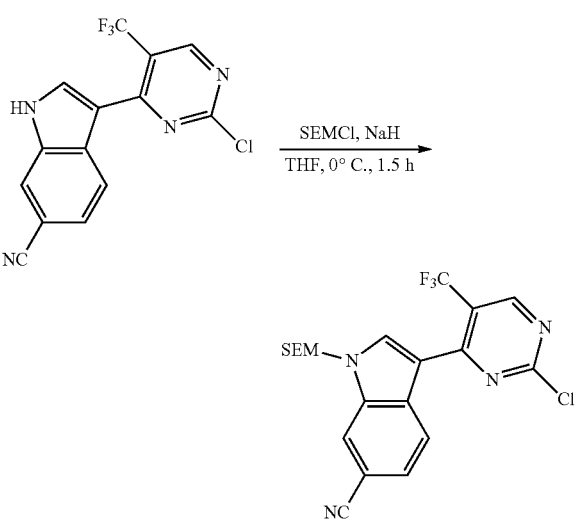

To a solution of 3-[2-chloro-5-(trifluoromethyl)pyrimidin-4-yl]-1H-indole-6-carbonitrile (1.99 g, 6.18 mmol, 1 eq) in THF (40 mL) was added NaH (370.76 mg, 9.27 mmol, 60% purity, 1.5 eq) at 0° C. under N$_2$ atmosphere. The mixture was stirred at 0° C. for 0.5 h under N$_2$ atmosphere. Then 2-(chloromethoxy) ethyl-trimethyl-silane (1.55 g, 9.27 mmol, 1.64 mL, 1.5 eq) was added and the mixture was stirred at 0° C. for 1 h under N$_2$ atmosphere. The reaction mixture changed from pink to brownish yellow. The reaction mixture was slowly poured into H$_2$O (40 mL), and extracted with EtOAc (20 mL×2). The combined organic layers were washed with brine (40 mL), dried over Na$_2$SO$_4$, filtered and concentrated under reduced pressure to give a residue. The residue was purified by column chromatography (SiO$_2$, PE/EtOAc=10/1 to 5/2) to afford the title compound (2.25 g, 4.96 mmol, 80.21% yield) as a yellow solid.

Step 2: 3-[2-[[(1S,2R)-2-hydroxycyclopentyl]-amino]-5-(trifluoromethyl)pyrimidin-4-yl]-1-(2-trimethylsilylethoxymethyl) indole-6-carbonitrile

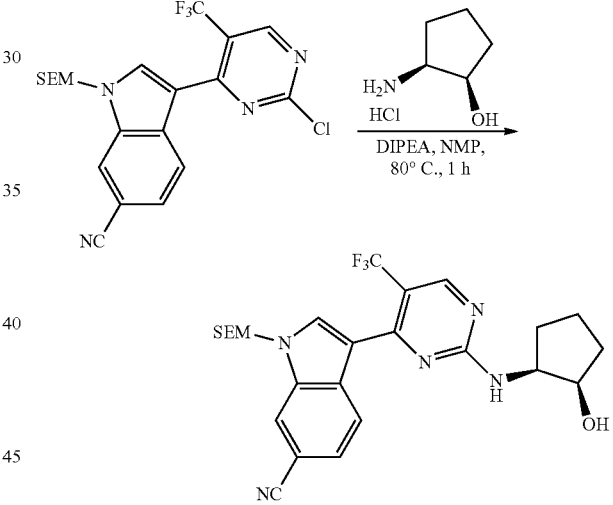

To a solution of 3-[2-chloro-5-(trifluoromethyl)pyrimidin-4-yl]-1-(2-trimethylsilyl ethoxymethyl) indole-6-carbonitrile (0.8 g, 1.77 mmol, 1 eq) in NMP (8 mL) was added (1R,2S)-2-aminocyclopentanol (267.36 mg, 1.94 mmol, 1.1 eq, HCl) and DIPEA (N,N-diisopropyl ethylamine; 913.11 mg, 7.07 mmol, 1.23 mL, 4 eq). The mixture was stirred at 80° C. for 1 h. The reaction mixture was diluted with H$_2$O 20 mL and extracted with EtOAc (20 mL×3). The combined organic layers were washed with brine (60 mL×2), dried over Na$_2$SO$_4$, filtered and concentrated under reduced pressure to give a residue. The residue was purified by column chromatography (SiO$_2$, PE/EtOAc=10/1 to 2/1) to afford the title compound (650 mg, 99% purity) was obtained as a white solid. The reaction was combined with another reaction in 20 mg scale for purification and work up

Step 3: [(1R,2S)-2-[[4-[6-cyano-1-(2-trimethylsilylethoxymethyl)indol-3-yl]-5-(trifluoromethyl)pyrimidin-2-yl]-amino]-cyclopentyl]-methane sulfonate

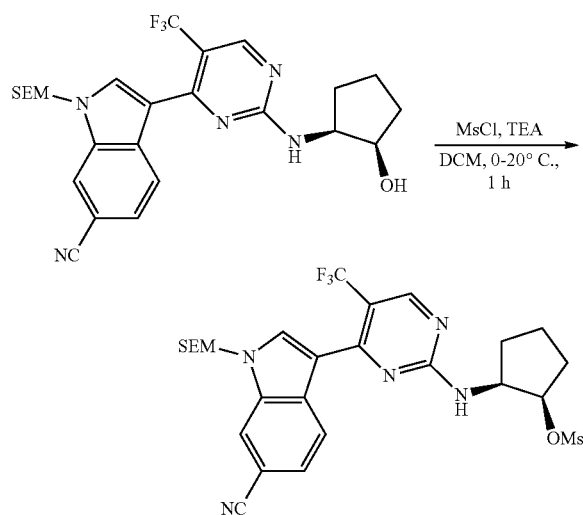

To a solution of 3-[2-[[(1S,2R)-2-hydroxycyclopentyl]-amino]-5-(trifluoromethyl)pyrimidin-4-yl]-1-(2-trimethylsilylethoxymethyl) indole-6-carbonitrile (0.45 g, 869.37 μmol, 1 eq) in DCM (10 mL) was added TEA (175.94 mg, 1.74 mmol, 242.01 μL, 2 eq). The mixture was cooled to 0° C., MsCl (129.46 mg, 1.13 mmol, 87.48 μL, 1.3 eq) was added dropwise to the above mixture and the resulting mixture was stirred at 20° C. for 1 h. The residue was poured into water (20 mL). The aqueous phase was extracted with DCM (20 mL×3). The combined organic phase was dried over anhydrous Na$_2$SO$_4$, filtered and concentrated in vacuum. The residue was purified by silica gel chromatography (100-200 mesh silica gel, Petroleum ether/Ethyl acetate=10/1,2/1) to afford the title compound (0.48 g, 725.19 μmol, 83.42% yield, 90% purity) as white solid.

Step 4: 3-[2-[[(1S,2S)-2-(2-methoxyethylamino)cyclopentyl]-amino]-5-(trifluoromethyl)pyrimidin-4-yl]-1-(2-trimethylsilylethoxymethyl) indole-6-carbonitrile

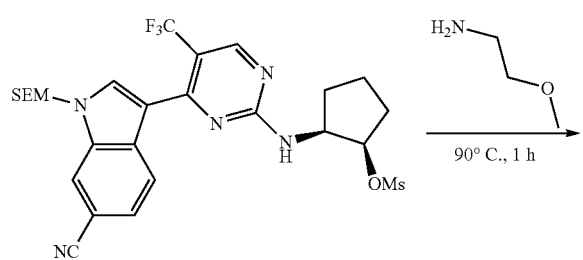

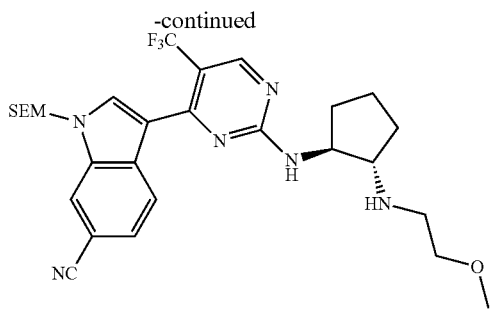

The solution of -[(1R,2S)-2-[[4-[6-cyano-1-(2-trimethylsilylethoxymethyl) indol-3-yl]-5-(trifluoromethyl)pyrimidin-2-yl]-amino]-cyclopentyl]-methanesulfonate (0.16 g, 268.59 μmol, 1 eq) in 2-methoxyethanamine (3.46 g, 46.01 mmol, 4.00 mL, 171.31 eq) was stirred at 90° C. for 1 h. The reaction mixture was diluted with EtOAc (20 mL) and washed with HCl (aqueous, 1N, 20 mL×3), brine (20 mL×2), dried over Na$_2$SO$_4$, filtered and concentrated under reduced pressure to give a residue. The residue was purified by column chromatography (SiO$_2$, PE:EtOAc=1:1) to afford the title compound (0.12 g, 204.62 μmol, 76.19% yield, 98% purity) as yellow solid.

Step 5: 3-[2-[[(1S,2S)-2-(2-methoxyethylamino)cyclopentyl]-amino]-5-(trifluoromethyl)pyrimidin-4-yl]-1H-indole-6-carbonitrile

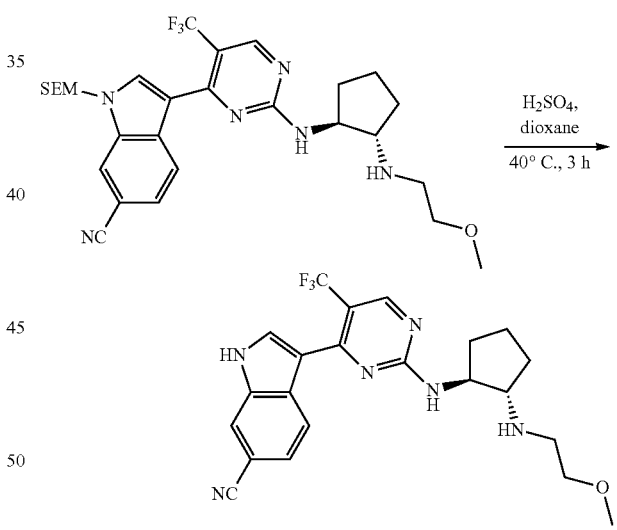

To a solution of 3-[2-[[(1S,2S)-2-(2-methoxyethylamino)cyclopentyl]-amino]-5-(trifluoromethyl)pyrimidin-4-yl]-1-(2-trimethylsilylethoxymethyl) indole-6-carbonitrile (0.1 g, 174.00 μmol, 1 eq) in dioxane (1 mL) was added H$_2$SO$_4$ (170.66 mg, 1.74 mmol, 92.75 μL, 10 eq). The mixture was stirred at 40° C. for 3 h. The reaction mixture was diluted with H$_2$O 10 mL and adjusted pH to 12 with NaOH(solid). Then the product was extracted with EtOAc (10 mL×4). The combined organic layers were washed with brine (50 mL×2), dried over Na$_2$SO$_4$, filtered and concentrated under reduced pressure to give a residue. The residue was purified by prep-HPLC (FA condition) to afford the title compound (24.3 mg, FA salt, 96.02% purity) as a white solid.

Example 6. 3-[2-[[(1S,2S)-2-pyrrolidin-1-ylcyclobutyl]-amino]-5-(trifluoromethyl)pyrimidin-4-yl]-1H-indole-6-carbonitrile (Compound 135) and 3-[2-[[(1R,2R)-2-pyrrolidin-1-ylcyclobutyl]-amino]-5-(trifluoromethyl)pyrimidin-4-yl]-1H-indole-6-carbonitrile (Compound 136)

Step 1: 3-[2-[(2-hydroxycyclobutyl)amino]-5-(trifluoromethyl)pyrimidin-4-yl]-1-(2-trimethylsilylethoxymethyl)indole-6-carbonitrile

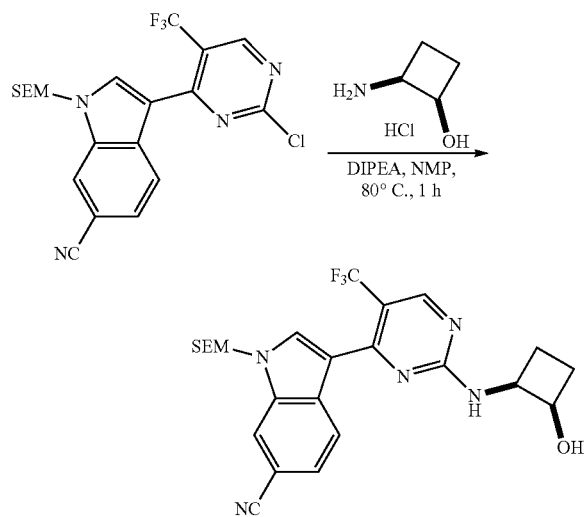

A mixture of 2-aminocyclobutanol (87.31 mg, 706.51 µmol, 1 eq, HCl), 3-[2-chloro-5-(trifluoromethyl)pyrimidin-4-yl]-1-(2-trimethylsilylethoxymethyl)indole-6-carbonitrile (320 mg, 706.51 µmol, 1 eq) and DIEA (456.56 mg, 3.53 mmol, 615.30 µL, 5 eq) in NMP (0.3 mF) was stirred for 1 h at 80° C. under N₂. It was poured into water (10 mF) and extracted with EtOAc (20 mL×3). The combined organic layer was washed with brine (20 mL×3), dried over Na₂SO₄, filtered. The filtrate was concentrated under reduced pressure to give a residue. The residue was purified by MPLC to afford the title compound (250 mg, 454.24 µmol, 64.29% yield, 91.5% purity) as light yellow solid.

Step 2: -[2-[[4-[6-cyano-1-(2-trimethylsilylethoxymethyl) indol-3-yl]-5-(trifluoromethyl)pyrimidin-2-yl]-amino]-cyclobutyl]-methane sulfonate

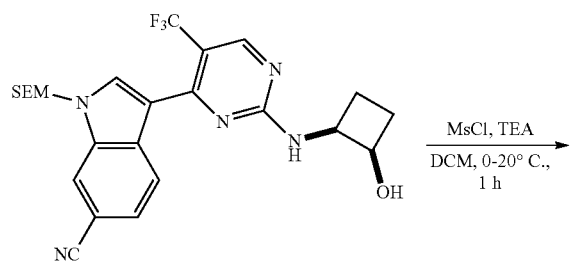

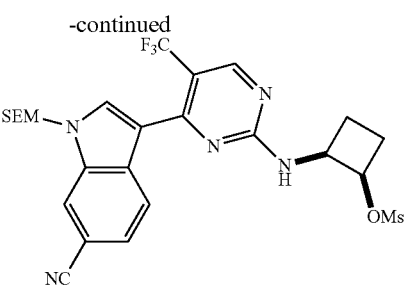

To a solution of 3-[2-[(2-hydroxycyclobutyl) amino]-5-(trifluoromethyl)pyrimidin-4-yl]-1-(2-trimethylsilylethoxymethyl) indole-6-carbonitrile (250 mg, 496.43 µmol, 1 eq) in DCM (0.5 mL) was added TEA (100.47 mg, 992.87 µmol, 138.20 µL, 2 eq). The mixture was cooled to 0° C. Then MsCl (73.93 mg, 645.36 µmol, 49.95 µL, 1.3 eq) was added. The resulting mixture was stirred for 1 h at 20° C. under N₂. The mixture was poured into water (5 mL) and then extracted with DCM (20 mL×3). The combined organic layer was washed with brine (50 mL), dried over Na₂SO₄, filtered and concentrated under reduced pressure to give a residue. The residue was purified by MPLC (SiO₂, PE/EtOAc=8/1 to 1/1) to afford the title compound (200 mg, 275.41 µmol, 55.48% yield, 80.1% purity) as yellow oil.

Step 3: 3-[2-[[(1S,2S)-2-pyrrolidin-1-ylcyclobutyl]-amino]-5-(trifluoromethyl)pyrimidin-4-yl]-1-(2-trimethylsilylethoxymethyl)indole-6-carbonitrile & 3-[2-[[(1R,2R)-2-pyrrolidin-1-ylcyclobutyl]-amino]-5-(trifluoromethyl)pyrimidin-4-yl]-1-(2-trimethylsilylethoxymethyl)indole-6-carbonitrile

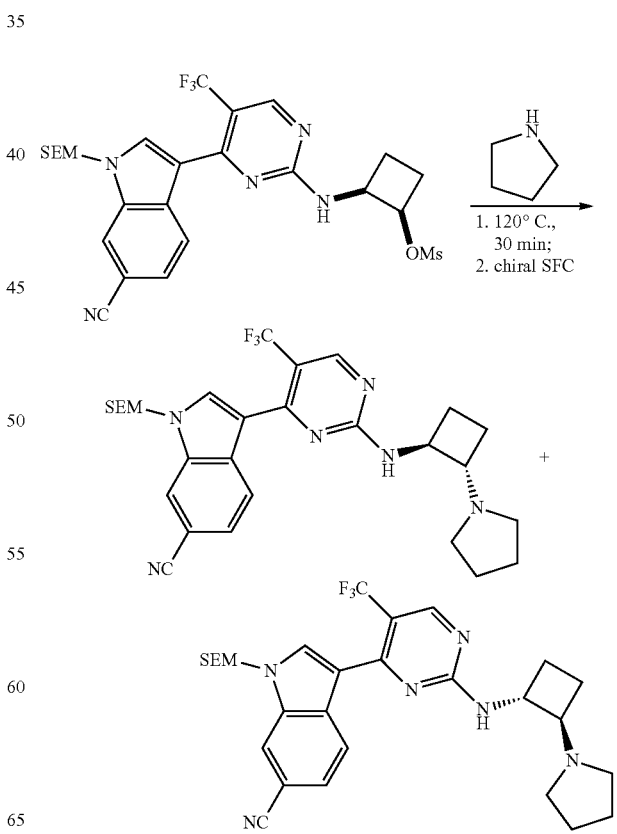

[2-[[4-[6-cyano-1-(2-trimethylsilylethoxymethyl)indol-3-yl]-5-(trifluoromethyl)pyrimidin-2-yl]-amino]-cyclobutyl]-methanesulfonate (180 mg, 309.45 µmol, 1 eq) and pyrrolidine (426.00 mg, 5.99 mmol, 0.5 mL, 19.36 eq) were taken up into a microwave tube. The sealed tube was heated at 120° C. for 30 min under microwave. The combined mixture was poured into water (5 mL) and then extracted with EtOAc (15 mL×3). The combined organic layer was washed with brine (40 mL), dried over $Na_2SO_4$, filtered and concentrated under reduced pressure to give a residue. The residue was purified by MPLC ($SiO_2$, DCM:MeOH=20:1 to 2:1) to give desired compound (Batch 1: 100 mg, 95.7% purity; Batch 2: 80 mg crude). The crude compound was purified by prep-HPLC to obtain the compound (50 mg) as brown solid (combined with another reaction in 80 mg scale for purification). The compound was combined with the compound from batch 1 for further SEC purification (column: DAICEL CHIRALPAK AD-H (250 mm×30 mm, 5 um); mobile phase: [0.1% $NH_3H_2O$ ETOH (ethanol)]; B %: 12%-12%, 4 min) to afford the title compound 1 (Rt=2.509 min, 15 mg) as yellow solid and title compound 2 (Rt=2.614 min, 15 mg) as yellow solid.

Step 4: 3-[2-[[(1S,2S)-2-pyrrolidin-1-ylcyclobutyl]-amino]-5-(trifluoromethyl)pyrimidin-4-yl]-1H-indole-6-carbonitrile

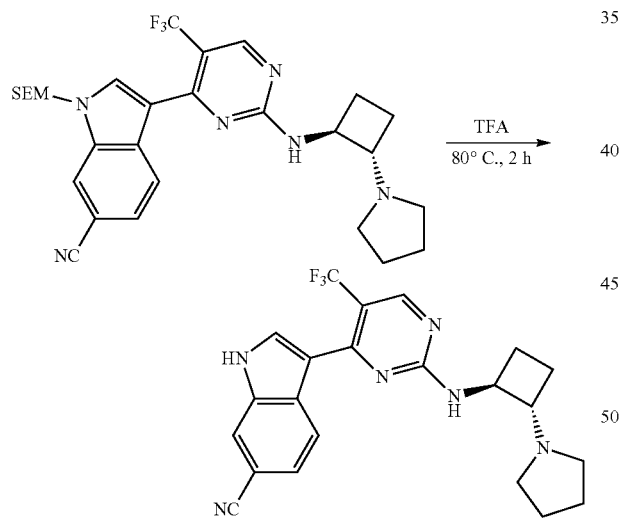

A solution of 3-[2-[[(1S,2S)-2-pyrrolidin-1-ylcyclobutyl]amino]-5-(trifluoromethyl)pyrimidin-4-yl]-1-(2-trimethylsilylethoxymethyl)indole-6-carbonitrile (15 mg, 26.94 µmol, 1 eq) in TFA (2 mL) was stirred at 80° C. for 2 h. It was poured into water (5 mL) and adjusted to pH=12 with NaOH solid, then extracted with DCM (10 mL×3). The combined organic layer was washed with brine (10 mL×3), dried over $Na_2SO_4$, filtered. The filtrate was concentrated under reduced pressure to give a residue. The residue was purified by prep-HPLC to afford the title compound (1.8 mg, 3.66 µmol, 13.60% yield, 94.24% purity, HCl salt) as yellow solid.

Step 5: 3-[2-[[(1R,2R)-2-pyrrolidin-1-ylcyclobutyl]amino]-5-(trifluoromethyl)pyrimidin-4-yl]-1H-indole-6-carbonitrile

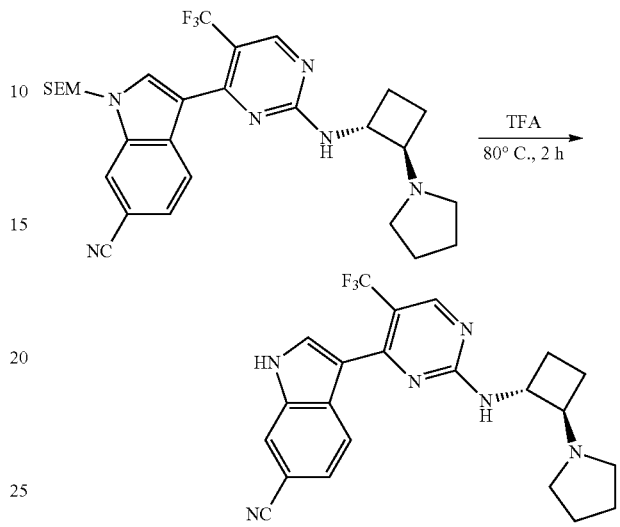

A solution of 3-[2-[[(1R,2R)-2-pyrrolidin-1-ylcyclobutyl]amino]-5-(trifluoromethyl)pyrimidin-4-yl]-1-(2-trimethylsilylethoxymethyl)indole-6-carbonitrile (15.00 mg, 26.94 µmol, 1 eq) in TFA (2 mL) was stirred at 80° C. for 2 h. The mixture was poured into water (5 mL) and adjusted to pH=12 with NaOH solid, then extracted with DCM (10 mL×3). The combined organic layer was washed with brine (10 mL×3), dried over $Na_2SO_4$, filtered. The filtrate was concentrated under reduced pressure to give a residue. The residue was purified by prep-HPLC to afford the title compound (1.8 mg, 3.80 µmol, 14.12% yield, 97.83% purity, HCl salt) as yellow solid.

Example 7. 3-[2-[[(1S,2S)-2-(dimethylamino)cyclobutyl]-amino]-5-(trifluoromethyl)pyrimidin-4-yl]-1H-indole-6-carbonitrile (Compound 126)

Step 1: N-[(1S,2S)-2-[[4-[6-cyano-1-(2-trimethylsilylethoxymethyl)indol-3-yl]-5-(trifluoromethyl)pyrimidin-2-yl]-amino]-cyclobutyl]-carbamate

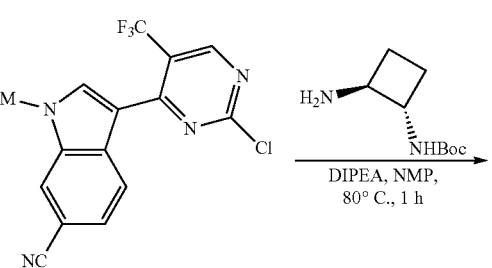

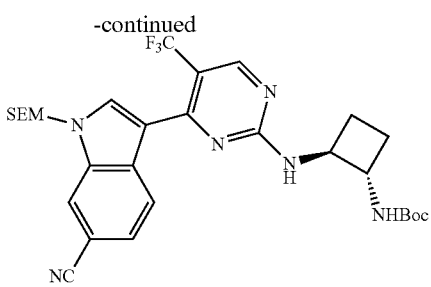

A mixture of 3-[[2-chloro-5-(trifluoromethyl)pyrimidin-4-yl]-1-(2-trimethylsilyl ethoxymethyl) indole-6-carbonitrile (170 mg, 375.33 µmol, 1 eq), tert-butyl N-[(1S,2S)-2-aminocyclobutyl]carbamate (83.89 mg, 450.40 µmol, 1.2 eq) and DIEA (58.21 mg, 450.40 µmol, 78.45 µL, 1.2 eq) in NMP (0.5 mL) was stirred for 1 hr at 80° C. The reaction mixture was poured into water (5 mL), and then extracted with EtOAc (10 mL×3). The combined organic layer was washed with brine (20 mL), dried over Na₂SO₄, filtered and concentrated under reduced pressure to give a residue. The residue was purified by MPLC (SiO₂, PE/EtOAc=10/1 to 3/1) to afford the title compound (160 mg, 87.6% purity) as light yellow solid. (The reaction was combined with another reaction in 40 mg scale for purification.)

Step 2: 3-[2-[[(1S,2S)-2-aminocyclobutyl]amino]-5-(trifluoromethyl)pyrimidin-4-yl]-1-(2-trimethylsilylethoxymethyl)indole-6-carbonitrile

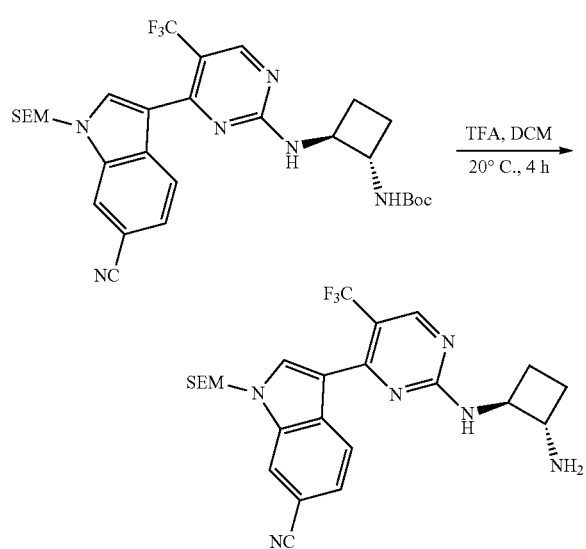

A mixture of tert-butyl N-[(1S,2S)-2-[[4-[6-cyano-1-(2-trimethylsilylethoxymethyl) indol-3-yl]-5-(trifluoromethyl) pyrimidin-2-yl]amino]cyclobutyl]carbamate (140 mg, 232.28 µmol, 1 eq) and TFA (264.85 mg, 2.32 mmol, 171.98 µL, 10 eq) in DCM (5 mL) was stirred for 4 hr at 20° C. under N₂. The reaction mixture was poured into water (5 mL) and adjusted to pH=9 with NaHCO₃ solid. Then the mixture was extracted with EtOAc (10 mL×3), the combined organic layer was washed with brine (20 mL), dried over Na₂SO₄, filtered and concentrated under reduced pressure to afford the title compound (135 mg, 74.9% purity) as yellow solid. The reaction was combined with another reaction in 30 mg scale for purification.

Step 3: 3-[2-[[(1S,2S)-2-(dimethylamino)cyclobutyl]amino]-5-(trifluoromethyl)pyrimidin-4-yl]-1-(2-trimethylsilylethoxymethyl)indole-6-carbonitrile

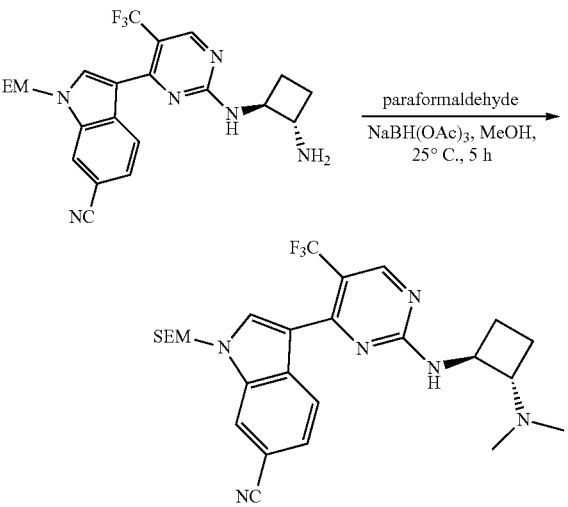

To a solution of 3-[2-[[(1S,2S)-2-aminocyclobutyl]amino]-5-(trifluoromethyl) pyrimidin-4-yl]-1-(2-trimethylsilylethoxymethyl)indole-6-carbonitrile (40 mg, 79.59 µmol, 1 eq) in MeOH (0.8 mL) was added HCHO (12.92 mg, 159.17 µmol, 11.85 µL, 2 eq) at 25° C. The mixture was stirred for 30 min at 25° C. Then NaBH(OAc)₃ (50.60 mg, 238.76 µmol, 3 eq) was added at 25° C. for 4.5 hr. The mixture was poured into water (5 mL) and then extracted with EtOAc (10 mL×3). The combined organic layer was washed with brine (20 mL), dried over Na₂SO₄, filtered and concentrated under reduced pressure to afford the title compound (70 mg, crude) as yellow solid. (The reaction was combined with another reaction in 30 mg scale for purification.)

Step 4: 3-[2-[[(1S,2S)-2-(dimethylamino) cyclobutyl]-amino]-5-(trifluoromethyl)pyrimidin-4-yl]-1H-indole-6-carbonitrile

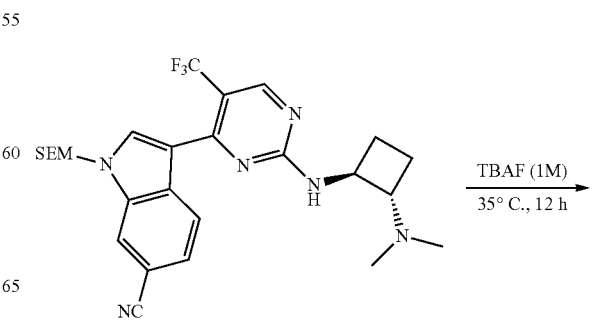

-continued

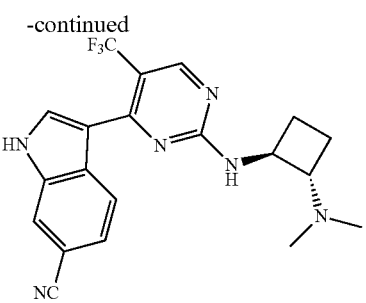

3-[2-[[(1S,2S)-2-(dimethylamino)cyclobutyl]amino]-5-(trifluoromethyl)pyrimidin-4-yl]-1-(2-trimethylsilylethoxymethyl)indole-6-carbonitrile (35 mg, 65.96 µmol, 1 eq) and TBAF (tetrabutylammonium fluoride; 1 M, 659.56 µL, 10 eq) were stirred at 35° C. for 12 hr under $N_2$. The reaction mixture was poured into water (10 mL), and then extracted with EtOAc (10 mL×3). The combined organic layer was washed with brine (20 mL), dried over $Na_2SO_4$, filtered and concentrated under reduced pressure to give a residue. The reaction was combined with another reaction in 35 mg scale for work up. The crude product was purified by prep-HPLC (HCl condition) to afford the title compound (12.2 mg, 96.81% purity, HCl salt) as yellow solid.

Example 8. N-[(1S,2S)-2-[[4-(6-cyano-1H-indol-3-yl)-5-(trifluoromethyl)pyrimidin-2-yl]-amino]-cyclobutyl]-acetamide (Compound 125)

Step 1: N-[(1S,2S)-2-[[4-[6-cyano-1-(2-trimethylsilylethoxymethyl)indol-3-yl]-5-(trifluoromethyl)pyrimidin-2-yl]amino]cyclobutyl]acetamide

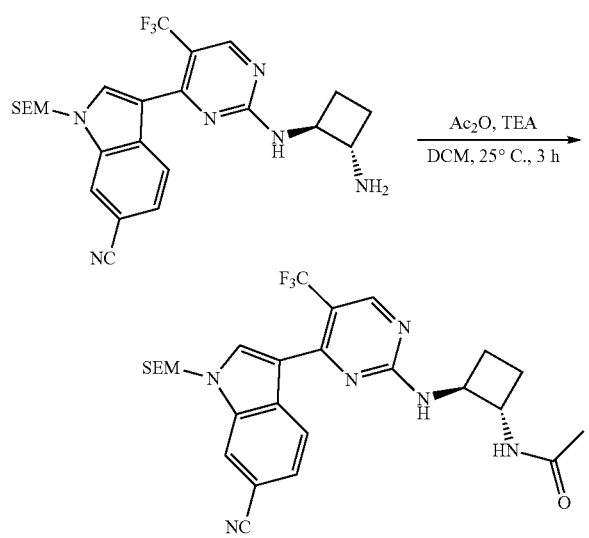

To a solution of 3-[2-[[(1S,2S)-2-aminocyclobutyl]amino]-5-(trifluoromethyl)pyrimidin-4-yl]-1-(2-trimethylsilylethoxymethyl)indole-6-carbonitrile (45 mg, 89.53 µmol, 1 eq) in DCM (0.5 mL) was added TEA (31.71 mg, 313.37 µmol, 43.62 µL, 3.5 eq) and $(CH_3CO)_2O$ (45.70 mg, 447.67 µmol, 5 eq). The mixture was stirred for 3 hr at 25° C. under $N_2$. The mixture was poured into $H_2O$ (5 mL) and then extracted with DCM (10 mL×3). The combined organic layer was washed with brine (20 mL), dried over $Na_2SO_4$, filtered and concentrated under reduced pressure to give a residue. The residue was purified by MPLC ($SiO_2$, PE/EtOAc=8/1 to 1/1) to afford the title compound (50 mg, 40.3% purity) as yellow solid. (The reaction was combined with another reaction in 30 mg scale for purification.)

Step 2: N-[(1S,2S)-2-[[4-(6-cyano-1H-indol-3-yl)-5-(trifluoromethyl)pyrimidin-2-yl]amino]cyclobutyl]acetamide

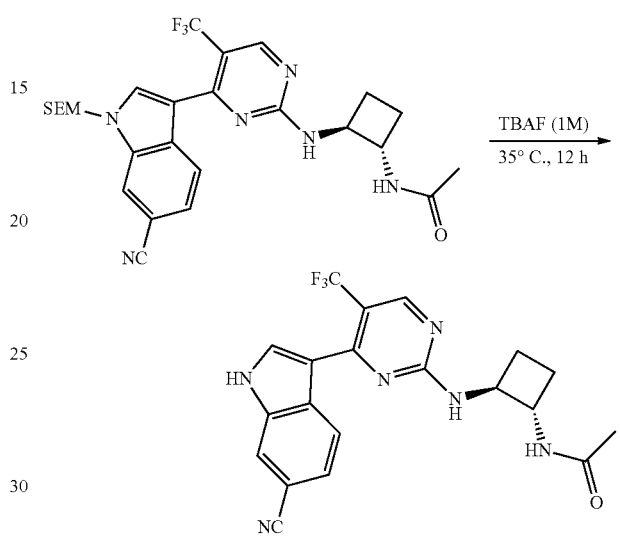

N-[(1S,2S)-2-[[4-[6-cyano-1-(2-trimethylsilylethoxymethyl)indol-3-yl]-5-(trifluoromethyl)pyrimidin-2-yl]amino]cyclobutyl]acetamide (25 mg, 45.90 µmol, 1 eq) and TBAF (1 M, 459.02 µL, 10 eq) were stirred at 35° C. for 12 hr under $N_2$. The mixture was concentrated to give the residue (80 mg). The residue (80 mg) was purified by prep-TLC (thin layer chromatography; EtOAC/MeOH=20:1) to provide the product (batch 1: 15 mg; batch 2: 30 mg, crude). The crude product (30 mg) was purified by MPLC ($SiO_2$, DCM/MeOH=50/1) to give the product (batch 3: 15 mg). Batch 1 and batch 3 were combined. The combined crude product (30 mg) was purified by prep-HPLC (HCl condition) to afford the title compound (8.3 mg, 97.96% purity, HCl salt) as yellow solid.

Example 9. 3-[2-[[(1S,2S)-2-(ethylamino)cyclobutyl]-amino]-5-(trifluoromethyl)pyrimidin-4-yl]-1H-indole-6-carbonitrile (Compound 131)

Step 1: 3-[2-[[(1S,2S)-2-(ethylamino) cyclobutyl]-amino]-5-(trifluoromethyl)pyrimidin-4-yl]-1-(2-trimethylsilylethoxymethyl) indole-6-carbonitrile

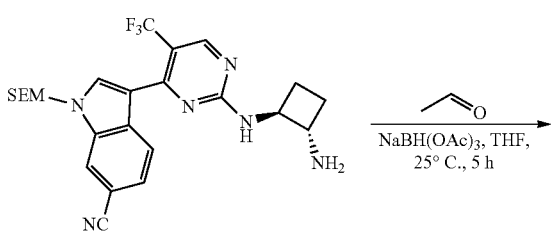

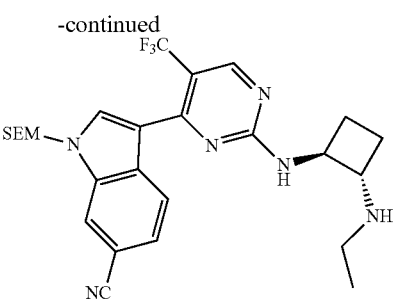

To a solution of 3-[2-[[(1S,2S)-2-aminocyclobutyl]-amino]-5-(trifluoromethyl)pyrimidin-4-yl]-1-(2-trimethylsilylethoxymethyl)indole-6-carbonitrile (0.06 g, 119.38 μmol, 1 eq) in THF (1 mL) was added HOAc (7.17 mg, 119.38 μmol, 6.83 μL, 1 eq) and acetaldehyde (2.63 mg, 59.69 μmol, 3.35 μL, 0.5 eq). The mixture was stirred at 15° C. for 1 h. Then NaBH(OAc)₃ (37.95 mg, 179.07 μmol, 1.5 eq) was added to the solution, the mixture was stirred at 15° C. for 11 h. The reaction mixture was diluted with water (10 mL) and extracted with EtOAc (5 mL×3). The combined organic layers were washed with brine (5 mL×3), dried over Na₂SO₄, filtered and concentrated under reduced pressure to give a residue. The residue was purified by prep-HPLC (TFA condition) and concentrated under reduced pressure to remove MeCN, then adjust pH to 9 with saturated aqueous of NaHCO₃ and extracted with EtOAc (5 mL×3). The combined organic layers were washed with brine (5 mL×3), dried over Na₂SO₄, filtered and concentrated under reduced pressure to afford the title compound (40 mg) as a yellow oil.

Step 2: 3-[2-[[(1S,2S)-2-(ethylamino) cyclobutyl]-amino]-5-(trifluoromethyl)pyrimidin-4-yl]-1H-indole-6-carbonitrile

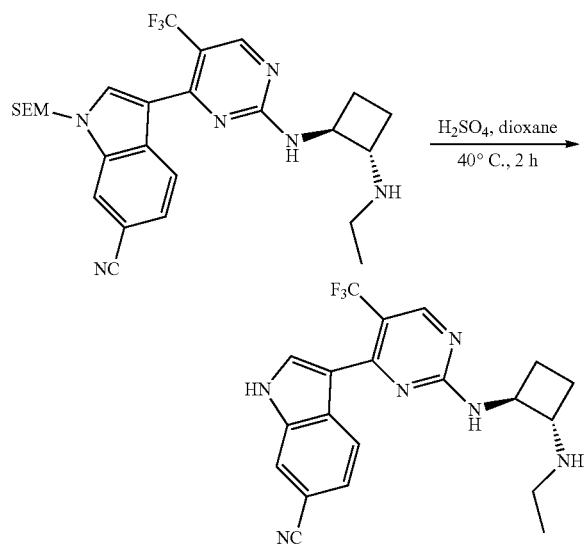

To a solution of 3-[2-[[(1S,2S)-2-(ethylamino) cyclobutyl]-amino]-5-(trifluoromethyl)Pyrimidin-4-yl]-1-(2-trimethylsilylethoxymethyl) indole-6-carbonitrile (0.03 g, 56.53 μmol, 1 eq) in dioxane (0.3 mL) was added H₂SO₄ (55.45 mg, 565.33 μmol, 30.13 μL, 10 eq). The mixture was stirred at 40° C. for 2 h. The reaction mixture was diluted with saturated aqueous of K₂CO₃ (10 mL) and extracted with EtOAc (5 mL×3). The combined organic layers were washed with brine (5 mL×3), dried over Na₂SO₄, filtered and concentrated under reduced pressure to give a residue. The residue was purified by prep-HPLC (HCl condition) to afford the title compound (3.1 mg, HCl salt, 91.1% purity) as a yellow solid.

Example 10. N-[(1S,2S)-2-[[4-(6-cyano-1H-indol-3-yl)-5-(trifluoromethyl)pyrimidin-2-yl]-amino]cyclopentyl]-acetamide (Compound 120)

Step 1: Tert-butyl N-[(2S)-2-[[4-[6-cyano-1-(2-trimethylsilylethoxymethyl) indol-3-yl]-5-(trifluoromethyl)pyrimidin-2-yl]-amino]-cyclopentyl]-carbamate

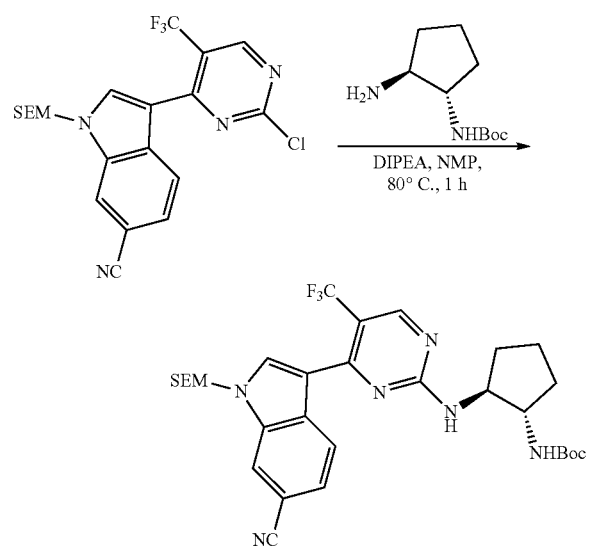

To a solution of 3-[2-chloro-5-(trifluoromethyl)pyrimidin-4-yl]-1-(2-trimethylsilyl ethoxymethyl)indole-6-carbonitrile (0.55 g, 1.21 mmol, 1 eq) in NMP (5 mL) was added DIPEA (187.66 mg, 1.45 mmol, 252.91 μL, 1.2 eq) and tert-butyl N-[(2S)-2-aminocyclopentyl]carbamate (290.80 mg, 1.45 mmol, 1.2 eq). The mixture was stirred at 80° C. for 1 h. The reaction mixture was diluted with water (100 mL) and extracted with EtOAc (10 mL×3). The combined organic layers were washed with brine (10 mL×3), dried over Na₂SO₄, filtered and concentrated under reduced pressure to give a residue. The residue was purified by column chromatography (SiO₂, PE/EtOAc=3/1) to afford the title compound (520 mg) as a yellow oil. (The reaction was combined with another reaction in 50 mg scale for purification.)

Step 2: 3-[2-[[(1S,2S)-2-aminocyclopentyl]amino]-5-(trifluoromethyl)pyrimidin-4-yl]-1-(2-trimethylsilylethoxymethyl)indole-6-carbonitrile

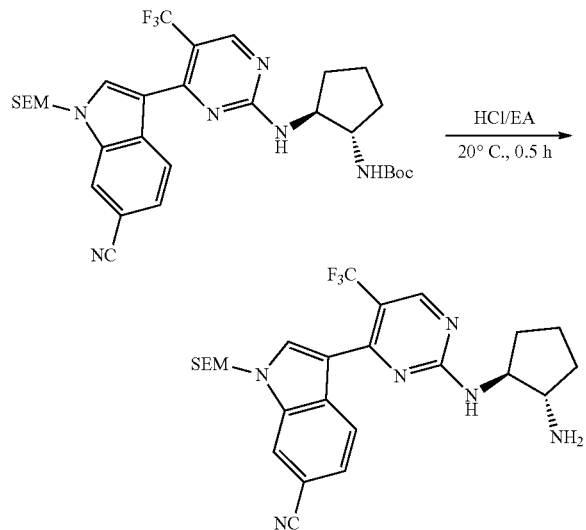

To a solution of tert-butyl N-[(2S)-2-[[4-[6-cyano-1-(2-trimethylsilylethoxymethyl) indol-3-yl]-5-(trifluoromethyl) pyrimidin-2-yl]amino]cyclopentyl]carbamate (0.46 g, 745.85 µmol, 1 eq) in EtOAc (5 mL) was added HCl/EtOAc (4 M, 4 mL, 21.45 eq). The mixture was stirred at 20° C. for 0.5 h. The reaction mixture was concentrated under reduced pressure to afford the title compound (450 mg) as a white solid. (The reaction was combined with another reaction in 50 mg scale for purification.)

Step 3: N-[(1S,2S)-2-[[4-[6-cyano-1-(2-trimethylsilylethoxymethyl)indol-3-yl]-5-(trifluoromethyl)pyrimidin-2-yl]amino]cyclopentyl]acetamide

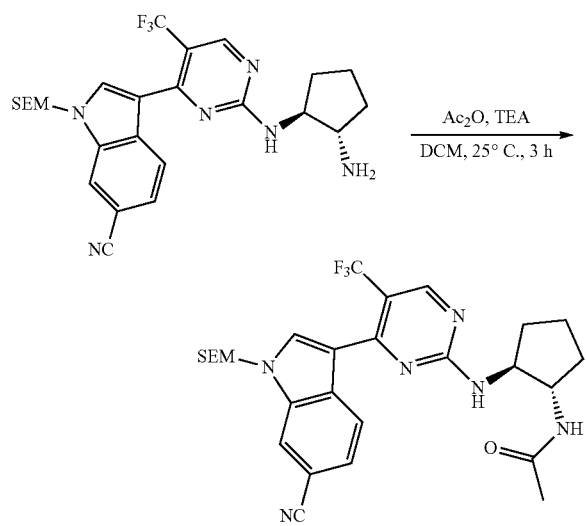

To a solution of 3-[2-[[(1S,2S)-2-aminocyclopentyl]-amino]-5-(trifluoromethyl)pyrimidin-4-yl]-1-(2-trimethylsilylethoxymethyl)indole-6-carbonitrile (0.1 g, 180.80 µmol, 1 eq, HCl) in DCM (1 mL) was added TEA (64.03 mg, 632.80 µmol, 88.08 µL, 3.5 eq) and $(CH_3CO)_2O$ (92.29 mg, 904.01 µmol, 5 eq). The mixture was stirred at 25° C. for 3 h. The reaction mixture was diluted with water (15 mL) and extracted with DCM (5 mL×3). The combined organic layers were washed with brine (5 mL×3), dried over $Na_2SO_4$, filtered and concentrated under reduced pressure to give a residue. The residue was purified by column chromatography ($SiO_2$, PE/EtOAc=2/1) to afford the title compound (100 mg) as a yellow oil. (The reaction was combined with another reaction in 20 mg scale for purification.)

Step 4: N-[(1S,2S)-2-[[4-(6-cyano-1H-indol-3-yl)-5-(trifluoromethyl)pyrimidin-2-yl]-amino]Cyclopentyl]-acetamide

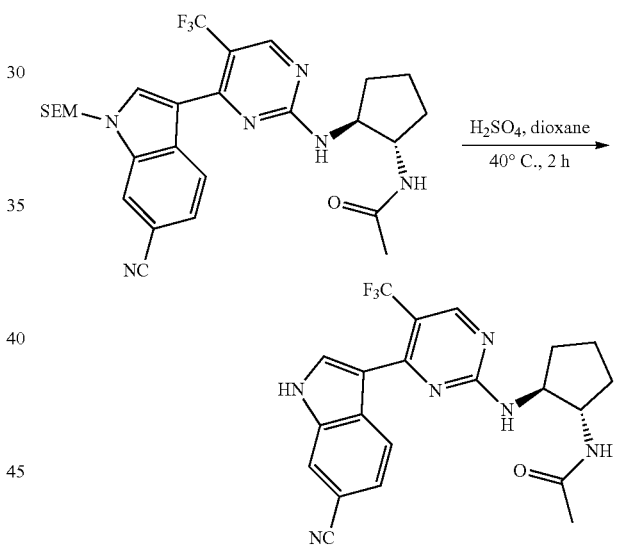

To a solution of N-[(1S,2S)-2-[[4-[6-cyano-1-(2-trimethylsilylethoxymethyl)indol-3-yl]-5-(trifluoromethyl)pyrimidin-2-yl]amino]cyclopentyl]acetamide (0.08 g, 143.20 µmol, 1 eq) in dioxane (1 mL) was added $H_2SO_4$ (140.45 mg, 1.43 mmol, 76.33 µL, 10 eq). The mixture was stirred at 40° C. for 2 h. The reaction mixture was diluted with saturated aqueous of $K_2CO_3$ (10 mL) and extracted with EtOAc (5 mL×3). The combined organic layers were washed with brine (5 mL×3), dried over $Na_2SO_4$, filtered and concentrated under reduced pressure to give a residue. The residue was purified by prep-HPLC (HCl condition) to afford the title compound (16.4 mg, HCl, 100% purity) as a white solid.

Example 11. 3-[2-[[(1S,2S)-2-(ethylamino) cyclopentyl]-amino]-5-(trifluoromethyl)pyrimidin-4-yl]-1H-indole-6-carbonitrile (Compound 128)

Step 1: 3-[2-[[(1S,2S)-2-(ethylamino)cyclopentyl]-amino]-5-(trifluoromethyl)pyrimidin-4-yl]-1-(2-trimethylsilylethoxymethyl) indole-6-carbonitrile

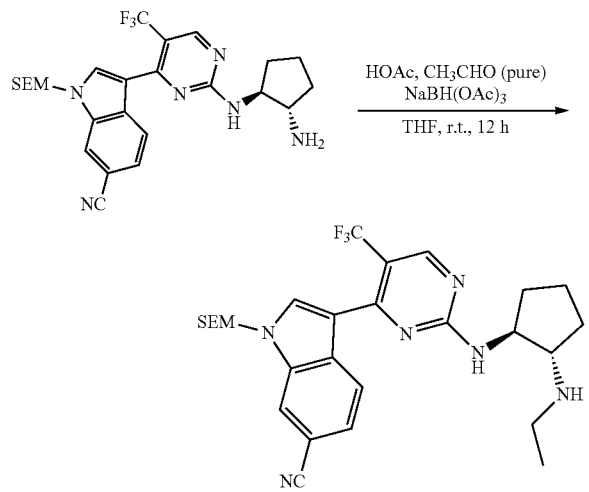

To a solution of 3-[2-[[(1S,2S)-2-aminocyclopentyl]-amino]-5-(trifluoromethyl)pyrimidin-4-yl]-1-(2-trimethylsilylethoxymethyl)indole-6-carbonitrile (0.08 g, 123.88 µmol, 1 eq) in THF (1 mL) was added HOAc (7.44 mg, 123.88 mol, 7.08 µL, 1 eq) and acetaldehyde (2.76 mg, 61.94 µmol, 3.51 µL, 99% purity, 0.5 eq). The mixture was stirred at 25° C. for 1 h. Then NaBH(OAc)$_3$ (39.38 mg, 185.82 µmol, 1.5 eq) was added to the solution at 25° C., the mixture was stirred at 25° C. for 11 h. The reaction mixture was concentrated under reduced pressure to give a residue.

The residue was purified by column chromatography (SiO$_2$, PE/EtOAc=1/1) to afford the title compound (55 mg) as a yellow oil.

Step 2: 3-[2-[[(1S,2S)-2-(ethylamino) cyclopentyl]-amino]-5-(trifluoromethyl)pyrimidin-4-yl]-1H-indole-6-carbonitrile

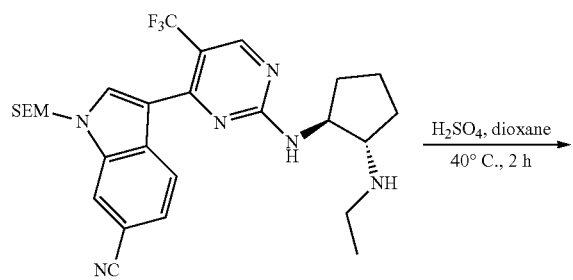

To a solution of 3-[2-[[(1S,2S)-2-(ethylamino)cyclopentyl]-amino]-5-(trifluoromethyl)pyrimidin-4-yl]-1-(2-trimethylsilylethoxymethyl)indole-6-carbonitrile (0.05 g, 91.80 µmol, 1 eq) in dioxane (0.5 mL) was added H$_2$SO$_4$ (90.03 mg, 917.96 µmol, 48.93 µL, 10 eq). The mixture was stirred at 40° C. for 2 h. The reaction mixture was diluted with saturated aqueous of K$_2$CO$_3$ 10 mL and extracted with EtOAc 15 mL (5 mL×3). The combined organic layers were washed with brine 15 mL (5 mL×3), dried over Na$_2$SO$_4$, filtered and concentrated under reduced pressure to give a residue. The residue was purified by prep-HPLC (HCl condition) to afford the title compound (HCl salt, 4.1 mg, 98.42% purity) as a yellow solid.

Example 12. (1S,2S)—N2-[4-[6-(3,5-dimethylisoxazol-4-yl)-1H-pyrrolo[2,3-b]pyridin-3-yl]-5-(trifluoromethyl)pyrimidin-2-yl]-cyclobutane-1,2-diamine (Compound 129)

Step 1: 3,5-dimethyl-4-(1H-pyrrolo-[2,3-b]-pyridin-6-yl) isoxazole

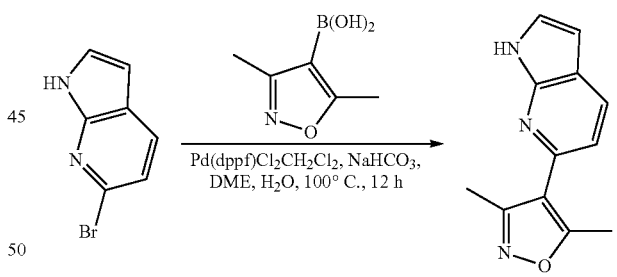

A mixture of 6-bromo-1H-pyrrolo-[2,3-b]-pyridine (1 g, 5.08 mmol, 1 eq), (3,5-dimethylisoxazol-4-yl) boronic acid (1.43 g, 10.15 mmol, 2 eq), Pd(dppf)Cl$_2$·CH$_2$Cl$_2$ (207.23 mg, 253.77 µmol, 0.05 eq), NaHCO$_3$ (1.28 g, 15.23 mmol, 592.17 µL, 3 eq) in DME (10 mL) and H$_2$O (3 mL) was degassed and purged with N$_2$ for 3 times, and then the mixture was stirred at 100° C. for 12 h under N$_2$ atmosphere. The reaction mixture was poured into H$_2$O (20 mL) and extracted with EtOAc (20 mL×3). The combined organic layers were washed with brine (20 mL×2), dried over Na$_2$SO$_4$, filtered and concentrated under reduced pressure to give a residue. The residue was purified by column chromatography (SiO$_2$, PE/EtOAc=10/1 to 2/1) to afford the title compound (1.1 g, 90% purity) as a white solid.

Step 2: 4-(3-bromo-1H-pyrrolo-[2,3-b]-pyridin-6-yl)-3,5-dimethyl-isoxazole

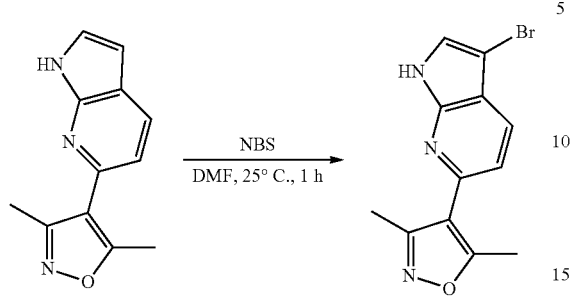

To a solution of 3,5-dimethyl-4-(1H-pyrrolo-[2,3-b]-pyridin-6-yl) isoxazole (0.9 g, 4.22 mmol, 1 eq) in DMF (dimethylformamide; 10 mL) was added NBS (N-bromosuccinimide; 676.10 mg, 3.80 mmol, 0.9 eq (equivalents)). The mixture was stirred at 25° C. for 1 h. The reaction mixture was poured into H$_2$O (20 mL), and extracted with EtOAc (20 mL×3). The combined organic layers were washed with brine (20 mL×2), dried over Na$_2$SO$_4$, filtered and concentrated under reduced pressure to give a residue. The residue was purified by column chromatography (SiO$_2$, PE/EtOAc=10/1 to 1/1) to afford the title compound (600 mg, crude) as pink solid which was used in the next step directly.

Step 3: 4-[1-(benzenesulfonyl)-3-bromo-pyrrolo-[2,3-b]-pyridin-6-yl]-3,5-dimethyl-isoxazole

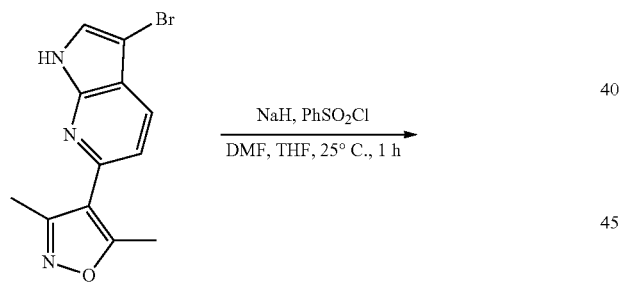

To a solution of 4-(3-bromo-1H-pyrrolo[2,3-b]-pyridin-6-yl)-3,5-dimethyl-isoxazole (0.6 g, 2.05 mmol, 1 eq) in DMF (9 mL) and THF (1 mL) was added NaH (98.58 mg, 2.46 mmol, 60% purity, 1.2 eq) and benzenesulfonyl chloride (471.58 mg, 2.67 mmol, 341.73 μL, 1.3 eq). The mixture was stirred at 25° C. for 1 h. The reaction mixture was poured into H$_2$O (20 mL) while white solid formed. The solid was filtered and concentrated under reduced pressure to afford the title compound (600 mg) as white solid, which used into the next step without further purification.

Step 4: 4-[1-(benzenesulfonyl) pyrrolo-[2,3-b]-pyridin-6-yl]-3,5-dimethyl-isoxazole; 4-[1-(benzenesulfonyl)-3-(4,4,5,5-tetramethyl-1,3,2-dioxaborolan-2-yl) pyrrolo-[2,3-b]-pyridin-6-yl]-3,5-dimethyl-isoxazole

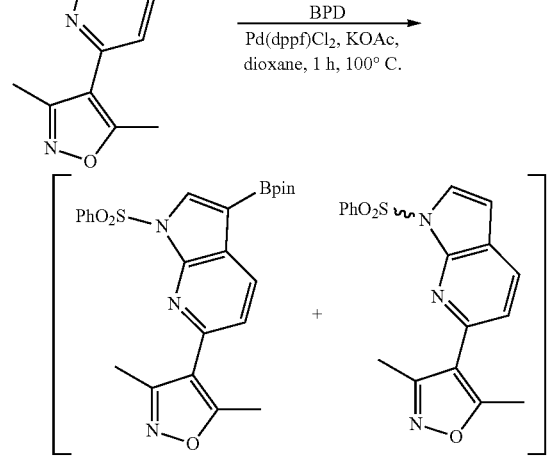

A mixture of 4-[1-(benzenesulfonyl)-3-bromo-pyrrolo-[2,3-b]-pyridin-6-yl]-3,5-dimethyl-isoxazole (0.27 g, 624.58 μmol, 1 eq), BPD (237.91 mg, 936.87 μmol, 1.5 eq), Pd(dppf)C$_{1-2}$ (45.70 mg, 62.46 μmol, 0.1 eq), KOAc (122.60 mg, 1.25 mmol, 2 eq) in dioxane (3 mL) was degassed and purged with N$_2$ for 3 times, and then the mixture was stirred at 100° C. for 1 h under N$_2$ atmosphere. The reaction mixture was poured into H$_2$O (20 mL) and extracted with EtOAc (20 mL×3). The combined organic layers were washed with brine (10 mL×2), dried over Na$_2$SO$_4$, filtered and concentrated under reduced pressure to afford the title compound (600 mg, crude, 2 Batches in parallel) as brown oil which was used into the next step without further purification.

Step 5: 4-chloro-2-methylsulfanyl-5-(trifluoromethyl)pyrimidine

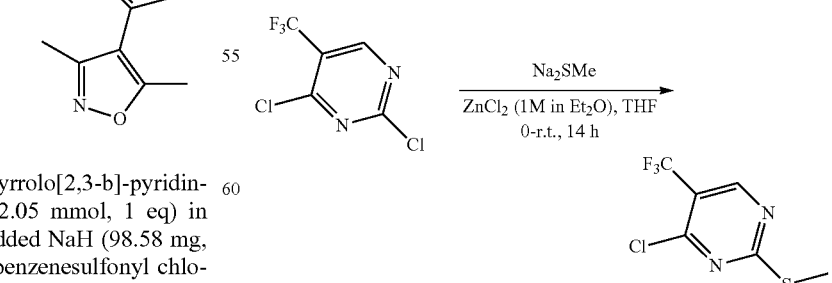

To a solution of 2,4-dichloro-5-(trifluoromethyl)pyrimidine (10 g, 46.09 mmol, 1 eq) in THF (200 mL) was added dropwise ZnCl₂ (1 M, 59.91 mL, 1.3 eq) at 0° C. After addition, the mixture was stirred at this temperature for 2 h, and then NaSMe (3.88 g, 55.31 mmol, 3.52 mL, 1.2 eq) was added dropwise at 0° C. The resulting mixture was stirred at 15° C. for 14 h. The mixture was quenched with aqueous HCl (150 mL, 1M), and then extracted with EtOAc (60 mL×3), dried over Na₂SO₄ and concentrated. The residue was purified by column chromatography (SiO₂, PE/DCM=1:0 to 50:1) to afford the title compound (10 g, 43.74 mmol, 94.91% yield) as a colorless oil.

Step 6: 4-[1-(benzenesulfonyl)-3-[2-methylsulfanyl-5-(trifluoromethyl)pyrimidin-4-yl]pyrrolo-[2,3-b]pyridin-6-yl]-3,5-dimethylisoxazole

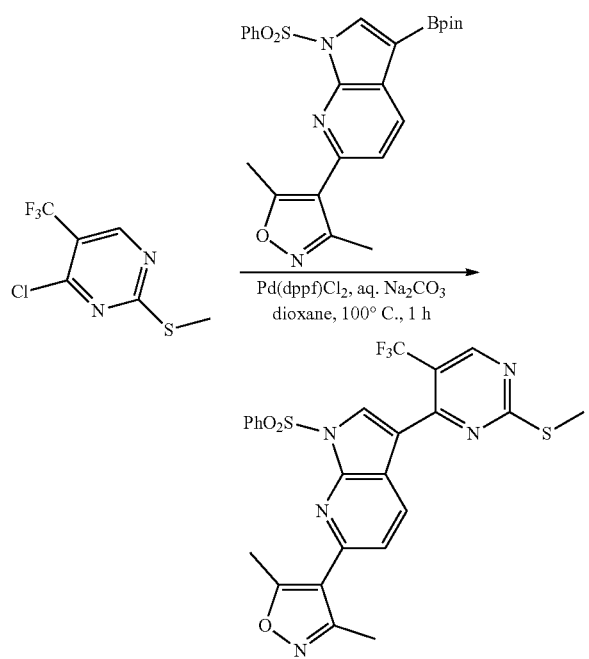

To a solution of 4-[1-(benzenesulfonyl)-3-(4,4,5,5-tetramethyl-1,3,2-dioxaborolan-2-yl)pyrrolo[2,3-b]pyridin-6-yl]-3,5-dimethyl-isoxazole (3 g, 3.76 mmol, 1 eq) and 4-chloro-2-methylsulfanyl-5-(trifluoromethyl)pyrimidine (1.43 g, 5.63 mmol, 1.5 eq) in dioxane (30 mL)/H₂O (6 mL) was added Na₂CO₃ (1.19 g, 11.27 mmol, 3 eq) and Pd(dppf)C₁₋₂ (274.76 mg, 375.50 µmol, 0.1 eq). The mixture was stirred at 100° C. under N₂ atmosphere for 1 h. The reaction mixture was poured into water (150 mL). The aqueous phase was extracted with ethyl acetate (50 mL×3). The combined organic phase was washed with brine (50 mL×2), dried over anhydrous Na₂SO₄, filtered and concentrated in vacuum. The residue was purified by silica gel chromatography (100-200 mesh silica gel, PE/EtOAc=10/1,4/1) to afford the title compound (0.7 g, 769.86 µmol, 20.50% yield, 60% purity) as a yellow solid.

Step 7: 4-[1-(benzenesulfonyl)-3-[2-methylsulfonyl-5-(trifluoromethyl)pyrimidin-4-yl]-pyrrolo[2,3-b]-pyridin-6-yl]-3,5-dimethylisoxazole

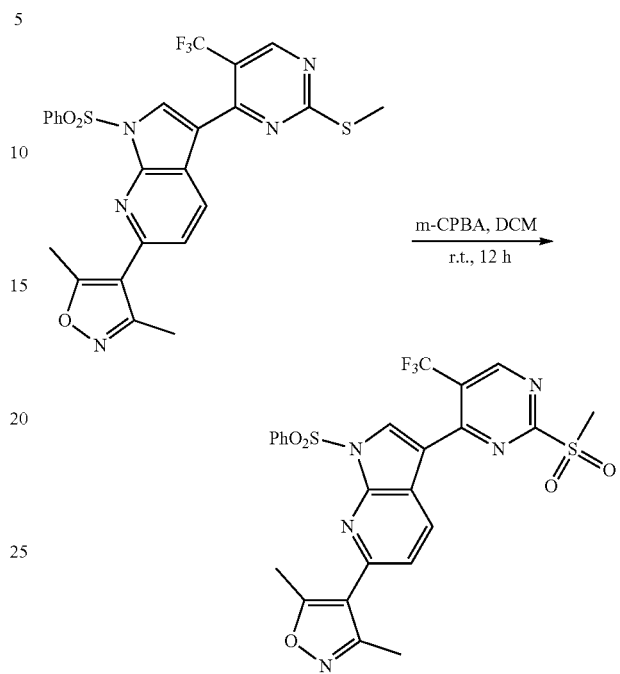

To a solution of 4-[1-(benzenesulfonyl)-3-[2-methylsulfanyl-5-(trifluoromethyl)pyrimidin-4-yl]pyrrolo[2,3-b]pyridin-6-yl]-3,5-dimethyl-isoxazole (0.7 g, 1.28 mmol, 1 eq) in DCM (50 mL) was added m-CPBA (3-chloroperbenzoic acid; 573.08 mg, 2.82 mmol, 2.2 eq). The mixture was stirred at 20° C. for 12 h. The residue was poured into a mixture of Sat.NaHCO₃ (20 mL) and Sat. Na₂SO₃ (20 mL), and the mixture was stirred for 5 min. The aqueous phase was extracted with DCM (30 mL×2). The combined organic phase was dried over anhydrous Na₂SO₄, filtered and concentrated in vacuum. The residue was purified by silica gel chromatography (100-200 mesh silica gel, PE/EtOAc=10/1,2/1, contained 10% DCM) to afford the title compound (0.5 g, 822.43 µmol, 64.10% yield, 95% purity) as a white solid.

Step 8: tert-butyl N-[(1S,2S)-2-[[4-[1-(benzenesulfonyl)-6-(3,5-dimethylisoxazol-4-yl) pyrrolo[2,3-b]pyridin-3-yl]-5-(trifluoromethyl)pyrimidin-2-yl]amino]cyclobutyl]carbamate

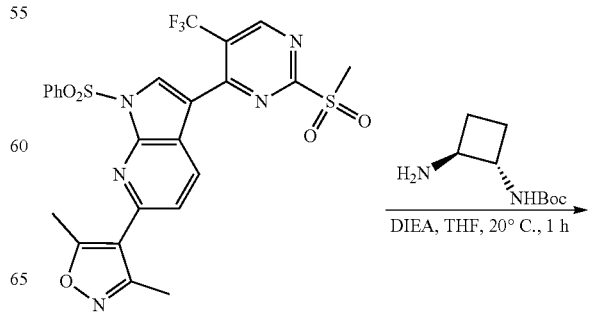

-continued

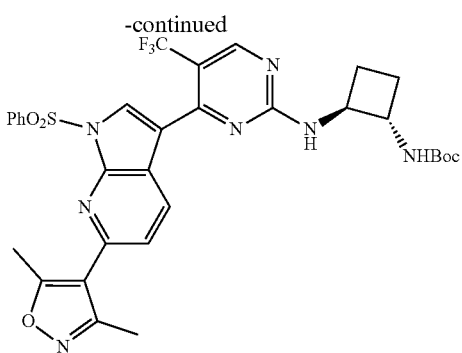

A solution of tert-butyl N-[(1S,2S)-2-aminocyclobutyl]carbamate (34.83 mg, 187.00 μmol, 1.2 eq), 4-[1-(benzenesulfonyl)-3-[2-methylsulfonyl-5-(trifluoromethyl)pyrimidin-4-yl]pyrrolo[2,3-b]pyridin-6-yl]-3,5-dimethyl-isoxazole (90 mg, 155.83 μmol, 1 eq) and DIEA (100.70 mg, 779.15 μmol, 135.71 μL, 5 eq) in THF (1 mL) was stirred at 20° C. for 1 h. The mixture was poured into water (10 mL) and then extracted with EtOAc (15 mL×3). The combined organic layer was washed with brine (20 mL), dried over Na$_2$SO$_4$, filtered and concentrated under reduced pressure to give a residue. The residue was purified by MPLC (SiO$_2$, PE/EtOAc=8/1 to 3/1) to afford the title compound (100 mg. 80.9% purity) as yellow solid. (The mixture was combined with another reaction in 10 mg scale for work up.)

Step 9: tert-butyl N-[(1S,2S)-2-[[4-[6-(3,5-dimethyl-isoxazol-4-yl)-1H-pyrrolo-[2,3-b]pyridin-3-yl]-5-(trifluoromethyl)pyrimidin-2-yl]amino]cyclobutyl]carbamate

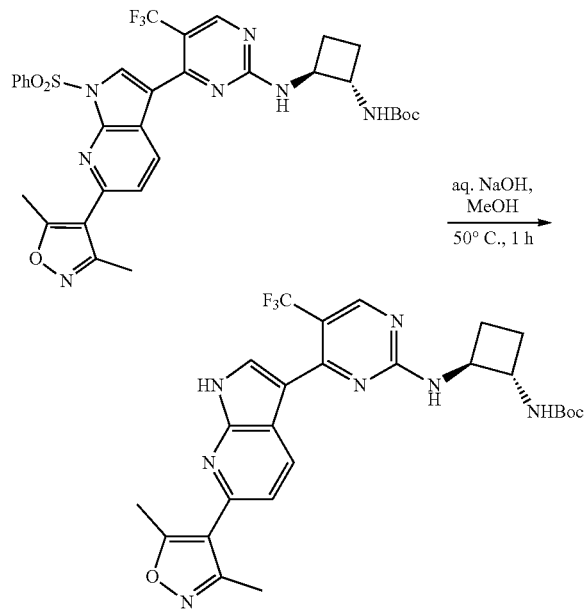

A mixture of tert-butyl N-[(1S,2S)-2-[[4-[1-(benzenesulfonyl)-6-(3,5-dimethylisoxazol-4-yl) pyrrolo-[2,3-b]-pyridin-3-yl]-5-(trifluoromethyl)pyrimidin-2-yl]-amino]-cyclobutyl]-carbamate (80 mg, 117.01 μmol, 1 eq) and NaOH (2 M, 292.53 μL, 5 eq) in MeOH (2 mL) was stirred at 50° C. for 1 h. The mixture was poured into water (10 mL) and then extracted with EtOAc (15 mL×3). The combined organic layer was washed with brine (20 mL), dried over Na$_2$SO$_4$, filtered and concentrated under reduced pressure to afford the title compound (60 mg, crude) as yellow solid. (The reaction was combined with another reaction in 20 mg scale for purification.)

Step 10: (1S,2S)—N2-[4-[6-(3,5-dimethylisoxazol-4-yl)-1H-pyrrolo[2,3-b]pyridin-3-yl]-5-(trifluoromethyl)pyrimidin-2-yl]-cyclobutane-1,2-diamine

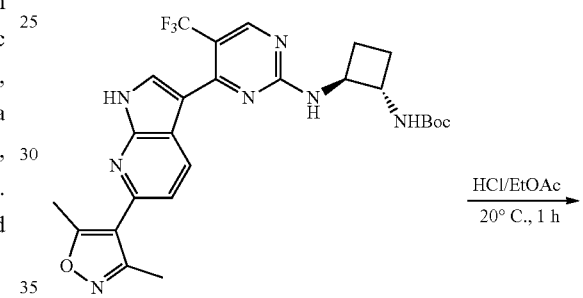

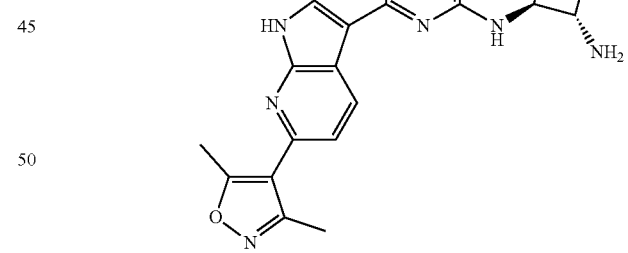

A solution of tert-butyl N-[(1S,2S)-2-[[4-[6-(3,5-dimethylisoxazol-4-yl)-1H-pyrrolo[2,3-b]pyridin-3-yl]-5-(trifluoromethyl)pyrimidin-2-yl]amino]cyclobutyl]carbamate (50 mg, 91.99 μmol, 1 eq) in HCl/EtOAc (4 mL) was stirred at 20° C. for 1 h. The mixture was concentrated to give the crude product, which was purified by prep-HPLC (HCl condition) to afford the title compound (33.6 mg, 69.56 μmol, 75.62% yield, 99.35% purity, HCl salt) as a yellow solid.

Example 13. (1S,2S,4R)—N-[4-[6-(3,5-dimethyl-isoxazol-4-yl)-1H-indol-3-yl]-5-(trifluoromethyl)pyrimidin-2-yl]-7-azabicyclo-[2.2.1]-heptan-3-amine (Compound 137) and (1R,2R,4S)—N-[4-[6-(3,5-dimethylisoxazol-4-yl)-1H-indol-3-yl]-5-(trifluoromethyl)pyrimidin-2-yl]-7-azabicyclo-[2.2.1]-heptan-3-amine (Compound 138)

Step 1: Tert-butyl 3-[[4-[6-bromo-1-(2-trimethylsilylethoxymethyl)indol-3-yl]-5-(trifluoromethyl)pyrimidin-2-yl]-amino]-7-azabicyclo-[2.2.1]-heptane-7-carboxylate

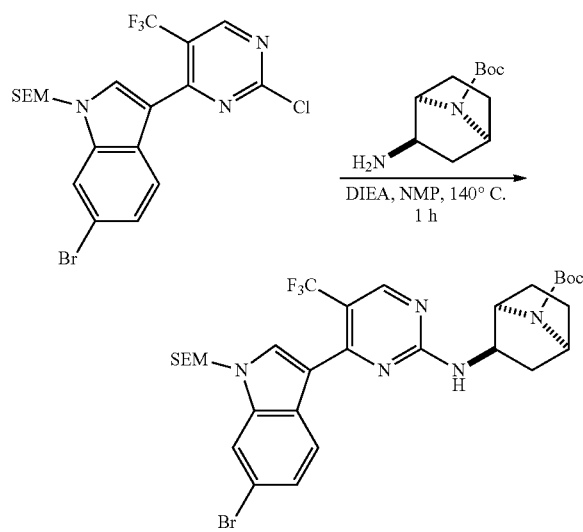

To a solution of 2-[[6-bromo-3-[2-chloro-5-(trifluoromethyl)pyrimidin-4-yl]-indol-1-yl]-methoxy]-ethyl-trimethyl-silane (271.30 mg, 535.29 μmol, 1 eq) in NMP (3 mL) was added DIPEA (103.77 mg, 802.94 μmol, 139.86 μL, 1.5 eq) and tert-butyl 3-amino-7-azabicyclo-[2.2.1]-heptane-7-carboxylate (125.00 mg, 588.82 μmol, 1.1 eq). The mixture was stirred at 140° C. for 1 h. The reaction mixture was diluted with water 50 mL and extracted with EtOAc (10 mL×3). The combined organic layers were washed with brine (10 mL×3), dried over Na₂SO₄, filtered and concentrated under reduced pressure to give a residue that was purified by column chromatography (SiO₂, PE/EtOAc=3/1) to afford the title compound (250 mg) as a white solid.

Step 2: 3-[[4-[6-(3,5-dimethylisoxazol-4-yl)-1-(2-trimethylsilylethoxymethyl)indol-3-yl]-5-(trifluoromethyl)pyrimidin-2-yl]amino]-7-azabicyclo[2.2H]heptane-7-carboxylate

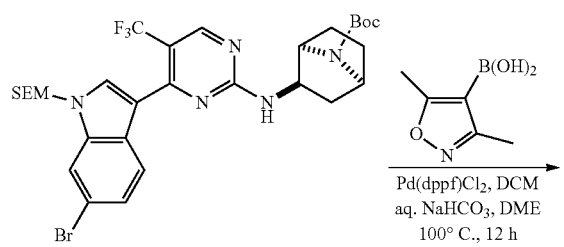

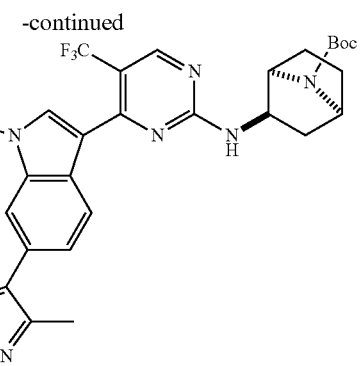

To a solution of tert-butyl 3-[[4-[6-bromo-1-(2-trimethylsilylethoxymethyl) indol-3-yl]-5-(trifluoromethyl)pyrimidin-2-yl]-amino]-7-azabicyclo-[2.2.1]heptane-7-carboxylate (200.00 mg, 292.98 μmol, 1 eq) in DME (0.3 mL) and H₂O (0.05 mL) was added (3,5-dimethylisoxazol-4-yl) boronic acid (82.58 mg, 585.96 μmol, 2 eq), NaHCO₃ (73.84 mg, 878.93 μmol, 34.18 μL, 3 eq) and Pd(dppf)Cl₂·CH₂Cl₂ (11.96 mg, 14.65 μmol, 0.05 eq). The mixture was stirred at 100° C. for 12 h under N₂. The reaction mixture was diluted with water (10 mL) and extracted with EtOAc (5 mL×3). The combined organic layers were washed with brine (5 mL×3), dried over Na₂SO₄, filtered and concentrated under reduced pressure to give a residue that was purified by column chromatography (SiO₂, PE/EtOAc=3/1) to afford the title compound (170 mg) as a yellow oil.

Step 3: Tert-butyl 3-[[4-[6-(3,5-dimethylisoxazol-4-yl)-1H-indol-3-yl]-5-(trifluoromethyl)pyrimidin-2-yl]-amino]-7-azabicyclo-[2.2H]heptane-7-carboxylate

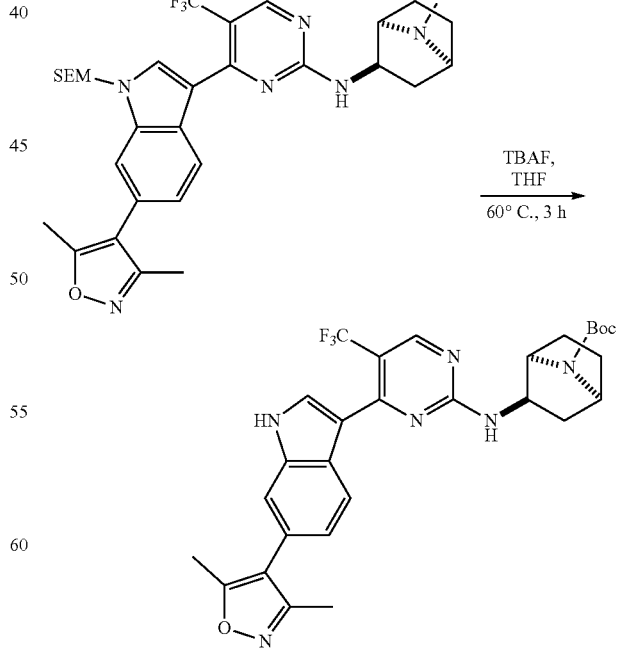

To a solution of tert-butyl 3-[[4-[6-(3,5-dimethylisoxazol-4-yl)-1-(2-trimethylsilyl ethoxymethyl) indol-3-yl]-5-(trifluoromethyl)pyrimidin-2-yl]-amino]-7-azabicyclo-[2.2.1]-heptane-7-carboxylate (0.1 g, 143.09 μmol, 1 eq) in THF (1 mL) was added TBAF (187.06 mg, 715.46 μmol, 5 eq). The mixture was stirred at 60° C. for 3 h. The reaction mixture was diluted with water (10 mL) and extracted with EtOAc (10 mL×3), then was washed with water (10 mL×3). The combined organic layers were washed with brine (10 m×3), dried over $Na_2SO_4$, filtered and concentrated under reduced pressure to give a residue. The residue was purified by column chromatography ($SiO_2$, PE/EtOAc=2/1) to afford the title compound (80 mg) as a yellow oil. The reaction was combined with another reaction in 10 mg scale for purification.

Step 4: Tert-butyl (1S,2S,4R)-3-[[4-[6-(3,5-dimethylisoxazol-4-yl)-1H-indol-3-yl]-5-(trifluoromethyl) pyrimidin-2-yl]-amino]-7-azabicyclo-[2.2.1]-heptane-7-carboxylate and Tert-butyl (1R,2R,4S)-3-[[4-[6-(3,5-dimethylisoxazol-4-yl)-1H-indol-3-yl]-5-(trifluoromethyl)pyrimidin-2-yl]-amino]-7-azabicyclo-[2.2H]heptane-7-carboxylate

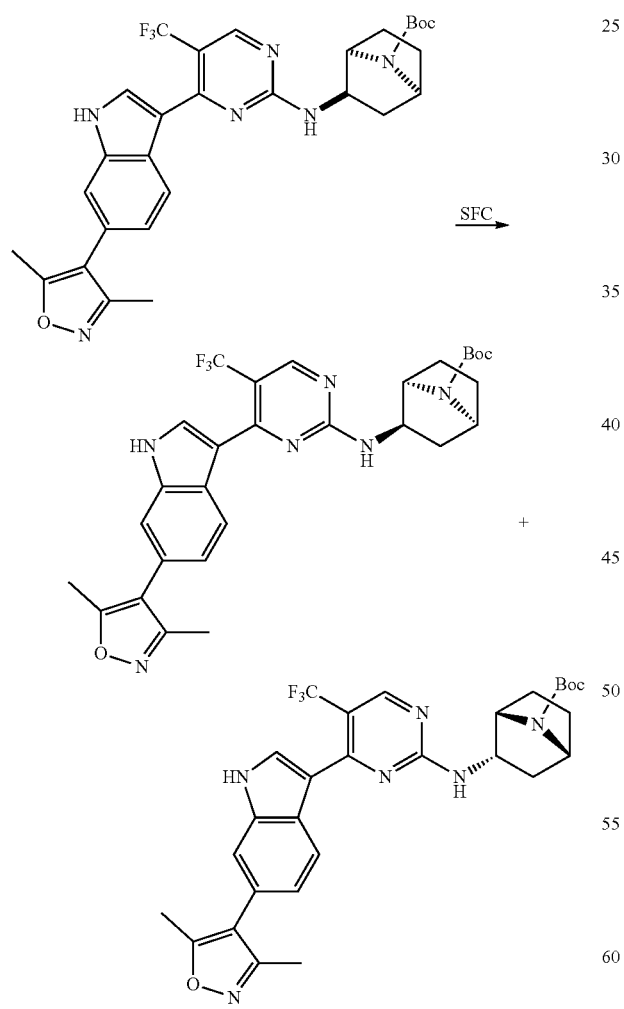

The tert-butyl 3-[[4-[6-(3,5-dimethylisoxazol-4-yl)-1H-indol-3-yl]-5-(trifluoromethyl)pyrimidin-2-yl]-amino]-7-azabicyclo-[2.2.1]-heptane-7-carboxylate (0.08 g, 140.70 μmol, 1 eq) isomers were separated by SFC (condition: column: DAICEL CHIRALPAK AD-H (250 mm*30 mm, 5 um); mobile phase: 0.1% $NH_3H_2O$ EtOH] B %: 30%-30%, 7 min) to afford the Compound 137 (25 mg) as a yellow oil and Compound 138 (30 mg) as a yellow oil. (Note: The absolute stereochemistry was assigned based on biochemical activity in analogy to other compounds in this series)

Step 5: (1S,2S,4R)—N-[4-[6-(3,5-dimethylisoxazol-4-yl)-1H-indol-3-yl]-5-(trifluoromethyl)pyrimidin-2-yl]-7-azabicyclo-[2.2.1]-heptan-3-amine

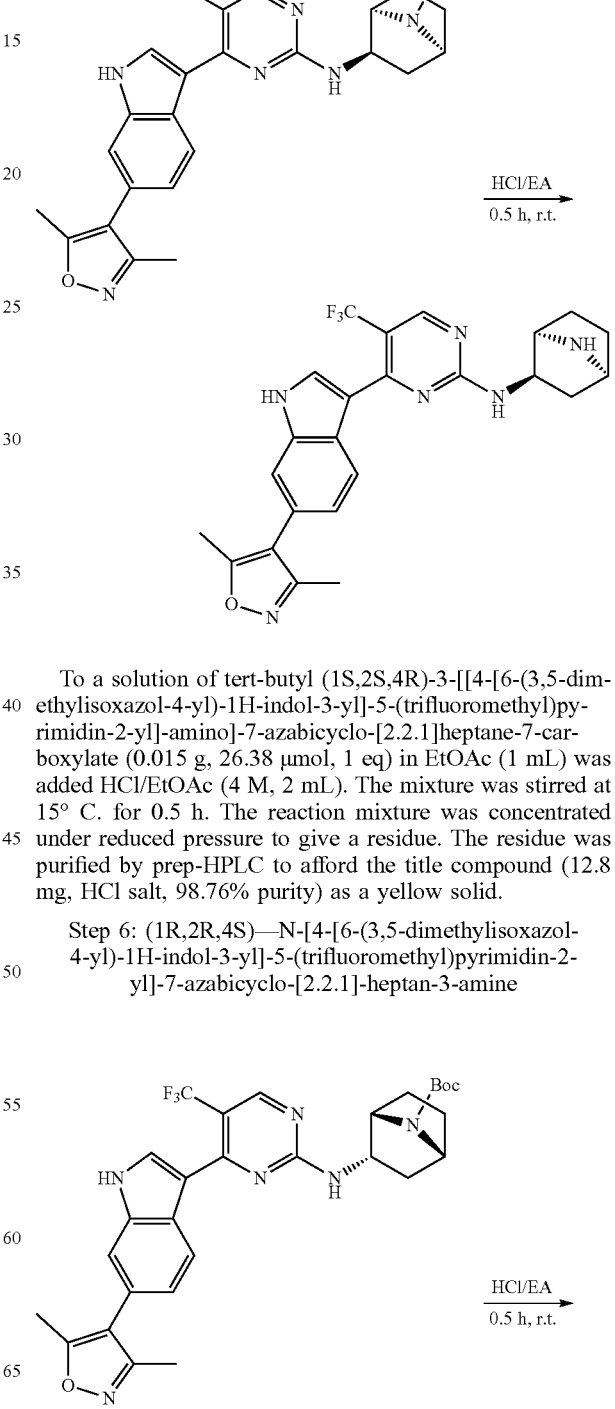

To a solution of tert-butyl (1S,2S,4R)-3-[[4-[6-(3,5-dimethylisoxazol-4-yl)-1H-indol-3-yl]-5-(trifluoromethyl)pyrimidin-2-yl]-amino]-7-azabicyclo-[2.2.1]heptane-7-carboxylate (0.015 g, 26.38 μmol, 1 eq) in EtOAc (1 mL) was added HCl/EtOAc (4 M, 2 mL). The mixture was stirred at 15° C. for 0.5 h. The reaction mixture was concentrated under reduced pressure to give a residue. The residue was purified by prep-HPLC to afford the title compound (12.8 mg, HCl salt, 98.76% purity) as a yellow solid.

Step 6: (1R,2R,4S)—N-[4-[6-(3,5-dimethylisoxazol-4-yl)-1H-indol-3-yl]-5-(trifluoromethyl)pyrimidin-2-yl]-7-azabicyclo-[2.2.1]-heptan-3-amine -continued

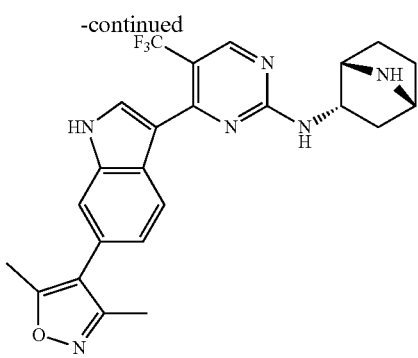

To a solution of tert-butyl (1R,2R,4S)-3-[[4-[6-(3,5-dimethylisoxazol-4-yl)-1H-indol-3-yl]-5-(trifluoromethyl)pyrimidin-2-yl]-amino]-7-azabicyclo-[2.2.1]-heptane-7-carboxylate (0.02 g, 35.17 μmol, 1 eq) in EtOAc (0.2 mL) was added HCl/EtOAc (4 M, 2 mL). The mixture was stirred at 15° C. for 0.5 h. The reaction mixture was concentrated under reduced pressure to give a residue. The residue was purified by prep-HPLC to afford the title compound (12.1 mg, HCl salt, 99.20% purity) as a yellow solid. The reaction was combined with another reaction in 10 mg scale for purification.

Example 14. 3-(2-[[(+/−)-exo-7-azabicyclo[2.2.1]heptan-2-yl]amino]-5-(trifluoromethyl)pyrimidin-4-yl)-1H-indole-6-carbonitrile (Compound 106), 3-[2-[[(1R,2R,4S)-7-azabicyclo[2.2.1]heptan-3-yl]amino]-5-(trifluoromethyl)pyrimidin-4-yl]-1H-indole-6-carbonitrile (Compound 115) and 3-[2-[[(1S,2S,4R)-7-azabicyclo[2.2.1]heptan-3-yl]-amino]-5-(trifluoromethyl)pyrimidin-4-yl]-1H-indole-6-carbonitrile (Compound 114)

Step 1: 3-[2-][[(+/−)-exo-7-azabicyclo[2.2.1]heptan-2-yl]amino)-5-(trifluoromethyl)pyrimidin-4-yl]-1H-indole-6-carbonitrile

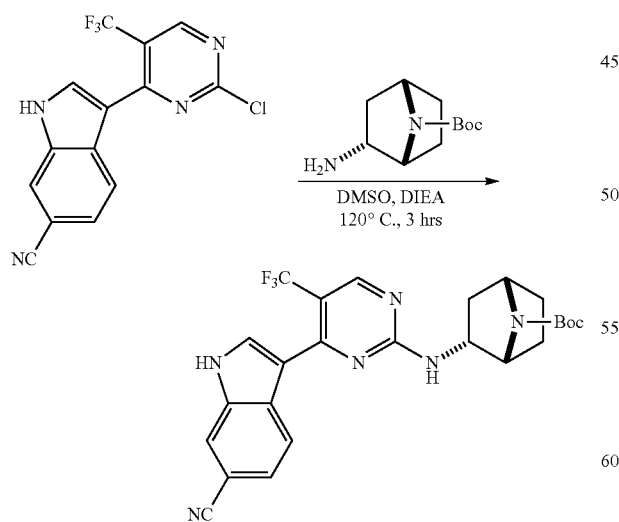

3-(2-chloro-5-(trifluoromethyl)pyrimidin-4-yl)-1H-indole-6-carbonitrile (130 mg, 1.0 eq) were dissolved in DMSO (dimethylsulfoxide; 3 ml) in a 40 ml vial. DIEA (62.48 mg, 0.485 umol, 1.2 eq) and (1R,2R,4S)-tert-butyl 2-amino-7-azabicyclo[2.2.1]heptane-7-carboxylate (85.71 mg, 0.404 umol, 1.0 eq) were added to the above vial. The resulting mixtures were shaken at 120° C. for 3 hrs. The reaction mixtures were purified directly by pre-HPLC to give the title compound (77.60 mg).

Step 2: 3-[2-[[(+/−)-exo-7-azabicyclo[2.2.1]heptan-2-yl]amino]-5-(trifluoromethyl) pyrimidin-4-yl]-1H-indole-6-carbonitrile

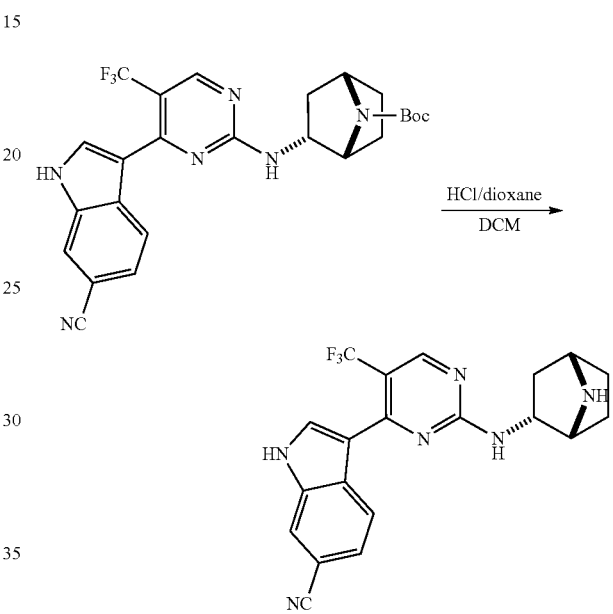

3-[2-[ ](+/−)-exo-7-azabicyclo[2.2.1]heptan-2-yl]amino]-5-(trifluoromethyl)pyrimidin-4-yl]-1H-indole-6-carbonitrile (77.60 mg, 155.67 umol, 1 eq) was dissolved in DCM (0.5 mL) in 40 ml vials. HCl/dioxane (2 mL) was added. The mixtures were shaken at 25° C. for 1 hr to give the title compound (72.15 mg, HCl, 98.24% purity).

Step 3: 3-[2-[[(1R,2R,4S)-7-azabicyclo[2.2.1]heptan-3-yl]amino]-5-(trifluoromethyl)pyrimidin-4-yl]-1H-indole-6-carbonitrile and 3-[2-[[(1S,2S,4R)-7-azabicyclo[2.2.1]heptan-3-yl]-amino]-5-(trifluoromethyl)pyrimidin-4-yl]-1H-indole-6-carbonitrile

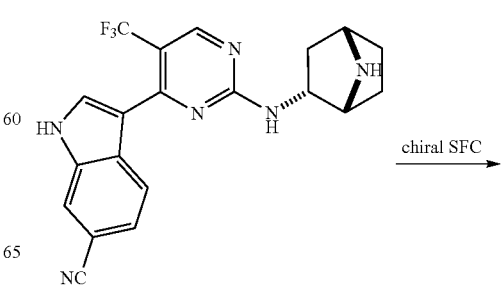

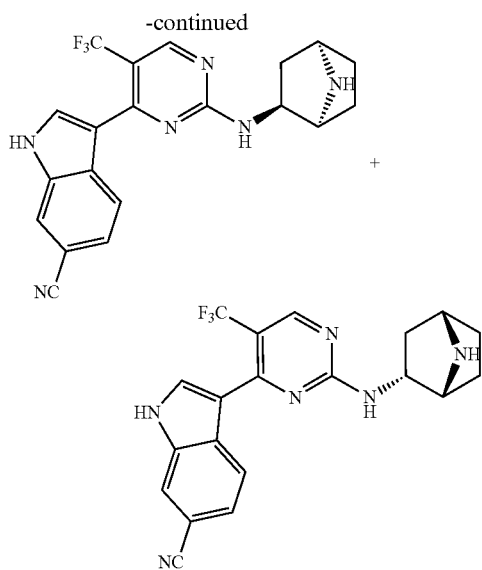

3-(2-(((+/−)-exo-7-azabicyclo[2.2.1]heptan-2-yl)amino)-5-(trifluoromethyl)pyrimidin-4-yl)-1H-indole-6-carbonitrile (65 mg, 149.48 μmol, 1 eq, HCl) was separated by SFC (method: column: AD (250 mm×30 mm, 5 um); mobile phase: [0.1% NH$_3$H$_2$O ETOH]; B %: 30%-30%, 5 min) to afford the title compound P1 (Rt=0.92 min, 14.6 mg, 35.89 μmol, 24.01% yield, 97.94% purity) as white solid and P2 (Rt=1.01 min, 30 mg). P2 peak was further separated by SFC (method: column: AD (250 mm×30 mm, 5 um); mobile phase: -[0.1% NH$_3$H$_2$O ETOH]; B %: 30%-30%, 6 min) to afford the title pure compound P2 (Rt=3.152, 18.9 mg, 45.17 μmol, 30.22% yield, 95.21% purity) as white solid. The absolute stereochemistries of P1 and P2 were assigned based on biochemical activity in analogy to other compounds in this series.

Example 15. (3S)—N-[4-[6-(3,5-dimethylisoxazol-4-yl)-1H-pyrrolo[2,3-b]pyridin-3-yl]-5-(trifluoromethyl)pyrimidin-2-yl]-1-azabicyclo[3.2.2]nonan-3-amine (Compound 141)

Step 1: 1-azabicyclo [3.2.2] nonan-3-one oxime

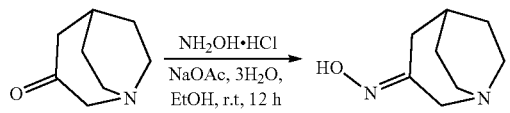

To a solution of 1-azabicyclo [3.2.2] nonan-3-one (0.4 g, 2.87 mmol, 1 eq) and NH$_2$OH·HCl (239.63 mg, 3.45 mmol, 1.2 eq) in EtOH (8 mL) was added NH$_2$OH·HCl (239.63 mg, 3.45 mmol, 1.2 eq) and sodium acetate trihydrate (782.10 mg, 5.75 mmol, 782.10 uL, 2 eq). The mixture was stirred at 15° C. for 12 h. The solution was filtered and the filtrate was concentrated in vacuum to afford the title compound (0.83 g, crude) as a yellow solid and used directly.

Step 2: 1-azabicyclo [3.2.2] nonan-3-amine

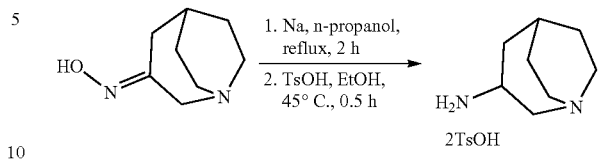

To a solution of 1-azabicyclo [3.2.2] nonan-3-one oxime (0.83 g, 5.38 mmol, 1 eq) in propan-1-ol (60 mL) was added Na (4.58 g, 199.15 mmol, 4.72 mL, 37 eq) in small portions over 0.5 h. The mixture was stirred at 100° C. for 2 h. It was cooled to 15° C., brine (200 mL) was added and extracted with propan-1-ol (50 mL×4). The combined organic phase was dried over anhydrous Na$_2$SO$_4$, filtered and concentrated in vacuum. The residue was dissolved into CHCl$_3$ (30 mL), filtered and the filtrate was concentrated in vacuum to give 800 mg of crude product. Then to a stirred solution of the 800 mg (crude product) in EtOH (10 mL) was added TsOH·H$_2$O (1.02 g, 5.38 mmol, 1 eq), and the mixture was stirred at 45° C. for 0.5 h. The reaction mixture was concentrated in vacuum. The residue was dissolved into water (5 mL) and lyophilized to afford the title compound (1 g, crude, TsOH) as a brown solid and used directly.

Step 3: (3S)—N-[4-[1-(benzenesulfonyl)-6-(3,5-dimethylisoxazol-4-yl)pyrrolo[2,3-b]pyridine-3-yl]-5-(trifluoromethyl)pyrimidin-2-yl]-1-azabicyclo[3.2.2]nonan-3-amine & (3R)—N-[4-[1-(benzenesulfonyl)-6-(3,5-dimethylisoxazol-4-yl)pyrrolo[2,3-b]pyridin-3-yl]-5-(trifluoromethyl)pyrimidin-2-yl]-1-azabicyclo[3.2.2]nonan-3-amine

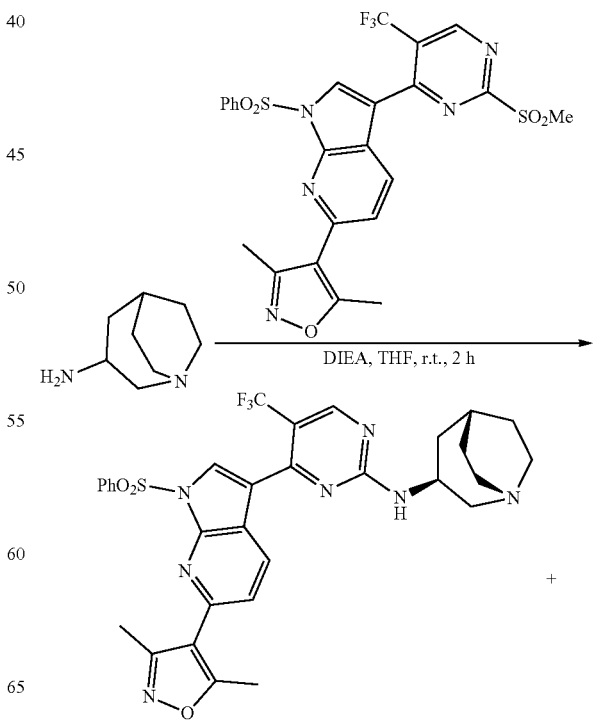

-continued

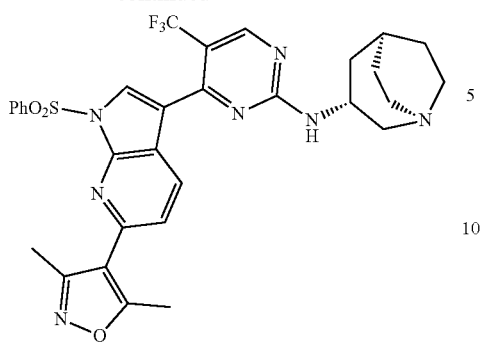

To a solution of 4-[1-(benzenesulfonyl)-3-[2-methylsulfonyl-5-(trifluoromethyl) pyrimidin-4-yl]pyrrolo[2,3-b]pyridin-6-yl]-3,5-dimethyl-isoxazole (0.25 g, 432.86 umol, 1 eq) and 1-azabicyclo[3.2.2]nonan-3-amine (946.66 mg, 3.03 mmol, 7 eq, TsOH) in THF (10 mL) was added DIEA (839.16 mg, 6.49 mmol, 1.13 mL, 15 eq). The mixture was stirred at 15° C. under N₂ for 2 h. The reaction mixture was poured into water (10 mL). The aqueous phase was extracted with EtOAc (15 mL×3). The combined organic phase was dried over anhydrous Na₂SO₄, filtered and concentrated in vacuum. The residue was purified by silica gel chromatography (100-200 mesh silica gel, PE/EtOAc=1/1, 0/1, contained 1% NH₄OH) to give a racemate compound (0.19 g) as a brown solid and separated by SFC (column: DAICEL CHIRALPAK AD-H (250 mm*30 mm, 5 um); mobile phase: [0.1% NH₃H₂O EtOH]; B %: 40%-40%, 6 min) to afford the title compound 1 (peak 1, RT=3.469 min, 0.1 g, 134.87 umol, 31.16% yield, 86% purity) and title compound 2 (peak 2, 60 mg, 89.39 umol, 20.65% yield, 95% purity), both as yellow solids. (Note: The reaction was combined with another reaction in 150 mg scale for work up.)

Step 4: (3S)—N-[4-[6-(3,5-dimethylisoxazol-4-yl)-1H-pyrrolo[2,3-b]pyridin-3-yl]-5-(trifluoromethyl) pyrimidin-2-yl]-1-azabicyclo[3.2.2]nonan-3-amine

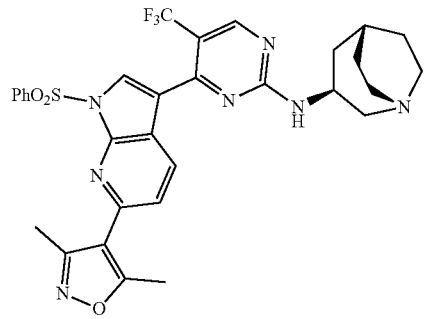

To a solution of (3S)—N-[4-[1-(benzenesulfonyl)-6-(3,5-dimethylisoxazol-4-yl)pyrrolo [2,3-b]pyridin-3-yl]-5-(trifluoromethyl)pyrimidin-2-yl]-1-azabicyclo[3.2.2]nonan-3-amine (80 mg, 125.46 umol, 1 eq) in dioxane (1 mL) was added NaOH (2 M, 627.28 uL, 10 eq). The mixture was stirred at 90° C. for 2 h, cooled to 15° C., and poured into water (10 mL). The aqueous phase was extracted with EtOAc (15 mL×3). The combined organic phase was dried over anhydrous Na₂SO₄, filtered and concentrated in vacuum. The residue was purified by prep-HPLC (HCl) to afford 20 mg crude product which contained impurity with MS=512. Then it was purified by prep-HPLC (neutral) to afford the title compound (7.5 mg, 99% purity) as a white solid. (Note: The reaction was combined with another reaction in 10 mg scale for purification.)

Example 16. (3R)—N-[4-[1-(benzenesulfonyl)-6-(3, 5-dimethylisoxazol-4-yl)pyrrolo[2,3-b]pyridin-3-yl]-5-(trifluoromethyl)pyrimidin-2-yl]-1-azabicyclo [3.2.2]nonan-3-amine (Compound 142)

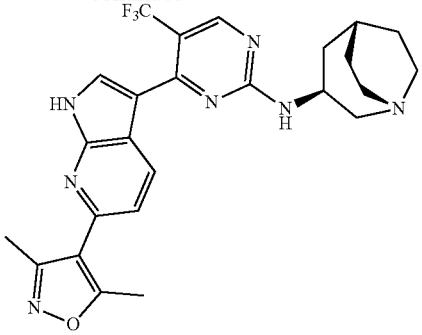

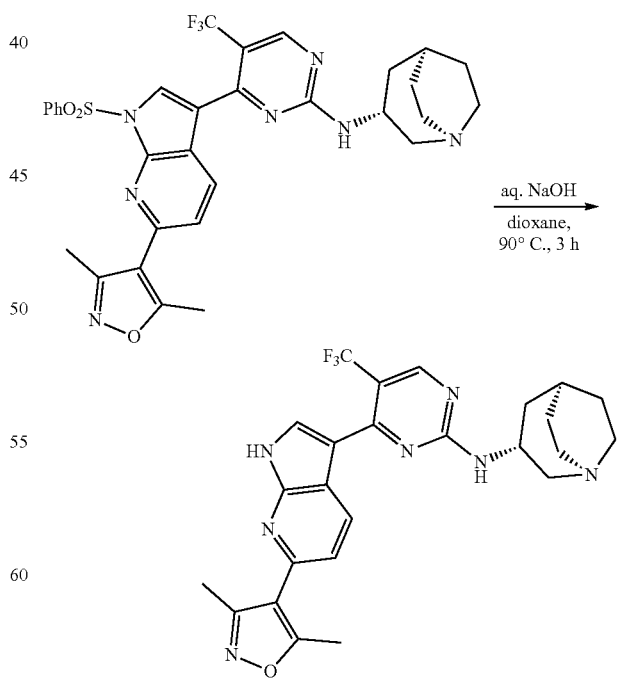

To a solution of (3R)—N-[4-[1-(benzenesulfonyl)-6-(3,5-dimethylisoxazol-4-yl)pyrrolo[2,3-b] pyridin-3-yl]-5-(trifluoromethyl)pyrimidin-2-yl]-1-azabicyclo[3.2.2]nonan-3-amine (60 mg, 94.09 umol, 1 eq) in dioxane (2 mL) was added NaOH (2 M, 470.46 uL, 10 eq). The mixture was stirred at 90° C. for 2 h. The solution was cooled to r.t. and diluted with water (15 mL). The aqueous phase was extracted with ethyl acetate (15 mL×3). The combined organic phase was dried over anhydrous Na₂SO₄, filtered and concentrated in vacuum. The residue was purified by prep-HPLC (HCl) to afford 15 mg crude product which contained impurity with MS=512. Then it was purified by prep-HPLC (neutral) to afford the title compound (4.9 mg, 9.75 umol, 10.36% yield, 99% purity) as a white solid.

Example 17. 4-[6-(3,5-dimethylisoxazol-4-yl)-1H-indol-3-yl]-N-[(1S,2S)-2-pyrrolidin-1-ylcyclopentyl]-5-(trifluoromethyl)pyrimidin-2-amine (Compound 143)

Step 1: (1R,2S)-2-[[4-[6-bromo-1-(2-trimethylsilylethoxymethyl)indol-3-yl]-5-(trifluoromethyl)pyrimidin-2-yl]amino]cyclopentanol

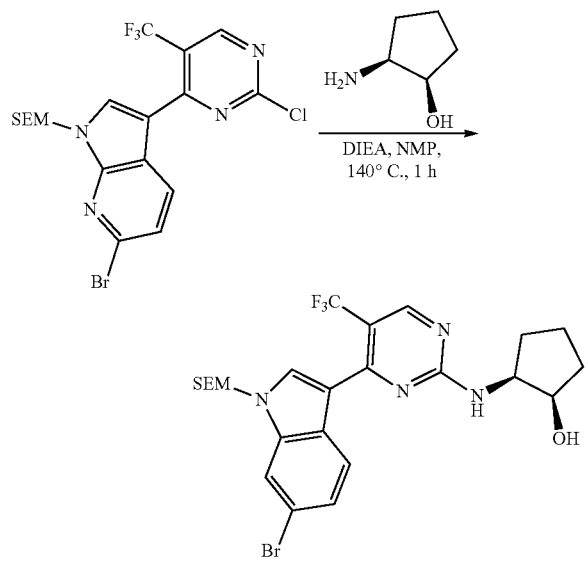

To a solution of 2-[[6-bromo-3-[2-chloro-5-(trifluoromethyl) pyrimidin-4-yl] indol-1-yl]methoxy] ethyl-trimethyl-silane (1.8 g, 3.55 mmol, 1 eq) and (1R,2S)-2-aminocyclopentanol (537.59 mg, 3.91 mmol, 1.1 eq, HCl) in NMP (15 mL) was added DIEA (1.84 g, 14.21 mmol, 2.47 mL, 4 eq). The mixture was stirred at 140° C. for 1 h then cooled to 15° C. and poured into water (100 mL). The aqueous phase was extracted with EtOAc (50 mL×3). The combined organic phase was washed with brine (50 mL×2), dried over anhydrous Na₂SO₄, filtered and concentrated in vacuum. The residue was purified by silica gel chromatography (100-200 mesh silica gel, PE/EtOAc=10/1, 1/1) to afford the title compound (2.0 g, 98% purity) as a yellow solid.

Step 2: (1R, 2S)-2-[[4-[6-(3,5-dimethylisoxazol-4-yl)-1-(2-trimethylsilylethoxymethyl) indol-3-yl]-5-(trifluoromethyl)pyrimidin-2-yl]amino]cyclopentanol

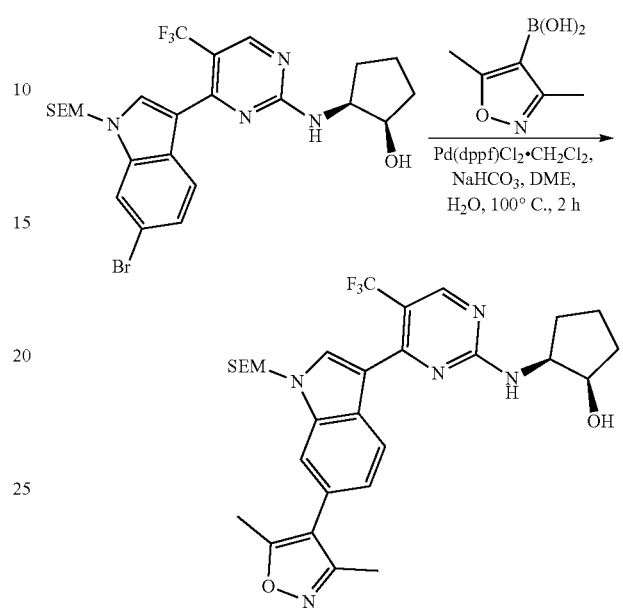

To a solution of (1R,2S)-2-[[4-[6-bromo-1-(2-trimethyl-silylethoxymethyl)indol-3-yl]-5-(trifluoromethyl)pyrimidin-2-yl]amino]cyclopentanol (0.3 g, 524.93 umol, 1 eq), (3,5-dimethylisoxazol-4-yl)boronic acid (147.96 mg, 1.05 mmol, 2 eq) in DME (10 mL) and H₂O (2 mL) was added Pd(dppf)Cl₂·CH₂Cl₂ (42.87 mg, 52.49 umol, 0.1 eq) and NaHCO₃ (132.29 mg, 1.57 mmol, 61.25 uL, 3 eq). The mixture was stirred at 100° C. for 2 h. It was cooled to 15° C. and poured into water (50 mL). The aqueous phase was extracted with EtOAc (30 mL×3). The combined organic phase was washed with brine (30 mL×2), dried over anhydrous Na₂SO₄, filtered and concentrated in vacuum. The residue was purified by silica gel chromatography (PE/EtOAc=10/1, 2/1) to afford the title compound (0.28 g, 428.79 umol, 81.68% yield, 90% purity) as a yellow solid.

Step 3: [(1R,2S)-2-[[4-[6-(3,5-dimethylisoxazol-4-yl)-1-(2-trimethylsilylethoxymethyl) indol-3-yl]-5-(trifluoromethyl) pyrimidin-2-yl] amino] cyclopentyl] methanesulfonate

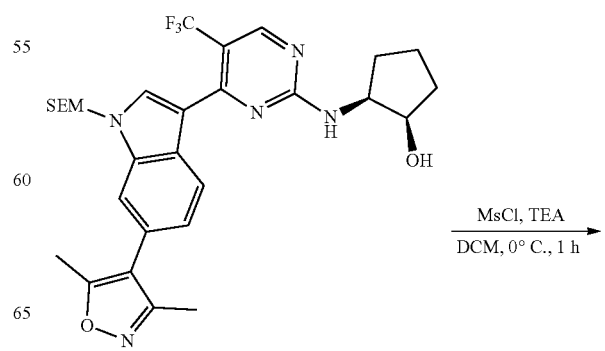

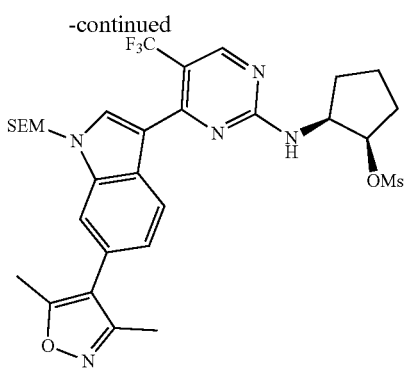

To a solution of (1R,2S)-2-[[4-[6-(3,5-dimethylisoxazol-4-yl)-1-(2-trimethylsilyl ethoxymethyl)indol-3-yl]-5-(trifluoromethyl)pyrimidin-2-yl]amino]cyclopentanol (0.28 g, 476.43 umol, 1 eq) and TEA (144.63 mg, 1.43 mmol, 198.94 uL, 3 eq) in DCM (10 mL) was added MsCl (70.95 mg, 619.36 umol, 47.94 uL, 1.3 eq) at 0° C. The mixture was stirred at 0° C. for 1 h. It was poured into water (20 mL). The aqueous phase was extracted with DCM (20 mL×2). The combined organic phase was dried over anhydrous Na₂SO₄, filtered and concentrated in vacuum. The residue was purified by silica gel chromatography (100-200 mesh silica gel, PE/EtOAc=10/1, 3/1) to afford the title compound (0.28 g, 378.49 umol, 79.44% yield, 90% purity) as a yellow solid.

Step 4: 4-[6-(3,5-dimethylisoxazol-4-yl)-1-(2-trimethylsilylethoxymethyl)indol-3-yl]-N-[(1S,2S)-2-pyrrolidin-1-ylcyclopentyl]-5-(trifluoromethyl)pyrimidin-2-amine

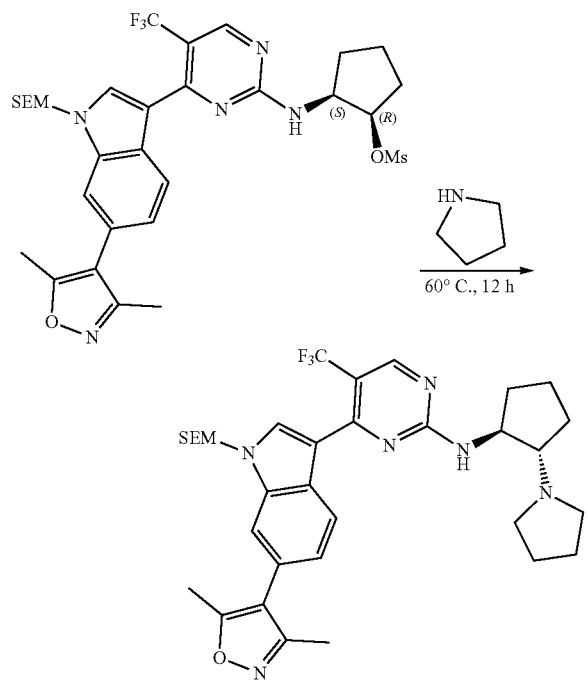

A solution of [(1R,2S)-2-[[4-[6-(3,5-dimethylisoxazol-4-yl)-1-(2-trimethylsilylethoxymethyl) indol-3-yl]-5-(trifluoromethyl)pyrimidin-2-yl]amino]cyclopentyl] methane sulfonate (0.2 g, 300.39 umol, 1 eq) and pyrrolidine (640.92 mg, 9.01 mmol, 752.25 uL, 30 eq) was stirred at 60° C. for 12 h. It was cooled to 15° C. and poured into water (30 mL), filtered and the filter cake was collected to afford the title compound (0.2 g, crude) as a yellow solid and used directly.

Step 5: 4-[6-(3,5-dimethylisoxazol-4-yl)-1H-indol-3-yl]-N-[(1S,2S)-2-pyrrolidin-1-ylcyclopentyl]-5-(trifluoromethyl)pyrimidin-2-amine

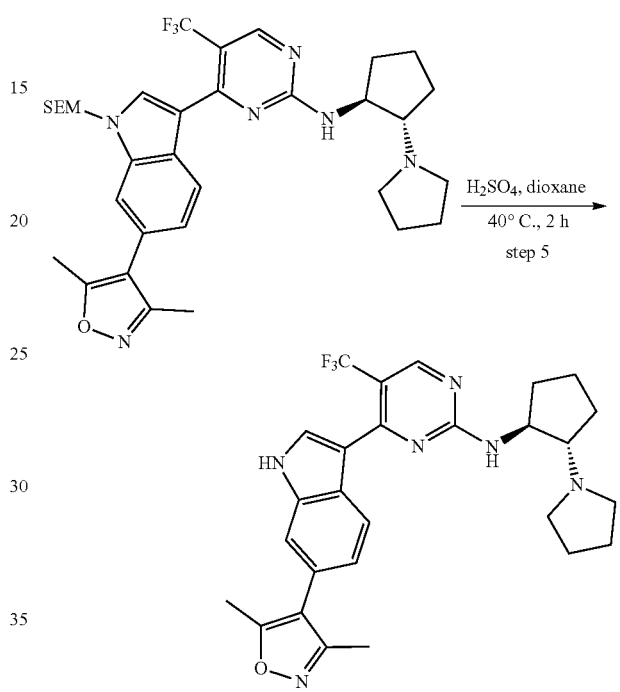

To a solution of 4-[6-(3,5-dimethylisoxazol-4-yl)-1-(2-trimethylsilylethoxymethyl) indol-3-yl]-N-[(1S,2S)-2-pyrrolidin-1-ylcyclopentyl]-5-(trifluoromethyl)pyrimidin-2-amine (0.18 g, 280.89 umol, 1 eq) in dioxane (5 mL) was added H₂SO₄ (413.24 mg, 4.21 mmol, 224.59 uL, 15 eq). The mixture was stirred at 40° C. for 2 h. It was cooled to 15° C. and adjusted pH to 10 with NaOH (2M), extracted with EtOAc (20 mL×3). The combined organic phase was dried over anhydrous Na₂SO₄, filtered and concentrated in vacuum to afford a mixture of 4-[6-(3,5-dimethylisoxazol-4-yl)-1H-indol-3-yl]-N-[(1S,2S)-2-pyrrolidin-1-ylcyclopentyl]-5-(trifluoromethyl)pyrimidin-2-amine; and [6-(3,5-dimethylisoxazol-4-yl)-3-[2-[[(1S,2S)-2-pyrrolidin-1-ylcyclopentyl]amino]-5-(trifluoromethyl)pyrimidin-4-yl]indol-1-yl]methanol (0.14 g, crude) as a yellow solid and used directly. It was dissolved into DCM (8 mL), and then ethane-1,2-diamine (77.91 mg, 1.30 mmol, 86.75 uL, 5 eq) was added. The mixture was stirred at 15° C. for 3 h. It was diluted with water (20 mL), the aqueous phase was extracted with EtOAc (15 mL×3). The combined organic phase was washed with brine (15 mL×2), dried over anhydrous Na₂SO₄, filtered and concentrated in vacuum. The residue was purified by prep-HPLC (Basicity) to afford the title compound (29.4 mg, 56.43 umol, 21.77% yield, 98% purity) as a white solid.

Example 18. 4-[6-(3, 5-dimethylisoxazol-4-yl)-1H-pyrrolo[2, 3-b]pyridin-3-yl]-N-[(1S)-2-pyrrolidin-1-ylcyclopentyl]-5-(trifluoromethyl) pyrimidin-2-amine (Compound 144)

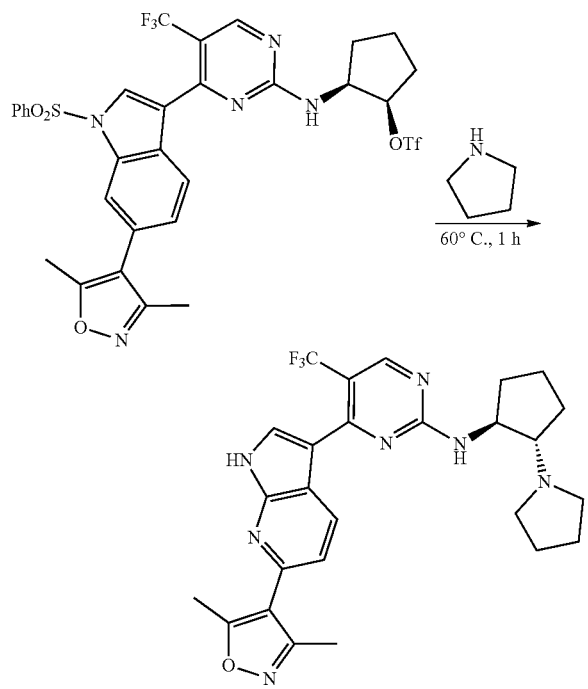

A solution of [(1R, 2S)-2-[[4-[1-(benzenesulfonyl)-6-(3, 5-dimethylisoxazol-4-yl) pyrrolo[2, 3-b] pyridin-3-yl]-5-(trifluoromethyl) pyrimidin-2-yl] amino] cyclopentyl]methanesulfonate (90 mg, 133.00 umol, 1 eq) in pyrrolidine (852.00 mg, 11.98 mmol, 1 mL, 90.07 eq) was stirred at 60° C. for 1 h. The resulting solution was concentrated under reduced pressure to remove pyrrolidine to give a residue. It was purified by prep-HPLC (FA condition) to afford the title compound (22.4 mg, FA, 99% purity) as white solid. (Note: The reaction was combined with another reaction in 50 mg scale for work-up and purification.)

Example 19. N-[(1S, 2S)-2-(azetidin-1-yl) cyclopentyl]-4-[6-(3, 5-dimethylisoxazol-4-yl)-1H-pyrrolo [2, 3-b] pyridin-3-yl]-5-(trifluoromethyl) pyrimidin-2-amine (Compound 145)

Step 1: (1R, 2S)-2-[[4-[1-(benzenesulfonyl)-6-(3, 5-dimethylisoxazol-4-yl) pyrrolo[2, 3-b] pyridin-3-yl]-5-(trifluoromethyl) pyrimidin-2-yl] amino] cyclopentanol

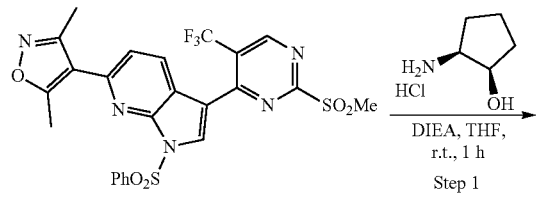

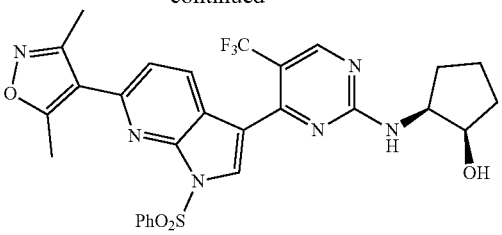

To a solution of 4-[1-(benzenesulfonyl)-3-[2-methylsulfonyl-5-(trifluoromethyl) pyrimidin-4-yl]pyrrolo[2,3-b] pyridin-6-yl]-3, 5-dimethyl-isoxazole (1.4 g, 2.42 mmol, 1 eq) in THF (14 mL) was added DIPEA (1.57 g, 12.12 mmol, 2.11 mL, 5 eq) and (1R,2S)-2-aminocyclopentanol; hydrochloride (400.27 mg, 2.91 mmol, 1.2 eq). The mixture was stirred at 15° C. for 1 h. The resulting solution was concentrated under reduced pressure to remove THF. The residue was diluted with H$_2$O (45 mL) and extracted with EtOAc (15 mL×3). The combined organic layers were washed with brine (60 mL), dried over Na$_2$SO$_4$, filtered and concentrated under reduced pressure to give a residue. It was purified by column chromatography (SiO$_2$, PE/EtOAc=5/1 to 1/1) to afford the title compound (880 mg, 88% purity) as yellow solid. (Note: The reaction was combined with another reaction in 200 mg scale for work up.)

Step 2: [(1R, 2S)-2-[[4-[1-(benzenesulfonyl)-6-(3, 5-dimethylisoxazol-4-yl) pyrrolo [2, 3-b] pyridin-3-yl]-5-(trifluoromethyl) pyrimidin-2-yl] amino] cyclopentyl]methanesulfonate

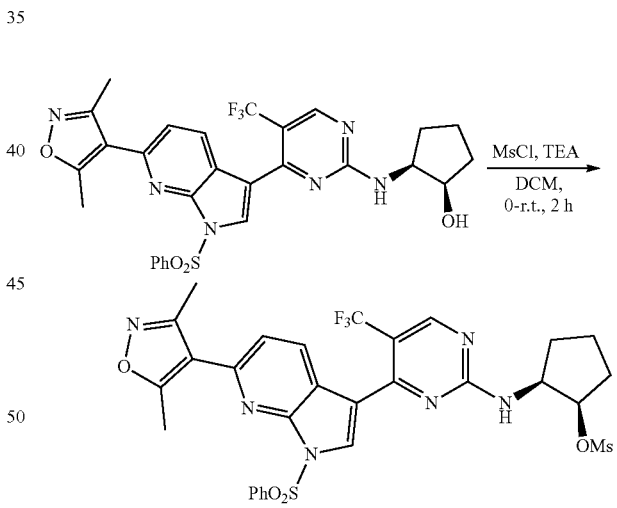

A mixture of (1R,2S)-2-[[4-[1-(benzenesulfonyl)-6-(3,5-dimethylisoxazol-4-yl) pyrrolo [2,3-b]pyridin-3-yl]-5-(trifluoromethyl) pyrimidin-2-yl]amino]cyclopentanol (150 mg, 250.59 umol, 1 eq) and TEA (63.39 mg, 626.47 umol, 87.20 uL, 2.5 eq) in DCM (1.5 mL) was added MsCl (34.45 mg, 300.70 umol, 23.27 uL, 1.2 eq) at 0° C. The mixture was stirred at 15° C. for 1 h. The resulting solution was quenched by addition water (15 mL), and extracted with EtOAc (5 mL×3).

The combined organic layers were washed with brine (15 mL), dried over Na$_2$SO$_4$, filtered and concentrated under reduced pressure to give a residue. It was purified by column chromatography (SiO₂, PE/EtOAc=3/1 to 1/1) to afford the title compound (110 mg, 149.55 umol, 59.68% yield, 92% purity) as yellow solid.

Step 3: (1S, 2S)—N1-[4-[6-(3, 5-dimethylisoxazol-4-yl)-1H-pyrrolo [2, 3-b] pyridin-3-yl]-5-(trifluoromethyl) pyrimidin-2-yl]-N2-ethyl-cyclopentane-1, 2-diamine

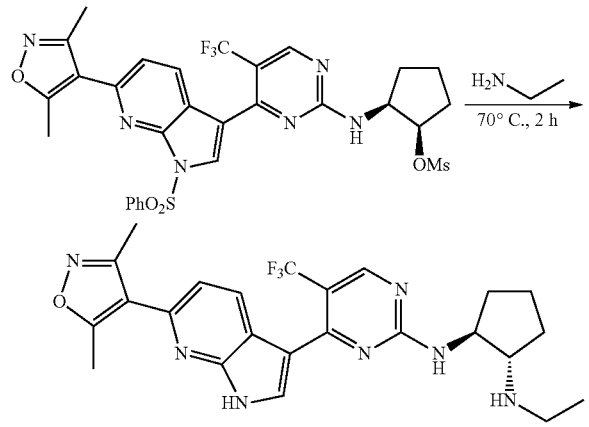

[(1R,2S)-2-[[4-[1-(benzenesulfonyl)-6-(3,5-dimethylisoxazol-4-yl)pyrrolo[2,3-b] pyridin-3-yl]-5-(trifluoromethyl)pyrimidin-2-yl] amino]cyclopentyl]methanesulfonate (150 mg, 221.67 umol, 1 eq), ethanamine (2 M, 3 mL, 27.07 eq) were taken up into a sealed tube. The sealed tube was heated at 70° C. for 2 h under microwave. LCMS (liquid chromatography mass spectrometry) showed the material did not convert completely so the sealed tube was heated at 100° C. for another 7 h under microwave. The resulting mixture was concentrated under reduced pressure to give a residue. It was purified by prep-HPLC (PA condition) to afford the title compound (4.1 mg, 7.56 umol, 3.41% yield, 98% purity, PA) as a white solid.

Example 20. N-[(1S, 2S)-2-(azetidin-1-yl) cyclopentyl]-4-[6-(3, 5-dimethylisoxazol-4-yl)-1H-pyrrolo [2, 3-b]pyridin-3-yl]-5-(trifluoromethyl) pyrimidin-2-amine (Compound 146)

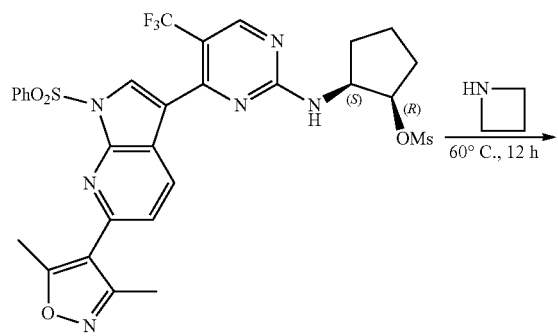

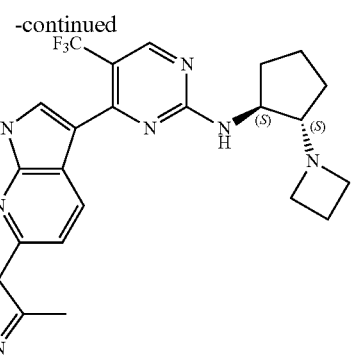

A solution of [(1R,2S)-2-[[4-[1-(benzenesulfonyl)-6-(3,5-dimethylisoxazol-4-yl) pyrrolo[2,3-b]pyridin-3-yl]-5-(trifluoromethyl)pyrimidin-2-yl]amino]cyclopentyl]methanesulfonate (90 mg, 133.00 umol, 1 eq) in azetidine (761.29 mg, 13.33 mmol, 899.87 uL, 100.25 eq) was stirred at 60° C. for 12 h. The resulting solution was concentrated under reduced pressure to give a residue. It was purified by prep-HPLC (FA condition) to afford the title compound (26.2 mg, FA, 98% purity) as white solid.

(Note: The reaction was combined with another reaction in 10 mg scale for work up)

Example 21. (1S, 2S)—N2-(2, 2-difluoroethyl)-N1-[4-[6-(3, 5-dimethylisoxazol-4-yl)-1H-pyrrolo[2, 3-b] pyridin-3-yl]-5-(trifluoromethyl) pyrimidin-2-yl] cyclopentane-1, 2-diamine (Compound 147)

Step 1: (1S, 2S)—N1-[4-[1-(benzenesulfonyl)-6-(3, 5-dimethylisoxazol-4-yl) pyrrolo [2, 3-b]pyridin-3-yl]-5-(trifluoromethyl) pyrimidin-2-yl]-N2-(2, 2-difluoroethyl) cyclopentane-1, 2-diamine

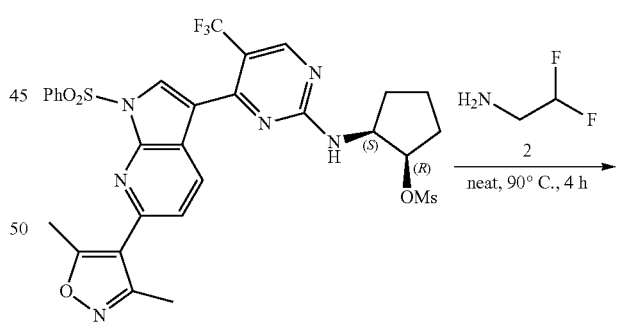

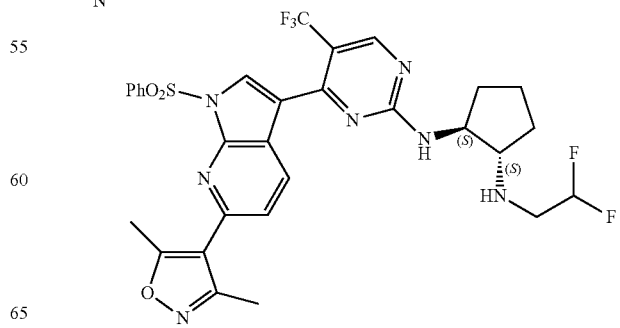

A solution of [(1R, 2S)-2-[[4-[1-(benzenesulfonyl)-6-(3, 5-dimethylisoxazol-4-yl) pyrrolo[2, 3-b] pyridin-3-yl]-5-(trifluoromethyl) pyrimidin-2-yl] amino] cyclopentyl] methanesulfonate (80 mg, 95.76 umol, 1 eq) in 2, 2-difluoroethanamine (1.77 g, 21.84 mmol, 1.5 mL, 228.02 eq) was stirred at 90° C. for 4 h. The solution was concentrated under reduced pressure to afford the title compound (90 mg, crude) as a brown solid that was used directly in the next step without purification.

Step 2: (1S, 2S)—N2-(2, 2-difluoroethyl)-N1-[4-[6-(3, 5-dimethylisoxazol-4-yl)-1H-pyrrolo [2, 3-b] pyridin-3-yl]-5-(trifluoromethyl) pyrimidin-2-yl] cyclopentane-1, 2-diamine

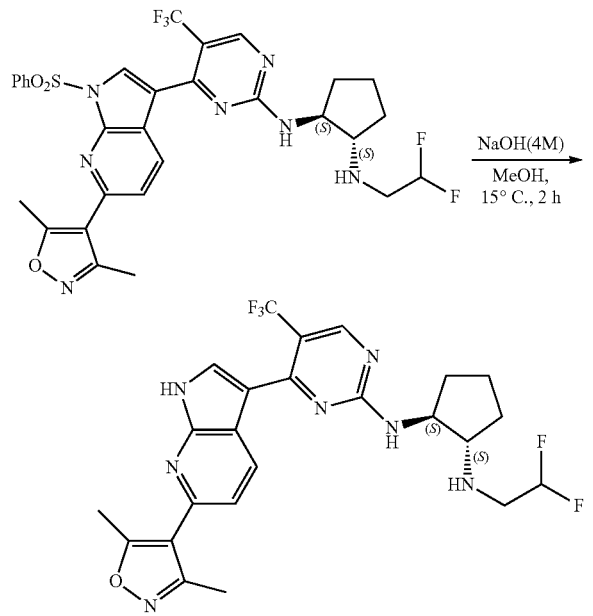

To a solution of (1S, 2S)—N1-[4-[1-(benzenesulfonyl)-6-(3, 5-dimethylisoxazol-4-yl) pyrrolo[2, 3-b] pyridin-3-yl]-5-(trifluoromethyl) pyrimidin-2-yl]-N2-(2, 2-difluoroethyl) cyclopentane-1, 2-diamine (90 mg, 136.02 umol, 1 eq) in MeOH (5 mL) was added NaOH (4 M, 1.80 mL, 52.93 eq). The mixture was stirred at 15° C. for 2 h. It was concentrated under reduced pressure to remove MeOH. The residue was diluted with water (50 mL) and extracted with EtOAc (25 mL×2). The combined organic layers were washed with brine (50 mL), dried over $Na_2SO_4$, filtered and concentrated under reduced pressure to give a residue. It was purified by prep-HPLC (FA condition) to afford the title compound (22.5 mg, FA, 91% purity, 100% ee value) as a white solid. (Note: The reaction was combined with another reaction in 5 mg scale for work up.)

Example 22. 4-[6-(3,5-dimethylisoxazol-4-yl)-1H-pyrrolo[2,3-b]pyridin-3-yl]-N-[(1S,2S)-2-[(3R)-3-fluoropyrrolidin-1-yl]cyclopentyl]-5-(trifluoromethyl)pyrimidin-2-amine (Compound 148)

Step 1: 4-[1-(benzenesulfonyl)-6-(3,5-dimethylisoxazol-4-yl)pyrrolo[2,3-b]pyridin-3-yl]-N-[(1S,2S)-2-[(3R)-3-fluoropyrrolidin-1-yl]cyclopentyl]-5-(trifluoromethyl)pyrimidin-2-amine

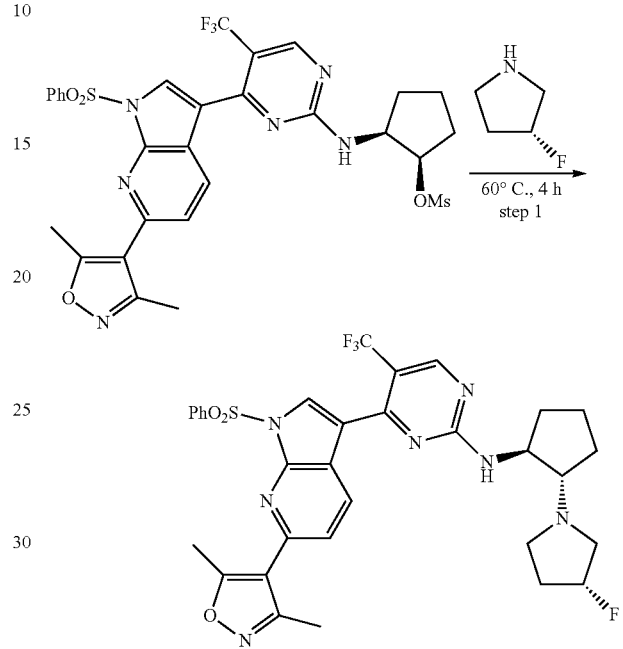

[(1R,2S)-2-[[4-[1-(benzenesulfonyl)-6-(3,5-dimethylisoxazol-4-yl)pyrrolo[2,3-b]pyridin-3-yl]-5-(trifluoromethyl)pyrimidin-2-yl]amino]cyclopentyl] methanesulfonate (80 mg, 118.22 umol, 1 eq) and (3R)-3-fluoropyrrolidine (52.67 mg, 591.10 umol, 5 eq) was stirred for 4 h at 60° C. It was cooled to the room temperature and poured into water (5 mF) and extracted with EtOAc (10 mL×3). The combined organic layer was washed with brine (10 mL×3) and sat. $NaHCO_3$ (20 mF), dried over $Na_2SO_4$, filtered and concentrated under reduced pressure to afford the title compound (60 mg, crude) as brown solid.

Step 2: 4-[6-(3,5-dimethylisoxazol-4-yl)-1H-pyrrolo[2,3-b]pyridin-3-yl]-N-[(1S,2S)-2-[(3R)-3-fluoropyrrolidin-1-yl]cyclopentyl]-5-(trifluoromethyl)pyrimidin-2-amine

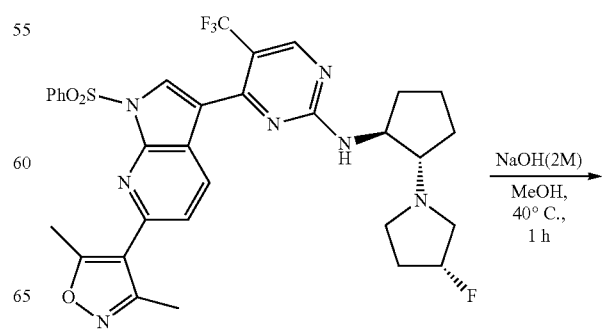

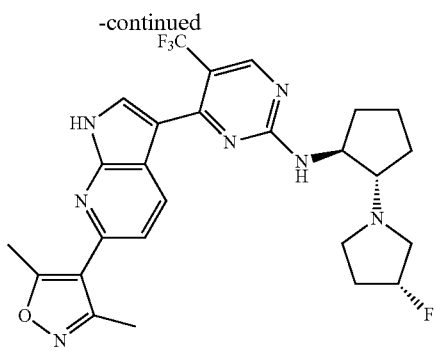

4-[1-(benzenesulfonyl)-6-(3,5-dimethylisoxazol-4-yl) pyrrolo[2,3-b]pyridin-3-yl]-N-[(1S,2S)-2-[(3R)-3-fluoropyrrolidin-1-yl]cyclopentyl]-5-(trifluoromethyl)pyrimidin-2-amine (60 mg, 89.59 umol, 1 eq) in MeOH (1 mL) was added NaOH (2 M, 223.98 uL, 5 eq). The mixture stirred for 1 h at 40° C. It was cooled to the room temperature and then poured into water (10 mL) and extracted with EtOAc (10 mL×3). The combined organic layer was washed with brine (10 mL×3), dried over Na₂SO₄, filtered. The filtrate was concentrated under reduced pressure to give a residue. It was purified by prep-HPLC (HCl condition) to afford the title compound (11.4 mg, 19.68 umol, 21.96% yield, 97.69% purity, HCl) as yellow solid.

Example 23. 4-[6-(3, 5-dimethylisoxazol-4-yl)-1H-pyrrolo[2, 3-b] pyridin-3-yl]-N-(2-pyrrolidin-1-ylcyclobutyl)-5-(trifluoromethyl) pyrimidin-2-amine (Compound 149)

Step 1: 2-[[4-[1-(benzenesulfonyl)-6-(3, 5-dimethyl-isoxazol-4-])pyrrolo [2, 3-b]pyridin-3-yl]-5-(trifluoromethyl) pyrimidin-2-yl] amino] cyclobutanol

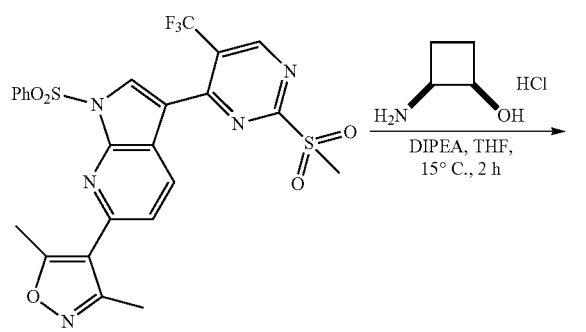

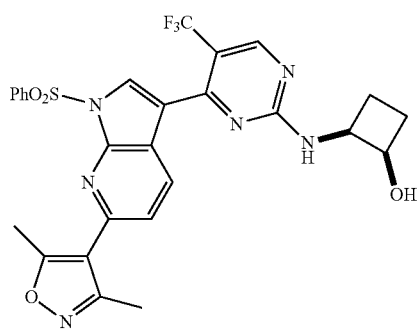

To a solution of 4-[1-(benzenesulfonyl)-3-[2-methylsulfonyl-5-(trifluoromethyl) pyrimidin-4-yl]pyrrolo [2, 3-b] pyridin-6-yl]-3, 5-dimethyl-isoxazole (0.25 g, 432.86 umol, 1 eq) in THF (2 mL) was added 2-aminocyclobutanol (64.19 mg, 519.43 umol, 1.2 eq, HCl) and DIPEA (167.83 mg, 1.30 mmol, 226.19 uL, 3 eq). The mixture was stirred at 15° C. for 2 h. It was concentrated under reduced pressure to give a residue. It was purified by column chromatography (SiO₂, PE/EtOAc=5/1 to 0/1) to afford the title compound (160 mg, 88% purity) as yellow solid. (Note: The reaction was combined with another reaction in 50 mg scale for work up.)

Step 2: [2-[[4-[1-(benzenesulfonyl)-6-(3, 5-dimethylisoxazol-4-yl) pyrrolo [2, 3-b]pyridin-3-yl]-5-(trifluoromethyl) pyrimidin-2-yl] amino] cyclobutyl] methanesulfonate

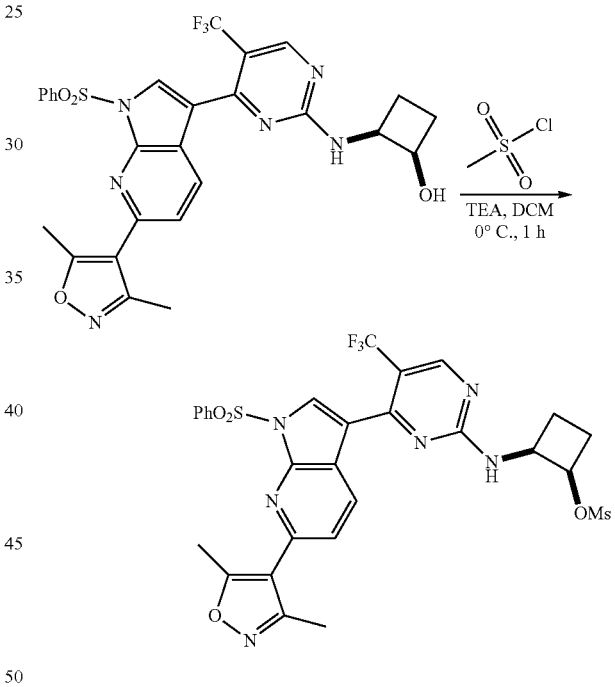

To a solution of 2-[[4-[1-(benzenesulfonyl)-6-(3, 5-dimethylisoxazol-4-yl) pyrrolo [2, 3-b]pyridin-3-yl]-5-(trifluoromethyl) pyrimidin-2-yl] amino] cyclobutanol (0.12 g, 205.28 umol, 1 eq) and TEA (62.32 mg, 615.84 umol, 85.72 uL, 3 eq) in DCM (2 mL) was added MsCl (28.22 mg, 246.34 umol, 19.07 uL, 1.2 eq) at 0° C. The mixture was stirred at 0° C. for 1 h, and concentrated under reduced pressure to give a residue that was purified by column chromatography (SiO₂, PE/EtOAc=5/1 to 1/1) to afford the title compound (180 mg) as a yellow solid. (Note: The reaction was combined with another reaction in 20 mg scale for work up.)

Step 3: 4-[6-(3, 5-dimethylisoxazol-4-yl)-1H-pyrrolo [2, 3-b] pyridin-3-yl]-N-(2-pyrrolidin-1-ylcyclobutyl)-5-(trifluoromethyl) pyrimidin-2-amine

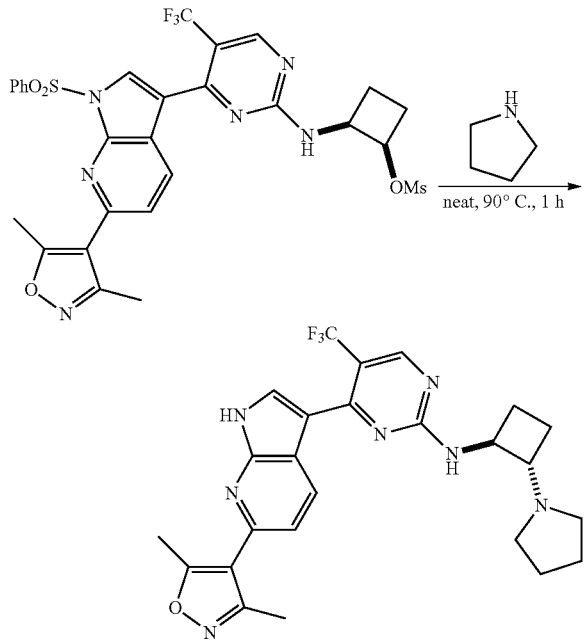

A solution of [2-[[4-[1-(benzenesulfonyl)-6-(3, 5-dimethylisoxazol-4-yl) pyrrolo [2, 3-b]pyridin-3-yl]-5-(trifluoromethyl) pyrimidin-2-yl] amino] cyclobutyl] methanesulfonate (85 mg, 128.27 umol, 1 eq) in pyrrolidine (1.70 g, 23.96 mmol, 2 mL, 186.79 eq) was stirred at 90° C. for 1 h. It was diluted with water (15 mL) and adjusted pH to 7 by added HCl (1M), then extracted with EtOAc (10 mL×2). The combined organic layers were washed with brine (20 mL), dried over $Na_2SO_4$, filtered and concentrated under reduced pressure to give a residue. The residue was purified by column chromatography (SiO₂, DCM/MeOH=20/1 to 10/1, added 1% NH₄OH) to afford a crude product, and then the crude product was purified by prep-HPLC (FA condition) to afford the title compound (12.1 mg, FA, 97.85% purity) as a white solid. (Note: The reaction was combined with another reaction in 20 mg scale for work up.)

Example 24. 4-[6-(3, 5-dimethylisoxazol-4-yl)-1H-pyrrolo[2,3-b]pyridin-3-yl]-N-[(1S,2S)-2-[(3S)-3-fluoropyrrolidin-1-yl]cyclopentyl]-5-(trifluoromethyl)pyrimidin-2-amine (Compound 150)

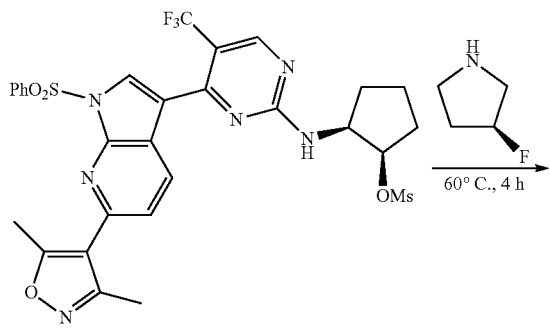

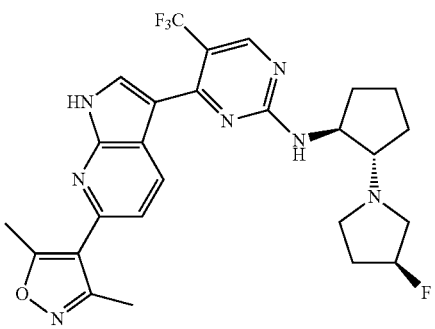

[(1R,2S)-2-[[4-[1-(benzenesulfonyl)-6-(3,5-dimethylisoxazol-4-yl) pyrrolo [2,3-b]pyridin-3-yl]-5-(trifluoromethyl) pyrimidin-2-yl] amino] cyclopentyl] methanesulfonate (80 mg, 118.22 umol, 1 eq) and (3S)-3-fluoropyrrolidine (52.68 mg, 591.12 umol, 5 eq) was stirred for 4 h at 60° C. It was cooled to the room temperature and poured into water (10 mL) and extracted with EtOAc (15 mL×3). The combined organic layer was washed with brine (15 mL×3), dried over $Na_2SO_4$ and filtered. The filtrate was concentrated under reduced pressure to give a residue. It was purified by prep-HPLC (HCl condition). The solution was lyophilized to give the desired product which is not pure enough. It was purified by prep-HPLC (HCl condition) to afford the title compound (18.4 mg, 99.44% purity, HCl) as yellow solid. (Note: The reaction was combined with another reaction in 20 mg scale for work up.)

Example 25. (1S,2S)—N1-[4-[6-(3, 5-dimethylisoxazol-4-yl)-1H-pyrrolo[2,3-b]pyridin-3-yl]-5-(trifluoromethyl)pyrimidin-2-yl]-N2-(2-fluoroethyl) cyclopentane-1, 2-diamine (Compound 151)

Step 1: Tert-butyl N-[(1S, 2S)-2-(2-fluoroethylamino) cyclopentyl] carbamate

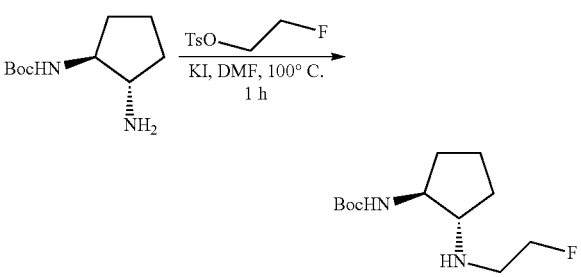

To a solution of tert-butyl N-[(1S,2S)-2-aminocyclopentyl] carbamate (0.2 g, 998.62 umol, 1 eq) in DMF (2 mL) was added KI (182.35 mg, 1.10 mmol, 1.1 eq) and 2-fluoroethyl 4-methylbenzenesulfonate (239.74 mg, 1.10 mmol, 1.1 eq). The mixture was stirred at 100° C. for 1 h then poured into aqueous LiCl (3%, 50 mL), extracted with EtOAc (30 mL×2), and the combined organic layers were washed with brine (50 mL), dried over $Na_2SO_4$, filtered and concentrated under reduced pressure to afford the title compound (250 mg, crude) as brown solid.

Step 2: Benzyl N-[(1S, 2S)-2-(tert-butoxycarbonylamino) cyclopentyl]-N-(2-fluoroethyl) carbamate

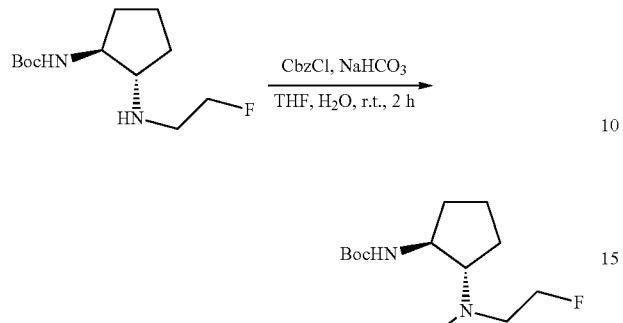

To a solution of tert-butyl N-[(1S, 2S)-2-(2-fluoroethylamino) cyclopentyl] carbamate (250.00 mg, 1.01 mmol, 1 eq) in THF (5 mL) and H₂O (1 mL) was added NaHCO₃ (170.52 mg, 2.03 mmol, 78.95 uL, 2 eq) and CbzCl (207.77 mg, 1.22 mmol, 173.14 uL, 1.2 eq). The mixture was stirred at 15° C. for 2 h. The solution was diluted with EtOAc (20 mL) and washed with brine (20 mL×2), dried over Na₂SO₄, filtered and concentrated under reduced pressure to afford the title compound (0.3 g, crude) as yellow solid which was used into the next step without further purification.

Step 3: Benzyl N-[(1S, 2S)-2-aminocyclopentyl]-N-(2-fluoroethyl) carbamate

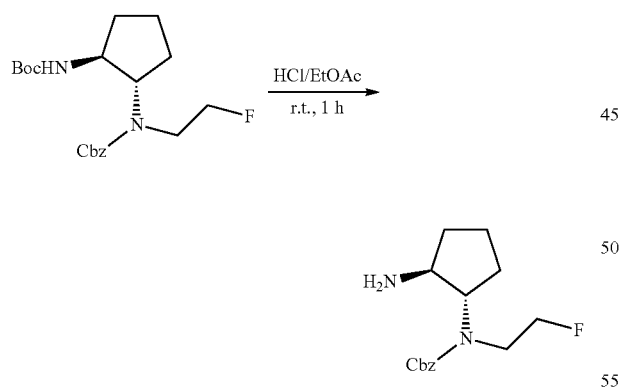

A solution of benzyl N-[(1S, 2S)-2-(tert-butoxycarbonylamino) cyclopentyl]-N-(2-fluoroethyl) carbamate (0.3 g, 788.53 umol, 1 eq) in HCl/EtOAc (4 M, 3 mL, 15.22 eq) was stirred at 15° C. for 0.5 h. The solution was filtered and washed by EtOAc (10 mL×3). The solid was dried under reduced pressure to afford the title compound (0.16 g, crude) as yellow solid, which was used into the next step without further purification.

Step 4: Benzyl N-[(1S, 2S)-2-[[4-[1-(benzenesulfonyl)-6-(3, 5-dimethylisoxazol-4-yl) pyrrolo [2, 3-b] pyridin-3-yl]-5-(trifluoromethyl) pyrimidin-2-yl] amino] cyclopentyl]-N-(2-fluoroethyl) carbamate

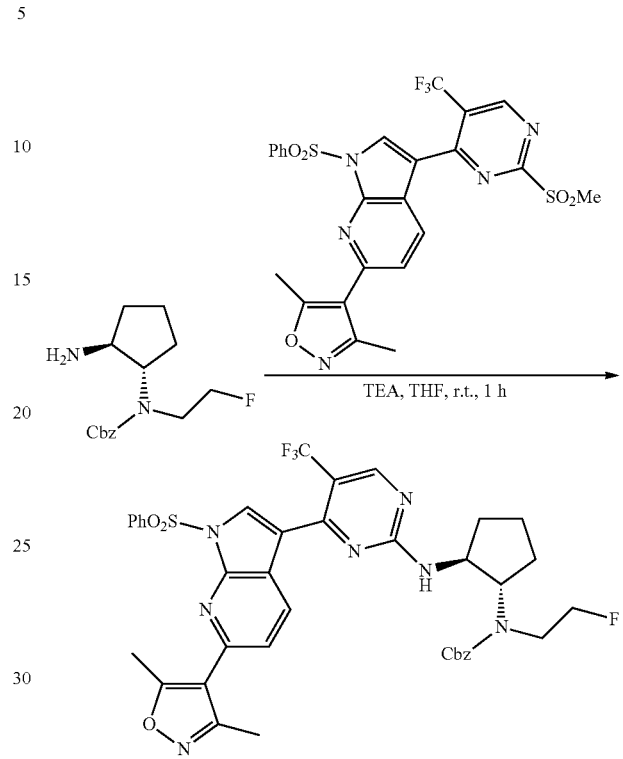

To a solution of 4-[1-(benzenesulfonyl)-3-[2-methylsulfonyl-5-(trifluoromethyl) pyrimidin-4-yl]pyrrolo [2, 3-b] pyridin-6-yl]-3, 5-dimethyl-isoxazole (0.2 g, 346.29 umol, 1 eq) in THF (4 mL) was added TEA (175.20 mg, 1.73 mmol, 241.00 uL, 5 eq) and benzyl N-[(1S, 2S)-2-aminocyclopentyl]-N-(2-fluoroethyl) carbamate (131.64 mg, 415.55 umol, 1.2 eq, HCl). The mixture was stirred at 15° C. for 1 h. The solution was concentrated under reduced pressure to give a residue. The residue was purified by column chromatography (SiO₂, PE/EtOAc=10/1 to 1/1) to afford the title compound (0.12 g, 80% purity) as yellow solid. (Note: The reaction was combined with another batch in 50 mg scale for work-up and purification.)

Step 5: Benzyl N-[(1S, 2S)-2-[[4-[6-(3, 5-dimethyl-isoxazol-4-yl)-1H-pyrrolo [2, 3-b]pyridin-3-yl]-5-(trifluoromethyl) pyrimidin-2-yl] amino] cyclopentyl]-N-(2-fluoroethyl) carbamate

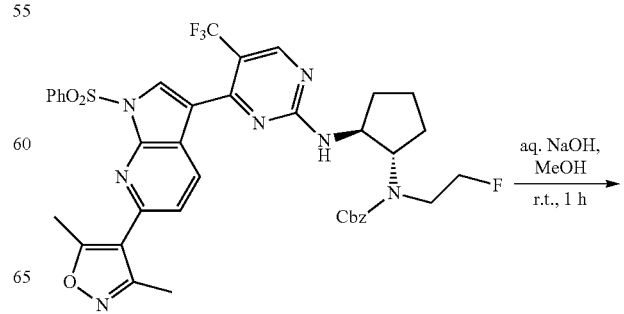

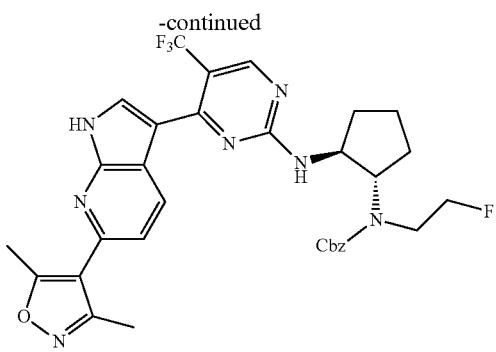

To a solution of benzyl N-[(1S,2S)-2-[[4-[1-(benzenesulfonyl)-6-(3,5-dimethylisoxazol-4-yl) pyrrolo [2,3-b] pyridin-3-yl]-5-(trifluoromethyl) pyrimidin-2-yl] amino] cyclopentyl]-N-(2-fluoroethyl) carbamate (0.1 g, 128.57 umol, 1 eq) in MeOH (5 mL) was added NaOH (2 M, 2.50 mL, 38.89 eq). The mixture was stirred at 15° C. for 1 h. The solution was concentrated under reduced pressure to afford the title compound (80 mg, crude) as yellow solid which was into the next step without further purification. (Note: The reaction mixture was combined with another batch in 20 mg scale for worked up and purification.)

Step 6: (1S, 2S)—N1-[4-[6-(3, 5-dimethylisoxazol-4-yl)-1H-pyrrolo [2, 3-b]pyridin-3-yl]-5-(trifluoromethyl) pyrimidin-2-yl]-N2-(2-fluoroethyl) cyclopentane-1, 2-diamine

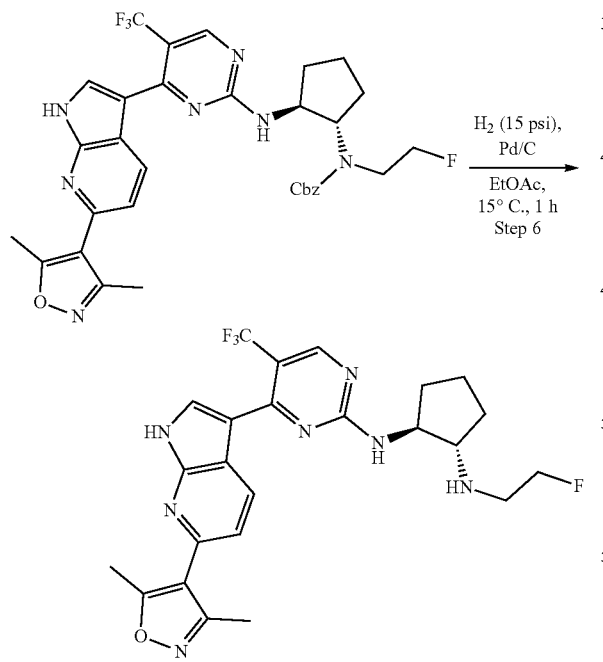

To a solution of benzyl N-[(1S, 2S)-2-[[4-[6-(3, 5-dimethylisoxazol-4-yl)-1H-pyrrolo [2, 3-b]pyridin-3-yl]-5-(trifluoromethyl) pyrimidin-2-yl] amino] cyclopentyl]-N-(2-fluoroethyl) carbamate (0.06 g, 94.10 umol, 1 eq) in EtOAc (5 mL) was added Pd/C (0.1 g, 10% purity) under $N_2$. The suspension was degassed under vacuum and purged with $H_2$ several times. The mixture was stirred under $H_2$ (15 psi) at 15° C. for 1 h. The suspension was filtered and washed by MeOH (5 mL×3). The filtrate was concentrated under reduced pressure to give the residue. The residue was purified by prep-HPLC (PA condition) to afford the title compound (14 mg, 98% purity, PA salt) as a white solid. (Note: The reaction was combined with another batch in 20 mg scale for worked up and purification.)

Example 26. (1S, 2R)—N1-[4-[6-(3, 5-dimethylisoxazol-4-yl)-1H-pyrrolo [2, 3-b] pyridin-3-yl]-5-(trifluoromethyl)pyrimidin-2-yl]-N2-(2-methoxyethyl)cyclopentane-1, 2-diamine (Compound 152)

Step 1: [(1S,2R)-2-[[4-[6-(3, 5-dimethylisoxazol-4-yl)-1H-pyrrolo[2,3-b]pyridin-3-yl]-5-(trifluoromethyl)pyrimidin-2-yl]amino]cyclopentyl]methane sulfonate

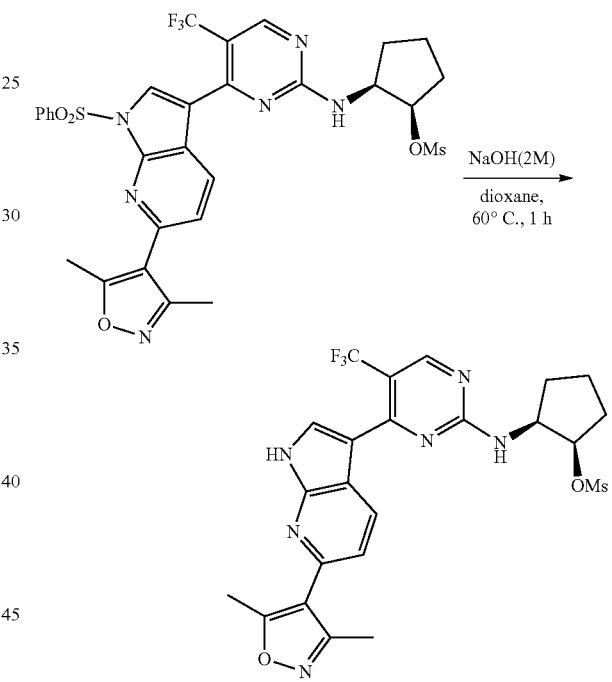

To a solution of [(1S,2R)-2-[[4-[1-(benzenesulfonyl)-6-(3,5-dimethylisoxazol-4-yl) pyrrolo[2,3-b]pyridin-3-yl]-5-(trifluoromethyl)pyrimidin-2-yl]amino]cyclopentyl] methanesulfonate (0.21 g, 310.34 umol, 1 eq) in dioxane (2 mL) was added NaOH (2 M, 1.05 mL, 6.77 eq). The mixture was stirred at 60° C. for 1 h. then concentrated under reduced pressure to remove solvent. The residue was diluted with water (200 mL), adjusted pH to 7 with HCl (1M), and then extracted with EtOAc (50 mL×3). The combined organic layers were washed with brine (150 mL), dried over $Na_2SO_4$, filtered and concentrated under reduced pressure to afford the title compound (170 mg, crude) as a white solid which was used directly into the next step without purification.

(Note: The reaction was combined with another reaction in 30 mg scale for work-up.)

Step 2: (1S, 2R)—N1-[4-[6-(3, 5-dimethylisoxazol-4-yl)-1H-pyrrolo [2, 3-b]pyridin-3-yl]-5-(trifluoromethyl) pyrimidin-2-yl]-N2-(2-methoxyethyl) cyclopentane-1, 2-diamine

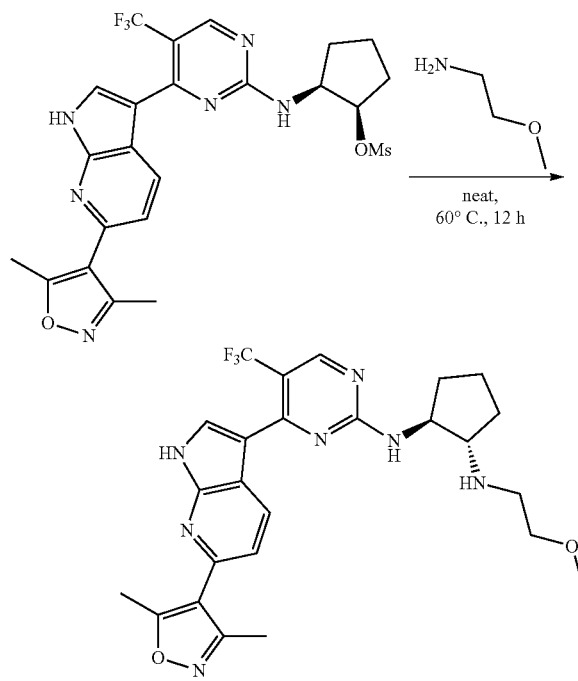

A solution of [(1R, 2S)-2-[[4-[6-(3,5-dimethylisoxazol-4-yl)-1H-pyrrolo[2, 3-b] pyridin-3-yl]-5-(trifluoromethyl) pyrimidin-2-yl] amino] cyclopentyl] methanesulfonate (65 mg, 121.15 umol, 1 eq) in 2-methoxyethanamine (842.40 mg, 11.22 mmol, 975.00 uL, 92.58 eq) was stirred at 60° C. for 12 h. It was concentrated under reduced pressure to give a residue. The residue was purified by prep-HPLC (FA condition) to afford the title compound (30.2 mg, 100% purity, 100% ee value) as a white solid. (Note: The reaction was combined with another reaction in 20 mg scale for work-up.)

Example 27. 4 4-[1-(benzenesulfonyl)-6-(3, 5-dimethylisoxazol-4-yl) pyrrolo [2, 3-b]pyridin-3-yl]-N-[(1S, 2S)-2-(3-methoxypyrrolidin-1-yl)cyclopentyl]-5-(trifluoromethyl) pyrimidin-2-amine (Compound 153)

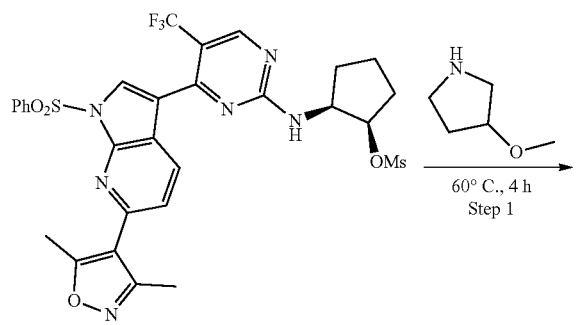

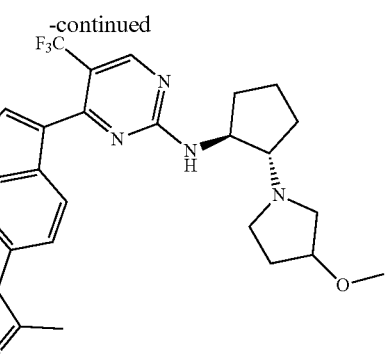

To a solution of [(1R,2S)-2-[[4-[1-(benzenesulfonyl)-6-(3,5-dimethylisoxazol-4-yl) pyrrolo[2,3-b]pyridin-3-yl]-5-(trifluoromethyl)pyrimidin-2-yl]amino]cyclopentyl]methanesulfonate (120 mg, 177.33 umol, 1 eq) and 3-methoxypyrrolidine (89.68 mg, 886.67 umol, 5 eq) was stirred for 4 h at 60° C. It was cooled to the room temperature and poured into water (5 mL) and extracted with EtOAc (10 mL×3). The combined organic layer was washed with brine (10 mL×3), dried over $Na_2SO_4$, filtered. The filtrate was concentrated under reduced pressure to give a residue. It was purified by prep-HPLC (neutral condition) to afford the title compound (15.3 mg, 20.96 umol, 11.82% yield, 93.4% purity) as yellow solid.

Example 28. 2-[[(1S,2S)-2-[[4-[6-(3,5-dimethylisoxazol-4-yl)-1H-pyrrolo [2,3-b] pyridin-3-yl]-5-(trifluoromethyl)pyrimidin-2-yl]amino]cyclopentyl]amino]ethanol (Compound 154)

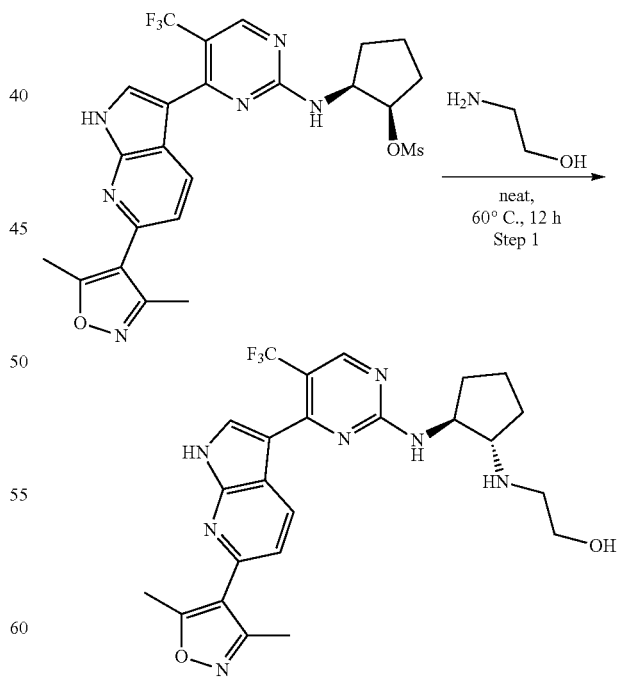

A solution of [(1R,2S)-2-[[4-[6-(3,5-dimethylisoxazol-4-yl)-1H-pyrrolo[2,3-b] pyridin-3-yl]-5-(trifluoromethyl)pyrimidin-2-yl]amino]cyclopentyl]methanesulfonate (0.075 g, 139.79 umol, 1 eq) in 2-aminoethanol (2.02 g, 33.07 mmol, 2 mL, 236.57 eq) was stirred at 60° C. for 12 h. It was concentrated under reduced pressure to give a residue. It was purified by prep-HPLC (LA condition) to afford the title compound (37.4 mg, LA salt, 100% purity) as a white solid. (Note: The reaction mixture was combined with another batch in 10 mg scale for worked up and purification).

Example 29. 4-[6-(3, 5-dimethylisoxazol-4-yl)-1H-pyrrolo [2, 3-b] pyridin-3-yl]-N-[(1S, 2S)-2-(3-fluoroazetidin-1-yl) cyclopentyl]-5-(trifluoromethyl) pyrimidin-2-amine (Compound 155)

Step 1: (2S)-2-[[4-[1-(benzenesulfonyl)-6-(3,5-dimethylisoxazol-4-yl)pyrrolo[2,3-b]pyridin-3-yl]-5-(trifluoromethyl)pyrimidin-2-yl]amino]cyclopentanone

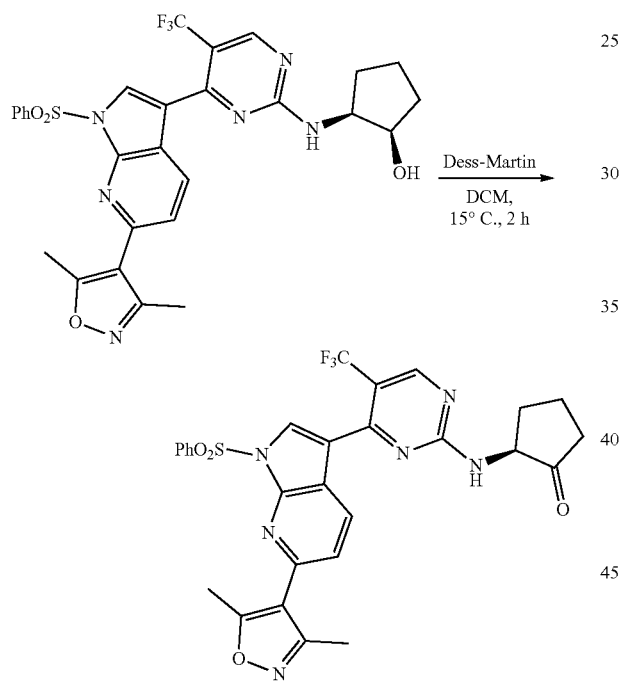

To a solution of (1R,2S)-2-[[4-[1-(benzenesulfonyl)-6-(3,5-dimethylisoxazol-4-yl)pyrrolo[2,3-b]pyridin-3-yl]-5-(trifluoromethyl)pyrimidin-2-yl]amino]cyclopentanol (0.5 g, 835.29 umol, 1 eq) in DCM (10 mL) was added Dess-Martin (708.56 mg, 1.67 mmol, 517.20 uL, 2 eq). The mixture was stirred at 15° C. for 2 h. The reaction mixture was diluted with DCM (20 mL) and washed with sat.NaHCO$_3$ (20 mL×2), brine (20 mL×2), dried over Na$_2$SO$_4$, filtered and concentrated under reduced pressure to give a residue. The residue was purified by column chromatography (SiO$_2$, PE:EtOAc=10:1 to 1:1) to afford the title compound (0.2 g, 335.24 umol, 40% yield) as yellow solid.

Step 2: 4-[1-(benzenesulfonyl)-6-(3, 5-dimethylisoxazol-4-yl) pyrrolo [2, 3-b] pyridin-3-yl]-N-[(1S, 2S)-2-(3-fluoroazetidin-1-yl) cyclopentyl]-5-(trifluoromethyl) pyrimidin-2-amine; 4-[1-(benzenesulfonyl)-6-(3, 5-dimethylisoxazol-4-yl) pyrrolo [2, 3-b] pyridin-3-yl]-N-[(1S, 2R)-2-(3-fluoroazetidin-1-yl) cyclopentyl]-5-(trifluoromethyl) pyrimidin-2-amine

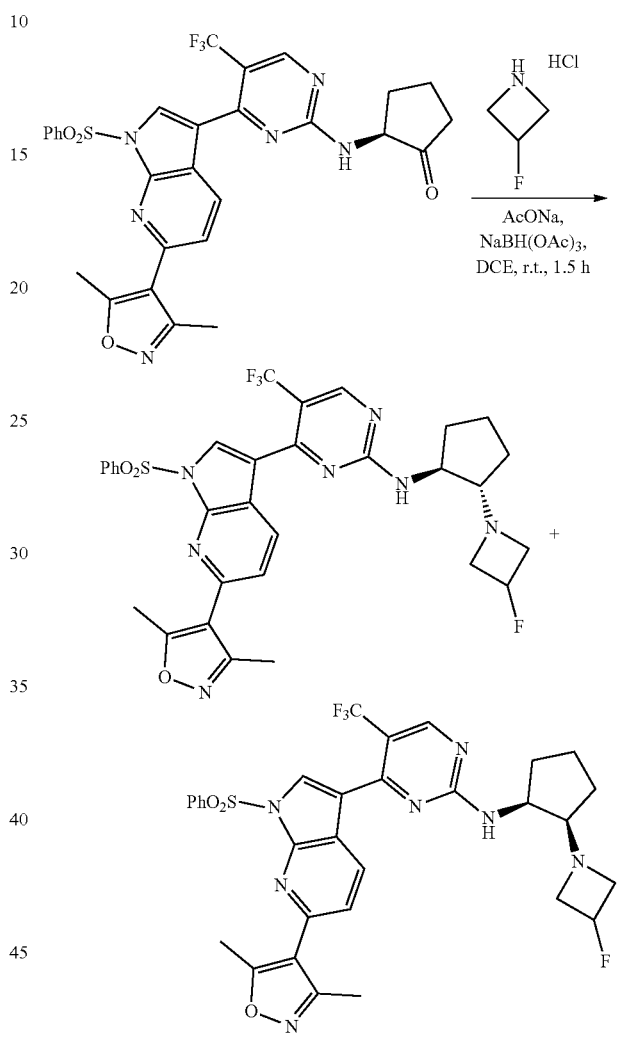

To a solution of (2S)-2-[[4-[1-(benzenesulfonyl)-6-(3, 5-dimethylisoxazol-4-yl) pyrrolo [2, 3-b]pyridin-3-yl]-5-(trifluoromethyl) pyrimidin-2-yl] amino] cyclopentanone (0.2 g, 335.24 umol, 1 eq) and 3-fluoroazetidine; hydrochloride (56.09 mg, 502.87 umol, 1.5 eq) in DCE (5 mL) was added NaBH(OAc)$_3$ (106.58 mg, 502.87 umol, 1.5 eq) and NaOAc (55.00 mg, 670.49 umol, 2 eq). The mixture was stirred at 20° C. for 1.5 h. The reaction was poured into sat.NaHCO$_3$ (20 mL). The aqueous phase was extracted with EtOAc (30 mL×3). The combined organic phase was washed with brine (30 mL×2), dried over anhydrous Na$_2$SO$_4$, filtered and concentrated in vacuum. The residue was purified by silica gel chromatography (100-200 mesh silica gel, Petroleum ether/Ethyl acetate=10/1, 0/1) to afford a racemate product (60 mg, 92% purity). Then the product was separated by SFC (column: DAICEL CHIRALPAK AD-H (250 mm*30 mm, 5 um); mobile phase: [0.1% NH₃H₂O IPA (isopropanol)]; B %: 40%-40%, 7 min: 50 min) to afford the title compound 1 (peak 1: 25 mg, 37.75 umol, 11.26% yield, 99% purity, 100% ee) as a yellow solid and title compound 2 (peak 2: 30 mg, 41.18 umol, 12.28% yield, 90% purity, 98% ee) was obtained as a yellow solid.

Step 3: 4-[6-(3,5-dimethylisoxazol-4-yl)-1H-pyrrolo[2,3-b]pyridin-3-yl]-N-[(1S,2S)-2-(3-fluoroazetidin-1-yl)cyclopentyl]-5-(trifluoromethyl)pyrimidin-2-amine

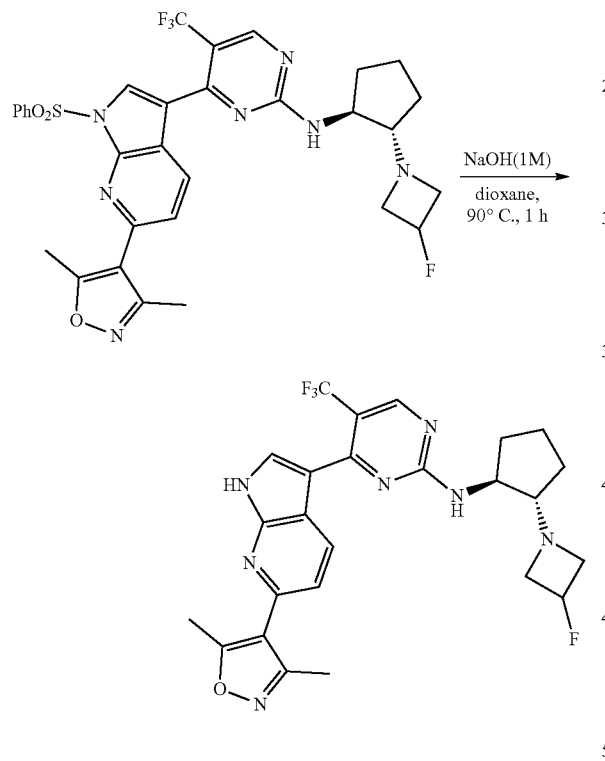

A solution of 4-[1-(benzenesulfonyl)-6-(3,5-dimethylisoxazol-4-yl)pyrrolo[2, 3-b] pyridin-3-yl]-N-[(1S, 2S)-2-(3-fluoroazetidin-1-yl)cyclopentyl]-5-(trifluoromethyl)pyrimidin-2-amine (24 mg, 36.60 umol, 1 eq) and NaOH (2 M, 54.91 uL, 3 eq) in dioxane (2 mL) was stirred at 90° C. for 1 h. It was cooled to r.t. and poured into water (20 mL). The aqueous phase was extracted with EtOAc (20 mL×2). The combined organic phase was washed with brine (30 mL×3), dried over anhydrous Na₂SO₄, filtered and concentrated in vacuum. The residue was purified by prep-HPLC (HCl) to afford the title compound (9.7 mg, 15.97 umol, 43.64% yield, 90.9% purity, HCl) as a yellow solid.

Example 30. 4-[6-(3, 5-dimethylisoxazol-4-yl)-1H-pyrrolo [2, 3-b] pyridin-3-yl]-N-[(1S, 2R)-2-(3-fluoroazetidin-1-yl) cyclopentyl]-5-(trifluoromethyl) pyrimidin-2-amine (Compound 156)

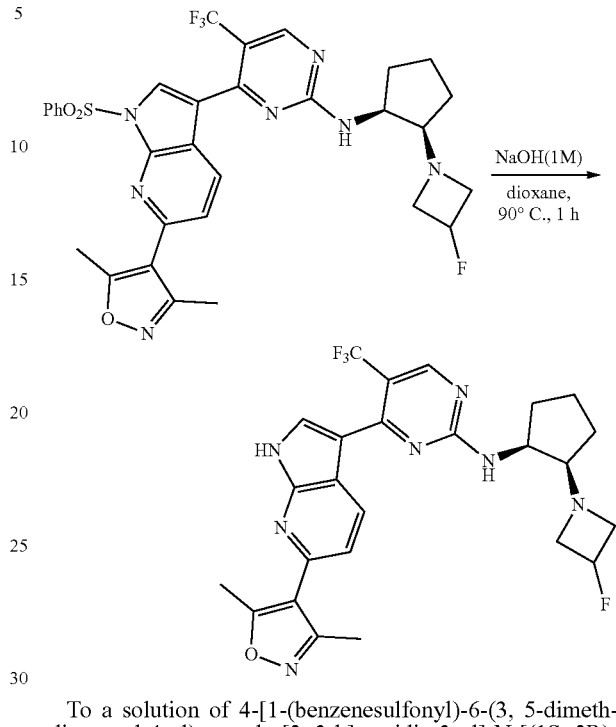

To a solution of 4-[1-(benzenesulfonyl)-6-(3, 5-dimethylisoxazol-4-yl) pyrrolo [2, 3-b] pyridin-3-yl]-N-[(1S, 2R)-2-(3-fluoroazetidin-1-yl) cyclopentyl]-5-(trifluoromethyl) pyrimidin-2-amine (25 mg, 38.13 umol, 1 eq) and NaOH (2 M, 57.19 uL, 3 eq) in dioxane (2 mL) was stirred at 90° C. for 1 h. then cooled to r.t. and poured into water (20 mL). The aqueous phase was extracted with EtOAc (20 mL×2). The combined organic phase was washed with brine (30 mL×3), dried over anhydrous Na₂SO₄, filtered and concentrated in vacuum. The residue was purified by prep-HPLC (neutral) to afford the title compound (7.2 mg, 99% purity) as a white solid.

Example 31. (1S,2S)—N1-[4-[6-(3, 5-dimethylisoxazol-4-yl)-1H-pyrazolo [3, 4-b] pyridin-3-yl]-5-(trifluoromethyl) pyrimidin-2-yl]cyclopentane-1,2-diamine (Compound 157)

Step 1: Tert-butyl N-[(1S,2S)-2-[[4-[6-(3,5-dimethylisoxazol-4-yl)-1-tetrahydropyran-2-yl-pyrazolo[3,4-b] pyridin-3-yl]-5-(trifluoromethyl)pyrimidin-2-yl]amino]cyclopentyl]carbamate

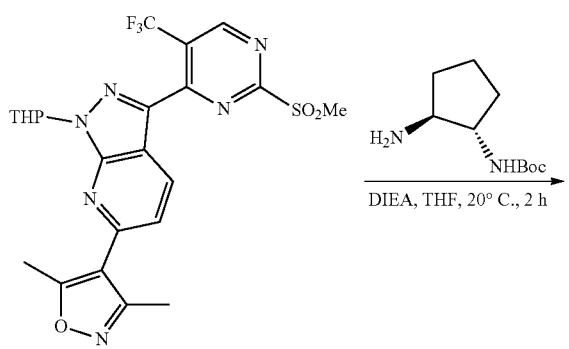

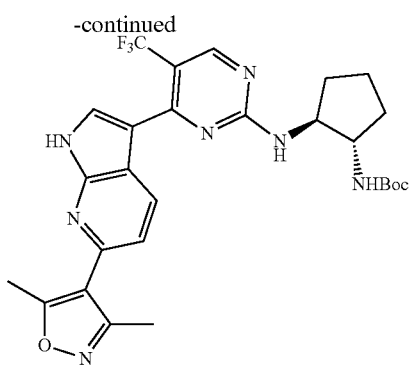

To a solution of 3,5-dimethyl-4-[3-[2-methylsulfonyl-5-(trifluoromethyl)pyrimidin-4-yl]-1-tetrahydropyran-2-yl-pyrazolo [3, 4-b] pyridin-6-yl] isoxazole (140 mg, 267.94 umol, 1 eq) in THF (4.5 mL) was added tert-butyl N-[(1S, 2S)-2-aminocyclopentyl] carbamate (53.66 mg, 267.94 umol, 1 eq) and DIPEA (103.89 mg, 803.83 umol, 140.01 uL, 3 eq). The mixture was stirred at 20° C. for 2 h. The solution was diluted with H$_2$O (10 mL) and extracted with DCM (15 mL×3). The combined organic layers were washed with brine (20 mL), dried over Na$_2$SO$_4$, filtered and concentrated under reduced pressure to give a residue. It was purified by column chromatography (SiO$_2$, DCM/MeOH=1/0 to 50/1) to afford the title compound (140 mg) as a yellow solid. (Note: The reaction was combined with another reaction in 10 mg scale for work up.)

Step 2: (1S, 2S)—N1-[4-[6-(3, 5-dimethylisoxazol-4-yl)-1H-pyrazolo [3, 4-b]pyridin-3-yl]-5-(trifluoromethyl) pyrimidin-2-yl] cyclopentane-1, 2-diamine

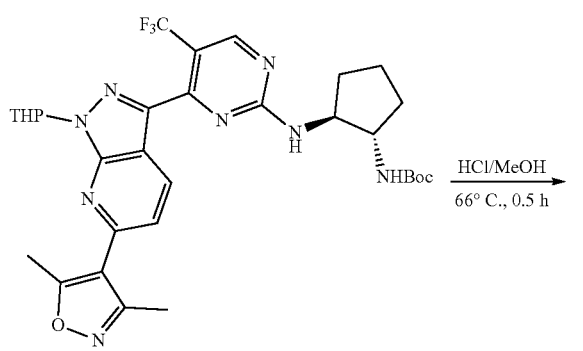

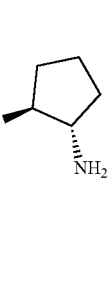

A solution of tert-butyl N-[(1S, 2S)-2-[[4-[6-(3, 5-dimethylisoxazol-4-yl)-1-tetrahydropyran-2-yl-pyrazolo [3, 4-b] pyridin-3-yl]-5-(trifluoromethyl) pyrimidin-2-yl] amino] cyclopentyl]carbamate (130 mg, 202.28 umol, 1 eq) in HCl/MeOH (4 M, 5 mL) was stirred at 66° C. for 0.5 h. The reaction mixture was concentrated under reduced pressure to remove solvent. The residue was purified by prep-HPLC (FA condition) to afford the title compound (FA, 50.3 mg, 99.61% purity) as a white solid. (Note: The reaction was combined with another reaction in 10 mg scale for work up.)

Example 32. (1S,2S)—N1-[4-[6-(3-methyl-1,2,4-thiadiazol-5-yl)-1H-pyrrolo [2,3-b] pyridin-3-yl]-5-(trifluoromethyl)pyrimidin-2-yl]cyclopentane-1,2-diamine (Compound 158)

Step 1: Trimethyl-[2-[[6-(3-methyl-1,2,4-thiadiazol-5-yl)pyrrolo[2,3-b]pyridin-1-yl]methoxy]ethyl]silane

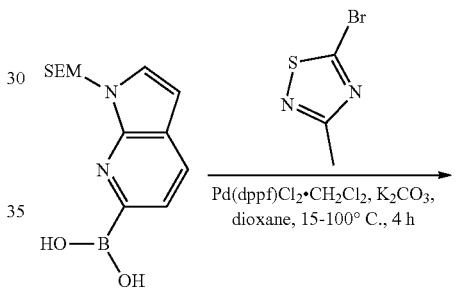

To a solution of [1-(2-trimethylsilylethoxymethyl)pyrrolo[2,3-b]pyridin-6-yl]boronic acid (3.92 g, 13.40 mmol, 1.6 eq), 5-bromo-3-methyl-1,2,4-thiadiazole (1.5 g, 8.38 mmol, 1 eq) in dioxane (40 mL) was added K$_2$CO$_3$ (2.89 g, 20.95 mmol, 2.5 eq) and Pd(dppf)C$_{1-2}$—CH$_2$Cl$_2$ (684.19 mg, 837.81 umol, 0.1 eq) at 15° C., the reaction mixture was degassed and purged with N$_2$ for 3 times and stirred at 100° C. for 2 h. The final reaction mixture was filtered and concentrated to give a residue. The residue was purified by silica gel column (PE/EtOAc=100/1 to 25/1) to afford the title compound (1.1 g, 3.17 mmol, 37.89% yield) as a colorless oil.

Step 2: 2-[[3-bromo-6-(3-methyl-1,2,4-thiadiazol-5-yl)pyrrolo[2,3-b]pyridin-1-yl]methoxy]ethyl-trimethyl-silane

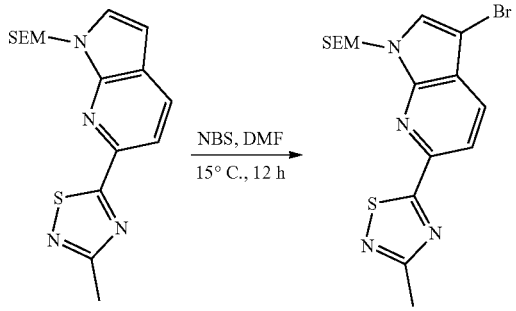 [SMILES: Cc1nsc(-c2ccc3ccn(COCC[Si](C)(C)C)c3n2)n1 ; Cc1nsc(-c2ccc3c(Br)cn(COCC[Si](C)(C)C)c3n2)n1]

To a stirred solution of trimethyl-[2-[[6-(3-methyl-1,2,4-thiadiazol-5-yl)pyrrolo[2,3-b] pyridin-1-yl]methoxy]ethyl] silane (1.1 g, 3.17 mmol, 1 eq) in DMF (30 mL) was added NBS (553.69 mg, 3.11 mmol, 0.98 eq), the reaction mixture was stirred at 15° C. for 2 h. The final reaction mixture was diluted with EtOAc (80 mL), washed with sub-saturated brine (50 mL×3) and saturated brine (50 mL). The organic layer was dried over Na$_2$SO$_4$ and concentrated to give a residue. The residue was purified by silica gel column (PE/EtOAc=50/1 to 20/1) to afford the title compound (1.15 g, 2.70 mmol, 85.16% yield) as a white solid.

Step 3: Trimethyl-[2-[[6-(3-methyl-1,2,4-thiadiazol-5-yl)-3-(4,4,5,5-tetramethyl-1,3,2-dioxaborolan-2-yl)pyrrolo[2,3-b]pyridin-1-yl]methoxy]ethyl]silane

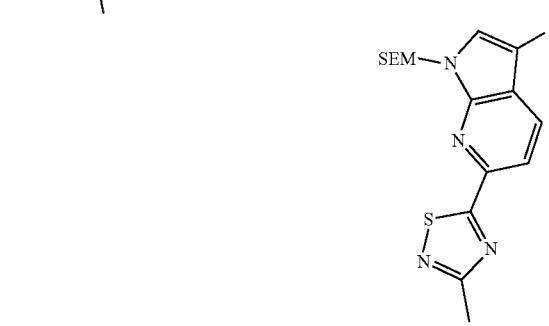

To a solution of 2-[[3-bromo-6-(3-methyl-1,2,4-thiadiazol-5-yl)pyrrolo[2,3-b]pyridin-1-yl]methoxy]ethyl-trimethyl-silane (1 g, 2.35 mmol, 1 eq) and 4,4,4',4',5,5,5',5'-octamethyl-2,2'-bi(1,3,2-dioxaborolane) (895.38 mg, 3.53 mmol, 1.5 eq) in dioxane (20 mL) was added KOAc (461.39 mg, 4.70 mmol, 2 eq) and Pd(dppf)Cl$_2$·CH$_2$Cl$_2$ (191.96 mg, 235.06 umol, 0.1 eq) at 15° C., the reaction mixture was degassed and purged with N$_2$ for 3 times and stirred at 100° C. for 3 h. The final reaction mixture was filtered and concentrated to give a residue. The residue was purified by silica gel column (PE/EtOAc=50/1) to afford the title compound (1.05 g) as a yellow solid which contained some de-Br byproduct. (Note: The reaction was combined with another reaction in 200 mg scale for work up.)

Step 4: Trimethyl-[2-[[3-[2-methylsulfanyl-5-(trifluoromethyl)pyrimidin-4-yl]-6-(3-methyl-1,2,4-thiadiazol-5-yl)pyrrolo [2,3-b]pyridin-1-yl]methoxy]ethyl] silane

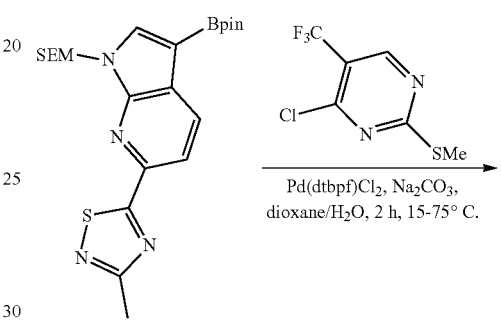

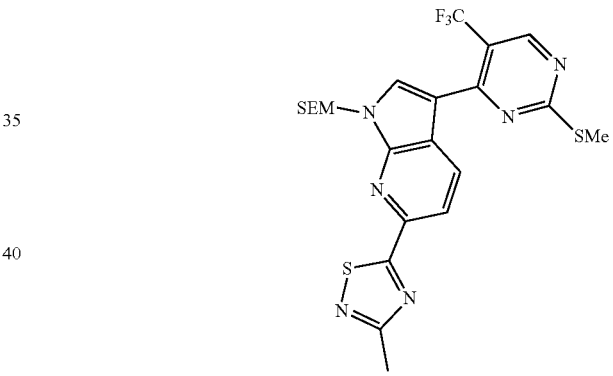

To a solution of trimethyl-[2-[[6-(3-methyl-1,2,4-thiadiazol-5-yl)-3-(4,4,5,5-tetramethyl-1,3,2-dioxaborolan-2-yl)pyrrolo[2,3-b]pyridin-1-yl]methoxy]ethyl]silane (929.99 mg, 1.97 mmol, 1 eq) and 4-chloro-2-methylsulfanyl-5-(trifluoromethyl)pyrimidine (0.45 g, 1.97 mmol, 1 eq) in H$_2$O (2.5 mL) and THF (12.5 mL) was added Na$_2$CO$_3$ (417.24 mg, 3.94 mmol, 2 eq) and ditert-butyl(cyclopentyl)phosphane:dichloropalladium:iron (128.28 mg, 196.83 umol, 0.1 eq) at 15° C., the reaction mixture was degassed and purged with N$_2$ for 3 times, and stirred at 75° C. for 2 h. The final reaction mixture was diluted with EtOAc (50 mL), washed with H$_2$O (20 mL). The organic layer was dried over Na$_2$SO$_4$ and concentrated to give a residue. It was purified by silica gel column (PE/EtOAc=50/1 to 10/1) to afford the title compound (550 mg) as a white solid. (Note: The reaction was combined with another reaction in 50 mg scale for work up.)

Step 5: Trimethyl-[2-[[3-[2-methylsulfonyl-5-(trifluoromethyl)pyrimidin-4-yl]-6-(3-methyl-1,2,4-thiadiazol-5-yl)pyrrolo[2,3-b]pyridin-1-yl]methoxy]ethyl]silane

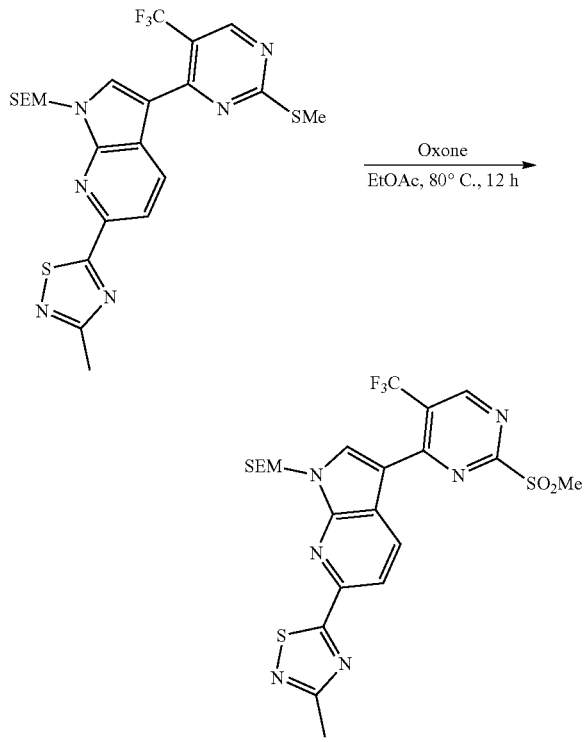

A mixture of trimethyl-[2-[[3-[2-methylsulfanyl-5-(trifluoromethyl)pyrimidin-4-yl]-6-(3-methyl-1,2,4-thiadiazol-5-yl)pyrrolo[2,3-b]pyridin-1-yl]methoxy]ethyl]silane (0.5 g, 928.19 umol, 1 eq) and Oxone (2.85 g, 4.64 mmol, 5 eq) in EtOAc (20 mL) was stirred at 80° C. for 12 h. The final reaction mixture was filtered and washed with EtOAc (30 mL). The organic layer was washed with Na$_2$SO$_3$ (aq, 10 mL×3), dried over Na$_2$SO$_4$ and concentrated to give a residue. The residue was purified by silica gel column (PE/EtOAc=15/1 to 5/1) to afford the title compound (120 mg) as a yellow solid.

Step 6: Tert-butyl N-[(1S,2S)-2-[[4-[6-(3-methyl-1,2,4-thiadiazol-5-yl)-1-(2-trimethylsilylethoxymethyl)pyrrolo[2,3-b]pyridin-3-yl]-5-(trifluoromethyl)pyrimidin-2-yl]amino]cyclopentyl]carbamate

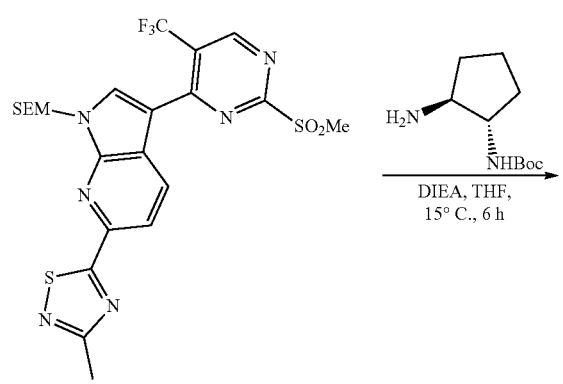

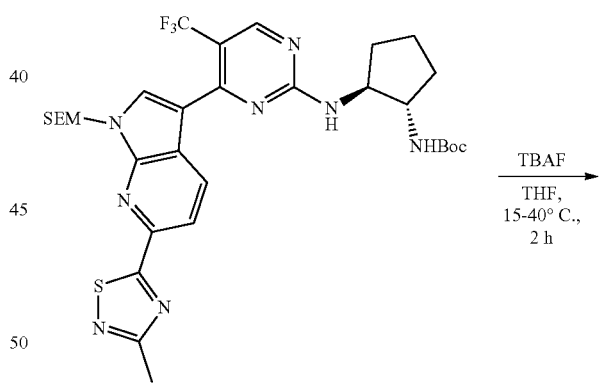

A mixture of trimethyl-[2-[[3-[2-methylsulfonyl-5-(trifluoromethyl)pyrimidin-4-yl]-6-(3-methyl-1,2,4-thiadiazol-5-yl)pyrrolo[2,3-b] pyridin-1-yl]methoxy]ethyl]silane (0.19 g, 332.93 umol, 1 eq), tert-butyl N-[(1S, 2S)-2-aminocyclopentyl] carbamate (66.68 mg, 332.93 umol, 1 eq) and DIEA (215.15 mg, 1.66 mmol, 289.96 uL, 5 eq) in THF (5 mL) was stirred at 15° C. for 6 h. The final reaction mixture was concentrated to give a residue. The residue was purified by silica gel column (PE/EtOAc=4/1) to afford the title compound (220 mg) as a light yellow solid. (Note: The reaction was combined with another reaction in 30 mg scale for work up.)

Step 7: Tert-butyl N-[(1S,2S)-2-[[4-[6-(3-methyl-1,2,4-thiadiazol-5-yl)-1H-pyrrolo[2,3-b]pyridin-3-yl]-5-(trifluoromethyl)pyrimidin-2-yl]amino]cyclopentyl]carbamate

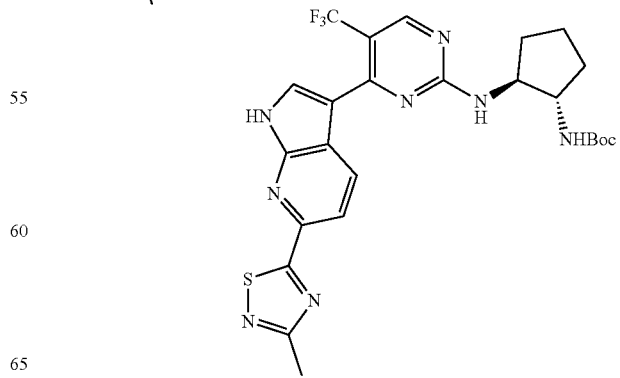

To a solution of tert-butyl N-[(1S, 2S)-2-[[4-[6-(3-methyl-1, 2, 4-thiadiazol-5-yl)-1-(2-trimethylsilylethoxymethyl) pyrrolo [2, 3-b] pyridin-3-yl]-5-(trifluoromethyl) pyrimidin-2-yl]amino] cyclopentyl] carbamate (180 mg, 260.55 umol, 1 eq) in THF (3 mL) was added TBAF (1 M, 5 mL, 19.19 eq) at 15° C., the reaction mixture was stirred at 40° C. for 2 h. The mixture was diluted with EtOAc (20 mL), washed with Sat.NaHCO₃ (10 mL×3). The organic layer was dried over Na₂SO₄ and concentrated to give a residue. The residue was purified by silica gel column (PE/EtOAc=20/1 to 5/1) to afford the title compound (85 mg) as a yellow solid. (Note: The reaction was combined with another reaction in 40 mg scale for work up.)

Step 8: (1S,2S)—N1-[4-[6-(3-methyl-1, 2, 4-thiadiazol-5-yl)-1H-pyrrolo [2, 3-b]pyridin-3-y-5-(trifluoromethyl)pyrimidin-2-yl] cyclopentane-1, 2-diamine

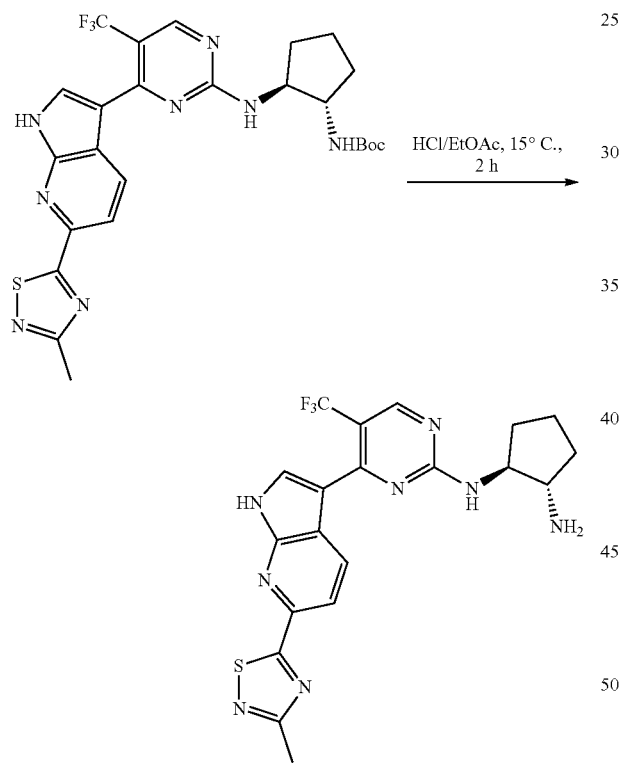

A mixture of tert-butyl N-[(1S,2S)-2-[[4-[6-(3-methyl-1, 2,4-thiadiazol-5-yl)-1H-pyrrolo [2,3-b]pyridin-3-yl]-5-(trifluoromethyl)pyrimidin-2-yl]amino]cyclopentyl]carbamate (0.07 g, 124.87 umol, 1 eq) and HCl/EtOAc (4 M, 15 mL, 480.51 eq) was stirred at 15° C. for 2 h. The resulting mixture was concentrated to give a residue. It was purified by prep-HPLC (HCl condition) to give the desired product which was not pure enough. Then, it was purified by prep-HPLC (neutral condition) to afford the title compound (7.9 mg 93.6% purity) as a white solid. (Note: The reaction was combined with another reaction in 15 mg scale for work up.)

Example 33. 1-[(1S,2S)-2-[[4-[6-(3,5-dimethyl-isoxazol-4-yl)-1H-pyrrolo[2,3-b] pyridin-3-yl]-5-(trifluoromethyl) pyrimidin-2-yl] amino] cyclopentyl] azetidin-3-ol (Compound 159)

Step 1: 1-[(1S,2S)-2-[[4-[1-(benzenesulfonyl)-6-(3, 5-dimethylisoxazol-4-yl)pyrrolo[2,3-b] pyridin-3-yl]-5-(trifluoromethyl)pyrimidin-2-yl]amino]cyclopentyl]azetidin-3-o;1[(1R, 2S)-2-[[4-[1-(benzenesulfonyl)-6-(3,5-dimethylisoxazol-4-yl) pyrrolo[2,3-b] pyridin-3-yl]-5-(trifluoromethyl) pyrimidin-2-yl]amino]cyclopentyl]azetidin-3-ol

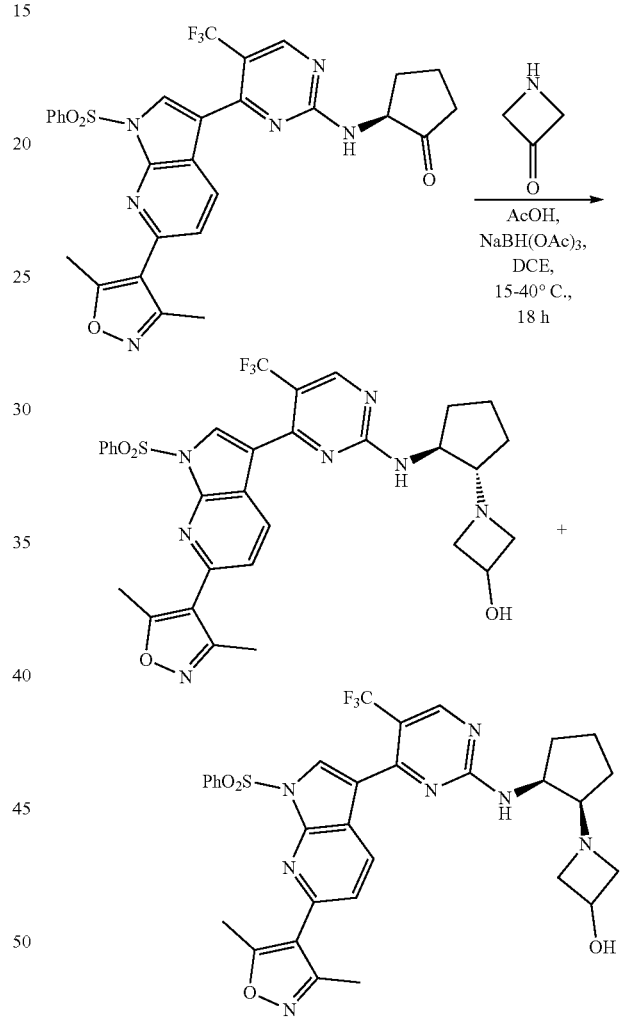

To a solution of (2S)-2-[[4-[1-(benzenesulfonyl)-6-(3, 5-dimethylisoxazol-4-yl) pyrrolo[2, 3-b]pyridin-3-yl]-5-(trifluoromethyl) pyrimidin-2-yl] amino] cyclopentanone (230 mg, 385.53 umol, 1 eq) and azetidin-3-ol (56.36 mg, 771.06 umol, 2 eq) in DCE (11 mL) was added NaBH(OAc)₃ (163.42 mg, 771.06 umol, 2 eq) and HOAc (23.15 mg, 385.53 umol, 22.05 uL, 1 eq). The mixture was stirred at 15° C. for 12 h. And then azetidin-3-ol (28.18 mg, 385.53 umol, 1 eq) and NaBH(OAc)₃ (81.71 mg, 385.53 umol, 1 eq) was added into the mixture, it was stirred at 40° C. for 6 h. It was concentrated under reduced pressure to remove solvent. The residue was diluted with water 50 mL and extracted with EtOAc (30 mL×2). The combined organic layers were washed with brine 50 mL, dried over Na$_2$SO$_4$, filtered and concentrated under reduced pressure to give a residue. The residue was purified by column chromatography (SiO$_2$, PE/EtOAc=1/1 to DCM/MeOH=15/l) to afford the mixture of two isomers (130 mg, 100% purity). It was separated twice by SFC to afford the title compound 1 (55 mg, 81.62 umol, 21.17% yield, 97% purity) was obtained as a brown solid and the title compound 2 (40 mg, 58.13 umol, 15.08% yield, 95% purity) was obtained as a brown solid. (Note: The reaction was combined with another reaction in 20 mg scale for work-up and purification.)

Step 2: 1-[(1S, 2S)-2-[[4-[6-(3, 5-dimethylisoxazol-4-yl)-1H-pyrrolo [2, 3-b] pyridin-3-yl]-5-(trifluoromethyl) pyrimidin-2-yl] amino] cyclopentyl] azetidin-3-ol

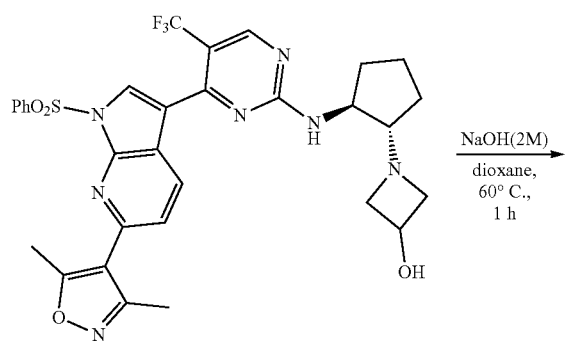

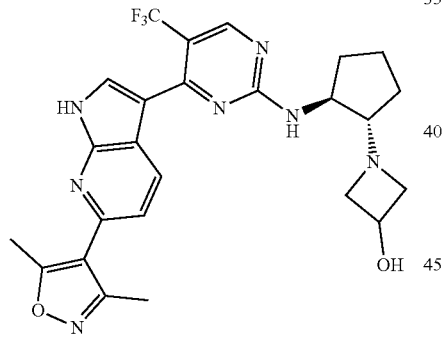

To a solution of 1-[(1S, 2S)-2-[[4-[1-(benzenesulfonyl)-6-(3, 5-dimethylisoxazol-4-yl) pyrrolo-[2,3b] pyridin-3-yl]-5-(trifluoromethyl) pyrimidin-2-yl] amino] cyclopentyl] azetidin-3-ol (50.00 mg, 76.49 umol, 1 eq) in dioxane (5 mL) was added NaOH (2 M, 573.68 uL, 15 eq). The mixture was stirred at 60° C. for 1 h. It was cooled to the room temperature and diluted with water 30 mL, and adjusted pH to 7 by added HCl (1M), then extracted with EtOAc (30 mL×2), the combined organic layers were washed with brine 50 mL, dried over Na$_2$SO$_4$, filtered and concentrated under reduced pressure to give a residue. It was purified by prep-HPLC (FA condition) to afford the title compound (12 mg, 99% purity) as a white solid. (Note: The reaction was combined with another reaction in 5 mg scale for work-up and purification.)

Example 34. (1S,2S)—N2-[4-[6-(3,5-dimethylisoxazol-4-yl)-1H-pyrrolo[2,3-b]pyridin-3-yl]-5-(trifluoromethyl)pyrimidin-2-yl]-N1-ethyl-cyclobutane-1, 2-diamine (Compound 160)

Step 1: Tert-butyl N-[(1S, 2S)-2-(ethylamino) cyclobutyl] carbamate

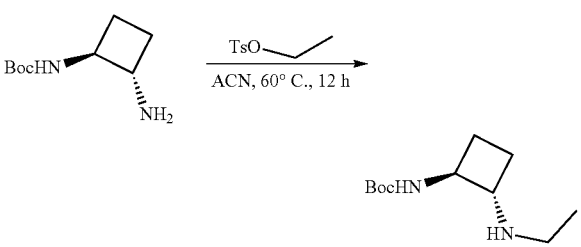

A solution of tert-butyl N-[(1S,2S)-2-aminocyclobutyl] carbamate (0.6 g, 3.22 mmol, 1 eq) and ethyl 4-methylbenzenesulfonate (645.11 mg, 3.22 mmol, 551.38 uL, 1 eq) in ACN (5 mL) was stirred at 65° C. for 12 h. It was concentrated under reduced pressure to afford the title compound (900 mg, crude) as yellow oil, which was used into the next step without further purification. (Note: The reaction was combined with another reaction in 50 mg scale for work up)

Step 2: Benzyl N-[(1S, 2S)-2-(tert-butoxycarbonylamino) cyclobutyl]-N-ethyl-carbamate

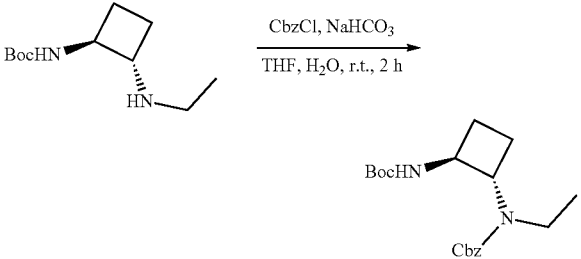

To a solution of tert-butyl N-[(1S, 2S)-2-(ethylamino) cyclobutyl] carbamate (900.00 mg, 4.20 mmol, 1 eq) in THF (18 mL) and H$_2$O (2 mL) was added NaHCO$_3$ (705.60 mg, 8.40 mmol, 326.66 uL, 2 eq) and CbzCl (859.71 mg, 5.04 mmol, 716.43 uL, 1.2 eq). The mixture was stirred at 20° C. for 1 h. The solution was diluted with EtOAc (30 mL), and washed with brine (30 mL×2), dried over Na$_2$SO$_4$, filtered and concentrated under reduced pressure to afford the title compound (0.8 g, crude) as yellow oil, which was used into the next step without further purification.

Step 3: Benzyl N-[(1S, 2S)-2-aminocyclobutyl]-N-ethyl-carbamate

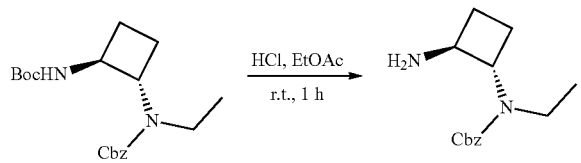 [SMILES: CCN(C(=O)OCc1ccccc1)[C@H]1CC[C@@H]1NC(=O)OC(C)(C)C ; CCN(C(=O)OCc1ccccc1)[C@H]1CC[C@@H]1N]

A solution of benzyl N-[(1S, 2S)-2-(tert-butoxycarbonylamino) cyclobutyl]-N-ethyl-carbamate (0.8 g, 2.30 mmol, 1 eq) in HCl/EtOAc (4 M, 8.00 mL, 13.94 eq) was stirred at 20° C. for 1 h. The solution was diluted with EtOAc (20 mL), and washed by H$_2$O (20 mL×2). The organic layer was discarded. The aqueous phase was adjusted pH to 10 with NaOH (solid). Then it was extracted by EtOAc (20 mL×4). The combined organic layer was washed by brine (20 mL×2), dried over Na$_2$SO$_4$, filtered and concentrated under reduced pressure to afford the title compound (0.4 g, crude) as yellow oil, which was used into the next step without further purification.

Step 4: Benzyl N-[(1S, 2S)-2-[[4-[1-(benzenesulfonyl)-6-(3, 5-dimethylisoxazol-4-yl) pyrrolo [2, 3-b] pyridin-3-yl]-5-(trifluoromethyl) pyrimidin-2-yl] amino] cyclobutyl]-N-ethyl-carbamate

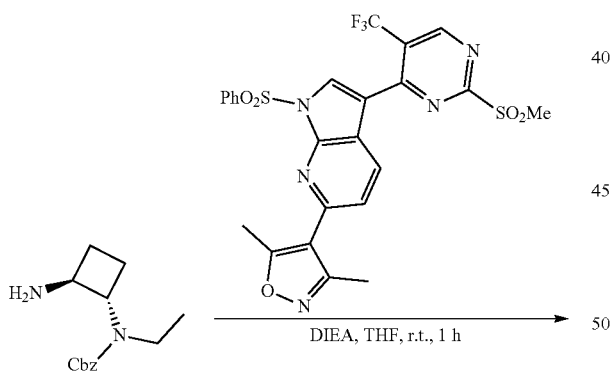

To a solution of 4-[1-(benzenesulfonyl)-3-[2-methylsulfonyl-5-(trifluoromethyl) pyrimidin-4-yl]pyrrolo [2, 3-b] pyridin-6-yl]-3, 5-dimethyl-isoxazole (0.3 g, 519.43 umol, 1 eq) in THF (3 mL) was added DIPEA (201.40 mg, 1.56 mmol, 271.43 uL, 3.00 eq) and benzyl N-[(1S, 2S)-2-aminocyclobutyl]-N-ethyl-carbamate (154.78 mg, 623.32 umol, 1.2 eq). The mixture was stirred at 20° C. for 1 h. It was concentrated under reduced pressure to give a residue. The residue was purified by column chromatography (SiO$_2$, Petroleum Ether/EtOAc=10/1 to 2/1) to afford the title compound (0.3 g, 402.27 umol, 77.44% yield) as yellow solid.

Step 5: Benzyl N-[(1S, 2S)-2-[[4-[6-(3, 5-dimethyl-isoxazol-4-yl)-1H-pyrrolo [2, 3-b]pyridin-3-yl]-5-(trifluoromethyl) pyrimidin-2-yl] amino] cyclobutyl]-N-ethyl-carbamate

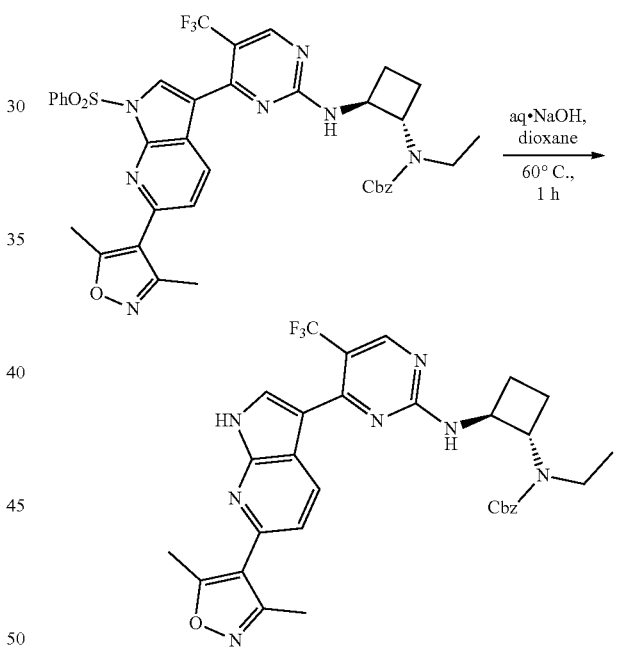

To a solution of benzyl N-[(1S, 2S)-2-[[4-[1-(benzenesulfonyl)-6-(3, 5-dimethylisoxazol-4-yl) pyrrolo [2, 3-b] pyridin-3-yl]-5-(trifluoromethyl) pyrimidin-2-yl] amino] cyclobutyl]-N-ethyl-carbamate (0.3 g, 402.27 umol, 1 eq) in dioxane (3 mL) was added NaOH (2 M, 3 mL, 14.92 eq). The mixture was stirred at 60° C. for 1 h. The solution was diluted with EtOAc (30 mL) and washed with brine (30 mL×2), dried over Na$_2$SO$_4$, filtered and concentrated under reduced pressure to afford the title compound (0.17 g, crude) as yellow solid, which was used into the next step without further purification.

115

Step 6: (1S, 2S)—N2-[4-[6-(3, 5-dimethylisoxazol-4-yl)-1H-pyrrolo [2, 3-b] pyridin-3-yl]-5-(trifluoromethyl) pyrimidin-2-yl]-N1-ethyl-cyclobutane-1, 2-diamine

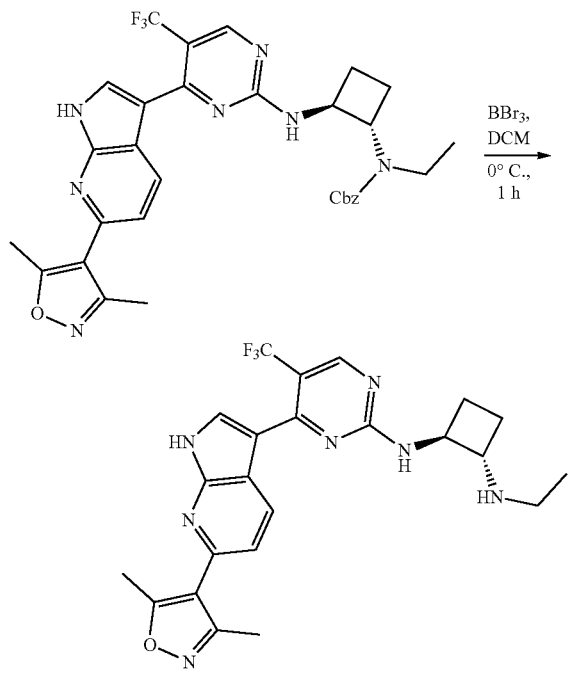

To a solution of benzyl N-[(1S, 2S)-2-[[4-[6-(3, 5-dimethylisoxazol-4-yl)-1H-pyrrolo [2, 3-b]pyridin-3-yl]-5-(trifluoromethyl) pyrimidin-2-yl] amino] cyclobutyl]-N-ethyl-carbamate (0.15 g, 247.68 umol, 1 eq) in DCM (2 mL) was added BBr₃ (310.25 mg, 1.24 mmol, 119.33 uL, 5 eq) at 0° C. The mixture was stirred at 0° C. for 1 h. It was concentrated under reduced pressure to remove DCM. The residue was triturated with Petroleum Ether (5 mL) and filtered. The solid was concentrated under reduced pressure to give a crude product. It was purified by prep-HPLC (FA condition) to afford the title compound (29.1 mg, FA salt, 99.39% purity) as a white solid.

Example 35. 3-[2-[[(1S,2S)-2-aminocyclopentyl] amino]-5-(trifluoromethyl) pyrimidin-4-yl]-7-dimethylphosphoryl-1H-indole-6-carbonitrile (Compound 161)

Step 1: 7-chloro-3-[2-chloro-5-(trifluoromethyl) pyrimidin-4-yl]-1H-indole-6-carbonitrile

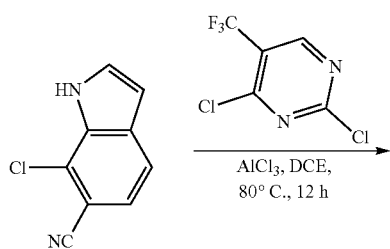

116

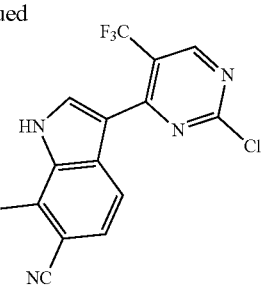

To a solution of 2, 4-dichloro-5-(trifluoromethyl) pyrimidine (5.53 g, 25.48 mmol, 3 eq) in DCE (20 mL) was added AlCl₃ (2.83 g, 21.23 mmol, 1.16 mL, 2.5 eq) at 80° C. After addition, the mixture was stirred at this temperature for 30 min, and then 7-chloro-1H-indole-6-carbonitrile (1.5 g, 8.49 mmol, 1 eq) was added at 80° C. The resulting mixture was stirred at 80° C. for 11.5 h. The reaction mixture was diluted with H₂O (200 mL) and extracted with EtOAc (100 mL×2). The combined organic layers were washed with brine (300 mL×2), dried over Na₂SO₄, filtered and concentrated under reduced pressure to give a residue. The residue was purified by column chromatography (SiO₂, PE/EtOAc=10/1 to 5/1) to give a crude product. It was washed with MeOH (10 mL) and filtered to afford the title compound (330 mg) as a white solid.

Step 2: 3-[5-(trifluoromethyl) pyrimidin-4-yl]-1H-indole-6-carbonitrile

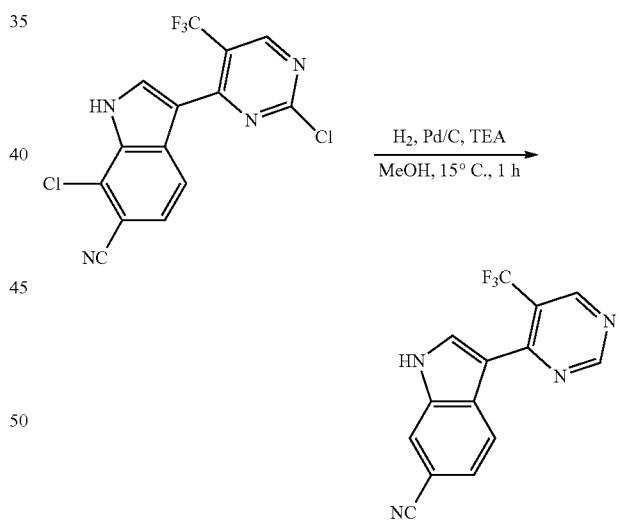

To a solution of 7-chloro-3-[2-chloro-5-(trifluoromethyl) pyrimidin-4-yl]-1H-indole-6-carbonitrile (40 mg, 112.01 umol, 1 eq) in MeOH (2 mL) was added Pd/C (25 mg, 10% purity), TEA (22.67 mg, 224.02 umol, 31.18 uL, 2 eq) under N₂. The suspension was degassed under vacuum and purged with H₂ several times. The mixture was stirred under H₂ (15 psi) at 15° C. for 1 h. The mixture was filtered and the filtrate was concentrated to give a residue. It was purified by prep-TLC (SiO₂, PE/EtOAc=3/1) to afford the title compound (10 mg, 31.23 umol, 27.88% yield, 90% purity) as a white solid. (Note: This reaction was done for the structure confirmation of the material.)

Step 3: Tert-butyl N-[(1S,2S)-2-[[4-(7-chloro-6-cyano-1H-indol-3-yl)-5-(trifluoromethyl) pyrimidin-2-yl]amino]cyclopentyl]carbamate

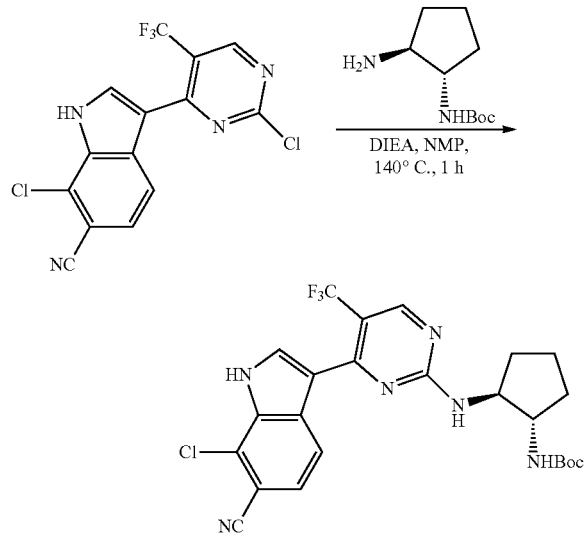

To a solution of 7-chloro-3-[2-chloro-5-(trifluoromethyl) pyrimidin-4-yl]-1H-indole-6-carbonitrile (0.3 g, 840.06 umol, 1 eq) and tert-butyl N-[(1S,2S)-2-aminocyclopentyl] carbamate (201.89 mg, 1.01 mmol, 1.2 eq) in NMP (5 mL) was added DIEA (325.72 mg, 2.52 mmol, 438.97 uL, 3 eq). The mixture was stirred at 140° C. for 1 h. It was poured into water (50 mL). The aqueous phase was extracted with EtOAc (50 mL×3). The combined organic phase was washed with brine (50 mL×2), dried over anhydrous Na₂SO₄, filtered and concentrated in vacuum. The residue was purified by silica gel chromatography (100-200 mesh silica gel, PE/EtOAc=5/1, 0/1) to afford the title compound (0.3 g) as a yellow solid. (Note: The reaction was combined with another reaction in 30 mg scale for purification.)

Step 4: Tert-buty 1N-[(1S,2S)-2-[[4-(6-cyano-7-dimethylphosphoryl-1H-indol-3-yl)-5-(trifluoromethyl)pyrimidin-2-yl]amino]cyclopentyl]carbamate

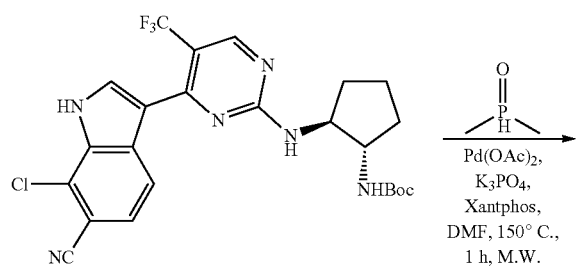

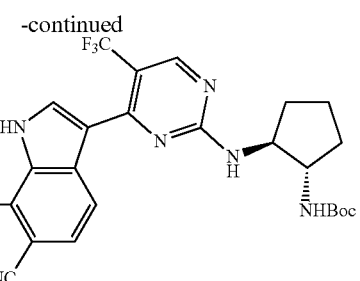

A mixture of tert-butyl N-[(1S,2S)-2-[[4-(7-chloro-6-cyano-1H-indol-3-yl)-5-(trifluoromethyl)pyrimidin-2-yl]amino]cyclopentyl]carbamate (280 mg, 537.50 umol, 1 eq), methylphosphonoylmethane (209.76 mg, 2.69 mmol, 5 eq), K₃PO₄ (228.19 mg, 1.07 mmol, 2 eq), Pd(OAc)₂ (12.07 mg, 53.75 umol, 0.1 eq), Xantphos (31.10 mg, 53.75 umol, 0.1 eq) and DMF (0.5 mL) in microwave sealed tube was degassed and purged with N₂ for 3 times, and then the mixture was stirred at 150° C. for 1 h in microwave. The reaction mixture was diluted with H₂O 200 mL and extracted with EtOAc (100 mL×2). The combined organic layers were washed with brine (300 mL×2), dried over Na₂SO₄, filtered and concentrated under reduced pressure to give a residue. It was purified by column chromatography (SiO₂, PE/EtOAc=10/1 to 4/1) to afford the title compound (210 mg) as a white solid. (Note: The reaction was combined with another reaction in 20 mg scale for purification.)

Step 5: 3-[2-[[(1S,2S)-2-aminocyclopentyl]amino]-5-(trifluoromethyl)pyrimidin-4-yl]-7-dimethylphosphoryl-1H-indole-6-carbonitrile

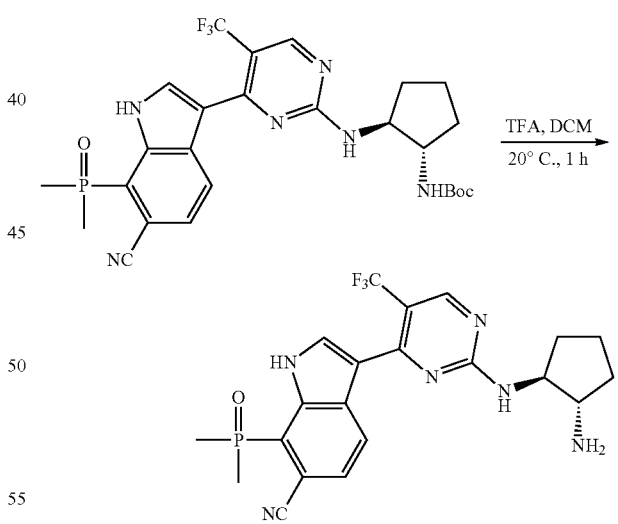

To a solution of tert-butyl N-[(1S, 2S)-2-[[4-(6-cyano-7-dimethylphosphoryl-1H-indol-3-yl)-5-(trifluoromethyl) pyrimidin-2-yl] amino]cyclopentyl] carbamate (180 mg, 319.99 umol, 1 eq) in DCM (3 mL) was added TFA (109.45 mg, 959.96 umol, 71.07 uL, 3 eq). The mixture was stirred at 20° C. for 1 h. The reaction mixture was adjusted pH to 8 with Sat.NaHCO₃ and extracted with EtOAc (30 mL×2). The combined organic layers were washed with brine (100 mL×2), dried over Na₂SO₄, filtered and concentrated under reduced pressure to give a residue. The residue was purified by prep-HPLC (neutral condition) to afford the title compound (62.1 mg) as a white solid. (Note: The reaction was combined with another reaction in 10 mg scale for purification.)

Example 36. 3-[2-[[(1S,2S)-2-aminocyclopentyl]amino]-5(trifluoromethyl)pyrimidin-4-yl]-7-dimethylphosphoryl-1H-indole-6-carboxamide (Compound 162)

Step 1: 7-chloro-3-[2-chloro-5-(trifluoromethyl)pyrimidin-4-yl]-1H-indole-6-carbonitrile

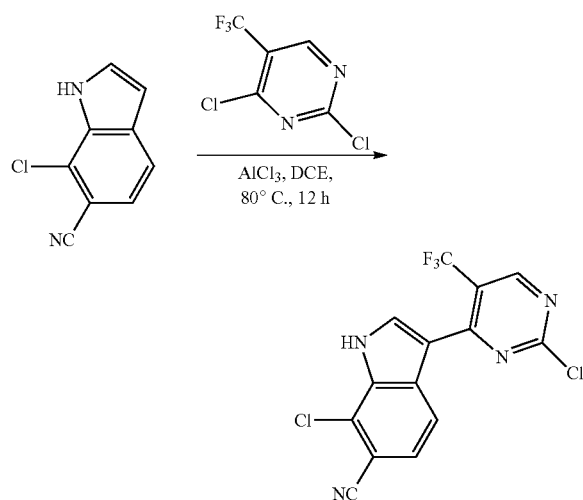

To a solution of 2, 4-dichloro-5-(trifluoromethyl)pyrimidine (5.53 g, 25.48 mmol, 3 eq) in DCE (20 mL) was added AlCl₃ (2.83 g, 21.23 mmol, 1.16 mL, 2.5 eq) at 80° C. After addition, the mixture was stirred at this temperature for 30 min, and then 7-chloro-1H-indole-6-carbonitrile (1.5 g, 8.49 mmol, 1 eq) was added at 80° C. The resulting mixture was stirred at 80° C. for 11.5 h. The reaction mixture was diluted with H₂O (200 mL) and extracted with EtOAc (100 mL×2). The combined organic layers were washed with brine (300 mL×2), dried over Na₂SO₄, filtered and concentrated under reduced pressure to give a residue. It was purified by column chromatography (SiO₂, Petroleum ether/Ethyl acetate=10/1 to 5/1) to give a residue. The residue was washed with MeOH (10 mL) and filtered to afford the title compound (330 mg) as a white solid. (Note: The reaction was combined with another reaction in 200 mg scale for work up.)

Step 2: Tert-butyl N-[(1S, 2S)-2-[[4-(7-chloro-6-cyano-1H-indol-3-yl)-5-(trifluoromethyl) pyrimidin-2-yl]amino]cyclopentyl]carbamate

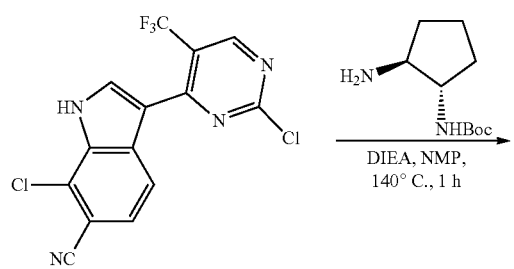

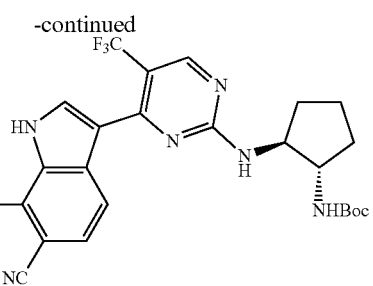

To a solution of 7-chloro-3-[2-chloro-5-(trifluoromethyl)pyrimidin-4-yl]-1H-indole-6-carbonitrile (0.3 g, 840.06 umol, 1 eq) and tert-butyl N-[(1S,2S)-2-aminocyclopentyl]carbamate (201.89 mg, 1.01 mmol, 1.2 eq) in NMP (5 mL) was added DIEA (325.72 mg, 2.52 mmol, 438.97 uL, 3 eq). The mixture was stirred at 140° C. for 1 h. It was poured into water (50 mL). The aqueous phase was extracted with EtOAc (50 mL×3). The combined organic phase was washed with brine (50 mL×2), dried over anhydrous Na₂SO₄, filtered and concentrated in vacuum. The residue was purified by silica gel chromatography (100-200 mesh silica gel, Petroleum ether/Ethyl acetate=5/1 to 0/1) to afford the title compound (0.3 g) as a yellow solid. (Note: The reaction was combined with another reaction in 30 mg scale for work up)

Step 3: Tert-butyl N-[(1S,2S)-2-[[4-(6-cyano-7-dimethylphosphoryl-1H-indol-3-yl)-5-(trifluoromethyl)pyrimidin-2-yl]amino]cyclopentyl]carbamate

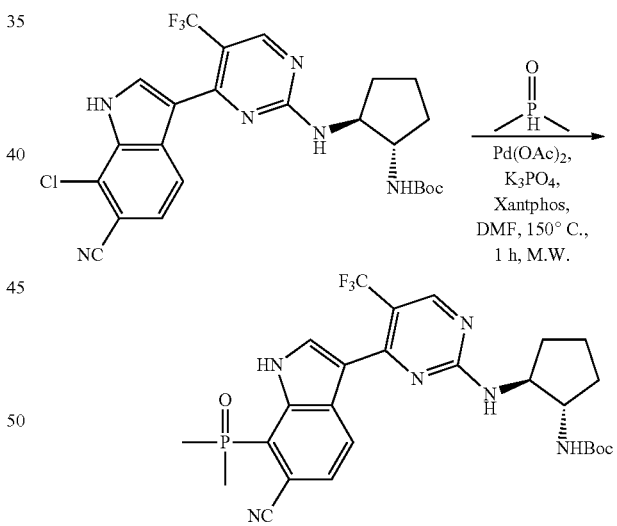

A mixture of tert-butyl N-[(1S,2S)-2-[[4-(7-chloro-6-cyano-1H-indol-3-yl)-5-(trifluoromethyl)pyrimidin-2-yl]amino]cyclopentyl]carbamate (280 mg, 537.50 umol, 1 eq), methylphosphonoylmethane (209.76 mg, 2.69 mmol, 5 eq), K₃PO₄ (228.19 mg, 1.07 mmol, 2 eq), Pd(OAc)₂ (12.07 mg, 53.75 umol, 0.1 eq), Xantphos (31.10 mg, 53.75 umol, 0.1 eq) and DMF (0.5 mL) in microwave sealed tube was degassed and purged with N₂ for 3 times, and then the mixture was stirred at 150° C. for 1 h in microwave. The reaction mixture was diluted with H₂O (200 mL) and extracted with EtOAc (100 mL×2). The combined organic layers were washed with brine (300 mL×2), dried over Na₂SO₄, filtered and concentrated under reduced pressure. It was purified by column chromatography (SiO₂, Petroleum ether/Ethyl acetate=10:1 to 4:1) to afford the title compound (210 mg) as a white solid. (Note: The reaction was combined with another reaction in 20 mg scale for work up.)

Step 4: 3-[2-[[(1S,2S)-2-aminocyclopentyl]amino]-5-(trifluoromethyl)pyrimidin-4-yl]-7-dimethylphosphoryl-1H-indole-6-carboxamide

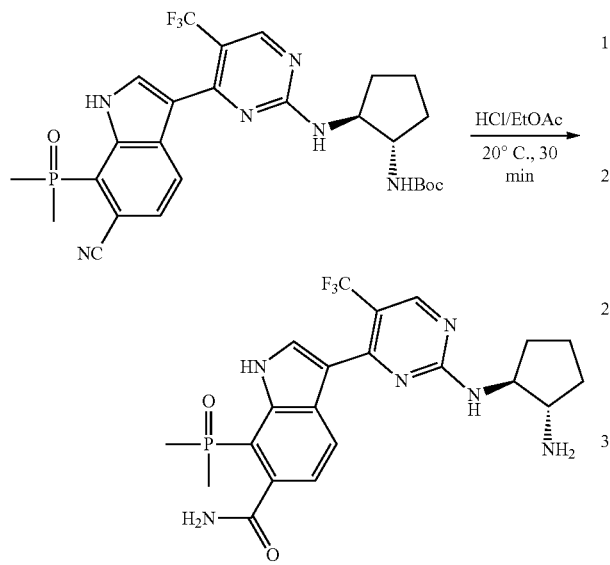

A mixture of tert-butyl N-[(1S, 2S)-2-[[4-(6-cyano-7-dimethylphosphoryl-1H-indol-3-yl)-5-(trifluoromethyl) pyrimidin-2-yl] amino]cyclopentyl]carbamate (10 mg, 17.78 umol, 1 eq) and HCl/EtOAc (4 M, TOO eq) was stirred at 20° C. for 30 min. The mixture was concentrated to give a residue. The residue was purified by prep-HPLC (HCl condition) to afford the title compound (5 mg, 9.67 umol, 54.41% yield, 100% purity, HCl) as a yellow solid.

Example 37. 1-[(1R,2S)-2-[[4-[6-(3,5-dimethylisoxazol-4-yl)-1H-pyrrolo[2,3-b]pyridin-3-yl]-5-(trifluoromethyl)pyrimidin-2-yl]amino]cyclopentyl] azetidin-3-ol (Compound 163)

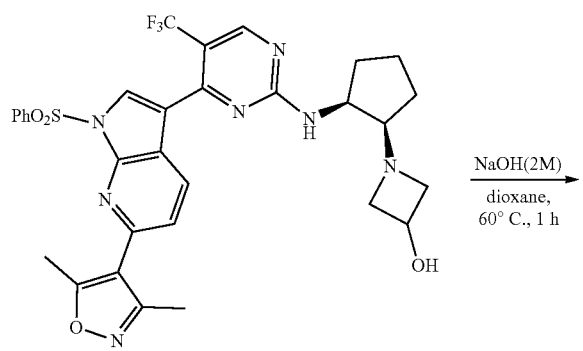

-continued

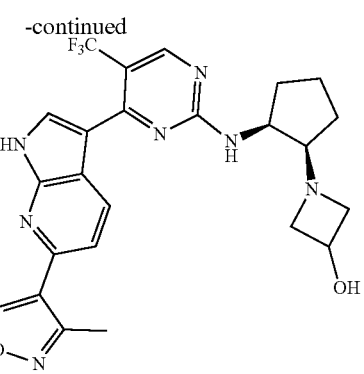

To a solution of 1-[(1R,2S)-2-[[4-[1-(benzenesulfonyl)-6-(3,5-dimethylisoxazol-4-yl) pyrrolo[2,3-b]pyridin-3-yl]-5-(trifluoromethyl)pyrimidin-2-yl]amino]cyclopentyl]azetidin-3-ol (0.04 g, 61.19 umol, 1 eq) in dioxane (0.5 mL) was added NaOH (2 M, 917.89 uL, 30 eq). The mixture was stirred at 60° C. for 1 h. It was cooled to the room temperature and poured into water (10 mL) and extracted with EtOAc (10 mL×3). The combined organic layer was washed with brine (10 mL×3), dried over Na₂SO₄, filtered. The filtrate was concentrated under reduced pressure to give a residue. It was purified by prep-HPLC (FA condition) to afford the tittle compound (7.9 mg, 14.12 umol, 23.07% yield, 100% purity, FA) as white solid.

Example 38. 4-[6-(3,5-dimethylisoxazol-4-yl)-1H-pyrrolo[2,3-b]pyridin-3-yl]-N-[(1S,2S)-2-(3-methoxyazetidin-1-yl)cyclopentyl]-5-(trifluoromethyl)pyrimidin-2-amine (Compound 164)

Step 1: Tert-butyl N-[(1S)-2-(3-methoxyazetidin-1-yl) cyclopentyl] carbamate

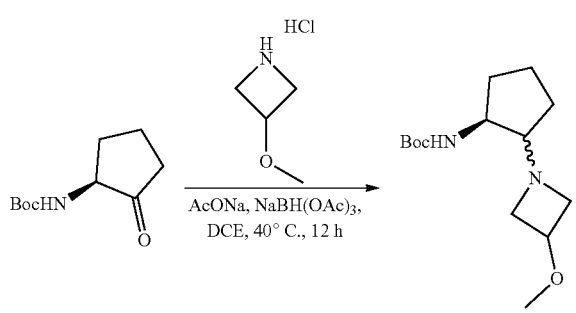

To a solution of tert-butyl N-[(1S)-2-oxocyclopentyl] carbamate (0.5 g, 2.51 mmol, 1 eq) in DCE (30 mL) was added 3-methoxyazetidine (620.24 mg, 5.02 mmol, 2 eq, HCl), NaOAc (514.63 mg, 6.27 mmol, 2.5 eq) and NaBH(OAc)₃ (1.60 g, 7.53 mmol, 3 eq). The mixture was stirred at 40° C. for 12 h. It was cooled to the room temperature and diluted with water (150 Ml), and then separation of organic and aqueous phases, the organic layers was discarded. The aqueous phases were adjusted pH to 7 by added NaHCO₃ solid, extracted with EtOAc (100 mL×2), combined all organic layers, washed with brine 200 mL, dried over Na₂SO₄, filtered and concentrated under reduced pressure to afford the title compound (690 mg, crude) as a white solid which was used directly into the next step without purification. (Note: The reaction was combined with another reaction in 50 mg scale for work-up and purification.)

Step 2: (1S)-2-(3-methoxyazetidin-1-yl) cyclopentanamine

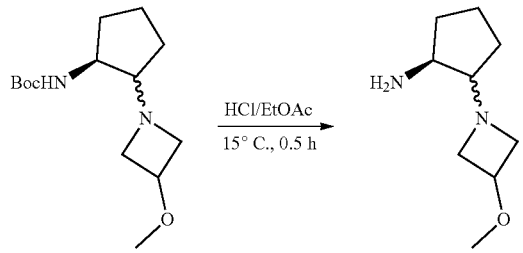 [SMILES: COC1CN(C2CCC[C@@H]2NC(=O)OC(C)(C)C)C1 ; COC1CN(C2CCC[C@@H]2N)C1]

To a solution of tert-butyl N-[(1S)-2-(3-methoxyazetidin-1-yl) cyclopentyl] carbamate (690 mg, 2.55 mmol, 1 eq) in EtOAc (5 mL) was added HCl/EtOAc (4 M, 60 mL, 94.04 eq). The mixture was stirred at 15° C. for 0.5 h. It was concentrated under reduced pressure to remove solvent. The residue was diluted with water (100 mL), adjusted pH to 10, and extracted with EtOAc (50 mL×15). The combined organic layers were washed with brine (200 mL), dried over Na$_2$SO$_4$, filtered and concentrated under reduced pressure to afford the title compound (300 mg, crude) as a yellow solid.

Step 3: 4-[1-(benzenesulfonyl)-6-(3,5-dimethyl-isoxazol-4-yl)pyrrolo[2,3-b]pyridin-3-yl]-N-[(1S, 2S)-2-(3-methoxyazetidin-1-yl)cyclopentyl]-5-(trifluoromethyl)pyrimidin-2-amine and 4-[1-(benzenesulfonyl)-6-(3,5-dimethylisoxazol-4-yl) pyrrolo[2,3-b]pyridin-3-yl]-N-[(1S,2R)-2-(3-methoxyazetidin-1-yl)cyclopentyl]-5-(trifluoromethyl)pyrimidin-2-amine

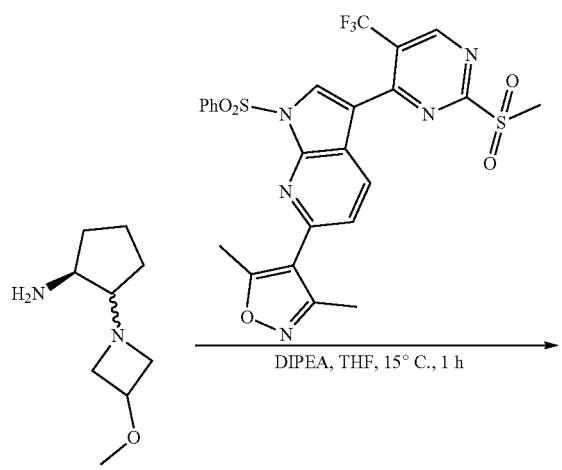

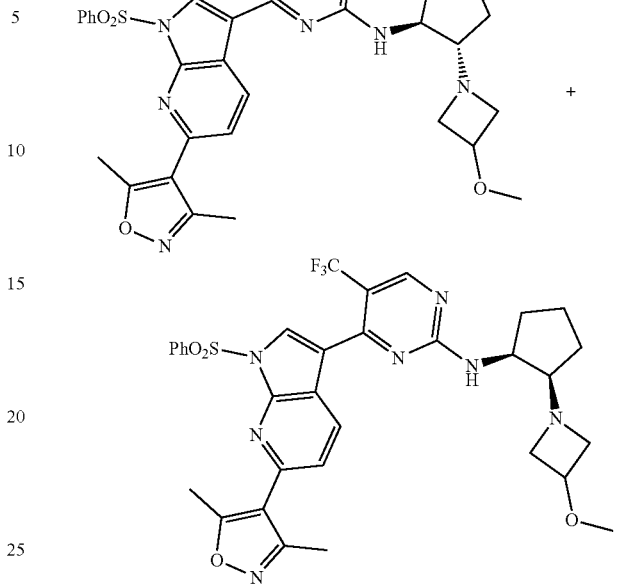

To a solution of 4-[1-(benzenesulfonyl)-3-[2-methylsulfonyl-5-(trifluoromethyl) pyrimidin-4-yl]pyrrolo[2, 3-b] pyridin-6-yl]-3, 5-dimethyl-isoxazole (0.5 g, 865.72 umol, 1 eq) in THF (5 mL) was added DIPEA (223.78 mg, 1.73 mmol, 301.59 uL, 2 eq) and (1S)-2-(3-methoxyazetidin-1-yl) cyclopentanamine (176.87 mg, 1.04 mmol, 1.2 eq). The mixture was stirred at 15° C. for 1 h. It was concentrated under reduced pressure to give a residue. The residue was purified by column chromatography (SiO$_2$, PE/EtOAc/EtOH=10/10/1) to obtain the residue (220 mg, 92% purity). The residue was separated of chiral isomers by SFC (column: DAICEL CHIRALPAK AD-H (250 mm×30 mm, 5 urn); mobile phase: [0.1% NH$_3$H$_2$O ETOH]; B %: 38%-38%, 14 min) to afford title compound 1 (90 mg, 133.04 umol, 40.38% yield, 98.7% purity) as brown solid and title compound 2 (85 mg, 123.61 umol, 37.52% yield, 97.1% purity) as yellow solid.

Step 4: 4-[6-(3,5-dimethylisoxazol-4-yl)-1H-pyrrolo[2,3-b]pyridin-3-yl]-N-[(1S,2S)-2-(3-methoxyazetidin-1-yl)cyclopentyl]-5-(trifluoromethyl)pyrimidin-2-amine

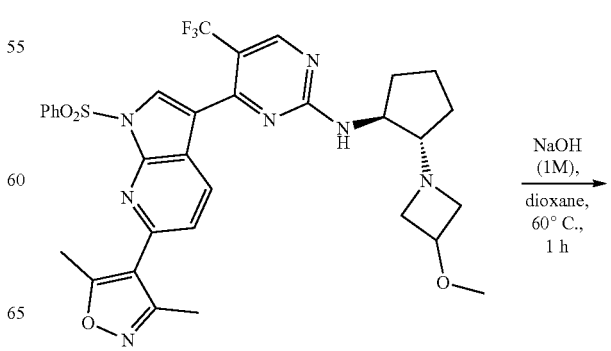

-continued

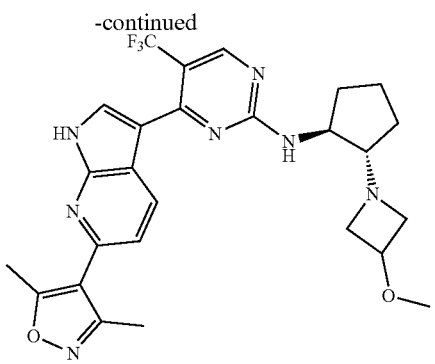

To a solution of 4-[1-(benzenesulfonyl)-6-(3,5-dimethylisoxazol-4-yl) pyrrolo[2,3-b]pyridin-3-yl]-N-[(1S,2S)-2-(3-methoxy azetidin-1-yl)cyclopentyl]-5-(trifluoromethyl)pyrimidin-2-amine (80 mg, 119.81 umol, 1 eq) in dioxane (1 mL) was added NaOH (2 M, 1.80 mL, 30 eq). The mixture was stirred at 60° C. for 1 h. It was cooled to the room temperature and poured into water (10 mL) and extracted with EtOAc (10 mL×3). The combined organic layer was washed with brine (10 mL×3), dried over Na$_2$SO$_4$, filtered. The filtrate was concentrated under reduced pressure to give a residue. It was purified by prep-HPLC (HCl condition) to afford the title compound 1 (25.7 mg, 43.52 umol, 36.32% yield, 95.5% purity, HCl) as yellow solid.

Example 39. 4-[6-(3,5-dimethylisoxazol-4-yl)-1H-pyrrolo[2,3-b]pyridin-3-yl]-N-[(1S,2R)-2-(3-methoxyazetidin-1-yl)cyclopentyl]-5-(trifluoromethyl)pyrimidin-2-amine (Compound 165)

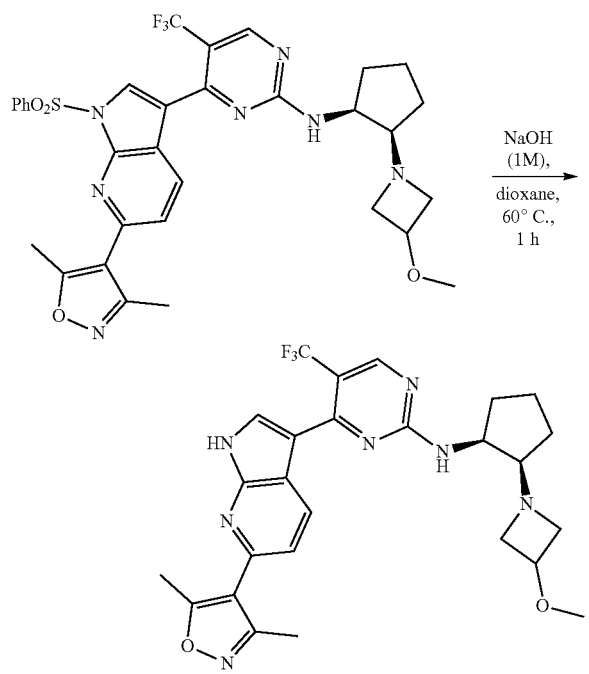

To a solution of 4-[1-(benzenesulfonyl)-6-(3, 5-dimethylisoxazol-4-yl) pyrrolo[2,3-b]pyridin-3-yl]-N-[(1S,2R)-2-(3-methoxy azetidin-1-yl)cyclopentyl]-5-(trifluoromethyl) pyrimidin-2-amine (80 mg, 119.81 umol, 1 eq) in dioxane (1 mL) was added NaOH (2 M, 299.54 uL, 5 eq). The mixture was stirred at 60° C. for 1 h. It was cooled to the room temperature and poured into water (10 mL) and extracted with EtOAc (10 mL×3). The combined organic layer was washed with brine (10 mL×3), dried over Na$_2$SO$_4$, filtered. The filtrate was concentrated under reduced pressure to give a residue. It was purified by prep-HPLC (HCl condition) to afford the title compound 2 (25.1 mg, 42.72 umol, 35.65% yield, 95.99% purity, HCl) as yellow solid.

Example 40. N-[(1S,2S)-2-(3,3-difluoroazetidin-1-yl)cyclopentyl]-4-[6-(3,5-dimethylisoxazol-4-yl)-1H-pyrrolo[2,3-b]pyridin-3-yl]-5-(trifluoromethyl) pyrimidin-2-amine (Compound 166)

Step 1: Tert-butyl N-[(1S, 2R)-2-hydroxycyclopentyl] carbamate

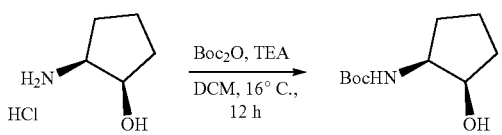 [SMILES: Cl ; N[C@H]1CCC[C@H]1O ; CC(C)(C)OC(=O)N[C@H]1CCC[C@H]1O]

To a solution of (1S, 2R)-2-aminocyclopentanol, hydrochloride (2 g, 14.53 mmol, 1 eq) in DCM (20 mL) was added TEA (4.41 g, 43.60 mmol, 6.07 mL, 3 eq) and Boc$_2$O (3.17 g, 14.53 mmol, 3.34 mL, 1 eq). The mixture was stirred at 16° C. for 12 h. It was concentrated under reduced pressure to remove DCM. The residue was diluted with water 50 mL, adjusted pH to 7 by added HCl (1 M), and then extracted with EtOAc (30 mL×3). The combined organic layers were washed with brine (50 mL), dried over Na$_2$SO$_4$, filtered and concentrated under reduced pressure to afford the title compound (2.5 g, crude) as a colorless oil which was used directly into the next step without purification.

Step 2: Tert-butyl N-[(1S)-2-oxocyclopentyl]carbamate

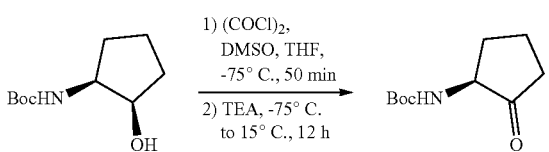 [SMILES: CC(C)(C)OC(=O)N[C@H]1CCC[C@H]1O ; CC(C)(C)OC(=O)N[C@H]1CCCC1=O]

A mixture of oxalyl chloride (1.18 g, 9.32 mmol, 815.49 uL, 1.5 eq) in THF (20 mL) is cooled to −72° C. under nitrogen and treated dropwise with DMSO (1.46 g, 18.63 mmol, 1.32 mL, 3 eq). It was stirred at this temperature for 5 min, and then tert-butyl N-[(1S, 2R)-2-hydroxycyclopentyl]carbamate (1.25 g, 6.21 mmol, 1 eq) was added into the mixture, stirred is continued at −75° C. for 45 min. TEA (3.39 g, 33.54 mmol, 4.67 mL, 5.4 eq) was added slowly keeping the temperature below −68° C., after the addition is complete the reaction is allowed to warm slowly to 15° C., stirred at this temperature for 12 h. It was quenched by addition water (100 mL) and concentrated under reduced pressure to remove THF, and then extracted with EtOAc (50 mL×2). The combined organic layers were washed with brine (100 mL), dried over Na$_2$SO$_4$, filtered and concentrated under reduced pressure to give a residue. The residue was purified by column chromatography (SiO₂, PE/EtOAc=100/1 to 15/1) to afford the title compound (1.1 g, 99% purity) as a yellow solid.

Step 3: Tert-butyl N-[(1S)-2-(3, 3-difluoroazetidin-1-yl) cyclopentyl] carbamate

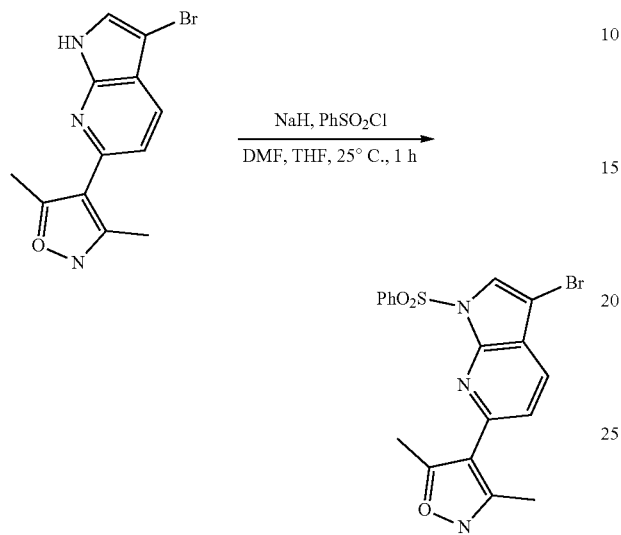

To a solution of tert-butyl N-[(1S)-2-oxocyclopentyl] carbamate (0.5 g, 2.51 mmol, 1 eq) in DCE (30 mL) was added 3,3-difluoroazetidin (650.13 mg, 5.02 mmol, 2 eq, HCl), NaOAc (514.65 mg, 6.27 mmol, 2.5 eq) and NaBH(OAc)₃ (1.60 g, 7.53 mmol, 3 eq). The mixture was stirred at 40° C. for 12 h. It was diluted with water 150 mL, and adjusted pH to 7 by added NaHCO₃ solid, and then separation of organic and aqueous phases, and the aqueous phases were extracted with EtOAc (100 mL×2), combined all of the organic layers, washed with brine (200 mL), dried over Na₂SO₄, filtered and concentrated under reduced pressure to afford the title compound (720 mg, crude) as a white solid which was used directly into the next step without purification. (Note: The reaction was combined with another reaction in 50 mg scale for work up.)

Step 4: (1S)-2-(3, 3-difluoroazetidin-1-yl) cyclopentanamine

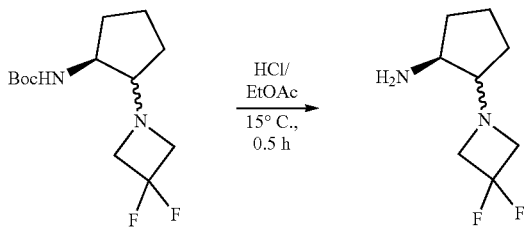 [SMILES: CC(C)(C)OC(=O)N[C@H]1CCCC1N1CC(F)(F)C1 ; N[C@H]1CCCC1N1CC(F)(F)C1]

To a solution of tert-butyl N-[(1S)-2-(3,3-difluoroazetidin-1-yl)cyclopentyl] carbamate (720 mg, 2.61 mmol, 1 eq) in EtOAc (5 mL) was added HCl/EtOAc (4 M, 40 mL, 61.40 eq). The mixture was stirred at 15° C. for 0.5 h. It was concentrated under reduced pressure to remove solvent. The residue was diluted with water (100 mL), adjusted pH to 10, and extracted with EtOAc (50 mL×15). The combined organic layers were washed with brine 200 mL, dried over Na₂SO₄, filtered and concentrated under reduced pressure to afford the title compound (230 mg, crude) as a yellow oil which was used directly into the next step without purification.

Step 5: 4-[1-(benzenesulfonyl)-6-(3,5-dimethyl-isoxazol-4-yl)pyrrolo[2, 3-b]pyridin-3-yl]-N-[(1S)-2-(3,3-difluoroazetidin-1-yl) cyclopentyl]-5-(trifluoromethyl)pyrimidin-2-amine

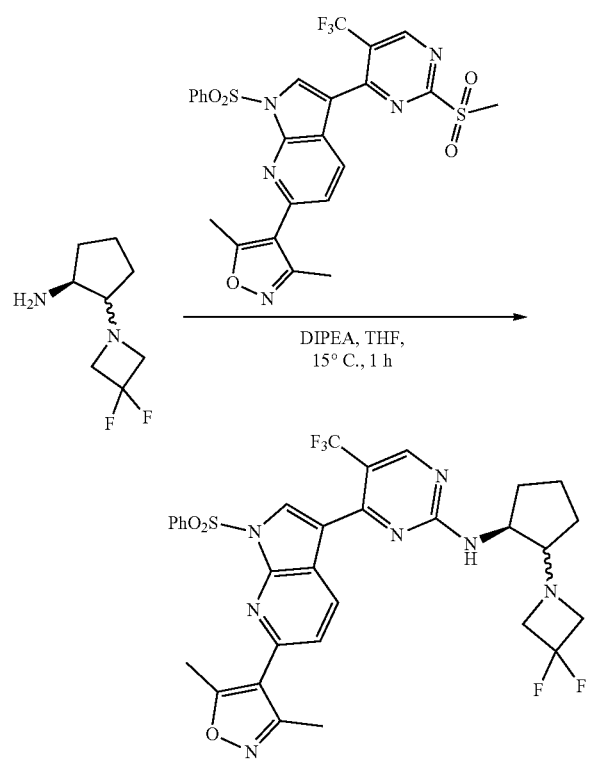

To a solution of 4-[1-(benzenesulfonyl)-3-[2-methylsulfonyl-5-(trifluoromethyl) pyrimidin-4-yl]pyrrolo[2,3-b]pyridin-6-yl]-3, 5-dimethyl-isoxazole (500 mg, 865.72 umol, 1 eq) in THF (5 mL) was added DIPEA (223.78 mg, 1.73 mmol, 301.59 uL, 2 eq) and (1S)-2-(3,3-difluoroazetidin-1-yl)cyclopentanamine (183.05 mg, 1.04 mmol, 1.2 eq). The mixture was stirred at 15° C. for 1 h. It was concentrated under reduced pressure to give a residue. It was purified by column chromatography (SiO₂, PE/EtOAc=5/1 to 2/1) to afford the title compound (220 mg, 85% purity) as a brown solid.

Step 6: 4-[1-(benzenesulfonyl)-6-(3,5-dimethyl-isoxazol-4-yl)pyrrolo[2,3-b]pyridin-3-yl]-N-[(1S,2R)-2-(3,3-difluoroazetidin-1-yl)cyclopentyl]-5-(trifluoromethyl)pyrimidin-2-amine And 4-[1-(benzenesulfonyl)-6-(3,5-dimethylisoxazol-4-yl)pyrrolo[2,3-b]pyridin-3-yl]-N-[(1S,2S)-2-(3,3-difluoroazetidin-1-yl)cyclopentyl]-5-(trifluoromethyl)pyrimidin-2-amine

Step 7: N-[(1S,2S)-2-(3,3-difluoroazetidin-1-yl)cyclopentyl]-4-[6-(3,5-dimethylisoxazol-4-yl)-1H-pyrrolo[2,3-b]pyridin-3-yl]-5-(trifluoromethyl)pyrimidin-2-amine

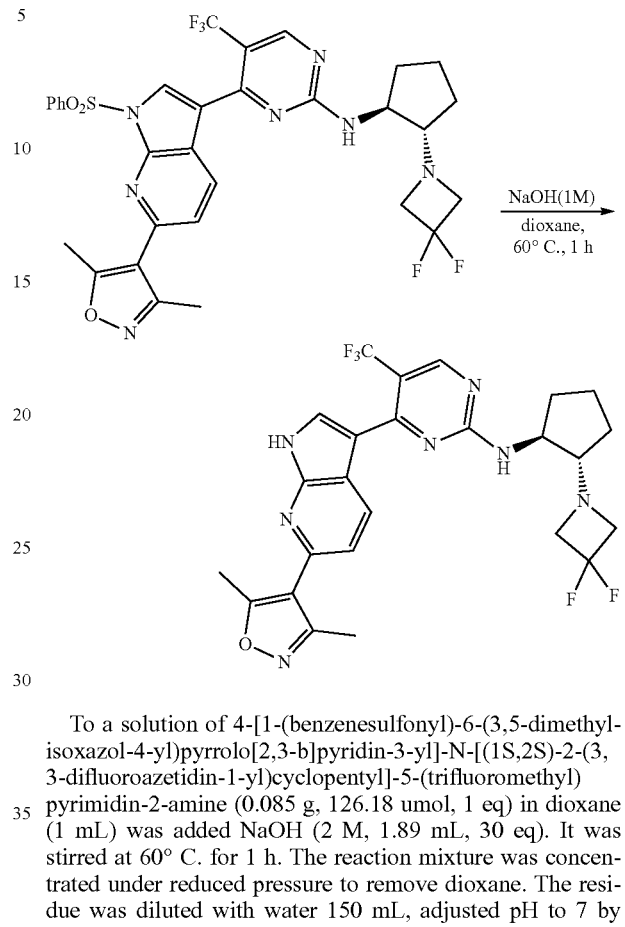

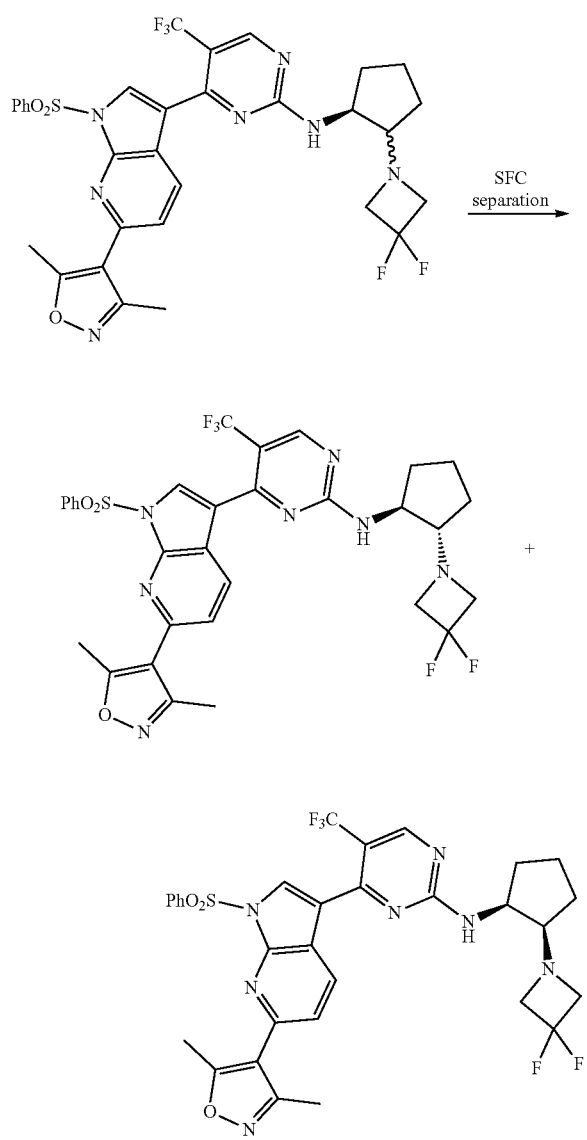

To a solution of 4-[1-(benzenesulfonyl)-6-(3,5-dimethylisoxazol-4-yl)pyrrolo[2,3-b]pyridin-3-yl]-N-[(1S,2S)-2-(3,3-difluoroazetidin-1-yl)cyclopentyl]-5-(trifluoromethyl)pyrimidin-2-amine (0.085 g, 126.18 umol, 1 eq) in dioxane (1 mL) was added NaOH (2 M, 1.89 mL, 30 eq). It was stirred at 60° C. for 1 h. The reaction mixture was concentrated under reduced pressure to remove dioxane. The residue was diluted with water 150 mL, adjusted pH to 7 by added HCl (1M), and then extracted with EtOAc (50 mL×2). The combined organic layers were washed with brine 100 mL, dried over $Na_2SO_4$, filtered and concentrated under reduced pressure to obtain the residue. The residue was purified by prep-HPLC (FA condition) to afford the title compound (25.2 mg, 42.74 umol, 28.50% yield, 98.29% purity, FA) as white solid.

Example 41. N-[(1S,2R)-2-(3,3-difluoroazetidin-1-yl)cyclopentyl]-4-[6-(3,5-dimethylisoxazol-4-yl)-1H-pyrrolo[2,3-b]pyridin-3-yl]-5-(trifluoromethyl)pyrimidin-2-amine (Compound 167)

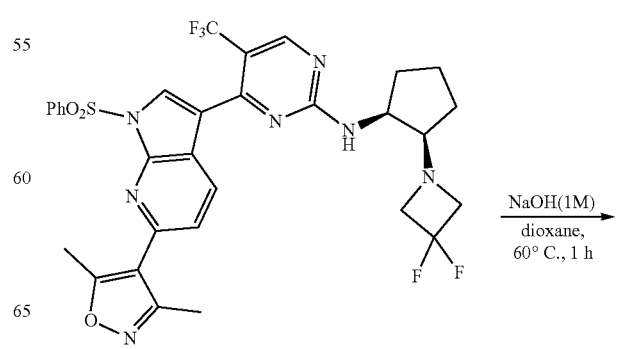

4-[1-(benzenesulfonyl)-6-(3,5-dimethylisoxazol-4-yl)pyrrolo[2,3-b]pyridin-3-yl]-N-[(1S)-2-(3,3-difluoroazetidin-1-yl)cyclopentyl]-5-(trifluoromethyl)pyrimidin-2-amine (220 mg, 326.58 umol, 1 eq) was separated of chiral isomers by SFC (column: DAICEL CHIRALPAK AD-H (250 mm×30 mm, 5 um); mobile phase: [0.1% $NH_3H_2O$ IPA]; B %: 38%-38%, 17 min) to afford title compound 1 (80 mg, 114.00 umol, 34.91% yield, 96% purity) as brown solid and title compound 2 (80 mg, 114.00 umol, 34.91% yield, 96% purity) as brown solid.

-continued

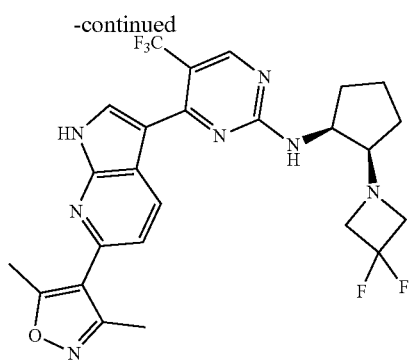

To a solution of 4-[1-(benzenesulfonyl)-6-(3,5-dimethyl-isoxazol-4-yl)pyrrolo[2,3-b]pyridin-3-yl]-N-[(1S,2R)-2-(3,3-difluoroazetidin-1-yl)cyclopentyl]-5-(trifluoromethyl)pyrimidin-2-amine (85.00 mg, 126.18 umol, 1 eq) in dioxane (1 mL) was added NaOH (2 M, 1.89 mL, 30 eq). The mixture was stirred at 60° C. for 1 h. The reaction mixture was concentrated under reduced pressure to remove dioxane. The residue was diluted with water 150 mL, adjusted pH to 7 by added HCl (1M), and then extracted with EtOAc (50 mL×2). The combined organic layers were washed with brine 100 mL, dried over Na$_2$SO$_4$, filtered and concentrated under reduced pressure to give a residue. The residue was purified by prep-HPLC (HCl condition) to obtain the residue, firstly. Then the residue was purified by prep-HPLC (neutral condition) secondly to afford the title compound (6.3 mg, 11.75 umol, 7.84% yield, 99.52% purity) as light yellow solid.

Example 42. 3-[2-[[(1S,2S)-2-aminocyclopentyl]amino]-5-(trifluoromethyl) pyrimidin-4-yl]-7-chloro-1H-indol-6-ol (Compound 168)

Step 1: 6-bromo-7-chloro-1H-indole

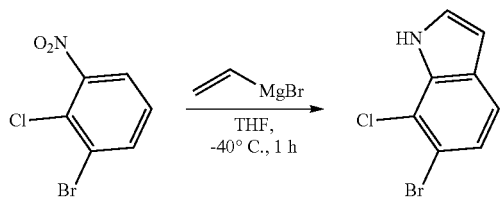

To a solution of 1-bromo-2-chloro-3-nitro-benzene (5 g, 21.15 mmol, 1 eq) in THF (50 mL) was added bromo(vinyl)magnesium (1 M, 105.73 mL, 5 eq) at −40° C. slowly. The mixture was stirred at −40° C. for 1 h. The reaction mixture was diluted with water (1000 Ml) and extracted with EtOAc (100 mL×3). The combined organic layers were washed with brine (100 mL×3), dried over Na$_2$SO$_4$, filtered and concentrated under reduced pressure to give a residue. It was purified by column chromatography (SiO$_2$, Petroleum ether/Ethyl acetate=8/1) to afford the title compound (13 g, 45.12 mmol, 42.68% yield, 80% purity) as white solid. (Note: The reaction was combined with other 4 batch in 5 g scale for work-up.)

Step 2: 6-bromo-7-chloro-3-[2-chloro-5-(trifluoromethyl)pyrimidin-4-yl]-1H-indole

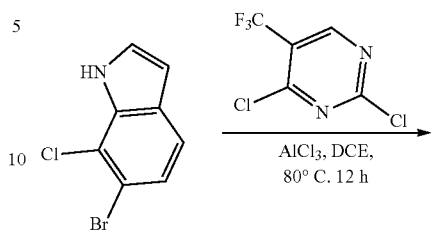

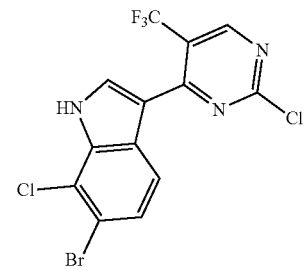

To a solution of 2,4-dichloro-5-(trifluoromethyl)pyrimidine (6.21 g, 28.63 mmol, 1.1 eq) in DCE (60 mL) was added AlCl$_3$ (4.17 g, 31.24 mmol, 1.71 mL, 1.2 eq), the reaction mixture was stirred at 80° C. for 0.5 h. before 6-bromo-7-chloro-1H-indole (6 g, 26.03 mmol, 1 eq) was added to the solution at 80° C. for 11.5 h. It was cooled to room temperature and diluted with water (200 mL) and extracted with EtOAc (50 mL×3). The combined organic layers were washed with brine (30 mL×3), dried over Na$_2$SO$_4$, filtered and concentrated under reduced pressure to give a residue that was purified by column chromatography (SiO$_2$, Petroleum ether/Ethyl acetate=3/1) then triturated with MeOH (30 mL) and filtered to collect the cake. The filtrate was purified by prep-HPLC. The 2 batch was combined to afford the title compound (2.4 g) as yellow solid.

Step 3: 2-[[6-bromo-7-chloro-3-[2-chloro-5-(trifluoromethyl)pyrimidin-4-yl]indol-1-yl]methoxy]ethyl-trimethyl-silane

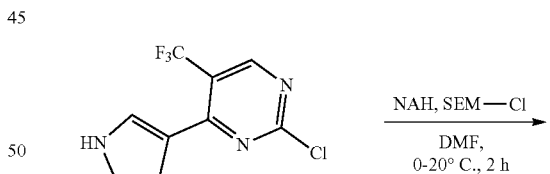

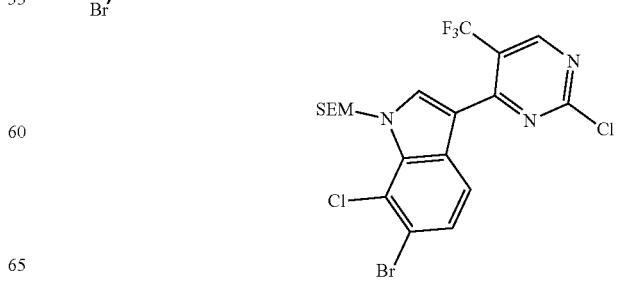

To a solution of 6-bromo-7-chloro-3-[2-chloro-5-(trifluoromethyl)pyrimidin-4-yl]-1H-indole (2.4 g, 5.84 mmol, 1 eq) in DMF (30 mL) was added NaH (303.62 mg, 7.59 mmol, 60% purity, 1.3 eq) at 0° C. for 0.5 h, then SEM-Cl (1.46 g, 8.76 mmol, 1.55 mL, 1.5 eq) was added to the solution. The mixture was stirred at 20° C. for 1.5 h. The reaction mixture was diluted with water (500 mL) and extracted with EtOAc (50 mL×3). The combined organic layers were washed with brine (50 mL×3), dried over Na$_2$SO$_4$, filtered and concentrated under reduced pressure to give a residue. It was purified by column chromatography (SiO$_2$, Petroleum ether/Ethyl acetate=5/1) to afford the title compound (2.7 g) as a brown solid.

Step 4: Tert-butyl N-[(1S,2S)-2-[[4-[6-bromo-7-chloro-1-(2-trimethylsilylethoxymethyl) indol-3-yl]-5-(trifluoromethyl)pyrimidin-2-yl]amino]cyclopentyl]carbamate

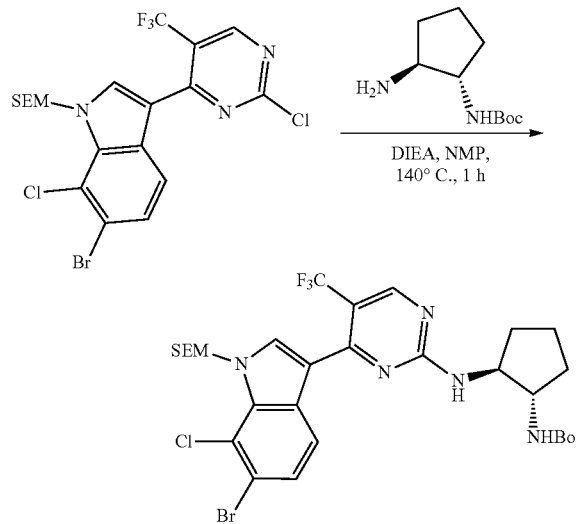

To a solution of 2-[[6-bromo-7-chloro-3-[2-chloro-5-(trifluoromethyl)pyrimidin-4-yl] indol-1-yl]methoxy]ethyl-trimethyl-silane(0.25 g, 461.88 umol, 1 eq) in NMP (2 mL) was added DIPEA (298.48 mg, 2.31 mmol, 402.26 uL, 5 eq) and tert-butyl N-[(1S,2S)-2-aminocyclopentyl]carbamate (111.01 mg, 554.26 umol, 1.2 eq). The mixture was stirred at 140° C. for 1 h. The mixture was concentrated under reduced pressure to give a residue. It was purified by column chromatography (SiO$_2$, PE/EtOAc=2/1) to afford the title compound (250 mg) as a yellow oil.

Step 5: Tert-butyl N-[(1S,2S)-2-[[4-[7-chloro-6-hydroxy-1-(2-trimethylsilylethoxymethyl) indol-3-yl]-5-(trifluoromethyl)pyrimidin-2-yl]amino]cyclopentyl]carbamate

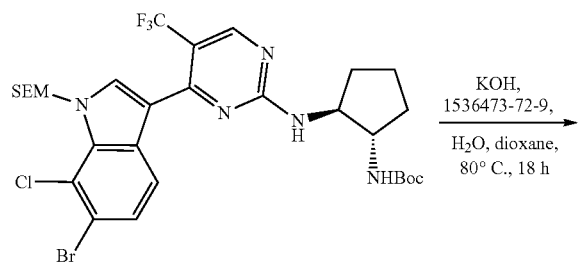

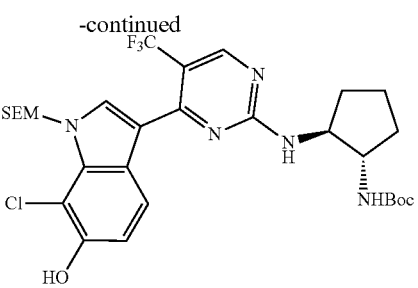

To a solution of tert-butyl N-[(1S,2S)-2-[[4-[6-bromo-7-chloro-1-(2-trimethylsilylethoxymethyl)indol-3-yl]-5-(trifluoromethyl)pyrimidin-2-yl]amino]cyclopentyl]carbamate (0.3 g, 425.48 umol, 1 eq) in dioxane (3 mL) was added KOH (119.36 mg, 2.13 mmol, 5 eq), H$_2$O (153.30 mg, 8.51 mmol, 153.30 uL, 20 eq) [2-(2-aminophenyl)phenyl]-methylsulfonyloxypalladium; ditert-butyl-[3,6-dimethoxy-2-(2,4,6 triisopropylphenyl) phenyl]phosphane (72.71 mg, 85.10 umol, 0.2 eq). The mixture was stirred at 80° C. for 18 h under N$_2$. It was diluted with water 50 mL and extracted with EtOAc (5 mL×3). The combined organic layers were washed with brine (5 mL×3), dried over Na$_2$SO$_4$, filtered and concentrated under reduced pressure to give a residue. It was purified by column chromatography (SiO$_2$, PE/EtOAc=2/1) to afford the title compound (150 mg) as a yellow oil.

Step 6: 3-[2-[[(1S, 2S)-2-aminocyclopentyl]amino]-5-(trifluoromethyl) pyrimidin-4-yl]-7-chloro-1H-indol-6-ol

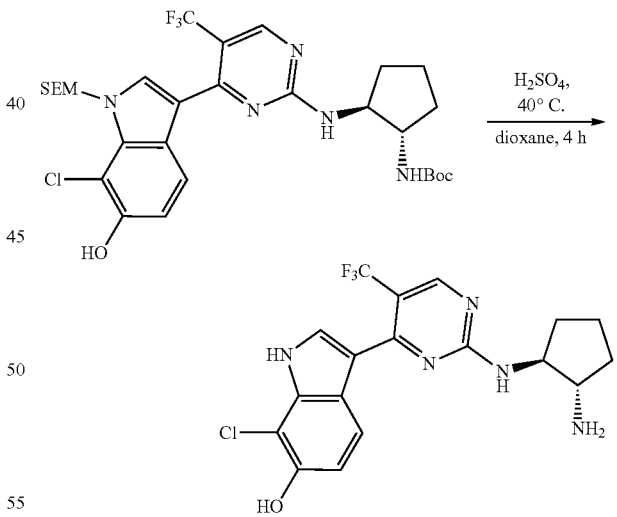

To a solution of tert-butyl N-[(1S,2S)-2-[[4-[7-chloro-6-hydroxy-1-(2-trimethylsilylethoxymethyl)indol-3-yl]-5-(trifluoromethyl)pyrimidin-2-yl]amino]cyclopentyl]carbamate (50 mg, 77.86 umol, 1 eq) in dioxane (3 mL) was added H$_2$SO$_4$ (152.73 mg, 1.56 mmol, 83.00 uL, 20 eq). The mixture was stirred at 40° C. for 4 h. It was cooled to r.t. and adjusted pH to 12 with NaOH (2N). The aqueous phase was extracted with ethyl acetate (30 mL×2). The combined organic phase was washed with brine (50 mL×2), dried over anhydrous Na$_2$SO$_4$, filtered and concentrated in vacuum.

The residue was purified by prep-HPLC (FA condition) to afford the title compound (9.2 mg, 96.04% purity, FA) as a light yellow solid.

Example 43. Inhibition of CDK Kinase Activity

Compounds of the invention were assayed for inhibition of CDK7, CDK9, CDK12, and CDK2 activity at Biortus Biosciences (Jiangyin, Jiangsu Province, P.R. of China) using kinase assays for each CDK developed with a Caliper/LabChip EZ Reader (Perkin Elmer, Waltham, MA). These assays measure the amount of phosphorylated peptide substrate produced as a fraction of the total peptide following an incubation period at 27° C. with the following components: test compounds (variable concentrations from 10 μM down to 0.508 nM in a series of 3-fold serial dilutions), active CDK kinase protein (with the indicated Cyclin, listed below for each CDK), ATP (2 mM), and substrate peptide (listed below) in the buffer 2-(N-morpholino)ethanesulfonate (MES buffer, 20 mM), pH 6.75, 0.01% (v/v) Tween 20 detergent, 0.05 mg/mL bovine serum albumin (BSA).

Specifically, the CDK7 inhibition assay used CDK7/Cyclin H/MAT1 complex (6 nM) and "5-FAM-CDK7tide" peptide substrate (2 μM, synthesized fluorophore-labeled peptide with the following sequence: 5-FAM-YSPTSPSYS-PTSPSYSPTSPSKKKK (SEQ ID NO: 1), where "5-FAM" means 5-carboxyfluorescein) with 6 mM $MgCl_2$ in the buffer composition listed above. Furthermore, the CDK9 inhibition assay used CDK9/Cyclin T1 complex (8 nM) and "5-FAM-CDK9tide" peptide substrate (2 μM, synthesized fluorophore-labeled peptide with the following sequence: 5-FAM-GSRTPMY-$NH_2$ (SEQ ID NO:2) where 5-FAM is defined above and $NH_2$ signifies a C-terminal amide) with 10 mM $MgCl_2$ in the buffer composition listed above. The CDK12 inhibition assay used CDK12 (aa686-1082)/Cyclin K complex (50 nM) and "5-FAM-CDK9tide" (2 μM) as defined above, with 2 mM $MgCl_2$ in the buffer composition above. Additionally, the CDK2 inhibition assay used CDK2/Cyclin E1 complex (0.5 nM) and "5-FAM-CDK7tide" (2 μM) as defined above, with 2 mM $MgCl_2$ in the buffer composition listed above.

The incubation period at 27° C. for each CDK inhibition assay was chosen such that the fraction of phosphorylated peptide product produced in each assay, relative to the total peptide concentration, was approximately 20% (±5%) for the uninhibited kinase (35 min. for CDK7, 35 min. for CDK2, 3 hr. for CDK12, 15 min. for CDK9). In cases where the compound titrations were tested and resulted in inhibition of peptide product formation, these data were fit to produce best-fit $IC_{50}$ values. The results of these assays are shown below in Table 3 where "A" represents a calculated $IC_{50}$ of less than 30 nM; "B" represents a calculated $IC_{50}$ of between 30 nM and less than 100 nM; "C" represents a calculated $IC_{50}$ of between 100 nM and less than 500 nM; "D" represents a calculated $IC_{50}$ of greater than or equal to 500 nM, and "NT" represents that the specified compound was not tested in the specified assay.

The inhibitory activity of selected compounds against CDK2, CDK7, CDK9, and CDK12 was found to be as follows.

| Compound | CDK 12 | CDK 2 | CDK 7 | CDK 9 |
|---|---|---|---|---|
| 100 | D | D | D | D |
| 101 | D | D | A | D |
| 102 | D | D | D | D |
| 103 | D | D | A | D |
| 104 | D | D | B | D |
| 105 | D | D | D | D |
| 106 | D | D | A | D |
| 107 | D | D | C | D |
| 108 | D | D | B | D |
| 109 | D | D | C | D |
| 110 | D | D | C | D |
| 111 | D | D | C | D |
| 112 | D | D | C | D |
| 113 | D | D | D | D |
| 114 | D | D | A | D |
| 115 | D | D | B | D |
| 116 | D | D | A | D |
| 117 | D | D | A | D |
| 118 | D | D | A | D |
| 119 | D | D | A | D |
| 120 | D | D | D | D |
| 121 | D | D | B | D |
| 122 | D | D | B | D |
| 123 | D | D | A | D |
| 124 | D | D | C | D |
| 125 | D | D | D | D |
| 126 | D | D | B | D |
| 127 | D | D | A | D |
| 128 | D | D | A | D |
| 129 | D | D | A | D |
| 130 | D | D | C | D |
| 131 | D | D | A | D |
| 132 | D | D | D | D |
| 133 | D | D | B | D |
| 134 | D | D | D | D |
| 135 | D | D | A | D |
| 136 | D | D | C | D |
| 137 | D | D | A | D |
| 138 | D | D | B | D |
| 139 | D | D | A | D |
| 140 | D | D | A | D |
| 141 | D | D | A | D |
| 142 | D | D | A | D |
| 143 | D | D | A | D |
| 144 | D | D | A | D |
| 145 | D | D | A | D |
| 146 | D | D | A | D |
| 147 | D | D | A | D |
| 148 | D | D | A | D |
| 149 | D | D | A | D |
| 150 | D | D | B | D |
| 151 | D | D | A | D |
| 152 | D | D | A | D |
| 153 | D | D | A | D |
| 154 | D | D | A | D |
| 155 | D | D | C | D |
| 156 | D | D | A | D |
| 157 | D | D | A | D |
| 158 | D | D | A | D |
| 159 | D | D | A | D |
| 160 | D | D | A | D |
| 161 | D | D | A | D |
| 162 | NT | D | A | D |
| 163 | D | D | B | D |
| 164 | D | D | A | D |
| 165 | D | D | B | D |
| 166 | D | D | D | D |
| 167 | D | D | D | D |
| 168 | D | D | A | D |

Example 44. Inhibition of Cell Proliferation

HCC70 and MB453 cells are cell lines derived from human triple negative breast cancer. COV318 and COV504 cells are cell lines derived from human ovarian cancer. Representative compounds of the invention were tested at different concentrations (from 4 μM to 126.4 pM; 0.5 log serial dilutions) for their ability to inhibit the proliferation of each of these cell lines. Known CDK inhibitors dinaciclib or N-((1S,3R)-3-((5-chloro-4-(1H-indol-3-yl) pyrimidin-2-yl)amino)cyclohexyl)-5-((E)-4-(dimethylamino)but-2-enamido)picolinamide and triptolide were used as positive controls. Cells were seeded at approximately 2,000 cells/well and grown in ATCC-formulated RPMI-1640 Medium (ATCC 30-2001)+10% FBS. The cells were cultured at 37° C. in a humidified chamber in the presence of 5% $CO_2$. Proliferation assays were conducted over a 72-hour time period. CyQUANT® Direct Cell Proliferation Assay (Life Technologies, Chicago, IL USA) was used to assess the anti-proliferative effects of the compounds following manufacturer's directions and utilizing the reagents supplied with the CyQUANT® Direct Cell kit. The results of the assay are shown below in the table below where "A" represents a calculated $IC_{50}$ of less than 100 nM; "B" represents a calculated $IC_{50}$ of between 100 nM and less than 500 nM; "C" represents a calculated $IC_{50}$ of between 500 nM and less than 2 µM; "D" represents a calculated $IC_{50}$ of greater than 2 µM.

The inhibition of proliferation of HCC70, MB453, COV318 and COV504 cells by compounds described herein was found to be as follows.

| Compound | HCC 70 | COV 318 | COV 504 | MB 453 |
|---|---|---|---|---|
| 100 | D | D | D | C |
| 101 | B | B | B | B |
| 102 | D | D | D | D |
| 103 | B | B | B | B |
| 104 | C | D | B | B |
| 105 | D | D | D | D |
| 106 | B | B | B | B |
| 107 | D | D | D | D |
| 108 | C | D | C | C |
| 109 | C | C | C | C |
| 110 | C | D | C | D |
| 111 | D | D | D | D |
| 112 | D | D | D | C |
| 113 | D | D | C | D |
| 114 | B | B | A | A |
| 115 | C | C | B | B |
| 116 | B | B | B | A |
| 117 | B | D | B | B |
| 118 | B | A | A | A |
| 119 | B | D | B | B |
| 120 | D | D | D | D |
| 121 | D | D | D | D |
| 122 | B | B | B | B |
| 123 | B | B | B | B |
| 124 | C | D | C | C |
| 125 | D | D | D | C |
| 126 | D | D | B | B |
| 127 | A | B | A | A |
| 128 | A | B | A | A |
| 129 | B | B | A | A |
| 130 | D | D | D | D |
| 131 | C | C | B | B |
| 132 | D | D | D | D |
| 133 | C | C | C | C |
| 134 | NT | NT | NT | NT |
| 135 | D | D | C | B |
| 136 | NT | NT | NT | NT |
| 137 | A | B | A | A |
| 138 | B | B | B | B |
| 139 | B | C | B | B |
| 140 | A | A | A | A |
| 141 | A | A | A | A |
| 142 | B | B | B | B |
| 143 | B | C | A | A |
| 144 | B | A | A | A |
| 145 | A | A | A | A |
| 146 | A | D | A | A |
| 147 | C | D | B | B |
| 148 | B | D | A | B |
| 149 | A | D | A | A |
| 150 | C | D | C | D |
| 151 | A | D | A | B |
| 152 | B | C | B | B |
| 153 | B | D | B | C |
| 154 | A | B | A | A |
| 155 | D | D | D | D |
| 156 | B | D | B | C |
| 157 | B | B | B | B |
| 158 | C | D | D | C |
| 159 | A | D | B | B |
| 160 | A | A | A | A |
| 161 | A | B | A | A |
| 162 | NT | NT | NT | NT |
| 163 | D | D | D | C |
| 164 | B | D | B | B |
| 165 | D | D | D | C |
| 166 | D | D | D | D |
| 167 | D | D | D | D |
| 168 | B | B | A | A |

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context (for example, where it is evident from the context that "A or B" can mean only "A" or, alternatively, only "B"). The invention includes embodiments in which exactly one member of the group is present in, employed in, or otherwise relevant to a given product or process as well as embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists every possible subgroup of the elements is also disclosed, and any element(s) can be removed from the group. In general, where the invention, or aspects or embodiments of the invention, is/are referred to as comprising or including particular elements and/or features, other aspects or embodiments of the invention consist of, or consist essentially of, such elements and/or features. For practicality and simplicity, not all of those aspects or embodiments have been specifically set forth in haec verba herein but are nevertheless within the scope of the present invention. Where ranges are given, endpoints are included. Furthermore, unless otherwise indicated or otherwise evident from the context, values that are expressed as ranges can assume any specific value or sub-range within the stated ranges in different embodiments of the invention, to the tenth of the unit of the lower limit of the range, and any value may be as stated or "about" the stated value.

One of ordinary skill in the art will recognize or be able to ascertain using no more than routine experimentation, many equivalents to the specific embodiments of the compositions and methods described and claimed herein. Such equivalents are intended to be encompassed by the following claims.

What is claimed is:

1. A compound of Formula I:

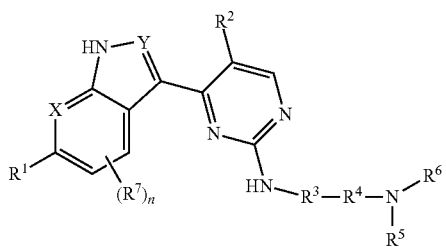

or a pharmaceutically acceptable salt, stereoisomer, or isotopic form thereof, wherein:

X is N, CH, or $C(R^{10})$, wherein $R^{10}$ is halo or $-P(O)(CH_3)_2$;

Y is N or CH;

$R^1$ is $-OH$, $-CN$, $-C(O)NH_2$, or one of the following heteroaryl groups

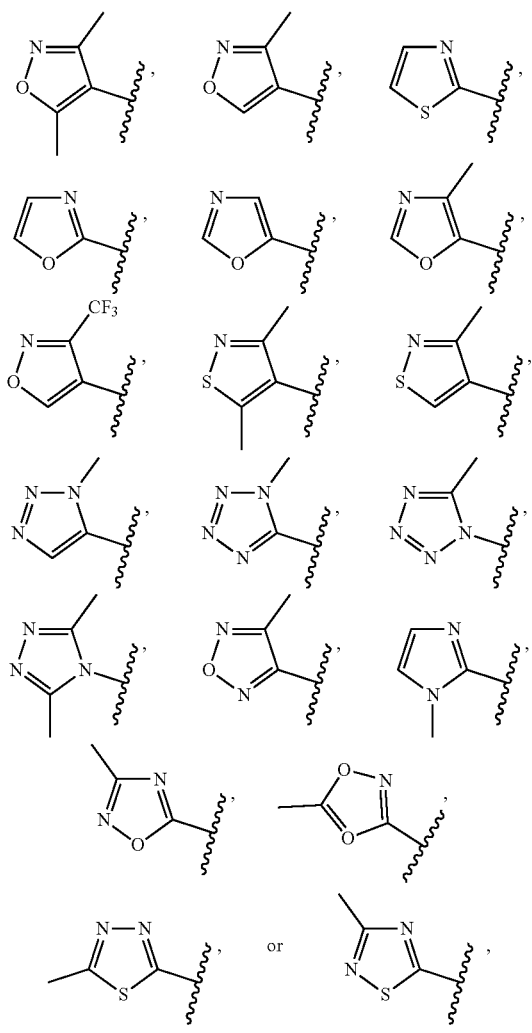

wherein any heteroaryl portion of $R^1$ is optionally substituted at up to two substitutable carbon atoms with a substituent independently selected from halo, $-CN$, $-OH$, $-NH_2$, $-NH(C_1$-$C_4$ alkyl), $-N(C_1$-$C_4$ alkyl)$_2$, $C_1$-$C_4$ alkyl, $-O-(C_1$-$C_4$ alkyl), $-(C_1$-$C_4$ alkylene)-$O-(C_1$-$C_4$ alkyl), and $-S(O)_2-(C_1$-$C_4$ alkyl);

$R^2$ is fluoro, chloro, $-CN$, or $C_1$-$C_4$ alkyl optionally substituted with fluoro;

$R^3$, $R^4$, and $R^5$ are as follows:

(i) $R^3$ is C or CH and $R^4$ is C or CH, wherein $R^3$ and $R^4$ are taken together to form an optionally substituted and optionally benzofused cycloalkyl, and $R^5$ is hydrogen, $C_1$-$C_4$ alkyl, or is taken together with $R^6$ to form an optionally substituted and optionally benzofused saturated monocyclic or bicyclic heterocyclyl; or (ii) $R^3$ is C or CH, $R^4$ is C, CH, or $CH_2$, and $R^5$ is C, CH or $CH_2$, wherein $R^3$ and $R^5$ are taken together with $R^4$ and the intervening nitrogen atom to form a saturated monocyclic heterocyclyl other than piperidine, wherein the saturated monocyclic heterocyclyl is optionally substituted and optionally fused to a cycloalkyl, saturated heterocyclyl, or phenyl ring, wherein $R^5$ and $R^6$ are optionally taken together to form a ring that is fused to the saturated monocyclic heterocyclyl formed when $R^3$ and $R^5$ are taken together; or (iii) $R^3$ is $CH_2$, $R^4$ is C or CH, and $R^5$ is C, CH or $CH_2$, wherein $R^4$ and $R^5$ are taken together with the intervening nitrogen atom to form an optionally substituted and optionally benzofused saturated monocyclic or bicyclic heterocyclyl;

$R^6$ is hydrogen, $-C_1$-$C_4$ alkyl, $-C(O)-(C_1$-$C_4$ alkyl), $-C(O)-(C_1$-$C_4$ alkylene)-$N(R^7)_2$, $-(C_1$-$C_4$ alkylene)-$O-(C_1$-$C_4$ alkyl), $-C(O)$-aryl, or $-S(O)_2$-aryl;

each $R^7$ is, independently, halo, $-CN$, $-OH$, $-NH_2$, $-NH(C_1$-$C_4$ alkyl), $N(C_1$-$C_4$ alkyl)$_2$, $-C_1$-$C_4$ alkyl, $-O-(C_1$-$C_4$ alkyl), $-(C_1$-$C_4$ alkylene)-$O-(C_1$-$C_4$ alkyl) or $-S(O)_2-(C_1$-$C_4$ alkyl);

n is 0, 1, 2, 3 or 4;

each saturated heterocyclyl, cycloalkyl, or aryl is optionally substituted with up to four substituents independently selected from halo, $-CN$, $-OH$, $-NH_2$, $-NH(C_1$-$C_4$ alkyl), $N(C_1$-$C_4$ alkyl)$_2$, $-C_1$-$C_4$ alkyl, $-O-(C_1$-$C_4$ alkyl), $-(C_1$-$C_4$ alkylene)-$O-(C_1$-$C_4$ alkyl), and an optionally substituted phenyl; and each $C_1$-$C_4$ alkyl and $C_1$-$C_4$ alkylene is optionally substituted with up to five substituents independently selected from halo, $-CN$, $-OH$, $-NH_2$, $-NH$(unsubstituted $C_1$-$C_4$ alkyl), N(unsubstituted $C_1$-$C_4$ alkyl)$_2$, and $-O$-(unsubstituted $C_1$-$C_4$ alkyl).

2. The compound of claim 1 or the pharmaceutically acceptable salt, stereoisomer, or isotopic form thereof, wherein $R^1$ is $-OH$, $-CN$, $-C(O)NH_2$,

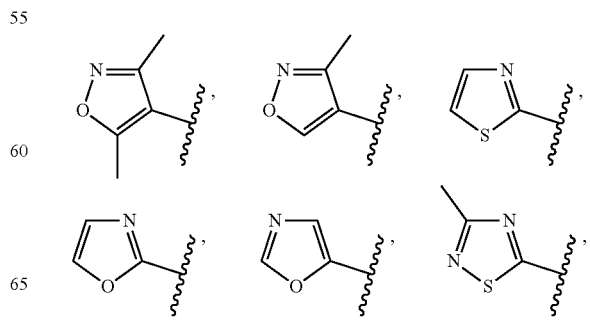

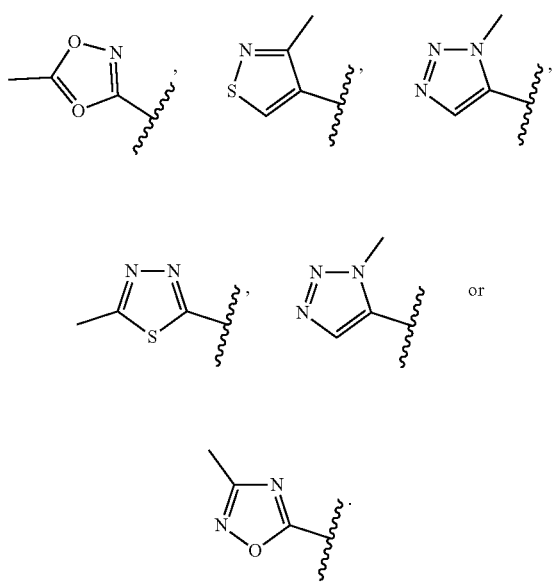

3. The compound of claim 1 or the pharmaceutically acceptable salt, stereoisomer, or isotopic form thereof, wherein $R^2$ is -chloro or —$CF_3$.

4. The compound of claim 1, wherein the compound is a compound of Formula Ia:

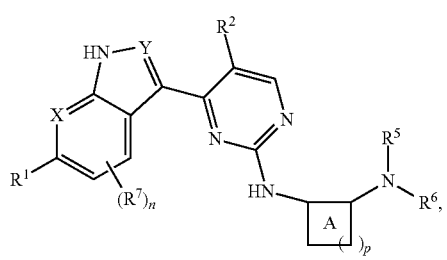

(Ia)

or a pharmaceutically acceptable salt, stereoisomer, or isotopic form thereof, wherein:

ring A is an optionally substituted and optionally benzofused cycloalkyl;

X, Y, $R^1$, $R^2$, $R^5$, $R^6$, $R^7$, and n are as defined in claim 1; and p is 0, 1, 2, 3, 4, or 5.

5. The compound of claim 4 or the pharmaceutically acceptable salt, stereoisomer, or isotopic form thereof, wherein $R^1$ is hydrogen or —$CH_3$, and $R^6$ is hydrogen, —$C_1$-$C_4$ alkyl, halo-substituted —$C_1$-$C_4$ alkyl, hydroxy-substituted —$C_1$-$C_4$ alkyl, or —($C_1$-$C_4$ alkylene)-O—($C_1$-$C_4$ alkyl), or $R^5$ and $R^6$ are taken together with the nitrogen atom to which they are bound to form a saturated heterocyclyl optionally substituted with 1-4 substituents independently selected from halo, —OH, —$C_1$-$C_4$ alkyl, and —O—($C_1$-$C_4$ alkyl).

6. The compound of claim 1 or the pharmaceutically acceptable salt, stereoisomer, or isotopic form thereof, wherein the compound is a compound of Formula Ib:

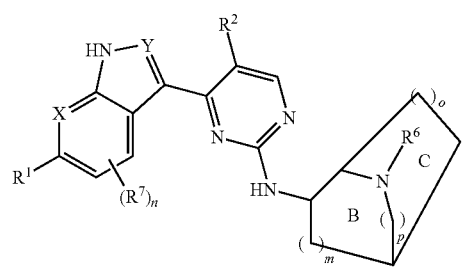

(Ib)

wherein:

ring B is an optionally substituted, saturated monocyclic heterocyclyl optionally fused to a cycloalkyl, saturated heterocyclyl, or phenyl ring X, Y, $R^1$, $R^2$, $R^6$, $R^7$, and n are as defined in claim 1; and m is 0, 1, 3, or 4.

7. The compound of claim 1 or the pharmaceutically acceptable salt, stereoisomer, or isotopic form thereof, wherein Y is CH and/or X is N, CH, C(Cl), or —C(P(O)(CH$_3$)$_2$).

8. The compound of claim 1 or the pharmaceutically acceptable salt, stereoisomer, or isotopic form thereof, wherein n is 0.

9. The compound of claim 6, wherein the compound is a compound of Formula II:

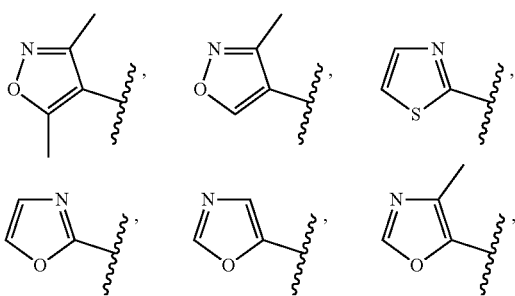

(II)

or a pharmaceutically acceptable salt, stereoisomer, or isotopic form thereof, wherein:

ring B is optionally substituted;

ring C is optionally substituted;

X is N, CH, or C($R^{10}$), wherein $R^{10}$ is halo or —P(O)(CH$_3$)$_2$;

Y is N or CH;

$R^1$ is —OH, —CN, —C(O)NH$_2$, or one of the following heteroaryl groups

-continued

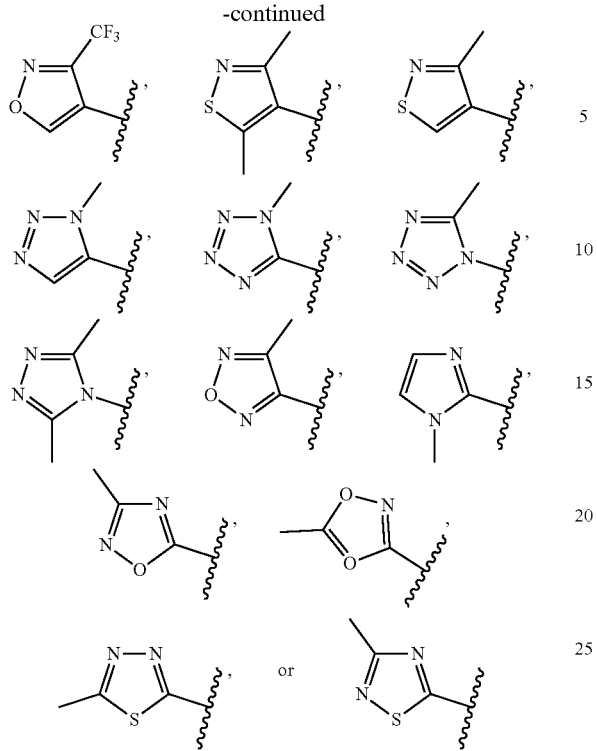

wherein any heteroaryl portion of R¹ is optionally substituted at up to two substitutable carbon atoms with a substituent independently selected from halo, —CN, —OH, —NH$_2$, —NH(C$_1$-C$_4$ alkyl), —N(C$_1$-C$_4$ alkyl)$_2$, C$_1$-C$_4$ alkyl, —O—(C$_1$-C$_4$ alkyl), —(C$_1$-C$_4$ alkylene)-O—(C$_1$-C$_4$ alkyl), and —S(O)$_2$—(C$_1$-C$_4$ alkyl);

R² is fluoro, chloro, —CN, or C$_1$-C$_4$ alkyl optionally substituted with fluoro;

R⁶ is hydrogen, —C$_1$-C$_4$ alkyl, —C(O)—(C$_1$-C$_4$ alkyl), —C(O)—(C$_1$-C$_4$ alkylene)-N(R⁷)$_2$, —(C$_1$-C$_4$ alkylene)-O—(C$_1$-C$_4$ alkyl), —C(O)-aryl, or —S(O)$_2$-aryl;

each R⁷ is, independently, halo, —CN, —OH, —NH$_2$, —NH(C$_1$-C$_4$ alkyl), N(C$_1$-C$_4$ alkyl)$_2$, —C$_1$-C$_4$ alkyl, —O—(C$_1$-C$_4$ alkyl), —(C$_1$-C$_4$ alkylene)-O—(C$_1$-C$_4$ alkyl) or —S(O)$_2$—(C$_1$-C$_4$ alkyl);

m is 0, 1, 2, 3 or 4;

n is 0, 1, 2, 3 or 4;

o is 0, 1, 2, 3 or 4;

p is 0, 1, 2, 3 or 4;

wherein m+p does not equal 2;

each saturated heterocyclyl, cycloalkyl, or aryl is optionally substituted with up to four substituents independently selected from halo, —CN, —OH, —NH$_2$, —NH(C$_1$-C$_4$ alkyl), N(C$_1$-C$_4$ alkyl)$_2$, —C$_1$-C$_4$ alkyl, —O—(C$_1$-C$_4$ alkyl), —(C$_1$-C$_4$ alkylene)-O—(C$_1$-C$_4$ alkyl), and an optionally substituted phenyl; and each C$_1$-C$_4$ alkyl and C$_1$-C$_4$ alkylene is optionally substituted with up to five substituents independently selected from halo, —CN, —OH, —NH$_2$, —NH(unsubstituted C$_1$-C$_4$ alkyl), N(unsubstituted C$_1$-C$_4$ alkyl)$_2$, and —O-(unsubstituted C$_1$-C$_4$ alkyl).

10. A compound selected from any one of the compounds set forth below or a pharmaceutically acceptable salt, stereoisomer, or isotopic form thereof:

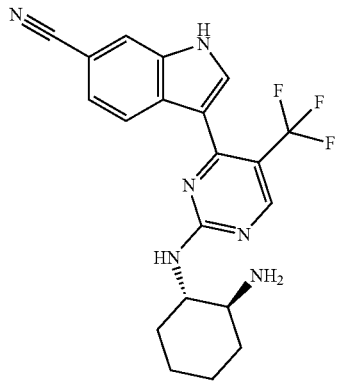

Compound 100

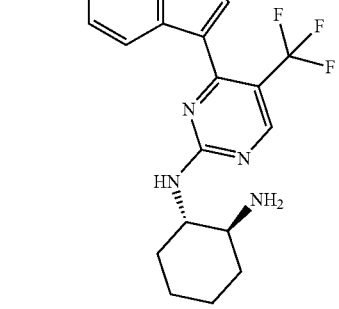

Compound 101

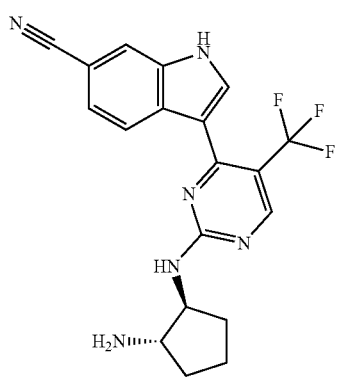

Compound 102

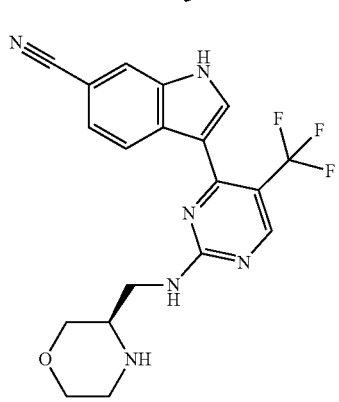

Compound 103

-continued
Compound 104
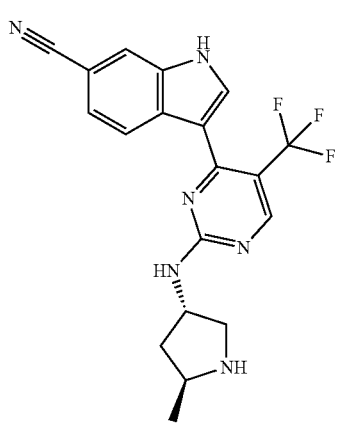
Compound 108
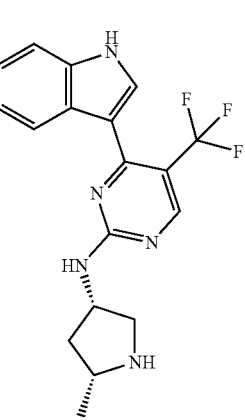
Compound 105
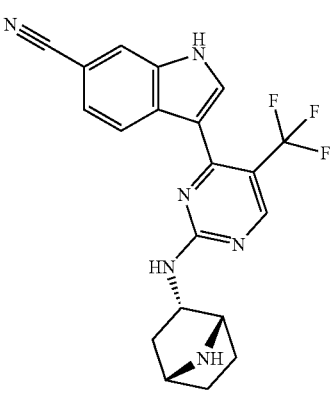
Compound 109
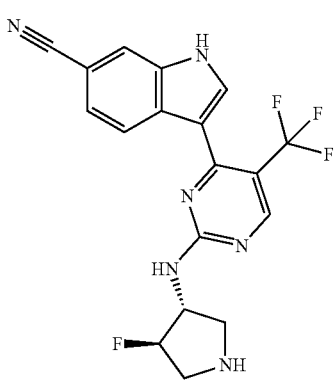
Compound 106*
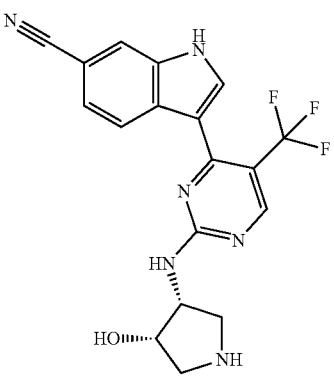
Compound 110*
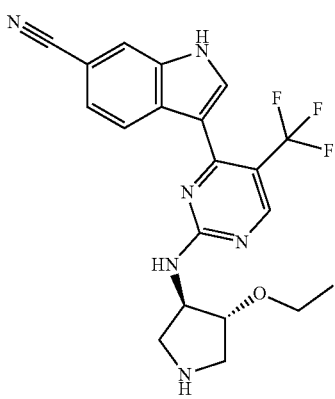
Compound 107*
Compound 111*

Compound 112
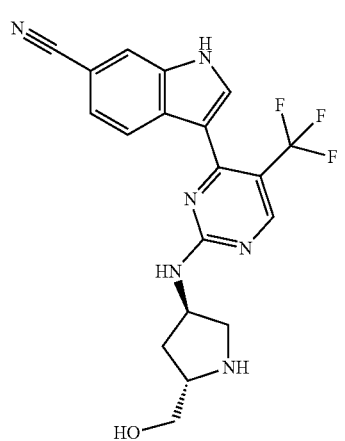
Compound 113*
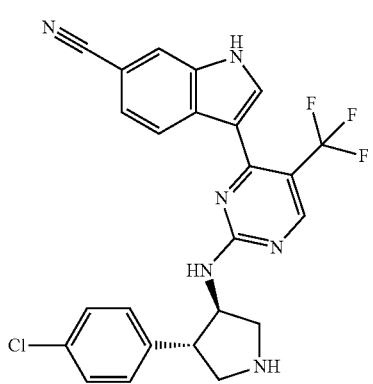
Compound 114
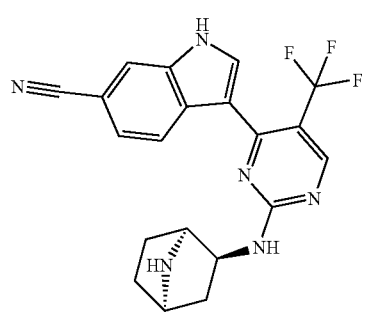
Compound 115
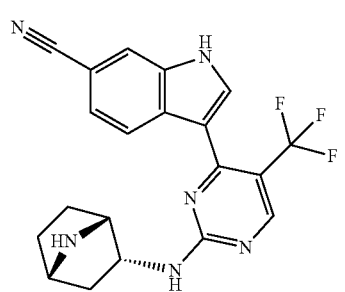
Compound 116
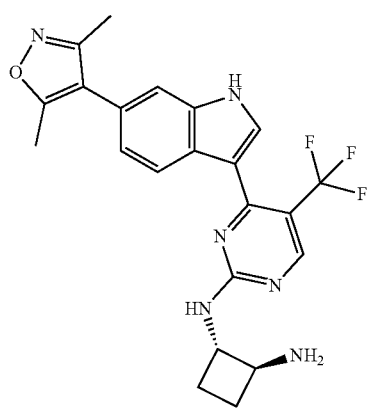
Compound 117
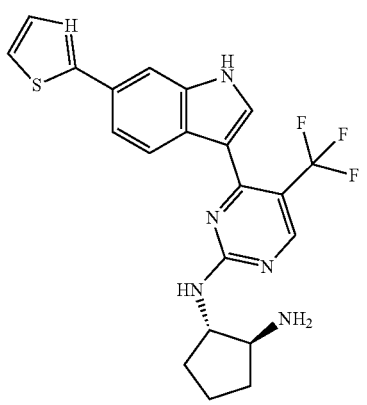
Compound 118
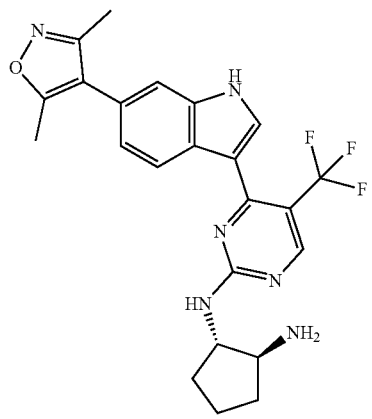
Compound 119
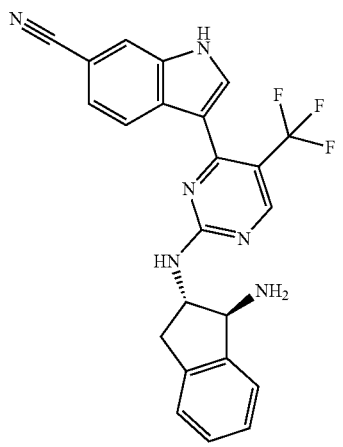

Compound 120
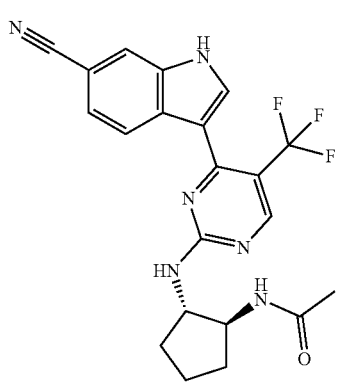
Compound 121
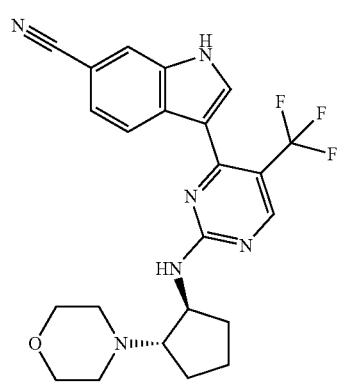
Compound 122
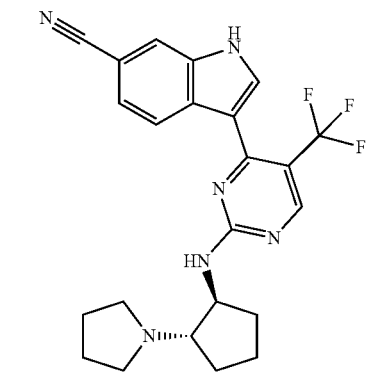
Compound 123
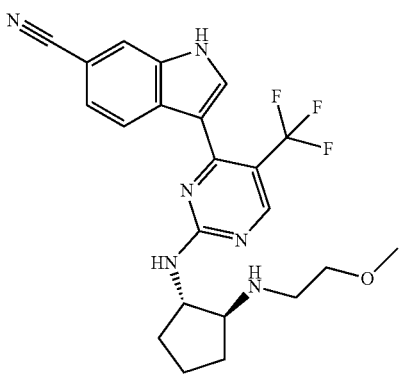
Compound 124
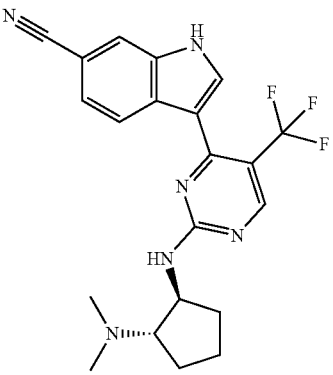
Compound 125
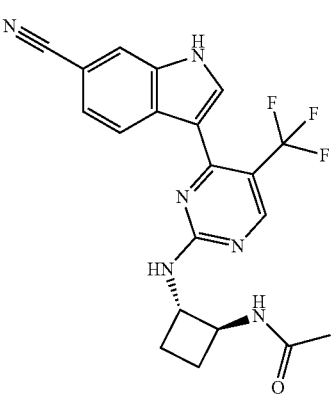
Compound 126
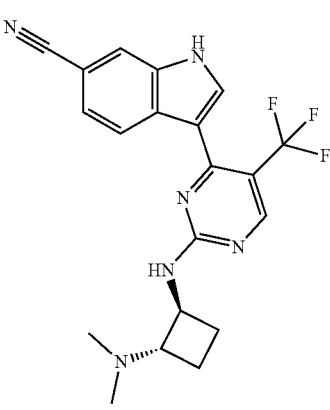
Compound 127
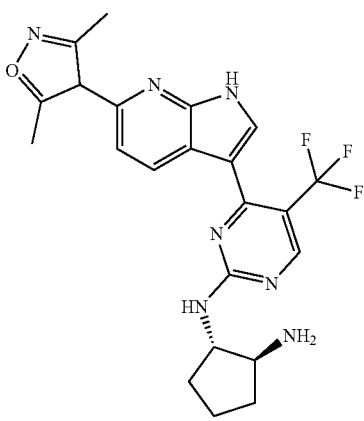

-continued
Compound 128
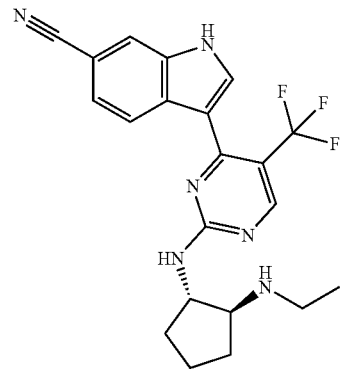
Compound 129
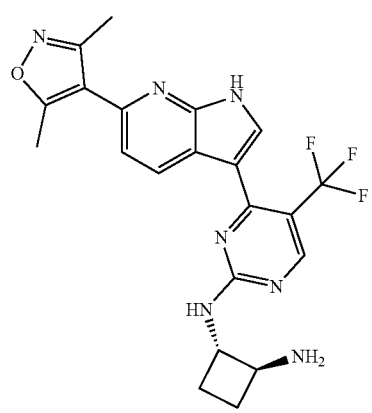
Compound 130
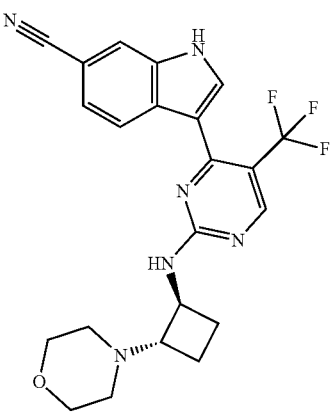
Compound 131
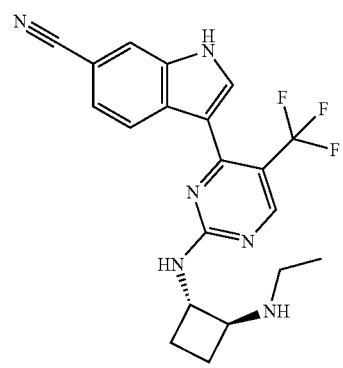
-continued
Compound 132
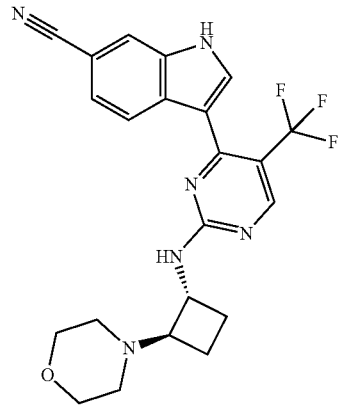
Compound 133
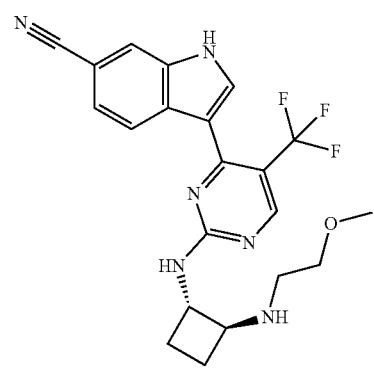
Compound 134
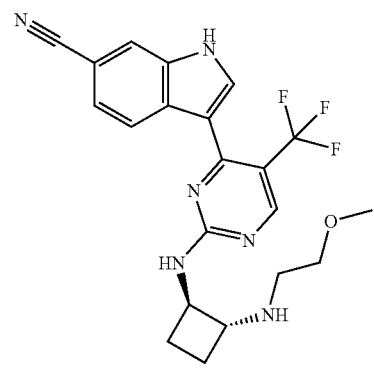
Compound 135

Compound 136
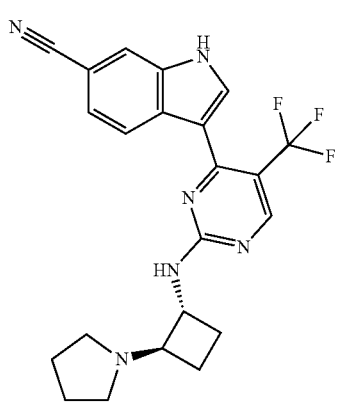
Compound 137
Compound 138
Compound 139
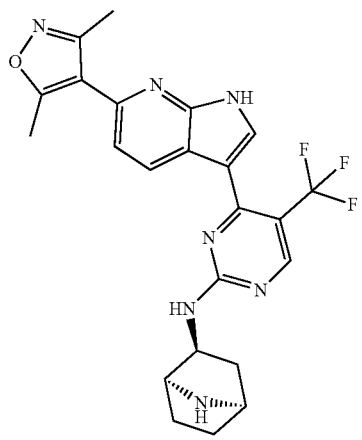
Compound 140
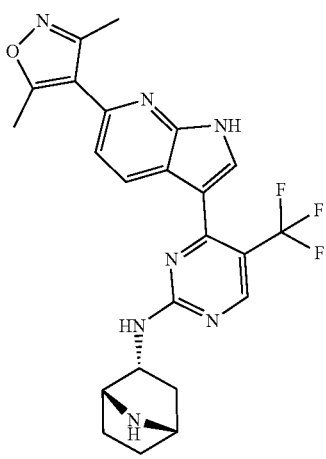
Compound 141
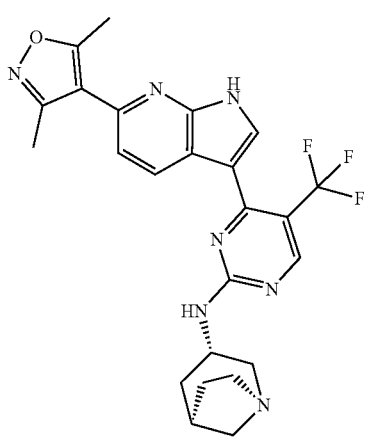

-continued
Compound 142
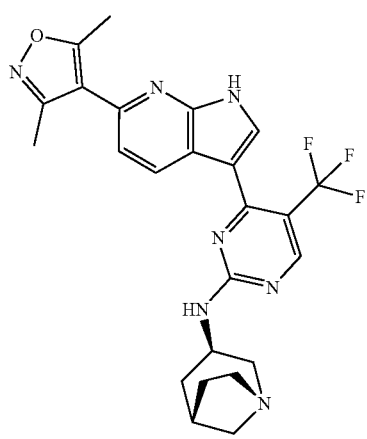
Compound 143
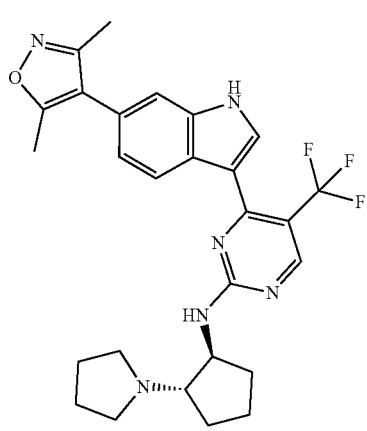
Compound 144
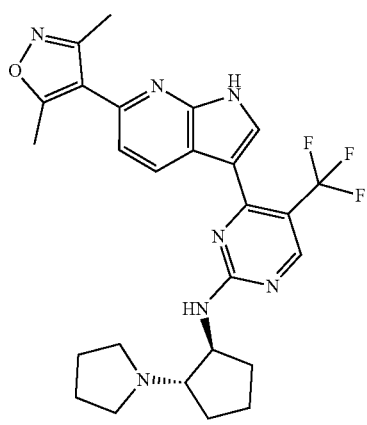
-continued
Compound 145
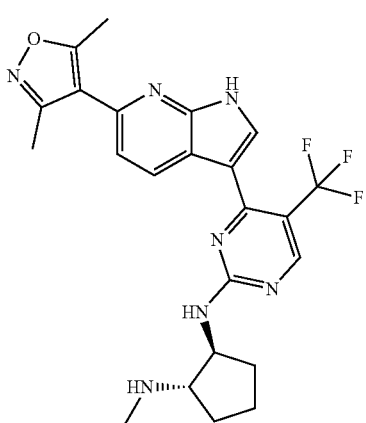
Compound 146
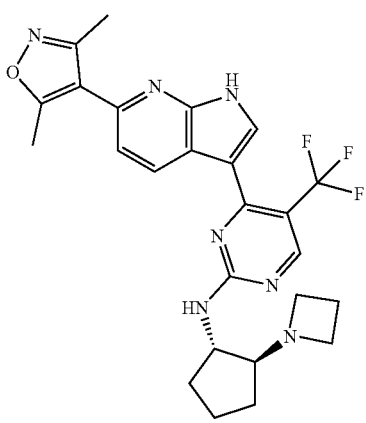
Compound 147
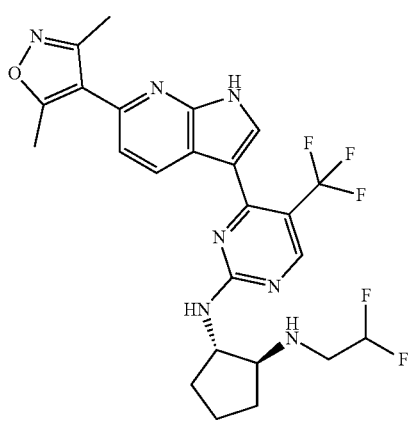

Compound 148
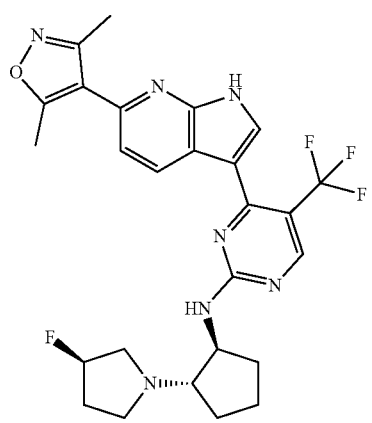
Compound 151
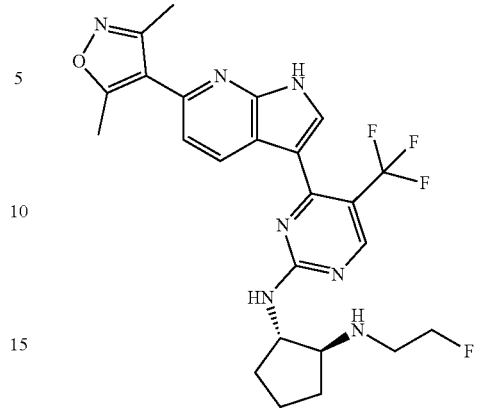
Compound 149
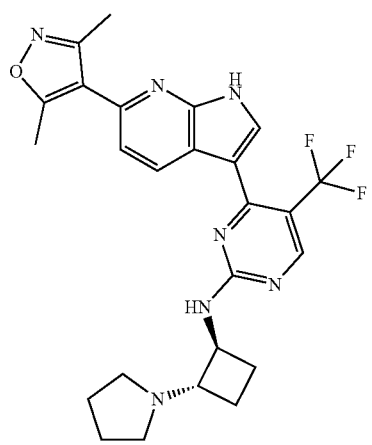
Compound 152
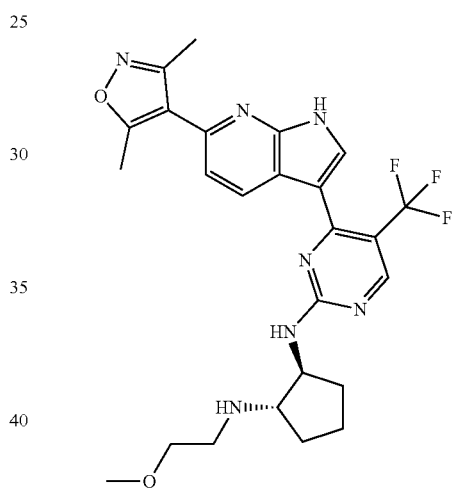
Compound 150
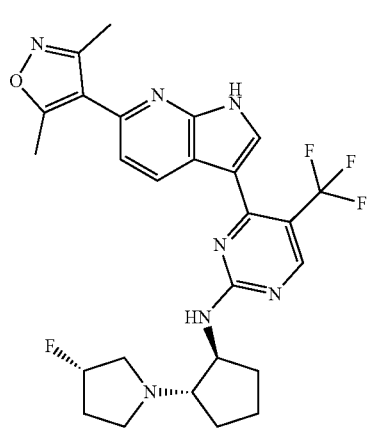
Compound 153
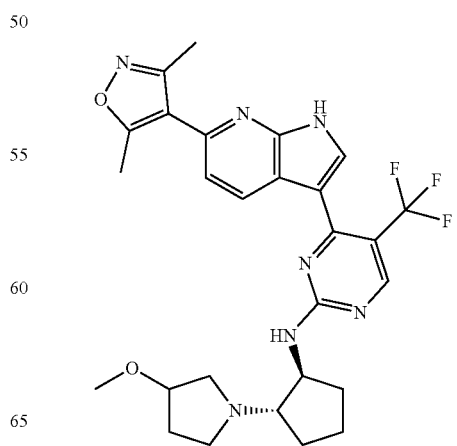

-continued
Compound 154
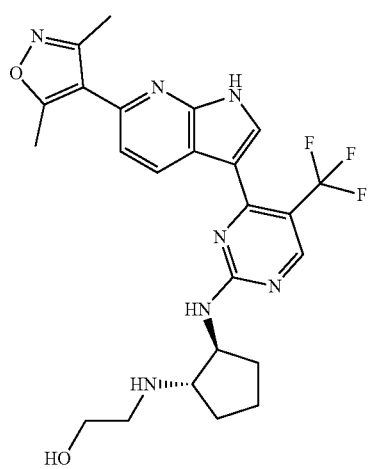
Compound 155
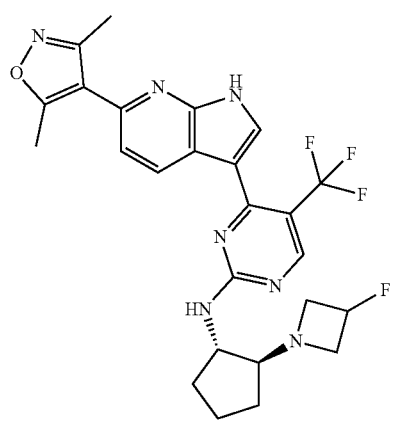
Compound 156
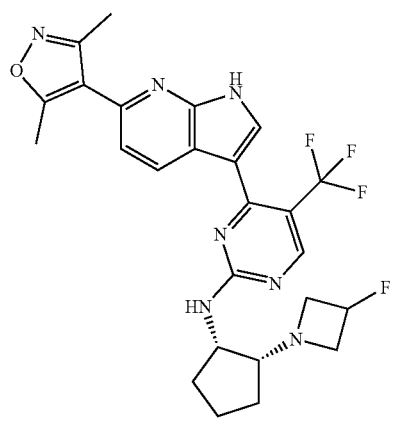
-continued
Compound 157
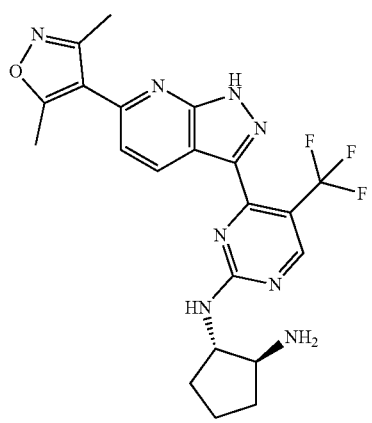
Compound 158
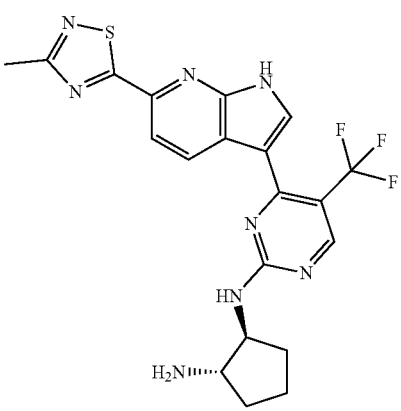
Compound 159
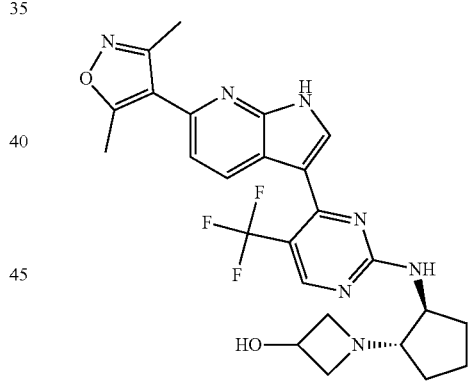
Compound 160
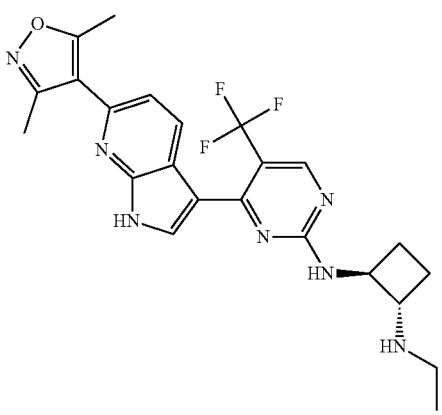

Compound 161
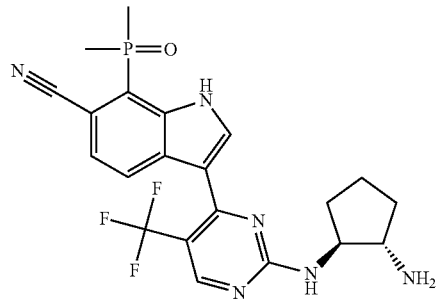
Compound 162
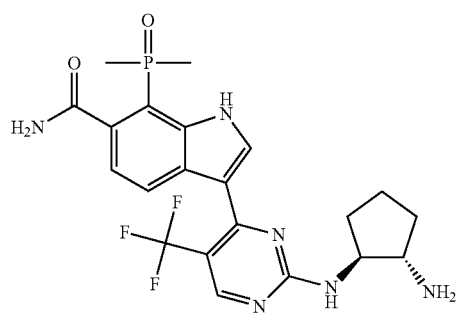
Compound 163
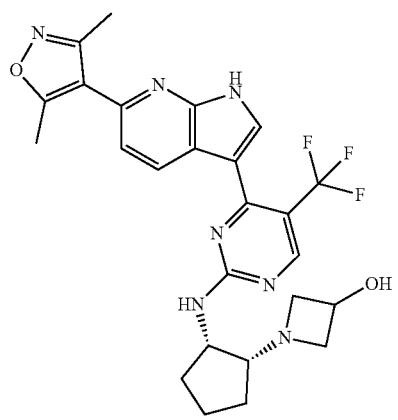
Compound 164
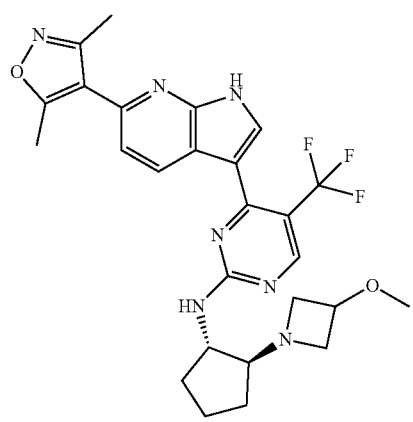
Compound 165
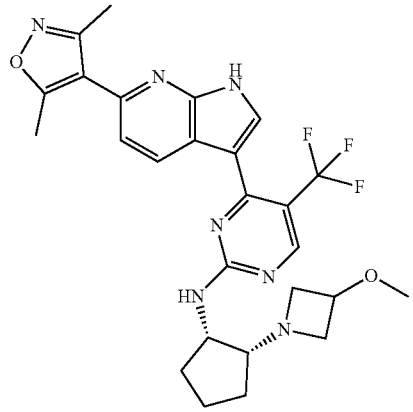
Compound 166
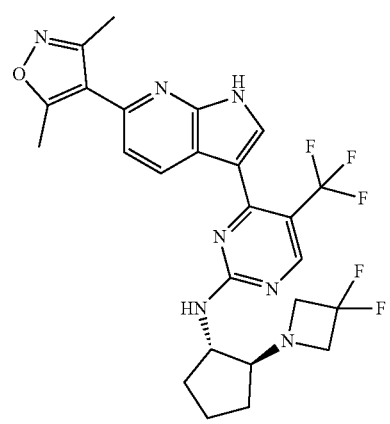
Compound 167
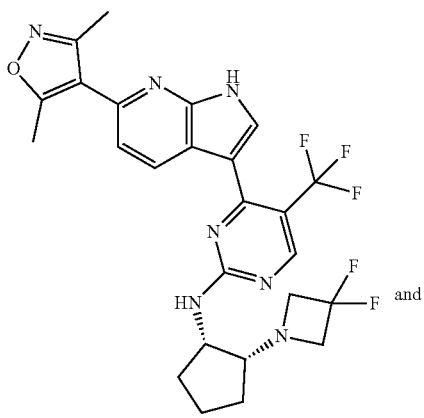
and
Compound 168
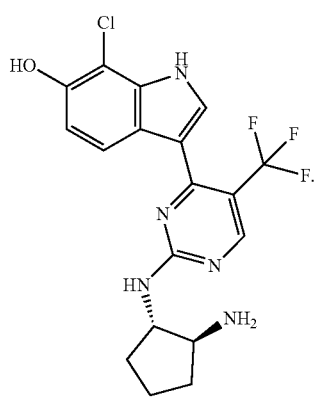

11. A pharmaceutical composition comprising the compound of claim 1 or the pharmaceutically acceptable salt, stereoisomer, or isotopic form thereof; and a pharmaceutically acceptable excipient.

12. A method of treating a patient suffering from a disease associated with aberrant activity of CDK7, the method comprising administering to the patient a therapeutically effective amount of the compound of claim 1 or the pharmaceutically acceptable salt, stereoisomer, or isotopic form thereof.

13. The method of claim 12, wherein the disease is a proliferative disease, an infectious disease, or a disease caused by or associated with expanded repeats of simple nucleotide tracts.

14. The method of claim 13, wherein the proliferative disease is cancer, a benign neoplasm, pathologic angiogenesis, or a fibrotic disease; the infectious disease is a viral infection caused by an influenza virus, a human immunodeficiency virus (HIV), a herpes virus, or a human papilloma virus (HPV)); and the disease caused by or associated with expanded repeats of simple nucleotide tracts is Huntington's Disease, myotonic dystrophy, or a form of amyotrophic lateral sclerosis (ALS).

15. The method of claim 14, wherein the proliferative disease is a cancer selected from the group consisting of a blood cancer, a bone cancer, a brain cancer, a breast cancer, a lung cancer, melanoma, neuroblastoma, and an ovarian cancer.

16. The method of claim 15, wherein the blood cancer is chronic lymphocytic leukemia (CLL), chronic myelomonocytic leukemia (CMML), acute lymphoblastic leukemia (ALL), T-cell acute lymphoblastic leukemia (T-ALL), chronic myelogenous leukemia (CML), acute myelogenous leukemia (AML), lymphoma, or multiple myeloma.

17. The method of claim 15, wherein the bone cancer is osteosarcoma or Ewing's sarcoma; the breast cancer is triple-negative breast cancer (TNBC); the brain cancer is a glioblastoma; and the lung cancer is small cell lung cancer (SCLC).

18. The method of claim 12, further comprising administering a second agent to the patient, wherein the second agent is an anti-proliferative agent, an anti-cancer agent, an immunosuppressant, or a pain-relieving agent.

19. A pharmaceutical composition comprising the compound of claim 10 or the pharmaceutically acceptable salt, stereoisomer, or isotopic form thereof; and a pharmaceutically acceptable excipient.

20. A method of treating a patient suffering from a disease associated with aberrant activity of CDK7, the method comprising administering to the patient a therapeutically effective amount of the compound of claim 10 or the pharmaceutically acceptable salt, stereoisomer, or isotopic form thereof.

21. The method of claim 20, wherein the disease is a proliferative disease, an infectious disease, or a disease caused by or associated with expanded repeats of simple nucleotide tracts.

22. The method of claim 21, wherein the proliferative disease is cancer, a benign neoplasm, pathologic angiogenesis, or a fibrotic disease; the infectious disease is a viral infection caused by an influenza virus, a human immunodeficiency virus (HIV), a herpes virus, or a human papilloma virus (HPV); and the disease caused by or associated with expanded repeats of simple nucleotide tracts is Huntington's Disease, myotonic dystrophy, or a form of amyotrophic lateral sclerosis (ALS).

23. The method of claim 22, wherein the proliferative disease is a cancer selected from the group consisting of a blood cancer, a bone cancer, a brain cancer, a breast cancer, a lung cancer, melanoma, neuroblastoma, and an ovarian cancer.

24. The method of claim 23, wherein the blood cancer is chronic lymphocytic leukemia (CLL), chronic myelomonocytic leukemia (CMML), acute lymphoblastic leukemia (ALL), T-cell acute lymphoblastic leukemia (T-ALL), chronic myelogenous leukemia (CML), acute myelogenous leukemia (AML), lymphoma, or multiple myeloma.

25. The method of claim 23, wherein the bone cancer is osteosarcoma or Ewing's sarcoma; the breast cancer is triple-negative breast cancer (TNBC); the brain cancer is a glioblastoma; and the lung cancer is small cell lung cancer (SCLC).

26. The method of claim 10, further comprising administering a second agent to the patient, wherein the second agent is an anti-proliferative agent, an anti-cancer agent, an immunosuppressant, or a pain-relieving agent.

* * * * *